US012444478B2

(12) United States Patent
Moufarrej et al.

(10) Patent No.: US 12,444,478 B2
(45) Date of Patent: Oct. 14, 2025

(54) NONINVASIVE MOLECULAR CLOCK FOR FETAL DEVELOPMENT PREDICTS GESTATIONAL AGE AND PRETERM DELIVERY

(71) Applicants: CZ Biohub SF, LLC, San Francisco, CA (US); The Board of Trustees of the Leland Stanford Junior University, Stanford, CA (US); Statens Serum Institut, Copenhagen (DK)

(72) Inventors: Mira N. Moufarrej, Stanford, CA (US); Thuy T. M. Ngo, Stanford, CA (US); Joan Camunas-Soler, Stanford, CA (US); Mads Melbye, Copenhagen (DK); Stephen R. Quake, San Francisco, CA (US)

(73) Assignees: CZ Biohub SF, LLC, San Francisco, CA (US); The Board of Trustees of the Leland Stanford Junior University, Stanford, CA (US); Statens Serum Institut, Copenhage (DK)

( * ) Notice: Subject to any disclaimer, the term of this patent is extended or adjusted under 35 U.S.C. 154(b) by 1369 days.

(21) Appl. No.: 16/758,844

(22) PCT Filed: Oct. 23, 2018

(86) PCT No.: PCT/US2018/057142
§ 371 (c)(1),
(2) Date: Apr. 23, 2020

(87) PCT Pub. No.: WO2019/084033
PCT Pub. Date: May 2, 2019

(65) Prior Publication Data

US 2023/0140653 A1 May 4, 2023

Related U.S. Application Data

(60) Provisional application No. 62/578,360, filed on Oct. 27, 2017, provisional application No. 62/576,033, filed on Oct. 23, 2017.

(51) Int. Cl.

| | |
|---|---|
| ***G16B 20/00*** | (2019.01) |
| ***C12Q 1/6876*** | (2018.01) |
| ***C12Q 1/6883*** | (2018.01) |
| ***G16B 40/20*** | (2019.01) |
| ***G16H 50/20*** | (2018.01) |

(52) U.S. Cl.
CPC ........... *G16B 20/00* (2019.02); *C12Q 1/6883* (2013.01); *G16B 40/20* (2019.02); *G16H 50/20* (2018.01); *C12Q 1/6876* (2013.01); *C12Q 2600/158* (2013.01)

(58) Field of Classification Search
CPC ...... G16B 20/00; G16B 40/20; C12Q 1/6883; C12Q 1/6876; C12Q 2600/158; C12Q 2600/16; G16H 50/20; A61P 15/00; G01N 2800/368; G01N 2800/50; G01N 33/689; G01N 2800/60
See application file for complete search history.

(56) References Cited

U.S. PATENT DOCUMENTS

2015/0366835 A1* 12/2015 Pogue-Geile ........ C12Q 1/6886 514/492

FOREIGN PATENT DOCUMENTS

| | | | |
|---|---|---|---|
| JP | 2011522272 | 7/2011 | |
| JP | 2015511122 | 4/2015 | |
| WO | 2009134452 A2 | 11/2009 | |
| WO | WO-2014105985 A1 * | 7/2014 | ............. A61K 31/57 |
| WO | 2015010442 A1 | 1/2015 | |
| WO | 2017/096405 A1 | 6/2017 | |

OTHER PUBLICATIONS

Linda K. Woolery, Jerzy Grzymala-Busse, Machine Learning for an Expert System to Predict Preterm Birth Risk, Journal of the American Medical Informatics Association, vol. 1, Issue 6, Nov. 1994, pp. 439-446, https://doi.org/10.1136/jamia.1994.95153433 (Year: 1994).*
Lan Yang et al. Maternal-Fetal Medicine Obstetrics & Gynecology Science 2015; 58(4): 261-267. Published online: Jul. 16, 2015 (Year: 2015).*
Spencer, K., Cowans, N.J. and Stamatopoulou, A. (2008), ADAM12s in maternal serum as a potential marker of pre-eclampsia. Prenat. Diagn., 28: 212-216. https://doi.org/10.1002/pd.1957 (Year: 2008).*
Emma L. Davies, Jacqueline S. Bell & Sohinee Bhattacharya (2016) Preeclampsia and preterm delivery: A population-based case-control study, Hypertension in Pregnancy, 35:4, 510-519, DOI: 10.1080/10641955.2016.1190846 (Year: 2016).*
Hendrix et al. ("An immunohistochemical analysis of Rab27B distribution in fetal and adult tissue", Int. J. Dev. Biol. 56: 363-368 (2012) https://doi.org/10.1387/ijdb.120008ah). (Year: 2012).*
Neofytou et al. ("Targeted capture enrichment assay for non-invasive prenatal testing of large and small size sub-chromosomal deletions and duplications." PLoS One. Feb. 3, 2017;12(2):e0171319. doi: 10.1371) (Year: 2017).*
Khurram et al.(Human myometrial adaptation to pregnancy: cDNA microarray gene expression profiling of myometrium from non-pregnant and pregnant women, Molecular Human Reproduction, vol. 9, Issue 11, Nov. 2003, pp. 681-700) https://academic.oup.com/molehr/article/9/11/681/1059654 (Year: 2003).*

(Continued)

*Primary Examiner* — Neil P Hammell
*Assistant Examiner* — Morgan Taylor Lindgren Baltzel
(74) *Attorney, Agent, or Firm* — Kilpatrick Townsend & Stockton LLP

(57) ABSTRACT

The invention is directed to methods of identifying woman is risk for preterm delivery. In some aspects, the methods include quantitating one or more placental or fetal-tissue specific genes in a biological sample from the woman.

11 Claims, 14 Drawing Sheets

Specification includes a Sequence Listing.

(56) References Cited

OTHER PUBLICATIONS

Conde-Agudelo, et al., “Novel biomarkers for the prediction of the spontaneous preterm birth phenotype: a systematic review and meta-analysis”, BJOG: An International Journal of Obstetrics & Gynaecology, Mar. 15, 2011, vol. 118, pp. 1042-1054.

Ngo, et al., “A Noninvasive Molecular Clock for Fetal Development Predicts Gestational Age and Preterm Delivery”, bioRxiv, Bioengineering, 2007, p. 212910-212914.

Siler-Khodr, et al., “Gonadotropin-releasing Hormone Effects on Placental Hormones during Gestation: I. Alpha-Human Chorionic Gonadotropin, Human Chorionic Gonadotropin and Human Chorionic Somatomammotropin”, Biology of Reproduction, 1986, vol. 34, pp. 245-254.

Westergaard, et al., “Single Measurements ofChorionic Gonadotropin and Schwangerschafts Protein for Assessing Gestational Age and Predicting the Day of Delivery”, The Journal of Reproductive Medicine, 1985, vol. 30, No. 1, pp. 57-60.

Application PCT/US2018/057142, International Search Report and Written Opinion. May 2, 2019, 19 pages.

EP18871519.7, “Extended European Search Report”, Oct. 15, 2021, 19 pages.

PCT/US2018/057142, “International Preliminary Report on Patentability”, May 7, 2020, 13 pages.

EP18871519.7 , “Partial Supplementary European Search Report”, Jul. 14, 2021, 22 pages.

Fiddes et al., “Isolation, Cloning and Sequence Analysis of the cDNA for the Alpha-Subunit of Human Chorionic Gonadotropin”, Nature. vol. 281, No. 5730 Available online at: https://www.ncbi.nlm.nih.gov/pubmed/?term=Nature%2C+1979%2C+Vol.+281%2C+No.+5730%2C+pages+351-356, 1979, pp. 351-356.

Fiddes et al., “The Gene Encoding the Common Alpha Subunit of the Four Human Glycoprotein Hormones”, Journal of Molecular and Applied Genetics. vol. 1, No. 1 Available online at: https://www.ncbi.nlm.nih.gov/pubmed/?term=Journal+of+Molecular+and+Applied+Genetics%2C+Vol.+1%2C+No.+1%2C+pages+3-18, 1982, pp. 3-18.

Heng et al., “Maternal Whole Blood Gene Expression at 18 and 28 Weeks of Gestation Associated with Spontaneous Preterm Birth in Asymptomatic Women”, PLOS One, vol. 11, No. 6, Jun. 22, 2016, 17 pages.

Heng et al., “Whole Blood Gene Expression Profile Associated with Spontaneous Preterm Birth in Women with Threatened Preterm Labor”, PLOS One, vol. 9, No. 5, May 14, 2014, pp. 1-13.

* cited by examiner

University of Pennsylvania positive fold change for preterm samples

| | gene | exact_test | exact_post_bh | permutation_test | perm_post_bh | wilcox_rank_test | wilcox_post_bh |
|---|---|---|---|---|---|---|---|
| 1 | CGB | 0.01459029 | 0.058209285 | 0.035708125 | 0.109981025 | 0.039532547 | 0.152269024 |
| 2 | PKHD1L1 | 0.01511929 | 0.058209285 | 0.002536219 | 0.011487581 | 0.030442576 | 0.130226577 |
| 3 | TBC1D15 | 0.00641979 | 0.037815074 | 0.000876735 | 0.006137142 | 0.017236068 | 0.082948578 |
| 4 | RGS18 | 3.3283E-06 | 0.000128138 | 1.14577E-05 | 0.000441122 | 1.95447E-06 | 7.5247E-05 |
| 5 | APLF | 0.01511929 | 0.058209285 | 0.005907478 | 0.023940831 | 0.050656999 | 0.185742328 |
| 6 | DGCR14 | 0.00207004 | 0.01771031 | 0.012834225 | 0.047058824 | 0.002315177 | 0.022537842 |
| 7 | DAPP1 | 0.00120009 | 0.011550824 | 0.002233135 | 0.011487581 | 0.068992313 | 0.230974266 |
| 8 | RAB27B | 0.00016903 | 0.003253888 | 0.000572857 | 0.005954874 | 0.009137491 | 0.056136526 |
| 9 | MMD | 0.00052594 | 0.006749511 | 0.000353348 | 0.005441558 | 1.54658E-05 | 0.000396955 |
| 10 | MOB1B | 0.00120009 | 0.011550824 | 0.000698623 | 0.005977108 | 0.003968674 | 0.033954212 |
| 11 | VCAN | 0.00602521 | 0.037815074 | 0.0609357 | 0.13405854 | 0.039550396 | 0.152269024 |
| 12 | PPBP | 4.0152E-05 | 0.001030557 | 0.000826726 | 0.006137142 | 0.010206641 | 0.056136526 |
| 13 | FAM212B.AS1 | 0.00641979 | 0.037815074 | 0.001060894 | 0.0068074 | 0.011941369 | 0.061299028 |
| 14 | P2RY12 | 0.01511929 | 0.058209285 | 0.000618688 | 0.005954874 | 0.007278664 | 0.056045715 |
| 15 | LYPLAL1 | 0.00326219 | 0.025118868 | 0.000510739 | 0.005954874 | 0.008163882 | 0.056136526 |
| 16 | RAB11A | 0.01511929 | 0.058209285 | 0.001908679 | 0.011305255 | 0.002039147 | 0.022537842 |
| 17 | MAP3K7CL | 3.1158E-06 | 0.000128138 | 2.62012E-06 | 0.000201749 | 1.95447E-06 | 7.5247E-05 |
| 18 | FRMD4B | 0.00736657 | 0.037815074 | 0.000129618 | 0.002495147 | 0.00153396 | 0.022537842 |
| 19 | CLCN3 | 0.00052594 | 0.006749511 | 0.002318622 | 0.011487581 | 0.002341594 | 0.022537842 |
| 20 | POLE2 | 0.00736657 | 0.037815074 | 2.73342E-05 | 0.000701578 | 9.73693E-05 | 0.001874359 |
| 21 | PLAC4 | 0.05513702 | 0.192979573 | 0.044377393 | 0.128269206 | 0.201252035 | 0.596015642 |
| 22 | ADAM12 | 0.16185096 | 0.346181214 | 0.023262032 | 0.081107685 | 0.34579949 | 0.832080024 |
| 23 | CYP3A7 | 0.36140374 | 0.556290502 | 0.002406417 | 0.011487581 | 0.068208318 | 0.230974266 |
| 24 | VGLL1 | 0.24188641 | 0.433145431 | 0.012834225 | 0.047058824 | 0.5 | 0.975090549 |
| 25 | GH2 | 0.09515475 | 0.261675555 | 0.025280317 | 0.081107685 | 0.447434697 | 0.975090549 |
| 26 | CAPN6 | 0.24188641 | 0.433145431 | 0.044977514 | 0.128269206 | 0.530096158 | 0.975090549 |
| 27 | PSG4 | 0.09515475 | 0.261675555 | 0.025280317 | 0.081107685 | 0.254408768 | 0.675617372 |
| 28 | RPL23AP7 | 0.147326 | 0.346181214 | 0.004511025 | 0.019297161 | 0.010206641 | 0.056136526 |
| 29 | ANXA3 | 0.21053349 | 0.426607336 | 0.064540772 | 0.138045541 | 0.02593043 | 0.117449593 |

| Key | |
|---|---|
| exact_testFisher | Fisher Exact test p-value |
| post_bh | Benjamani Hochberg corrected p-value |
| permutation_test | Permutation test p-value |

| Key | |
|---|---|
| wilcox_rank_test | Mann-Whitney Test p-value |
| Indicates p-value < 0.05 | |

FIG. 10A

University of Alabama positive fold change for preterm samples

| | gene | exact_test | exact_post_bh | permutation_test | perm_post_bh | wilcox_rank_test | wilcox_post_bh |
|---|---|---|---|---|---|---|---|
| 1 | HSPB8 | 0.02383408 | 0.126867083 | 0.015893192 | 0.123029787 | 0.047323387 | 0.162797869 |
| 2 | PKHD1L1 | 0.00198525 | 0.076763093 | 0.099912585 | 0.404908897 | 0.028954115 | 0.131145107 |
| 3 | TBC1D15 | 0.00598154 | 0.076763093 | 0.18255593 | 0.466961829 | 0.011781743 | 0.113399272 |
| 4 | RGS18 | 0.00311968 | 0.076763093 | 0.143881199 | 0.466961829 | 0.022486636 | 0.120460045 |
| 5 | AVPR1A | 0.01644923 | 0.105549253 | 0.288787682 | 0.55380658 | 0.022486636 | 0.120460045 |
| 6 | DAPP1 | 0.00526700 | 0.0143557 | 0.017165128 | 0.123029787 | 0.007032729 | 0.113399272 |
| 7 | RAB27B | 0.01031300 | 0.01767943 | 0.017575684 | 0.123029787 | 0.010667079 | 0.113399272 |
| 8 | MMD | 0.01644923 | 0.105549253 | 0.14845526 | 0.466961829 | 0.057218854 | 0.162797869 |
| 9 | MOB1B | 0.00598154 | 0.076763093 | 0.108193801 | 0.416546133 | 0.009640813 | 0.113399272 |
| 10 | KLF9 | 0.02471437 | 0.126867083 | 0.00368039 | 0.068414004 | 0.003984992 | 0.113399272 |
| 11 | PPBP | 0.00311968 | 0.0143557 | 0.002403543 | 0.068414004 | 0.008695455 | 0.113399272 |
| 12 | P2RY12 | 0.02471437 | 0.126867083 | 0.348357287 | 0.55380658 | 0.018851672 | 0.120460045 |
| 13 | LYPLAL1 | 0.01031300 | 0.08823344 | 0.128476156 | 0.466961829 | 0.00630554 | 0.113399272 |
| 14 | RAB11A | 0.01031300 | 0.08823344 | 0.355072277 | 0.55380658 | 0.017219517 | 0.120460045 |
| 15 | FRMD4B | 0.03541042 | 0.170412649 | 0.199587112 | 0.466961829 | 0.049644693 | 0.162797869 |
| 16 | CLCN3 | 0.01644923 | 0.105549253 | 0.355017029 | 0.55380658 | 0.020606232 | 0.120460045 |
| 17 | CSHL1 | 0.08394782 | 0.258559274 | 0.005330961 | 0.068414004 | 0.051420738 | 0.162797869 |
| 18 | PSG7 | 0.05940288 | 0.21781055 | 0.004873997 | 0.068414004 | 0.088118285 | 0.21887445 |
| 19 | CGA | 0.34429949 | 0.602524107 | 0.042163103 | 0.21643726 | 0.330029859 | 0.529422898 |
| 20 | ADAM12 | 0.14593631 | 0.374569862 | 0.003632877 | 0.068414004 | 0.059501717 | 0.162797869 |
| 21 | PAPPA | 0.05940288 | 0.21781055 | 0.01485784 | 0.123029787 | 0.041604381 | 0.160176869 |
| 22 | GH2 | 0.11287578 | 0.321905002 | 0.002206859 | 0.068414004 | 0.016200179 | 0.120460045 |
| 23 | PSG1 | 0.18277827 | 0.41393903 | 0.020835083 | 0.124286982 | 0.049168007 | 0.162797869 |
| 24 | CSH2 | 0.34429949 | 0.602524107 | 0.020983516 | 0.124286982 | 0.114690254 | 0.275973424 |
| 25 | LGALS14 | 0.05940288 | 0.21781055 | 0.012258228 | 0.123029787 | 0.023466243 | 0.120460045 |
| 26 | KRT8 | 0.12481676 | 0.331410018 | 0.038074367 | 0.209409016 | 0.053332327 | 0.162797869 |
| 27 | CD180 | 0.59943536 | 0.824223625 | 0.204605614 | 0.466961829 | 0.011781743 | 0.113399272 |
| 28 | APLF | 0.08394782 | 0.258559274 | 0.217366723 | 0.466961829 | 0.031404066 | 0.134339615 |
| 29 | NFATC2 | 0.22968339 | 0.431356612 | 0.162361726 | 0.466961829 | 0.036785978 | 0.149080017 |
| 30 | MAP3K7CL | 0.05940288 | 0.21781055 | 0.357075209 | 0.55380658 | 0.026654193 | 0.128273303 |
| 31 | POLE2 | 0.08394782 | 0.2585593 | 0.2183198 | 0.4669618 | 0.06131348 | 0.1627979 |

| Key | |
|---|---|
| exact_test | Fisher Exact test p-value |
| post_bh | Benjamani Hochberg corrected p-value |

| Key | |
|---|---|
| permutation_test | Permutation test p-value |
| wilcox_rank_test | Mann-Whitney Test p-value |

| Key |
|---|
| Indicates p-value < 0.05 |

FIG. 10B

University of Pennsylvania negative fold change for preterm samples

| | gene | exact_test | exact_post_bh | permutation_test | perm_post_bh | wilcox_rank_test | wilcox_post_bh |
|---|---|---|---|---|---|---|---|
| 1 | PLAC1 | 0.000688596 | 0.053021876 | 0.000688596 | 0.053021876 | 5.20464E-05 | 0.004007574 |
| 2 | RAP1GAP | 0.546218487 | 1 | 0.00150385 | 0.057898209 | 0.000707175 | 0.027226229 |
| 3 | CAMP | 0.4059576 | 1 | 0.183714752 | 1 | 0.033271782 | 0.512385439 |
| 4 | ENAH | 1 | 1 | 0.081465655 | 1 | 0.028316466 | 0.512385439 |
| 5 | CPVL | 0.617098746 | 1 | 0.825751004 | 1 | 0.001793488 | 0.046032854 |
| 6 | ELANE | 0.987165775 | 1 | 0.607518681 | 1 | 0.046477206 | 0.596457475 |

| Key | |
|---|---|
| exact_testFisher | Fisher Exact test p-value |
| post_bh | Benjamani Hochberg corrected p-value |
| permutation_test | Permutation test p-value |
| wilcox_rank_test | Mann-Whitney Test p-value |
| Indicates p-value < 0.05 | |

FIG. 10C

University of Alabama negative fold change for preterm samples

| | gene | exact_test | exact_post_bh | permutation_test | perm_post_bh | wilcox_rank_test | wilcox_post_bh |
|---|---|---|---|---|---|---|---|
| 1 | PLAC1 | 0.0462538 | 1 | 0.046253803 | 0.998095901 | 0.026492205 | 0.931480085 |
| 2 | CYP3A7 | 0.11125664 | 1 | 0.748484848 | 0.998095901 | 0.016583809 | 0.931480085 |
| 3 | LTF | 0.48564406 | 1 | 0.852924595 | 0.998095901 | 0.049644693 | 0.931480085 |
| 4 | PGLYRP1 | 0.65570051 | 1 | 0.383217312 | 0.998095901 | 0.03973034 | 0.931480085 |

| Key | |
|---|---|
| exact_testFisher | Fisher Exact test p-value |
| post_bh | Benjamani Hochberg corrected p-value |
| permutation_test | Permutation test p-value |
| wilcox_rank_test | Mann-Whitney Test p-value |
| Indicates p-value < 0.05 | |

FIG. 10D

SEQUENCE LISTING

<160> NUMBER OF SEQ ID NOS: 299

<210> SEQ ID NO 1
<211> LENGTH: 861
<212> TYPE: DNA
<213> ORGANISM: Homo sapiens

<400> SEQUENCE: 1
acactctgct ggtataaaag caggtgagga cttcattaac tgcagttact gagaactcat 60
aagacgaagc taaaatccct cttcggatcc acagtcaacc gccctgaaca catcctgcaa 120

```
aaagcccaga gaaaggagcg ccatggatta ctacagaaaa tatgcagcta tctttctggt    180
cacattgtcg gtgtttctgc atgttctcca ttccgctcct gatgtgcagg agacagggtt    240
tcaccatgtt gcccaggctg ctctcaaact cctgagctca agcaatccac ccactaaggc    300
ctcccaaagt gctaggatta cagattgccc agaatgcacg ctacaggaaa acccattctt    360
ctcccagccg ggtgccccaa tacttcagtg catgggctgc tgcttctcta gagcatatcc    420
cactccacta aggtccaaga agacgatgtt ggtccaaaag aacgtcacct cagagtccac    480
ttgctgtgta gctaaatcat ataacagggt cacagtaatg gggggtttca aagtggagaa    540
ccacacggcg tgccactgca gtacttgtta ttatcacaaa tcttaaatgt tttaccaagt    600
gctgtcttga tgactgctga ttttctggaa tggaaaatta agttgtttag tgtttatggc    660
tttgtgagat aaaactctcc ttttccttac cataccactt tgacacgctt caaggatata    720
ctgcagcttt actgccttcc tccttatcct acagtacaat cagcagtcta gttcttttca    780
tttggaatga atacagcatt tagcttgttc cactgcaaat aaagcctttt aaatcatcat    840
tcaaaaaaaa aaaaaaaaaa a                                              861
```

<210> SEQ ID NO 2
<211> LENGTH: 3604
<212> TYPE: DNA
<213> ORGANISM: Homo sapiens

<400> SEQUENCE: 2

```
gagcagagct tggtacagcc caaatagttt tcaggttaag aaagccagaa tctttgttca     60
gccacactga ctgaacagac ttttagtggg gttacctggc taacagcagc agcggcaacg    120
gcagcagcag cagcagcagc agcagcagca gcagcagggc tcctgggata actcaggcat    180
agttcaacac tatgggtcct cctctgaagc tcttcaaaaa ccagaaatac caggaactga    240
agcaggaatg catcaaagac agcagacttt tctgtgatcc aacatttctg cctgagaatg    300
attctctttt ctacaaccga ctgcttcctg gaaaggtggt gtggaaacgt ccccaggaca    360
tctgtgatga cccccatctg attgtgggca acattagcaa ccaccagctg acccaaggga    420
gactggggca caagccaatg gtttctgcat ttcctgtttt ggctgttcag gagtctcatt    480
ggacaaagac aattcccaac cataaggaac aggaatggga ccctcaaaaa acagaaaaat    540
acgctgggat atttcacttt cgtttctggc attttggaga atggactgaa gtggtgattg    600
atgacttgtt gcccaccatt aacggagatc tggtcttctc tttctccact tccatgaatg    660
agttttggaa tgctctgctg gaaaaagctt atgcaaagct gctaggctgt tatgaggccc    720
tggatggttt gaccatcact gatattattg tggacttcac gggcacattg gctgaaactg    780
ttgacatgca gaaaggaaga tacactgagc ttgttgagga gaagtacaag ctattcggag    840
aactgtacaa aacatttacc aaaggtggtc tgatctgctg ttccattgag tctcccaatc    900
aggaggagca agaagttgaa actgattggg gtctgctgaa gggccatacc tataccatga    960
ctgatattcg caaaattcgt cttggagaga gacttgtgga agtcttcagt gctgagaagg   1020
tgtatatggt tcgcctgaga aaccccttgg gaagacagga atggagtggc ccctggagtg   1080
aaatttctga agagtggcag caactgactg catcagatcg caagaacctg gggcttgtta   1140
tgtctgatga tggagagttt tggatgagct tggaggactt ttgccgcaac tttcacaaac   1200
tgaatgtctg ccgcaatgtg aacaacccta tttttggccg aaaggagctg gaatcggtgt   1260
tgggatgctg gactgtggat gatgatcccc tgatgaaccg ctcaggaggc tgctataaca   1320
```

```
accgtgatac cttcctgcag aatccccagt acatcttcac tgtgcctgag gatgggcaca   1380
aggtcattat gtcactgcag cagaaggacc tgcgcactta ccgccgaatg ggaagacctg   1440
acaattacat cattggcttt gagctcttca aggtggagat gaaccgcaaa ttccgcctcc   1500
accacctcta catccaggag cgtgctggga cttccaccta tattgacacc cgcacagtgt   1560
ttctgagcaa gtacctgaag aagggcaact atgtgcttgt cccaaccatg ttccagcatg   1620
gtcgcaccag cgagtttctc ctgagaatct tctctgaagt gcctgtccag ctcagggaac   1680
tgactctgga catgcccaaa atgtcctgct ggaacctggc tcgtggctac ccgaaagtag   1740
ttactcagat cactgttcac agtgctgagg acctggagaa gaagtatgcc aatgaaactg   1800
taaacccata tttggtcatc aaatgtggaa aggaggaagt ccgttctcct gtccagaaga   1860
atacagttca tgccattttt gacacccagg ccattttcta cagaaggacc actgacattc   1920
ctattatagt acaggtctgg aacagccgaa aattctgtga tcagttcttg gggcaggtta   1980
ctctggatgc tgaccccagc gactgccgtg atctgaagtc tctgtacctg cgtaagaagg   2040
gtggtccaac tgccaaagtc aagcaaggcc acatcagctt caaggttatt tccagcgatg   2100
atctcactga gctctaaatc tgcaatccca gagaatcctg acaaagcgtg ccaccctttt   2160
attttccgtc aggtgccagg tcttagttaa gattcacaat ctttagaaag aatgagattc   2220
acaataatta actcttcctc tcttctgata aattccccat acctcccaat ccaagtagca   2280
tctgtagcta cataacctat atacctccag cagctggaca tggggaggcg acagtcctat   2340
ctagacatca tacacatttg ccaagaaagg atctctgggg cttccggggg tgagattcaa   2400
gcaggacaat aacaagaggc tggacaccct acagatgtct ttgatgtttt cagttgtttg   2460
atatatctcc cctgtagggc atgttgagga aggaggaggg ctgatcaagg ccaagctggt   2520
ctagcctgac atcctagctc ctgactgaac actatagact tcccagcagc atttcaccca   2580
gcagccagag ccggctttaa gtccccaacc cttacagaca ccactgccac caccaccaac   2640
cacgaccacc accaccacca ccactcacca ccatcatcac ctccggaaag tgtagtcctg   2700
ccctaaccca agtcaccccc gacagtaaat tttaccttca tgttgagaaa gcttcctggt   2760
gcttaatcaa gagctggagt tcaatgagtc ctagacagtg agaggggcct gagcttcagc   2820
tcaatggaag cctgctgtgt gccacaagac ggaaaagtgg aagaagctgc agtgggagac   2880
aaagcctcgg tcccccaccc atccacacac acctacactc acacacgcgc acatgggcgc   2940
gcacgaacta ccattcaggc agtcagtggg caagaggaaa gataagtaag taccatacac   3000
acctaaaaga tgagagaatt catccagaca tattacagcc agtttggggc ccctgactgc   3060
aatgtgaaac ctctcgctgc tgctaggttt acaaacaagc ccattgtcct gtgcctccta   3120
atatcatttg tactgaagac cccatctggg gacttgagac tttggtccca gcccagactc   3180
ctcagacttt tctctcagtt gggatgcttc actcgctggg ggtgtttgtt tgccctctca   3240
tttttcagta cttctacaga attttctcta gagtcagtca ttatgaaatg tacttccctc   3300
catcttaacc tatcaacttt ctgcccctcc ttcaaggccc agtataaatg ccacctcctc   3360
catgaagcct tccctaattc caccccaaac ccccaccttc aacaatattt caacgcttct   3420
gcaatgatga aaaagaaaca tagttgtagt acttagccta cctagaccag caagcattca   3480
tttttagctc gctcattttt taccatgttt tccagtctgt ttaacttctg cagtgccttc   3540
actacactgc cttacataaa ccaaatcaca ataaagttca tattcagtac attgaaaaaa   3600
aaaa                                                                3604
```

<210> SEQ ID NO 3
<211> LENGTH: 933
<212> TYPE: DNA
<213> ORGANISM: Homo sapiens

<400> SEQUENCE: 3
tgcaggaaag cctcaagtag aggagggttg aggcttcagt ccagcacctt tctcgggtca 60
cggcctcctc ctggctccca ggaccccacc ataggcagag gcaggccttc ctacacccta 120
ctccctgtgc ctccagcctc gactagtccc tagcactcga cgactgagtc tctgaggtca 180
cttcaccgtg gtctccgcct caccccttggc gctggaccag tgagaggaga gggctggggc 240
gctccgctga gccactcctg cgccccccctg gccttgtcta cctcttgccc cccgaggggt 300
tagtgtcgag ctcaccccag catcctatca cctcctggtg gccttgccgc ccccacaacc 360
ccgaggtata aagccaggta cacgaggcag gggacgcacc aaggatggag atgttccagg 420
ggctgctgct gttgctgctg ctgagcatgg gcgggacatg ggcatccaag gagccgcttc 480
ggccacggtg ccgccccatc aatgccaccc tggctgtgga gaaggagggc tgccccgtgt 540
gcatcaccgt caacaccacc atctgtgccg gctactgccc caccatgacc cgcgtgctgc 600
agggggtcct gccggccctg cctcaggtgg tgtgcaacta ccgcgatgtg cgcttcgagt 660
ccatccggct ccctggctgc ccgcgcggcg tgaaccccgt ggtctcctac gccgtggctc 720
tcagctgtca atgtgcactc tgccgccgca gcaccactga ctgcgggggt cccaaggacc 780 acccccttgac ctgtgatgac ccccgcttcc aggactcctc ttcctcaaag gcccctcccc 840
ccagccttcc aagcccatcc cgactcccgg ggccctcgga cacccccgatc ctcccacaat 900 aaaggcttct caatccgcaa aaaaaaaaaa aaa 933

<210> SEQ ID NO 4
<211> LENGTH: 2883
<212> TYPE: DNA
<213> ORGANISM: Homo sapiens

<400> SEQUENCE: 4
tcagccagtg tggcttcagg tcaagaggct gggcagggtc aaggtggcaa cgaggggaga 60
agccgggaca cagttctccc tgatttaaac ccgggcagcc tggagtgcag ctcatactcc 120
atgcccagaa ttcctgcctc gccactgtcc tgctgccctc cagacatgct ggggccctgc 180
atgctgctgc tgctgctgct gctgggcctg aggctacagc tctccctggg catcatccca 240
gttgaggagg agaacccgga cttctggaac cgcgaggcag ccgaggccct gggtgccgcc 300
aagaagctgc agcctgcaca gacagccgcc aagaacctca tcatcttcct gggcgatggg 360
atgggggtgt ctacggtgac agctgccagg atcctaaaag ggcagaagaa ggacaaactg 420
gggcctgaga taccccctggc catggaccgc ttcccatatg tggctctgtc caagacatac 480
aatgtagaca aacatgtgcc agacagtgga gccacagcca cggcctacct gtgcggggtc 540
aagggcaact tccagaccat tggcttgagt gcagccgccc gctttaacca gtgcaacacg 600
acacgcggca acgaggtcat ctccgtgatg aatcgggcca agaaagcagg gaagtcagtg 660
ggagtggtaa ccaccacacg agtgcagcac gcctcgccag ccggcaccta cgcccacacg 720
gtgaaccgca actggtactc ggacgccgac gtgcctgcct ccgcccgcca ggaggggtgc 780
caggacatcg ctacgcagct catctccaac atggacattg acgtgatcct aggtggaggc 840
cgaaagtaca tgtttcgcat gggaacccca gaccctgagt acccagatga ctacagccaa 900
ggtgggacca ggctggacgg gaagaatctg gtgcaggaat ggctggcgaa gcgccagggt 960

```
gcccggtatg tgtggaaccg cactgagctc atgcaggctt ccctggaccc gtctgtgacc   1020
catctcatgg gtctctttga gcctggagac atgaaatacg agatccaccg agactccaca   1080
ctggacccct ccctgatgga gatgacagag gctgccctgc gcctgctgag caggaacccc   1140
cgcggcttct tcctcttcgt ggagggtggt cgcatcgacc atggtcatca tgaaagcagg   1200
gcttaccggg cactgactga gacgatcatg ttcgacgacg ccattgagag ggcgggccag   1260
ctcaccagcg aggaggacac gctgagcctc gtcactgccg accactccca cgtcttctcc   1320
ttcggaggct accccctgcg agggagctcc atcttcgggc tggcccctgg caaggcccgg   1380
gacaggaagg cctacacggt cctcctatac ggaaacggtc caggctatgt gctcaaggac   1440
ggcgcccggc cggatgttac cgagagcgag agcgggagcc ccgagtatcg gcagcagtca   1500
gcagtgcccc tggacgaaga gacccacgca ggcgaggacg tggcggtgtt cgcgcgcggc   1560
ccgcaggcgc acctggttca cggcgtgcag gagcagacct tcatagcgca cgtcatggcc   1620
ttcgccgcct gcctggagcc ctacaccgcc tgcgacctgg cgccccccgc cggcaccacc   1680
gacgccgcgc acccggggcg gtccgtggtc cccgcgttgc ttcctctgct ggccgggacc   1740
ctgctgctgc tggagacggc cactgctccc tgagtgtccc gtccctgggg ctcctgcttc   1800
cccatcccgg agttctcctg ctccccacct cctgtcgtcc tgcctggcct ccagcccgag   1860
tcgtcatccc cggagtccct atacagaggt cctgccatgg aaccttcccc tccccgtgcg   1920
ctctggggac tgagcccatg acaccaaacc tgccccttgg ctgctctcgg actccctacc   1980
ccaaccccag ggactgcagg ttgtgccctg tggctgcctg caccccagga aaggaggggg   2040
ctcaggccat ccagccacca cctacagccc agtgggtacc aggcaggctc ccttcctggg   2100
gaaaagaagc acccagaccc cgcgccccgc tgatctttgc ttcagtcctt gaatcacctg   2160
tgggacttga ggactcggga tcttcaggac gcctggagaa gggtggtttc ctgccaccct   2220
gctggccaag gaggctcctg ggtggggat caccaggggg attttgacac agccttcggc   2280
tgccccccac taagctaatt ccacacccct gtaccccccc agggggccct ctgcctcatg   2340
gcaaaggctt gccccaaatc tcaacttctc agacgttcca taccccccaca tgccaatttc   2400
agcacccaac tgagatccga ggagctcctg ggaagccctg ggtgcaggac actggtcgag   2460
agccaaaggt ccctccccag acatctggac actgggcata gatttctcaa gaaggaagac   2520
tcccctgcct ccccagggcc tctgctctcc tgggagacaa agcaataata aaaggaagtg   2580
tttgtaatcc cagcactttg ggaggccgag gtgggcggat cacgaggtca ggagatggag   2640
accatcctgg ctaacacggt gaaaccccctt atctatgcgc ctgtagtccc agctacccag   2700
gaggctgaag caggataatc gcttgaaccc gggcggcgga gattgcagtg agccgaggtc   2760
atgccactgc actgcagcct gggcgacaga gcgagattct gcctcaaaaa taaacaaata   2820
aattttaaaa ataaataaat aataaaagga agtgttagac aatgtaaaaa aaaaaaaaaa   2880
aaa                                                                 2883
```

```
<210> SEQ ID NO 5
<211> LENGTH: 661
<212> TYPE: DNA
<213> ORGANISM: Homo sapiens

<400> SEQUENCE: 5

agcatcccaa ggcccgactc cccgcaccac tcagggtcct gtggacagct cacctagcgg     60
caatggctgc aggaagaagc ctatatcaca aaggaacaga agtattcatt cctgcatgac    120
tcccagacct ccttctgctt ctcagactct attccgacat cctccaacat ggaggaaacg    180
```

cagcagaaat ccaacttaga gctgctccac atctccctgc tgctcatcga gtcgcggctg 240
gagcccgtgc ggttcctcag gagtaccttc accaacaacc tggtgtatga cacctcggac 300
agcgatgact atcacctcct aaaggaccta gaggaaggca tccaaatgct gatggggagg 360
ctggaagacg gcagccacct gactgggcag accctcaagc agacctacag caagtttgac 420
acaaactcgc acaaccatga cgcactgctc aagaactacg ggctgctcca ctgcttcagg 480
aaggacatgg acaaggtcga gacattcctg cgcatggtgc agtgccgctc tgtggagggc 540
agctgtggct tctaggggcc cgcgtggcat cctgtgaccc ctccccagtg cctctcctgg 600
ccctgaaggt gccactccag tgcccaccag ccttgtctta ataaaattaa gttgtattgt 660
t 661

<210> SEQ ID NO 6
<211> LENGTH: 10009
<212> TYPE: DNA
<213> ORGANISM: Homo sapiens

<400> SEQUENCE: 6
cgtagctcat aatccatttt tataacacct tgctatctat atttacacct ttaaagaaca 60
cgggaattta agagggaaga gtaactaggc ttttgctaaa cttgggctaa taaaaccctc 120
tgtagagaga tccttaatat aggcatgggg acaacaagga gtatcccaag ggactcgccg 180
ctagggtgtc ttttaagcta ttggagcaaa ttcaaatttg gcttaaagaa aaagaaactc 240
attttgtatt gcaacaccat ttgggttaaa tacaagttag atgacgaata tatctggcct 300
aaacatggtt ctatatacta tagtgatatt ttacgattag gcttattttg taaaagagaa 360
ggaaaatggg aagagatccc ttatgtacag gcttttatgg ctctatactg gatcacgtta 420
cttccaggca ttagaatgcc atgcataagg gatccccacc tagctgctcc ccatagaaag 480
ttcataagcc tccccagagt ctcttcagtc ccccagtcct gagtgggggt tctcgccaat 540
tccctaatga gattccaccc caatatcatc aggcaccttt ccccttatc caactagccc 600 tagcctatac cctctgctgc ccaagaaaat gagcccaacc agtacaccag gagtggggct 660
ccatatcagc ccctaaggtc aagcctgtgt ccactgtgga aagtagttga tggaaatgag 720
ggaacactca aagagtacat atgccacttt ccatgtctaa ttagacctta taaaaggaaa 780
gaattggcca gttttcagat aaaccagaaa agcttataca agagtttgtt acgttgacta 840
tgttcttcaa attgccacga tttacaaata ttgtcatccg cttgctgtgc tgtggggaaa 900
aaaaagtaga ggaaaaagtg tgtggttaag ccagtcaatt atgacaaggt taaagaagta 960
actcggggaa aagatgaaaa tcccgctctg tttcagggtc ttttagttga agcactcagg 1020
aaatatacta atgcaggccc agacacccca gaagggcaag ctctcctggg tatacatttt 1080
ctcattcaat cttctcctga cattaggagg aatctacaaa aagcagcaat gggaccttca 1140
agtcctatga aacgacgctt aaacatagcc tttaaagttt acaacaacag ggacagggca 1200
aaagagggga gtaaaaagaa atagccaaaa agtacaattg ttaacagtga ctttaagcct 1260
ccttgcccct caggattact catcttgaga aaatgttaca aaattagcat ctgggatgcc 1320
tagacaagac ttgatgcctg acttgctgac ccctgggcca gaatcactgc gcctactata 1380
cgcaaaaggg cccctggcaa tgcaaatgtc ctaactgctc tggtgagaga gaacaataac 1440
aacaaaaagc ttccatcaat actagagcta accttctcct actagcccca gtgagctgct 1500
tagctcaagt aagtttactg tcccagagga cagctttcca cagtggcaga taagcagccg 1560

-continued

```
cctgaacatt tttctttggt atttccacca ctgagtgtgc tctccagtgg cgtggggact   1620
ccagaatctc cttttgagca atgcagtttg cttcctcccc tttttagttg atgctatggg   1680
attccctgtc ctgccttttc ctgttttcca tacctatcgg ggcaaacaaa atttggccag   1740
gtagatgggt cccagttctg taaataactt gaatccagtt gtcttgtata ggtcatttta   1800
tttaatatgt ttttgggtat atgtacatgt attgtgatgt gtgttacatc tagcgtgctg   1860
tcaaactggc ttatagataa aagaacactc atacattcaa caaataagac tactgaaagc   1920
ttattagttt gaagagaatc ttgtatcttc taaaatttaa ctttaggatt tttacctagg   1980
taagtcactg atgttcatag gctttaaaat ggttaaaatg gctttaaatg gtgaccagct   2040
ttgcatggta ccttggttct cggtgatcta gataaagtta aaagtgaaat aattaaatac   2100
acgtaaatgg gatatgctta atgtgtggtt taaaatcata aaatggtaga atggttctca   2160
gttatagaat gacaatgtct agtgtgaagt tcatgacttc ttccttccta ggtttccata   2220
aaatgtgcta aagaaatgta ttctttattg agaaaaaatt ttttgtctaa tccggaagtt   2280
actaaatggg aggttcaaaa catgagtgaa ccagtgagta gaaaagagag atgtaaagaa   2340
tattatgaat agaaaatgta ttttttgttt gttttgcaag gaaggatata aagaaagagt   2400
aattttatat gtggaggaat cctgtatagt aaattcccta tcctagagta aaataacttt   2460
aagaaagagg tagtatagaa catgtcagga aattcagcta tgttgtagat ggtctgtgta   2520
agtcatctgc acagtgcatg agtgtggagg tgggcgggca ctcattggcc cttgaactcc   2580
ttttgagcag tatggaagcc aagaactaga agccaggaaa tggggttgta aaactgattt   2640
gtctatggat tttatgtgtt gagctgctgt ggtcttggct tgtagtaatt acctatatga   2700
accttccccc ctccccttta gaatttagga caggttcaaa aggccctcca atataaaaat   2760
aaaatactgt ccttccccac aaaggaaaaa atagctcccc ggttcaacca ggagacttag   2820
tcttgctaaa accttaaaga cagggtaaag acagggatac cccaagaatc aattacaatg   2880
aaatggaagg ggccttatca ggtattgtta agtacccca ctgctgttaa acttcaggga    2940
acacctactt gggcacacag atccaggact aaacctgttt cttatgagtc acaggcacaa   3000
aggaagggca ctacaaccac aaccaatatc agtaaagctt tggaagacct ctgctaccta   3060
tttaaaataa tcaacactca gccagaagag gtaatgtaat gctgtagatg ggaataggag   3120
cattgatctt gctcttcttc ctgactgtag tacttccttt ctatggcttt aaccagccac   3180
ctcctcctgg gaaacatctc ctgtgggctt gttgggtata gaagctactc taagacccaa   3240
ccagatacca tgatgccact gttaattctg tttgctcttc taattaacct aagctagtgt   3300
gtatgtggac agggagggtg gacaaaattc tacagtaaat atttcaaaaa ttatagcatc   3360
atagaatcat ctttatggct gccagatttg tcatcaacac ccccaggata gacagtttca   3420
tcttccgacc tatctggaaa atctcaggac catgtcccca gacctcctaa ctaaccatag   3480
caccccaaaa tacccaaacc cctattgtga agtggaactc ttccccactt agtggatccc   3540
ccctggaccc tgctgtcccc ctgccctgac cactattatc ggaatctggg aagttgggca   3600
tctatatctc cagtgcactc ataactctaa catttgcatc cactcttgca ttaatgacac   3660
aaaagtggaa gcttccctgc gatgctctgg tccaactcta gttgccaagt ttccaagacc   3720
acggggaggt aaatgagatt ccatttgtga gtgaaaagac catatatggt accttctccc   3780
ggatgggaac atacaaagga aaaacaactg cctgatctgg gaaggtgaca gtactacctt   3840
cttctagaaa acaaagattg ttcaaccacc accatgagaa caggtggaaa atatctctat   3900
agacccaacc tggcaatgaa gtataaacat cgcaccccgc agggcttctc ttggtgccct   3960
```

```
agttgggttc atttttgttt gtgactatga atgggaagaa gtcacaccct gtaaccactc   4020
caactcccta aggagtcacc tcttctttaa ggaatagctt tcccttgtat ctaaaaaact   4080
tggaactgac atgaatgaac gttggccact cttacccctc caggggtcac aatctataac   4140
gcctaggacc caagaatatc agaaataagt aagcaataaa actaattctg gcaggaatca   4200
gggtggcaat aggactagca gcaccctggg gtggctttgc ctaccatgag ttaacgctaa   4260
agaacttggc tcaaatccta gaatccttag ccaccaacgg agatcaggca ttaaagagaa   4320
ttcaagagtt ccccagactc tggaaaatgt agttgttgat aacagactag cattggatta   4380
tttactagct gaacaaggtg gggtcttgtg cagttattaa taaaacctgc tgcacatata   4440
ttaactctgg acaggttgag gttaacattc aaaagatcta tgagcaagct acctagttac   4500
atagatataa ccagggcact gcccccaact atatctggtc aaccatcaaa agtgccttcc   4560
caagtctcac ctgtttttca cctcttctag gacctttgac aactgtcttg ttacaaatgt   4620
ttggtccttg cttctttaac ctcttagtaa agtttgtgta ttctagatta ccacagttcc   4680
agagacaatg ctggcacaag gcttccagcc catcctgtcc actgacacgg agaatgaaat   4740
cgtcctgcct ctgggctcct tagatcaggt atccagagat ttttactcct ccagtgccag   4800
gcagggccta cgtccataaa ctcagcagga agtagttacg gaaaacagat ctccgccctt   4860
ctgcagcccc cttaagatta aggaggagta tctaatctct gaagggggaa tgaggtagga   4920
ggtgggactc aactctggaa gtggggctca ggcactcaga ccaaactgag cactagctaa   4980
aataggtcca gggcagatgc tagtttccat aggacacacc gacctgtgtc aagtcagttc   5040
accatggctc tggcagcacc cagaagttac caccctcacc ctggaaatgt ctgcataaac   5100
tgccccttca tttgcatata attaaaagtg gatacaaata ccactgcaga actgcctctg   5160
agctgctact gtgggcgcac agcctgtagg gcagccctgc tttgcaagga gcagcgcctc   5220
tgctgctgct gtgcacagcc ggccgcttca ataaaagttg ctaacaccac tggcttgccc   5280
ttgagttcct tcctgggcaa agctaagaac cctcccgggc tatgcttcaa tcttagggct   5340
cgcctgtcct gcatcactgg gatcatctcc cagtaaacta gccacactta catccatgtg   5400
tcagggacat ttctggagaa agcagcccag gacactgttg aataaaacac acaatagtct   5460
ctgtggtctt ctccacccca ccccacacca ggcaccctca gcttgattct cctttttaat   5520
tgcctgtaag cagggaagca caatgttttc acattctttg taaggccttt gttctactaa   5580
aatctaacct cagagcacaa ttttaaacta gatgaaagag ttgctgcgcc tgaagcactg   5640
caaacacctc ctcaccacac atgtgcactc accctggaca ccctcactca ccctgacacc   5700
ctcactcctc accctggaca ccctcactca ccccagacac cgtcactcct caccctggac   5760
acctcactct gcaccctgga caccctcact caccctggac acgttcactc accctgacac   5820
cctcactcac cctggacacc ctcactcacc ctggataccc tcactcctca ccctggacac   5880
cctcactcac cctggatacc ctcactcctc accctggaca ctctcactca ccctgacacc   5940
ctcaatcctc accctggact ccctcactcc tcaccctgga ctccctcact cctcaccctg   6000
gacaccctca ctcctcatcc tggacaccct cactcaacct ggacaccctc actcctcacc   6060
ctgacaccct cactcctcac cctggacacc ctcactcctc accctgacac cctcactcct   6120
caccctggca ccctcagtca ccctgacacc ctcactcctc accctgacac cctcaagtct   6180
tcacctccct ggctgcagcc tgggacacgc tttccctaac ttctgaaggc tcagtcctcc   6240
tcaagccaat ctcatctcaa attgcacctc ctcagagagg tcttccataa ccgcccttat   6300
```

-continued

```
aaagcaggat tctttcacca ataccccttc ccacatggca ctgtctcaca gcactcctct   6360
aaaagtctgt ttacttcctt gacaatctgt cttccttata aggggaggtt ctgtaaaagc   6420
caagactctc tctgtctagt tgactgttgc ataccagggc ttagaccaag gccctgacat   6480
gcagtaggtg cttaatatgt tttgaggcaa ggtcttgctc tgttgcacat gctggagtgc   6540
agtggcacaa tcgtaattca ttgcagcctt gaactcctga gctcaagtga tcctcctgcc   6600
tcagcctcct gagtagctgg gactacaggc atgcaccacc aagcttggct aatttaaaaa   6660
aaaaattata tagataggga cttgctatgt tgcctaggct gatcttgaac tcctaacctc   6720
aagcaatcct cccacctcgg ccttccaaag tgctgggata ataggcatgg agccgccaca   6780
cccagccaat gtgccgaaga aagaaagaaa aacatgctca tcctttgagt caggttcaaa   6840
ttttttctcc tctttaaccc ccagtcactc cagttataag tgatttttaa ctcttctcac   6900
actttaatgc atctggcaag aagatccacg tggtgttagg aacaatacag gaccttaagg   6960
atgggggaat cagcaggtgt cagcgtgccc tgtatgctca gggcagctgt ttccactgga   7020
cattctccct ttgcctctct gggcagcaac tcctaggcca gccgacctgc tgtgtcgagt   7080
aaccaggatt tctcaatctt ggcatggttg ccattttgga ccagatcgtt ctttgttgtg   7140
ggggctgccc tgtacggcaa agaatgccga gcagcacttc cagtctccac ccacaggacg   7200
ccagtagcac cctctaagtt gtgagaactc aaaatgtccc cagaggatgc cagatgtccc   7260
ctggggtggg gacacaatca ccccaggttg agatccatgg agccaggtct gtttgccacc   7320
aaggggtaaa gctccattcc caccttagga gggctaggag gcagcatcgt ggggccacag   7380
aaggcctggg tttgcagtca gaggacagga tgcacattcc ttcaagatac agacccagat   7440
tgttgggcat ctagttcttg ggttttctgt tgttgctgtt ccgttttgtc tgtcttccct   7500
cctttgttta ctagcagcct ggaatttgcc actttttcta aacgaagatt tatggaacac   7560
ttaccacacg gctgacgctg cgcgaggcta aggttctaat acaccgcagc tcacttaact   7620
ctcgcaatac cataaacgca cactgtttca tcttgaccct ttcttgggaa ggtgacagag   7680
aggtaggagg gcaaacatct tgtgtgcccc gtcccaaggg tattactggt ggaataatat   7740
ccgcccccca ccccagtttc taatttgctg taggctgtga cgctgtgggg caagactagg   7800
agtcctgttg aaattaggaa taagtgtgct gtgagggaag ggctgcctta ttttagagca   7860
cagattttct gaatatctat tttgacaggt tcgatcctct ccccttcctg ccttccttct   7920
gtcgattttc aatgtcttga tggtgtccca cctgagtggc ctttagagat gtgagttgtg   7980
aggcactggg gaggcaggca cacgtcctcc agcccaagac tgcctaattt aacagggatt   8040
tctgcattct ggaacaagcc tccattttcc ccaagcagga ttactccaga gggcaaaaca   8100
cagcccaata gtatcacatt tcctttctgc tttagcaaaa ataaccactg tctcattcat   8160
gggaaaaggc cgccaaacaa atttgttact ggaaccattt gtaacaactt ctagtttgca   8220
ctgccttgga gcaagcacac tttgtagagg agggatttgc agttacttgg gcaacaaggt   8280
aaccactgat cattacagga agcttcagaa accgtgggac cagtgtagaa gaatggacta   8340
tctgtccaaa ctaagaataa aaagaatgac acttgtattt tgtatgtctt tttcactttg   8400
cctttctagt aattcatttt tcttgatatt tacaccttgt ggccctgtga tagactggaa   8460
atctcaaaaa cacacgttca gcaccaagat tttcagcagc accgcctcag aatgagaccc   8520
ctagaaaaaa ctgcgtgttt tccacttgcc caacacgagg agtttttgga acacgacctg   8580
cttgaggtgg agattttcta gatgggcaaa gagaaggaaa cacttaacct aggaagagta   8640
tttaggaaga agaaagaaca cagcctttct gcacaggaaa ccgccgagca gaggggcatc   8700
```

```
tggcctctgc agtggcctcc aaatagagtc caatggctgg ggccagcgtg gctgcttaaa   8760

ggggactcaa gggatataat aaaatgcaga ttctcaggtc ctagtgcaga caggctcacc   8820

caataagtct ggactgcata tgggaatctc tatttctagg cccttctgca aggtattcct   8880

gctctttcca ggaaccatcg gcagctggtt tggggaaaga agcaacgact ccaagtgtga   8940

cctgtgagct ggcagcagcc accctcagct ctgctctcgg tcactgaatc cgattctgca   9000

ttttaacagg accccaggtg ttgcacccac acaaagctga agcagattgg tctgggggca   9060

aaaaattaga gctatggaga ttctctcaaa tgaaatagat gatatcattg actgttagag   9120

cttctagaag gaatctgagg tcacttgttc aaattccctg atttacagat gaggaaacag   9180

aggctcagac agctcaaatg acttctctcc aatacccaac attcgacaag tagcagctct   9240

gggactagta cccaaagcac ctagctctcc aatcactgcg caagccacac aattctgtct   9300

gcttgtcagt ggcttttctg attcaaaaaa agcttaggaa tttccccagg aggcagcacg   9360

atgtagtggg aagggctctg gatgtctctc caaggcttct ggaattcatg cccacctcca   9420

ccaagaagcc actttcctgc cagctacagg tgctcacctg aaaagcaagc cagaccatat   9480

taaccctggc attgctggta cctggaagac tttctgattc aatgctttcc acctcctcct   9540

acccctcacc acccccgtgg catgaaatcc tgggggctgc tttagaaatt gttttctttg   9600

gctgctggtg ggggtgctgc tggtgggggt ttgcacagct ggcacactgc accagtctgg   9660

tgggggtttg cacagctggc acactgcacc agtctcctgc ctgctgccaa caaggccatt   9720

tcccaagcac tggctttgga gaagttgggg ctctgaagtg ggaacacaag gctgcctttt   9780

gcaggccagg tgtaaattct ccccctgcca ctttcagcct agcgtgaaac agatggagtg   9840

tgcattccca cttcccttta tggtaccctg gaatgatgga gctgcccagg gcatcgccac   9900

gttactctct agacagtctc tttgtcttcc tgcaatggca gcgccgaggt tgtatatttc   9960

taggtgcagg tatatgattg ccatataata aaaatctgaa aacatccca             10009
```

<210> SEQ ID NO 7
<211> LENGTH: 2046
<212> TYPE: DNA
<213> ORGANISM: Homo sapiens

<400> SEQUENCE: 7

```
agtgcagaag gaggaaggac agcacagctg acagccgtgc tcaggaagat tctggatcct     60

aggctcatct ccacagagga gaacacgcag ggagcagaga ccatggggcc cctctcagcc    120

cctccctgca cacagcatat aacctggaaa gggctcctgc tcacagcatc acttttaaac    180

ttctggaacc cgcccaccac agcccaagtc acgattgaag cccagccacc aaaagtttcc    240

gaggggaagg atgttcttct acttgtccac aatttgcccc agaatcttac tggctacatc    300

tggtacaaag gacaaatcag ggacctctac cattatgtta catcatatat agtagacggt    360

caaataatta aatatgggcc tgcatacagt ggacgagaaa cagtatattc caatgcatcc    420

ctgctgatcc agaatgtcac ccaggaagac acaggatcct acactttaca catcataaag    480

cgaggtgatg ggactggagg agtaactgga cgtttcacct tcaccttata cctggagact    540

cccaaaccct ccatctccag cagcaatttc aaccccaggg aggccacgga ggctgtgatt    600

ttaacctgtg atcctgagac tccagatgca agctacctgt ggtggatgaa tggtcagagc    660

ctccctatga ctcacagctt gcagctgtct gaaaccaaca ggaccctcta cctatttggt    720

gtcacaaact atactgcagg accctatgaa tgtgaaatac ggaacccagt gagtgccagc    780
```

cgcagtgacc cagtcaccct gaatctcctc ccgaagctgc ccaagcccta catcaccatc 840
aataacttaa accccaggga gaataaggat gtctcaacct tcacctgtga acctaagagt 900
gagaactaca cctacatttg gtggctaaat ggtcagagcc tcccggtcag tcccagggta 960
aagcgacgca ttgaaaacag gatcctcatt ctacccagtg tcacgagaaa tgaaacagga 1020
ccctatcaat gtgaaatacg ggaccgatat ggtggcatcc gcagtgaccc agtcaccctg 1080
aatgtcctct atggtccaga cctccccaga atttaccctt cattcaccta ttaccattca 1140
ggacaaaacc tctacttgtc ctgctttgcg gactctaacc caccggcaca gtattcttgg 1200
acaattaatg ggaagtttca gctatcagga caaaagcttt ctatccccca gattactaca 1260
aagcatagcg ggctctatgc ttgctctgtt cgtaactcag ccactggcaa ggaaagctcc 1320
aaatccgtga cagtcagagt ctctgactgg acattaccct gaattctact agttcctcca 1380
attccatctt ctcccatgga acctcaaaga gcaagaccca ctctgttcca gaagccctat 1440
aagtcagagt tggacaactc aatgtaaatt tcatgggaaa atccttgtac ctgatgtctg 1500
agccactcag aactcaccaa aatgttcaac accataacaa cagctgctca aactgtaaac 1560
aaggaaaaca agttgatgac ttcacactgt ggacagcttt tcccaagatg tcagaataag 1620
actccccatc atgatgaggc tctcacccct cttagctgtc cttgcttgtg cctgcctctt 1680
tcacttggca ggataatgca gtcattagaa tttcacatgt agtataggag cttctgaggg 1740
taacaacaga gtgtcagata tgtcatctca acctcagact tttacataac atctcaggag 1800
gaaatgtggc tctctccatc ttgcatacag ggctcccaat agaaatgaac acagagatat 1860
tgcctgtgtg tttgcagaga agatggtttc tataaagagt aggaaagctg aaattatagt 1920
agactcccct ttaaatgcac attgtgtgga tggctctcac catttcctaa gagatacatt 1980
gtaaaacgtg acagtaagac tgattctagc agaataaaac atgtactaca tttgctaaaa 2040
aaaaaa 2046

<210> SEQ ID NO 8
<211> LENGTH: 11025
<212> TYPE: DNA
<213> ORGANISM: Homo sapiens

<400> SEQUENCE: 8
gagcatcttt tggggggagg gaattcagcg gatcagtctt aagaggagct ttttttgga 60 gcgagaaatc atataaaata aaatgaaata aaacaaggag gaaggcaacc agctgttagg 120
ggaaaaataa ggcagataaa ggagcgggga gagaaattaa ttgccaacca ggaggagttg 180
ggctgtattt ttcaaaggtg gggagagtgg agcacacacc ttgaggagga aagcgagaaa 240
gaaaagaaaa aagcaagtgg aaaggggggc tcgcccaaga agggtgaaga agcgaagaaa 300
gtcgaggcgc cgaggctccc aaagctggca gctccgggtg gcggtgcagg ggcgaagggg 360
gggcgggggg aaccgtcgga catgcggctc tggagttggg tgctgcacct ggggctgctg 420
agcgccgcgc tgggctgcgg gctggccgag cgtccccgcc gggcccggag agacccgcgg 480
gccggccgac ccccgcgccc cgccgccggc ccggccacct gcgccacccg ggcggcccgc 540
ggccgccgcg cctcgccgcc gccgccgccg ccgccgggcg gtgcctggga agccgtgcgc 600
gtcccccggc ggcggcagca gcgggaggcg aggggcgcca ccgaggagcc gagcccgccg 660
agccgggcgc tctatttcag cgggcgaggc gagcagctgc gcctccgggc cgacctcgag 720
ctgccccggg acgcgttcac gctgcaagtg tggctgcgag cggagggggg ccagaggtct 780
ccggcagtga tcacagggct gtatgacaaa tgttcttata tctcacgtga ccgaggatgg 840

```
gtcgtgggca ttcacaccat cagtgaccaa gacaacaaag acccacgcta ctttttctcc    900
ttgaagacag accgagcccg gcaagtgacc accatcaatg cccaccgcag ctacctccca    960
ggccagtggg tatacctagc tgccacctat gatgggcagt tcatgaagct ctatgtgaat   1020
ggtgcccagg tggccacctc tggggaacaa gtgggtggca tattcagccc actgacccag   1080
aagtgcaaag tgctcatgtt agggggcagt gccctgaatc acaactaccg gggctacatc   1140
gagcacttca gtctgtggaa ggtggccagg actcagcggg agatactgtc tgacatggaa   1200
acccatggcg cccacactgc tctacctcag ctcctcctcc aggagaactg ggacaatgtg   1260
aagcatgcct ggtcccccat gaaggatggc agcagcccca aagtggaatt cagcaatgcc   1320
cacggctttc tgctggacac gagtctggag cctcctctgt gcggacagac attgtgtgac   1380
aacacagagg tcattgccag ctacaatcag ctctcaagtt tccgccagcc caaggtggtg   1440
cgctaccgcg tggtcaacct ctatgaagat gatcataaga acccgacggt gacgcgcgag   1500
caggtggact tccagcacca tcagctggct gaggccttca agcaatacaa catctcctgg   1560
gagctggacg tgctggaggt gagcaactcc tcccttcgcc gccgcctcat cctggccaac   1620
tgtgacatca gcaagattgg ggatgagaac tgtgaccccg agtgcaacca cacgctgacg   1680
ggccacgacg gcggggattg ccgccacctg cgccaccctg ccttcgtgaa gaagcagcac   1740
aacggggtgt gtgacatgga ctgcaactat gaacggttca actttgatgg tggagagtgc   1800
tgtgaccctg aaatcaccaa tgtcactcag acttgctttg accccgactc tccacacaga   1860
gcctacttgg atgttaatga gctgaagaac attcttaaat tggatggatc aacacatctc   1920
aatattttct ttgcaaaatc ctcagaggag gagttggcag gagtagcaac ttggccatgg   1980
gacaaggagg ccctgatgca cttaggtggc attgtcttga acccatcttt ctatggcatg   2040
cctgggcaca cccacaccat gatccatgag attggtcaca gcctgggcct ctatcacgtc   2100
ttccgaggca tctcagaaat ccagtcctgc agtgacccct gcatggagac agagccctcc   2160
ttcgagactg gagacctctg caatgatacc aacccagccc ctaaacacaa gtcctgtggt   2220
gacccagggc caggaaatga cacctgtggc tttcatagct tcttcaacac tccttacaac   2280
aacttcatga gctatgcaga tgacgactgt acggactcct tcacgcccaa tcaagtcgcc   2340
agaatgcact gttacctgga cctggtctac cagggctggc agccctccag gaaaccagcg   2400
cctgttgccc tcgcccccca agttctgggc cacacaacgg actctgtgac actggagtgg   2460
ttcccaccta tagatggcca tttctttgaa agagaattgg gatcagcatg tcatctttgc   2520
ctggaaggga gaatcctggt gcagtatgct tccaacgctt cctccccaat gccctgcagc   2580
ccatcaggac actggagccc tcgtgaagca gaaggtcatc ctgatgttga acagccctgt   2640
aagtccagtg tccgcacctg gagcccaaat tcagctgtca acccacacac ggttcctcca   2700
gcctgccctg agcctcaagg ctgctacctc gagctggagt tcctctaccc cttggtccct   2760
gagtctctga ccatttgggt gacctttgtc tccactgact gggactctag tggagctgtc   2820
aatgacatca aactgttggc tgtcagtggg aagaacatct ccctgggtcc tcagaatgtc   2880
ttctgtgatg tcccactgac catcagactc tgggacgtgg gcgaggaggt gtatggcatc   2940
caaatctaca cgctggatga gcacctggag atcgatgctg ccatgttgac ctccactgca   3000
gacaccccac tctgtctaca gtgtaagccc ctgaagtata aggtggtccg ggaccctcct   3060
ctccagatgg atgtggcctc catcctacat ctcaatagga aattcgtaga catggatcta   3120
aatcttggca gtgtgtacca gtattgggtc ataactattt caggaactga agagagtgag   3180
```

```
ccatcacctg ctgtcacata catccatgga agtgggtact gtggcgatgg cattatacaa   3240
aaagaccaag gtgaacaatg cgacgacatg aataagatca atggtgatgg ctgctccctt   3300
ttctgccgac aagaagtctc cttcaattgt attgatgaac ccagccggtg ctatttccat   3360
gatggtgatg gggtatgtga ggagtttgaa caaaaaacca gcattaagga ctgtggtgtc   3420
tacacgcccc agggattcct ggatcagtgg gcatccaatg cttcagtatc tcatcaagac   3480
cagcaatgcc caggctgggt catcatcgga cagccagcag catcccaggt gtgtcgaacc   3540
aaggtgatag atctcagtga aggcatttcc cagcatgcct ggtacccttg caccatcagc   3600
tacccatatt cccagctggc tcagaccact ttttggctcc gggcgtattt ttctcaacca   3660
atggttgccg cagctgtcat tgtccacctg gtgacggatg ggacatatta tggggaccaa   3720
aagcaggaga ccatcagcgt gcagctgctt gataccaaag atcagagcca cgatctaggc   3780
ctccatgtcc tgagctgcag gaacaatccc ctgattatcc ctgtggtcca tgacctcagc   3840
cagcccttct accacagcca ggcggtacgt gtgagcttca gttcgcccct ggtcgccatc   3900
tcgggggtgg ccctccgttc cttcgacaac tttgaccccg tcaccctgag cagctgccag   3960
agaggggaga cctacagccc tgccgagcag agctgcgtgc acttcgcatg tgagaaaact   4020
gactgtccag agctggctgt ggagaatgct tctctcaatt gctccagcag cgaccgctac   4080
cacggtgccc agtgtactgt gagctgccgg acaggctacg tgctccagat acggcgggat   4140
gatgagctga tcaagagcca gacgggaccc agcgtcacag tgacctgtac agagggcaag   4200
tggaataagc aggtggcctg tgagccagtc gactgcagca tcccagatca ccatcaagtc   4260
tatgctgcct ccttctcctg ccctgagggc accacctttg gcagtcaatg ttccttccag   4320
tgccgtcacc ctgcacaatt gaaaggcaac aacagcctcc tgacctgcat ggaggatggg   4380
ctgtggtcct tcccagaggc cctgtgtgag ctcatgtgcc tcgctccacc ccctgtgccc   4440
aatgcagacc tccagaccgc ccggtgccga gagaataagc acaaggtggg ctccttctgc   4500
aaatacaaat gcaagcctgg ataccatgtg cctggatcct ctcggaagtc aaagaaacgg   4560
gccttcaaga ctcagtgtac ccaggatggc agctggcagg agggagcttg tgttcctgtg   4620
acctgtgacc cacctccacc aaaattccat gggctctacc agtgtactaa tggcttccag   4680
ttcaacagtg agtgtaggat caagtgtgaa gacagtgatg cctcccaggg acttgggagc   4740
aatgtcattc attgccggaa agatggcacc tggaacggct ccttccatgt ctgccaggag   4800
atgcaaggcc agtgctcggt tccaaacgag ctcaacagca acctcaaact gcagtgccct   4860
gatggctatg ccatagggtc ggagtgtgcc acctcgtgcc tggaccacaa cagcgagtcc   4920
atcatcctgc caatgaacgt gaccgtgcgt gacatccccc actggctgaa ccccacacgg   4980
gtagagagag ttgtctgcac tgctggtctc aagtggtatc ctcaccctgc tctgattcac   5040
tgtgtcaaag gctgtgagcc cttcatggga gacaattatt gtgatgccat caacaaccga   5100
gccttttgca actatgacgg tggggattgc tgcacctcca cagtgaagac caaaaaggtc   5160
accccattcc ctatgtcctg tgatctacaa ggtgactgtg cttgtcggga cccccaggcc   5220
caagaacaca gccggaaaga cctccgggga tacagccatg gctaaggaag gacaagaagt   5280
tgtcaaagaa ttcccaacgc caggacccac atccctttgg tattgatttc acagtcagct   5340
gctcaacgga atggcctctc cacaccaggg atccttagca cccaaccggt ctgcctttaa   5400
ttttacccag gaaggactca cattggggcg aatgaaccaa gtttcgccat gctggatgat   5460
gaaatggatt cccatcccaa agtctgagat ggattgcata tacagtgtgc agtcccagag   5520
cctcctaaaa ttctagccat ttgtcacaca accacagcaa gaaacgtgtt ctatatctag   5580
```

```
agtgtgccca tctgtgttta gtacacatgc atgcatacac acccatacaa acatctgtgt   5640
gagggcagtt ctggagatga gcagagagag accggaataa actcaatctt ttctttccca   5700
agctcctagc caacactatc cttgggagaa agaaatttgc agaaactgct aagaccaagt   5760
gtggagatgt caagctagtt cacactctga ggctcagaat atgtaggaca tgcacaattg   5820
tgcagtcctt tgggattgga agtgaaacag tctgtgatcc cctaccttct agggaactag   5880
gacctaggaa gaggtaaaga ttatcaggta tgcaaagcgc cccaattctt ctgctgccat   5940
gggggatttt accccaactc cagggttcga ggccaatctg agaatggctt aggattgcaa   6000
tgtcaaggta ttatatcagc cccttgcttg aggcttgagg tcataatatc cctctaggac   6060
ttacctgttc ccccagatct tgccttggga ccacatttgc tgctactttt cctgctgctc   6120
tatcctatac attgaataat ccaagatggt agaactaggt taggaaaaat tccacacaac   6180
caaacagtct gccttaaaag tgacccacat ttttccatag ctcctcactt tttagccctt   6240
ctgcaagaga aaaaccctca tgggtccaca tggtgagaag ttaagtttcc tgtaagtggg   6300
cctctcaccc tggaaaggag ttgagggaca tcagatgctg gaaccctcac tgaaagtcca   6360
gaatgtctaa gccagtgtta gattttgtaa acaagtggaa cagtgttaaa tttctatgat   6420
gttggagcca tccagagact actggaattg tcgagacttt tggattatta tccttatcct   6480
tatcctaatc ttcctagccc ttcaggctag agtaggcttc gatcctgaga accttgctgt   6540
tgctctgagg agatataatt ctgggagaaa gaatctttta taagaacagt acagattgtt   6600
ctcaagaggg ccatcagaag gaagccaaag agttcacagc ctcagcacca acaactcaac   6660
atggtcatca tgtttctat atggtttttc cagctagcag tactcccttc catacctgtg    6720
actgggcagt gcttttctct ctcccatgtc tagcctccaa aagttaagtg aaaattagtc   6780
aactgcacgt ggaagccccc accactttgg ggatctcttt atttcttttc agccagggac   6840
ctgtccactc cctttgaatt aatatgggaa gaaattaata caggatgaac tggagagaag   6900
ggttgagtgt ggcatacttt ctgaaacctg gagctgggaa ttgcggagaa gggaaggtct   6960
agactagtta catcacatag ggattactgt aaatcaagtc atctcaagtc tagtgaagac   7020
agccaacaga aacaaaacct agcataggga tagaaaatac catgcacgtg tgcagcccca   7080
cctaattcct gcatccaagg caggtgttgt taatctatca tagcacttaa aaaaaaaaaa   7140
aaaaagagac caaaaataac tttaggaacc accatattat atcactccca atagcactga   7200
cctggtgatc aaaaacactt gagaagacat ctattggcca tctctggcca attacactaa   7260
gaaacatatc aaggtgcttt tggcacaggt gcccacaaat acggatgcag tgctgagata   7320
gtttatgaga cttgtaccat ttcacaaact ctgaaattgg gttccatatt ggcaaggctg   7380
ccacagttgt taagaataat cctctatgtt tcttcctcac aaaaccatat ctcatttata   7440
tccagaccat tacttcacta taattacaag gacaaattat tagcaagaaa taagaatagt   7500
attagaagaa ttgatcctat tttgaacccc tctccagtat cttcacactc ttgtcaactc   7560
tccaggcctc tctcttgccc tgagttatca gcctgtgtgg tgttaactac cttagaaggt   7620
acaagctaag aaatgtaaca gtatcaaccc tcccagttgc ttaattatac ccataggtaa   7680
tacaaaaagc tctgaagacc caaagatgac attactaatg atgtgatttc aggagccaca   7740
gaagaacctt accagcttcc ctcaaatcag tccttatcct ctttctatct tcactcccat   7800
catcatctat tttcacacta tccagctaag caaagattcc tggaggctga cttgtatctt   7860
cagactcaca gagtgaattc agctcttctg aatcaagacc cacccagtct ctttcattca   7920
```

gacctgttgc taacaaattt atatttgcca aggatattag gcaaaagagg ctacttgatt 7980
ggtggccaac ctcgtgccca catggaaggt atctttaata gggtcttttc aaaccttagt 8040
ggaggagggt cagctcaatt tgggcaatgc atttgttccc agtttcattt tcttcctggg 8100
aattaactcg tcatttcatt ccttcagtca tcttctgtgt aggtgaccgg agcactgaga 8160
ggcagctctg atgcactatt gtgtgtcagc agctcaaagg ccctaaaaca ctgaaggttc 8220
tgcatctgaa gtattagatt gttagcagca aaatatgaaa gatgaggtgg acagtcctct 8280
aagccctatt tagggaagct tttccaagcc acaatcttaa ctacctaccc aaaggatttg 8340
cattaccccc agattctgtg ccaacaacct tttaaggaaa tacagtcctt gggaaatgag 8400
ttttgatggt gaattggggt gttaaggaag ggaaagattg tcatagatgg tagggctttg 8460
aaaatgcagg gtatcagctg ccactcctgg cttcaacaca ttgagtcact gcctagacgg 8520
ttctcttggt cttattccca tcctggccaa tgcttaaata ctatttgttg aaaataattc 8580
tttgagacag atttcagcta cctcccttcc aggttcgatt taacttggtt gtaattgtca 8640
atttgttgtt ataggtctta cctgtgtgaa agaaagaaaa agaaagaaag aaagaaagag 8700
aaaggaaatt ataaggtcaa gttaacagtt ttgaggtttt gtgttttttt ctggaactac 8760
ttcaagtgag aaaataaaaa aaaatggtga caaagctgta cagatagaga taatagaaga 8820
caaagagatt aaaaggaaat aaaaatgcat gattaaaaac taagaataaa aaacctattt 8880
ttatgtttcc taaaggaaat tgtttattct acagcctcag taggtagaca caaacataaa 8940
gatttcccta gaagacatag agtgggattt gataacactg tctgttattt tctgtacatt 9000
gtggtaggtc caggaaatat gacattttcc cccttgatgt gttattgttg ttgttgggtg 9060
gggtgggcat tttgtttatt tgtttggtgg caatcagtgg tagtagggag tgggagggct 9120
tatattggtt tttccagcta ttaaggggac atattgtgtc gttgtgcttt tcacgttata 9180
aaatgtttat atttaccagt acagcactgg gctttataaa gactgcactc agaaccacac 9240
tgcacagtcc agttttttaa aaagctgcta catgacagac aggtaatccc actgagtgag 9300
ttttgagaaa caaatcaaac gaagtaaaca agaaacataa aaaccaaata gcaaatgaat 9360
aaaagcctgt tcttgtaact tattcaactt ttgccaaatt cctaccaatc acttgctttt 9420
taaaagaaat gtataatagc caaaagagaa attatgtccc tgttgtacag aagttagaat 9480
ttttgactcc aggcagcagt ttgctcagtg atcttgaaca agttatccaa ttgcctctac 9540
atttgcatca gtttctctag ctgcaaaatg gggataatac tatataccta cctcacagtg 9600
ggagggcagg agattttgag gccctgaggt tttaggtggg ctgtgagggc caacgcttga 9660
cacaaagtcc atgggttatt attcaagaat gcacaggccc atcggccttt tagaaagaca 9720
agacagggag tgcttgtttg atatttcaag gaataaagcc ggagctcctg aattgtagtc 9780
caccttaaaa gagagacctg tattggagaa tattttattt ttttggcaaa tttgatctta 9840
ccctttacca gttctataat ttggttaaaa gctgattatg tcctacaatg tcaaagtcag 9900
ctaactgtcg tctacttaag acttctggtc atttccaact tatagaggaa gggagtctct 9960
aaaatctctt cttcagaagg cacctcactt ctcagactta aaattccaca tcaagtgttc 10020
cattaaaaga agataaggca ttctgagtgc aaacaaatgg gggcttctta aactacacac 10080
cagcagtcag tgaggaaaac tttgaacaat tattgagttg ctttcttggg tctctataat 10140
caataacctg tctgcagata tctatctata taaagatatt atatataaat ataaatttac 10200
atatatatgc acatgtatat atagttgtac atatatgtgt gtatatatat acttaaatgt 10260
aatatttaca aaataaaact gtgatctcgt ctagagaaaa tgtattcata ttacaaactg 10320

```
ctcttccata tttatgtacc atattatacc tttttattat tgttataatt attatgggta  10380

tttctaatta atatgatgtt gaaacctgtt tggcaccttc tggaagctac caaaaaaatg  10440

acactccatt gaagtgctta aaagctgttc tcataagaat tctactggcc tattgtaaaa  10500

aagaaaaaaa aaaagaaaaa gaagaaagac acaaagaaaa taatctaaac accaaaaact  10560

aaacacaatt ccaatccttt ttctgtacct cacgcgcata aatttgctgc tcctattttt  10620

ttttctgttt atgtgttttt atggatctaa gttaaatctt ttggcaatat ataaaaatgt  10680

aaatagtaaa ctttatttat taagaatgtc atctttttta atttatattt acacaattgt  10740

tcatctaatt tatttttttct atacagtttt aaatactcag acatattttg ctgttcatga  10800

tatttttatc ctgttctcat ggatttgttt tcccatactg ttttctctga tctcaattac  10860

aggttggatc tcacaaataa taatgtcaga gacagaaata ttttgccact gttgattact  10920

atactttaaa gttctatatt atgaaaatat ataatagctt gtacgcttca aaaaaaaaaa  10980

aaaaaaaaaa aaaaaaaaaa aaaaaaaaaa aaaaaaaaaa aaaaa                 11025
```

<210> SEQ ID NO 9
<211> LENGTH: 794
<212> TYPE: DNA
<213> ORGANISM: Homo sapiens

<400> SEQUENCE: 9

```
gctgcattac agacacagac ctgcaaacat ctatggttgt gacagagttt ctttctgaca     60

cctgagtctt tctcctgctg cacggaaagc ttgctgggag gggcttggaa tctggcatga    120

agccaaaggg catctctgag ttgcagcatt taaatgatcc cactcagaga ttcacacaga    180

agactggaca caattccgaa gagctgccca gaaggagaga acaatgtcat cactacccgt    240

accatacaca ctgcctgttt ccttgcctgt tggttcgtgc gtgataatca cagggacacc    300

gatcctcact tttgtcaagg acccacagct ggaggtgaat ttctacactg ggatggatga    360

ggactcagat attgctttcc aattccgact gcactttggt catcctgcaa tcatgaacag    420

ttgtgtgttt ggcatatgga gatatgagga gaaatgctac tatttaccct ttgaagatgg    480

caaaccattt gagctgtgca tctatgtgcg tcacaaggaa tacaaggtaa tggtaaatgg    540

ccaacgcatt tacaactttg cccatcgatt cccgccagca tctgtgaaga tgctgcaagt    600

cttcagagat atctccctga ccagagtgct tatcagcgat tgagggagat gatcagactc    660

ctcattgttg aggaatccct ctttctacct gaccatggga ttcccagagc ctactaacag    720

aataatccct cctcacccct tcccctacac ttgatcatta aaacagcacc aaacttcaaa    780

aaaaaaaaaa aaaa                                                      794
```

<210> SEQ ID NO 10
<211> LENGTH: 6299
<212> TYPE: DNA
<213> ORGANISM: Homo sapiens

<400> SEQUENCE: 10

```
gtgacgtcac gcgtcgacgc tggggcgtac ctttcgggct cctgactcct gccgcttctc     60

ttccccttcc gtgggtcagg gccggtccgg tccggaacct gcagcccctt tcccagtgtt    120

ctagttcgcc cgtgacccgg aataatgagc aaggagggtg tggtgggttg aaagccatcc    180

tactttactc ccgagttaga gcatggattc agttttagtc ttaaggggga agtgagattg    240

gagattttta tttttaattt tgggcagaag caggttgact ctagggatct ccagagcgag    300
```

-continued

```
aggatttaac ttcatgttgc tcccgtgttt gaaggaggac aataaaagtc ccaccgggca    360
aaattttcgt aacctctgcg gtagaaaacg tcaggtatct tttaaatcgc gatagttttc    420
gctgtgtcag gctttcttcg gtggagctcc gagggtagct aggttctagg tttgaaacag    480
atgcagaatc caaaggcagc gcaaaaaaca gccaccgatt ttgctatgtc tctgagctgc    540
gagataatca gacagctaaa tggagtctga gcagctgttc catagaggct actatagaaa    600
cagctacaac agtataacaa gtgcaagtag tgatgaggaa cttttagatg gagcaggtgt    660
tattatggac tttcaaacat ctgaagatga caatttatta gatggtgaca ctgcagttgg    720
aactcattat acaatgacaa atggaggcag cattaacagt tctacacatt tactggatct    780
tttggatgaa ccaattccag gtgttggtac atatgatgat ttccatacta ttgattgggt    840
gcgagaaaaa tgtaaagaca gagaaaggca tagacggatc aacagcaaaa agaaagaatc    900
agcatgggaa atgacaaaaa gtttgtatga tgcgtggtca ggatggctag tagtaacact    960
aacaggattg gcatcagggg cactggccgg attaatagac attgctgccg attggatgac   1020
tgacctaaag gagggcattt gccttagtgc gttgtggtac aaccacgaac agtgctgttg   1080
gggatctaat gaaacaacat ttgaagagag ggataaatgt ccacagtgga aaacatgggc   1140
agaattaatc ataggtcaag cagagggtcc tggttcttat atcatgaact acataatgta   1200
catcttctgg gccttgagtt ttgcctttct tgcagtttcc ctggtaaagg tatttgctcc   1260
atatgcctgt ggctctggaa ttccagagat taaaactatt ttaagtggat tcatcatcag   1320
aggttacttg ggaaaatgga ctttaatgat taaaaccatc acattagtcc tggctgtggc   1380
atcaggtttg agtttaggaa aagaaggtcc cctggtacat gttgcctgtt gctgcggaaa   1440
tatcttttcc tacctctttc caaagtatag cacaaacgaa gctaaaaaaa gggaggtgct   1500
atcagctgcc tcagctgcag gggtttctgt agcttttggt gcaccaattg gaggagttct   1560
ttttagcctg gaagaggtta gctattattt tcctctcaaa actttatgga gatcattttt   1620
tgctgcttta gtggctgcat ttgttttgag gtccatcaat ccatttggta acagccgtct   1680
ggtccttttt tatgtggagt atcatacacc atggtacctt tttgaactgt ttcctttat    1740
tcttctaggg gtatttggag ggctttgggg agccttttc attagggcaa atattgcctg    1800
gtgtcgtcga cgcaagtcca cgaaatttgg aaagtatccc gttctggaag tcattattgt   1860
tgcagccatt actgctgtga tagccttccc taatccatac actaggctaa acaccagtga   1920
actgatcaaa gagcttttta cagactgtgg tcccctggaa tcctcttctc tttgtgacta   1980
cagaaatgac atgaatgcca gtaaaattgt cgatgacatt cctgatcgtc cagcaggcat   2040
tggagtatat tcagctatat ggcagttatg cctggcactc atatttaaaa tcataatgac   2100
agtattcact tttggcatca aggttccatc aggcttgttc atccccagca tggccattgg   2160
agcgatcgca ggaaggattg tggggattgc ggtggagcag cttgcctact atcaccacga   2220
ctggtttatc tttaaggagt ggtgtgaggt cggggctgat tgcattacac ctggccttta   2280
tgccatggtt ggtgctgctg catgcttagg tggtgtgaca agaatgactg tctccctggt   2340
ggttattgtt tttgagctta ctggaggctt ggaatatatt gttcccctta tggctgcagt   2400
catgaccagt aaatgggttg gagatgcctt tggcagggaa ggcatttatg aagcacacat   2460
ccgattaaat ggataccctt tcttggatgc aaaagaagaa ttcactcata ccaccctggc   2520
tgctgacgtt atgagacctc gaaggaatga tcctccctta gctgtcctga cacaggacaa   2580
tatgacagtg gatgatatag aaaacatgat taatgaaacc agctacaatg gatttcctgt   2640
cataatgtca aaagaatctc agagattagt gggatttgcc ctcagaagag acctgacaat   2700
```

tgcaatagaa agtgccagga aaaaacaaga aggtatcgtt ggcagttctc gggtgtgttt 2760
tgcacagcac accccatctc ttccagcaga aagtcctcgg ccattgaagc ttcgaagcat 2820
tcttgacatg agccctttta cagtgacaga ccacacccca atggagatcg tggtggatat 2880
tttccgaaag ctgggactga ggcagtgcct tgtaactcac aatgggattg tcttggggat 2940
catcacaaag aagaacatat tagagcatct cgagcaacta aagcagcacg tcgaaccctt 3000
ggcgcctcct tggcattata acaaaaaaag atatcctccg gcatatggcc cagacggcaa 3060
accaagaccc cgcttcaata atgttcaact gaatctcaca gatgaggaga gagaagaaac 3120
ggaagaggaa gtttatttgt tgaatagcac aactctttaa cctgagggag tcatctactt 3180
tttttcctc ctttacaaaa aaagaaagga aatataaaag ccgggttttt gcaacatggt 3240
ttgcaaataa tgctggtgga atggaggagt tgtttgggga gggaaaggag agagaaggaa 3300
aggagtgagg tatttcccgt ctaacagaaa gcagcgtatc aactcctatt gttctgcact 3360
ggatgcattc agctgaggat gtgcctgata gtgcaggctt gcgcctcaac agagatgaca 3420
gcagagtcct cgagcacctg gcctgttgct ccaacattgc aaagacacat tatcagtccc 3480
tatttctaga gggattactt tgaattgagc catctataaa actgcaaggt cttgcccttt 3540
tttttaatca aaactgttct gtttaattca tgaattgtat agttaagcat tacctttcta 3600
cattccagaa gagcctttat ttctctctct ctctctctct ctctctctct ctctactgag 3660
ctgtaacaaa gcctctttaa atcggtgtat ccttttgaag cagtcctttc tcatattgag 3720
atgtactgtg attttactga ggtttcatca caagaaggga gtgtttcttg tgccattaac 3780
catgtagttt gtaccatcac taaatgcttg gaacagtaca catgcaccac aacaaaggct 3840
catcaaacag gtaaagtctc gaaggaagcg agaacgaaat ctctcattgt gtgccgtgtg 3900
gctcaaaacc gaaaacaatg aagcttggtt ttaaaggata aagttttctt ttttgttttc 3960
ctctcagact ttatggataa tgtgaccggg tcttatgcaa attttctatt tctaaaacta 4020
ctactatgat atacaagtgc tgttgagcat aattaaataa aatgctgctg ctttgacagt 4080
aaagagaagg aagtattctg attagctgta tctggtatta attgcatgtt aaaacactgg 4140
aatttttaaa attgaaatta gatcagtcat tcttttcttt tctcaagata tctcatggct 4200
gacactgaag aagaaatgta attcataact tgcactaaat gtatattttt tttcttaaaa 4260
atttaccatt cttatttata tttttatgga ttaaaattta taaaatacag atcagttaat 4320
attgcactta agtaatttta ccttttttaat gtgattttta tagaataatt cagacttaca 4380
aatacagaga tatgaacaaa gtttacagtg ggaacaaagg tttaaaaaaa ggttgtggtt 4440
ctctctctgt gatccagtgt gcacataaac ctttctctga tctttcactg ccatcctctg 4500
gattatgtct tctgacctgt ccattttgac ccattaactg gaaagttgaa aaactacatt 4560
aactggaaag ttgaaaaact acattacttt ggagaataaa accgaaagtt cgtgtatacc 4620
ttcttaaaaa aaaaatcaaa ccaaaaatgt gaaaacaata gaattgcaaa gatagcagtt 4680
aaaattttaa tctgaaaata acctttgaat ctcgggctag gttacgtcca tatttgaagt 4740
ggtcagtgat ggtttgaaca ttttttgcag gatgagtgaa aatgcactgg attatatttg 4800
ggatttttgt ttttggaatt gtctgtttta atcacagcct taattcacaa ttggcaaagg 4860
cagtttactc aaaggactgg gctaaatatt ctgtaattat gcatttttga taggaaaatg 4920
aaatttttgc aaacagacat tttctttttt tttggctgga gtgcagtggg gcatggtctt 4980
ggctcactgc agcgttgacc acctgggctc aagtgatact cccgcctcag ccacccaagt 5040
agctggcact acgggcacac gccaccatgc ccagctaatt tttttgtatt tttagtagag 5100
atggggtttt gccatgctgc ccaggctggt ctcaactcct cagctcaagc aatctgcctg 5160
cgtgagcctc ccaaagtggt ggaattacag gcgtgggcca ctgcgcctgg cccagacaga 5220
cattttctga aacacaactg gcaatgagct gtttttacat tttgaaagtg attcttcact 5280
tcctagttct taattatagt atacctatta agatctgtaa gatcctgaag acataagatc 5340
atgaagccat ataagaatga ggattgaaag ttgagcaaaa ttttcgggat tttgggaaac 5400
attcttagct gtgctatctg cctaaaatta ttccttatta cttctctcct ttgacagact 5460
tcaagttttc ttcatagccc tttcaaagtt ttttgagcca tccagagtaa aatcatttct 5520
aaatgatagt tctgtatatc tccaactcgt cttaagtgta tttgcctgtg tgcaacgtat 5580
tgctagacta tgaactcctc agcatggctg ctggataact taattgtcct gagttaatag 5640
ccttcaaagg acaaatcggt ttctttgcag atagcttcgt aaaacttcac atggagttta 5700
ttttatcata tttccctttt ttatttctgc tcctccttta attgcccatc ttgcttcaga 5760
gactgacatt tcagggtgga tattaattaa agcattaatt ttgttttttg gtatatttct 5820
atccctagta tttctatctt actgctaaaa tacaggaaaa gtgccgtatt tttaatgcat 5880
ttagtggttt tctttggtgt tatctgttcc atttttcttt ttcatacatt gaagtgtgtc 5940
tccttttcaa ccaaaataat gaaatagtgg agaccatgaa attgttgtgc ctggctaatt 6000
ggcaaattaa tttaccaata taataagtgt agcgccttgt ttgaataccc tttttgagaa 6060
ggtatgatga gaatgggcaa gggtgtcagc atctcttctt cttaataatt aattgttttc 6120
agttttggtt cacgaagaat gcttagttaa tctgtaatgt tgcctagagc tgtatttatc 6180
tgtttttatt tatactagtg tagtaaagct gcatatcatt acagtaaaaa cgactactgt 6240
gatgagttaa tcagaaaatc tattaaaatc tatatgacaa tgaaaaaaaa aaaaaaaaa 6299

<210> SEQ ID NO 11
<211> LENGTH: 3006
<212> TYPE: DNA
<213> ORGANISM: Homo sapiens

<400> SEQUENCE: 11
gcaggctgct gtctcacaga gcgagaaggt gtcaggagca gcccagttgt gtctctctct 60
ctacctctgt gaagggcgcg aatgggcaga gcagaacttc tagaagggaa gatgagcacc 120
caggatccct cagatctgtg gagcagatcc gatggagagg ctgagctgct ccaggacttg 180
gggtggtatc acggcaacct cacacgccat gctgctgaag ctcttctcct ctcaaatgga 240
tgtgacggca gctaccttct gagggacagc aatgagacca ccgggctgta ctctctctct 300
gtgagggcca aagattctgt taaacacttt catgttgaat atactggata ttcatttaaa 360
tttggcttta atgaattctc atctttgaag gattttgtca agcattttgc aaatcagcct 420
ttgattggaa gcgagacagg cactctgatg gttctaaaac atccctaccc aagaaaagtg 480
gaagaaccct ccatttatga atctgtccgg gttcacacag caatgcagac aggaagaaca 540
gaagatgacc ttgtgcccac agcaccttct ctgggcacca aagaaggtta cctcaccaaa 600
cagggaggcc tggtcaagac ctggaaaaca agatggttta ctctgcacag gaatgaactg 660
aaatacttca aagaccagat gtcaccagaa ccaattcgga tcctagacct aacagaatgt 720
tcagctgtac aattcgatta ttcacaagaa agggtaaact gtttttgttt ggtatttcca 780
ttcaggacat tttatctctg tgcaaagacc ggagtagaag ctgatgagtg gatcaagata 840
ttacgctgga aattggtcaa ggacaaaagc tgatttattt tgtctgctct ctgtatatct 900

```
cccgaggaga agactgatca caaataagaa aacagctcaa ccaaggggaa ggcacgatcc    960
gatctcggtc gttcatcttt aaatagatct ttcttgccaa ggaatgctct ggcccaggag   1020
caaggtggaa tgtttccctg acgctgtgat ctgcagcagg cttcaaatga aaaccgacta   1080
aggattttct ttcaaaaaca aatcagaagc agatgctgat tgggacccat ataccacgtt   1140
gctgactcac gttgctgccc ttccatgatg ttgccatctc cttgagaaca ctgaagcaat   1200
caccattctg atagaaagtg cttaaaccac cactcttagg tctgctcact cttagaacac   1260
acaatggaag aggaagggtt tttgttttca ctcattgtgg tccccaagcc tattgacact   1320
agttgcctag agtcccactg tgagtcatgg tcagcctgtc tgacatccag gttgtgctat   1380
taaccaagaa ggaaacagat acttggaggc ttagatgact tctgcaggat ttatattcag   1440
atagaaaaca tcaaatattt tcaggggaga ggtttttttt tttaattttt ccccctttat   1500
acaaaaaaaa aagaacattt ccaaaactaa aatagaaaat gcttgtggca tttattttct   1560
ctttttaaaa ggttcagaaa tttggcaggt cctttgcttc taatgacaaa actgtgagag   1620
ctagatgtcc tatgggcaat taggtagtat aataaaggta aatgaaggta caatttttaa   1680
accattattt tcaccctgtt ggggtaaatg ttttaaagag tgagaaaaca taaattgaga   1740
aagggtgata aagtaataga taacttttag tttaataata attattgtta ttatactact   1800
aataatagag cacttgtaag cactaagtta tctttatcca acatttctcc aaatggactg   1860
aaagaaactt ttcaaggaca gtgtattata acaatccctt tcccagaatt agttgtatag   1920
ggttggccca agagatgtaa gaaaaatctc gcattgctcc ctaagcaccc tgggccttat   1980
taaagagcaa cttctatttc cagtcggggg agtaacacta aagctacaag aaatatgtaa   2040
taatgatagg taataatgtg ttccaaagct ttttcaaact agaataagga ggcaaataga   2100
agaatgagat actgatgtcc acagttcatt ggcagaatct aacccccttct gttatctttt   2160
ttaatactat ttttgtttag atagaagttt caaagaagat aaaaatgctt gaagagcctg   2220
agagtaaaaa gattatgctg caaagctatg atataaactg ctcttgcagt ccaaagggat   2280
acctgattaa agaagtttct tatttaaaca tctcagacgc aaaaattaca ttaaattttt   2340
gtatatttca acaacatttt aaatgtattt tgttatgttt gtattatata ggataaagca   2400
aatgtcaagt taaaatgtat tgtgttgttt gtaaagtaag aagttactgg ccaggagcgg   2460
cggctcatgc ctgtaatccc aggactttgg taggccaaga caagcagatc acttgaggtc   2520
aggagttcaa catcagcctg gccaacatga tgaaaccttg tctttactaa aaatacaaaa   2580
attagctggg catggtggca ggcgcctgta atcccagcta ctcaggaggc tgaggcagga   2640
gaattgcttg aacccgggag gtggaggttg cagtgaacca agatcgcggc gctgcactct   2700
agcctgggtg acagagtcag actccgtccc aaaaaaacaa acaaacaaaa caaaacaaaa   2760
aaaaacagaa gttacaaatg aatactcacg gatatgtata gttttatgtt tgttttctta   2820
gaaacaaatg tgtttctttg ggtgggtaat attgtgtttt actatgttta ccttttataa   2880
aacataacct gtttatttat attctttggc tttgtttatt aaaaagcatg attttgctgt   2940
gcatgtacca ttttgctatt aaaatttatt tttaatattt gtaacttgaa aaaaaaaaaa   3000
aaaaaa                                                              3006
```

<210> SEQ ID NO 12
<211> LENGTH: 1861
<212> TYPE: DNA
<213> ORGANISM: Homo sapiens

<400> SEQUENCE: 12
agcctactcg gtccggggtt gcgaactgta aggtctgagt tgctgcggcg caggcagcgg 60
agaccaagca gggatcttaa cagggtttag cgccacgcgg gccagggccg aggccggagc 120
tgggaggggc gcgcccggga aggggcggag ctgcggcggt ggcgccaaat cgcaaatatg 180
gcgccggagc ggctgcggag ccgggcgctc tccgccttca agttgcgggg cttgctgctc 240
cgtggtgaag ctattaagta cctcacagaa gctcttcagt ctatcagtga attagagctt 300
gaagataaac tggaaaagat aattaatgca gttgagaagc aacccttgtc atcaaacatg 360
attgaacgat ctgtggtgga agcagcagtc caggaatgca gtcagtctgt tgatgaaact 420
atagagcacg ttttcaatat cataggagca tttgatattc cacgctttgt gtacaattca 480
gaaagaaaaa aatttcttcc tctgttaatg accaaccacc ctgcaccaaa tttatttgga 540
acaccaagag ataaagcaga gatgtttcgt gagcgatata ccattttgca ccagaggacc 600
cacaggcatg aattatttac tcctccggtg ataggttctc accctgatga aagcggaagc 660
aaattccagc ttaaaacaat agaaacctta ttgggtagta caaccaaaat cggagatgcg 720
attgttcttg gaatgataac gcagttaaaa gagggaaaat tttttctgga agatcctact 780
ggaacagtcc aactagacct tagtaaagct cagttccata gtggtttata cacagaggca 840
tgctttgtct tagcagaagg ttggtttgaa gatcaagtgt ttcatgtcaa tgcctttgga 900
tttccaccca ctgagccctc tagtactact agggcatact atggaaatat taattttttt 960
ggaggtcctt ctaatacatc tgtgaagact tctgcaaaac taaaacagct agaagaggag 1020
aataaagatg ctatgtttgt gtttttatct gatgtttggt tggaccaggt ggaagtattg 1080
gaaaaacttc gcataatgtt tgctggttat tcaccagcac ctccaacctg ctttattctg 1140
tgtggtaatt tttcatctgc accatatgga aaaaatcaag ttcaagcttt gaaagattcc 1200
ctaaaaactt tggcagatat aatatgtgaa tacccagata ttcaccaaag tagtcgtttt 1260
gtgtttgtac ctggtccaga ggatcctgga tttggttcca tcttaccaag gccaccactt 1320
gctgaaagca tcactaatga attcagacaa agggtaccat tttcagtttt tactactaat 1380
ccttgcagaa ttcagtactg tacacaggaa attactgtct tccgtgaaga cttagtaaat 1440
aaaatgtgca gaaactgcgt ccgttttcct agcagcaatt tggctattcc taatcacttt 1500
gtaaagacta tcttatccca aggacatctg actcccctac ctctttatgt ctgcccagtg 1560
tattgggcat atgactatgc tttgagagtg tatcctgtgc ccgatctact tgtcattgca 1620
gacaaatatg atcctttcac tacgacaaat accgaatgcc tctgcataaa ccctggctct 1680
tttccaagaa gtggattttc attcaaagtt ttttatcctt ctaataagac agtagaagat 1740
agcaaacttc aaggcttttg agattcttaa agatcatctg aagaaaattc atcagttttc 1800
tgcttaactc tatatcttat gtgattctga tattacaata aaattatggt aaactttagg 1860
a 1861

<210> SEQ ID NO 13
<211> LENGTH: 1307
<212> TYPE: DNA
<213> ORGANISM: Homo sapiens

<400> SEQUENCE: 13
acttatctgc agacttgtag gcagcaactc accctcactc agaggtcttc tggttctgga 60
aacaactcta gctcagcctt ctccaccatg agcctcagac ttgataccac cccttcctgt 120
aacagtgcga gaccacttca tgccttgcag gtgctgctgc ttctgtcatt gctgctgact 180

```
gctctggctt cctccaccaa aggacaaact aagagaaact tggcgaaagg caaagaggaa    240
agtctagaca gtgacttgta tgctgaactc cgctgcatgt gtataaagac aacctctgga    300
attcatccca aaaacatcca aagtttggaa gtgatcggga aaggaaccca ttgcaaccaa    360
gtcgaagtga tagccacact gaaggatggg aggaaaatct gcctggaccc agatgctccc    420
agaatcaaga aaattgtaca gaaaaaattg gcaggtgatg aatctgctga ttaatttgtt    480
ctgtttctgc caaacttctt taactcccag gaagggtaga attttgaaac cttgattttc    540
tagagttctc atttattcag gatacctatt cttactgtat taaaatttgg atatgtgttt    600
cattctgtct caaaaatcac attttattct gagaaggttg gttaaaagat ggcagaaaga    660
agatgaaaat aaataagcct ggtttcaacc ctctaattct tgcctaaaca ttggactgta    720
ctttgcattt ttttctttaa aaatttctat tctaacacaa cttggttgat tttcctggt     780
ctactttatg gttattagac atactcatgg gtattattag atttcataat ggtcaatgat    840
aataggaatt acatggagcc caacagagaa tatttgctca atacattttt gttaatatat    900
ttaggaactt aatggagtct ctcagtgtct tagtcctagg atgtcttatt taaaatactc    960
cctgaaagtt tattctgatg tttattttag ccatcaaaca ctaaaataat aaattggtga   1020
atatgaatct tataaactgt ggttagctgg tttaaagtga atatatttgc cactagtaga   1080
acaaaaatag atgatgaaaa tgaattaaca tatctacata gttataattc tatcattaga   1140
atgagcctta taaataagta caatatagga cttcaacctt actagactcc taattctaaa   1200
ttctactttt ttcatcaaca gaactttcat tcattttta aaccctaaaa cttataccca    1260
cactattctt acaaaaatat tcacatgaaa taaaaatttg ctattga                 1307
```

<210> SEQ ID NO 14
<211> LENGTH: 1922
<212> TYPE: DNA
<213> ORGANISM: Homo sapiens

<400> SEQUENCE: 14

```
gtgcgcggcc ccgcgcggca acgcaggggc ggaaccgcat gactggcagt ggcatcagcg     60
atggcggctg cgtcggggtc ggttctgcag cgctgtatcg tgtcgccggc agggaggcat    120
agcgcctctc tgatcttcct gcatggctca ggtgattctg gacaaggatt aagaatgtgg    180
atcaagcagg ttttaaatca agatttaaca ttccaacaca taaaaattat ttatccaaca    240
gctcctccca gatcatatac tcctatgaaa ggaggaatct ccaatgtatg gtttgacaga    300
tttaaaataa ccaatgactg cccagaacac cttgaatcaa ttgatgtcat gtgtcaagtg    360
cttactgatt tgattgatga agaagtaaaa agtggcatca agaagaacag gatattaata    420
ggaggattct ctatgggagg atgcatggca atacatttag catatagaaa tcatcaagat    480
gtggcaggag tatttgctct ttctagtttt ctgaataaag catctgctgt ttaccaggct    540
cttcagaaga gtaatggtgt acttcctgaa ttatttcagt gtcatggtac tgcagatgag    600
ttagttcttc attcttgggc agaagagaca aactcaatgt taaaatctct aggagtgacc    660
acgaagtttc atagttttcc aaatgtttac catgagctaa gcaaaactga gttagacata    720
ttgaagttat ggattcttac aaagctgcca ggagaaatgg aaaaacaaaa atgaatgaat    780
caagagtgat ttgttaatgt aagtgtaatg tctttgtgaa aagtgatttt tactgccaaa    840
ttataatgat aattaaaata ttaagaaata acactttcct gactttttta ttattaaaat    900
gcttatcact gtagacagta gctaatctta ttaatgaaaa acaatagaca aacatctgtg    960
```

cataatttt cagacacaat tctgtaaata tttggaaacc ttttaagtat ttaaactttt 1020
aaatttttga aataaagtat tctaaactaa tataaataag gacaatgaaa aaacatgaaa 1080
ggacttagca taatgttatt ttatcttttc tacaactttg tttaaattac ctttccaaag 1140
atatttgtgt ttatgtaatt ttccacggaa taacattaat actctaggtt tataaaccgg 1200
tttcacatta tttcatttga tcatcacaag agctttgtga agtaagccga gaagttgtta 1260
ctggtattta ataatagcaa tagaggagtt aaagactttc ccacagcttg caggtcaaga 1320
caagaaattc aggtctccta attctcagtg gagctctatt tctgttaacc caaattgctg 1380
ctctgtttta ggtctcaatt tcatctgtaa aatgatacta atagtactta tcccattgga 1440
tttttgttga gatttaaata aatagccaaa agccaataca taataaacac tcaataaaga 1500
ttaaccataa ggagagtcat gatctggttc caggaataca ttgttagatg actgaaaaat 1560
tgtattactt caatgaaaat actataaata ataacatttt catatattag ttggttctca 1620
tgcatacata atctaatttt atttgatcct cacaactgtt taagttttat taaatataca 1680
ttatccctat ttgtataaat agaatcatac aatacctgcc tgctttcatt caacaaaatt 1740
atcatgagat ttttccatgt tgtgtacatc aatagttcat ctattttatt gctcagtaat 1800
attccattgt gtggatgtat cactatttgt ttacacattc accactgata tataagttgc 1860
ttccagtgtg aggctgtttt aaataaagct gctatgaata ttcatgtaag aaaaaaaaaa 1920
aa 1922

<210> SEQ ID NO 15
<211> LENGTH: 2269
<212> TYPE: DNA
<213> ORGANISM: Homo sapiens

<400> SEQUENCE: 15
cgcagccccg gttcctgccc gcacctctcc ctccacacct ccccgcaagc tgagggagcc 60
ggctccggcc tcggccagcc caggaaggcg ctcccacagc gcagtggtgg gctgaagggc 120
tcctcaagtg ccgccaaagt gggagcccag gcagaggagg cgccgagagc gagggagggc 180
tgtgaggact gccagcacgc tgtcacctct caatagcagc ccaaacagat taagacatgg 240
gaggtgaaag acaacttgag tggttaaatt actgtcatgc aaagcgacta gatggttcag 300
ctgattgcac ctttagaagt tatgtggaac gaggcagcag atcttaagcc ccttgctctg 360
tcacgcaggc tggaatgcag tggtggaatc atggctcact acagccctga cctcctgggc 420
ccagagatgg agtctcgcta ttttgcccag gttggtcttg aacacctggc ttcaagcagt 480
cctcctgctt ttggcttctt gaagtgcttg gattacagta tttcagtttt atgctctgca 540
acaagtttgg ccatgttgga ggacaatcca aaggtcagca agttggctac tggcgattgg 600
atgctcactc tgaagccaaa gtctattact gtgcccgtgg aaatccccag ctcccctctg 660
gattgtcagt ggctgctatg cagcaggtgc agcctggtct ctcactgagt ctctactcca 720
caaaggcaac gactggccaa ggcagtggct ggctctgggt tacacaagtg cagacactca 780
actaagtgag ctggaagacc caggagaagg cggaggctca ggtgcccaca tgatcagcac 840
agccagggta cctgctgaca agcctgtacg catcgccttt agcctcaatg acgcctcaga 900
tgatacaccc cctgaagact ccattccttt ggtctttcca gaattagacc agcagctaca 960
gcccctgccg ccttgtcatg actccgagga atccatggag gtgttcaaac agcactgcca 1020
aatagcagaa gaataccatg aggtcaaaaa ggaaatcacc ctgcttgagc aaaggaagaa 1080
ggagctcatt gccaagttag atcaggcaga aaaggagaag gtggatgctg ctgagctggt 1140
tcgggaattc gaggctctga cggaggagaa tcggacgttg aggttggccc agtctcaatg 1200
tgtggaacaa ctggagaaac ttcgaataca gtatcagaag aggcagggct cgtcctaact 1260
ttaaattttt cagtgtgagc atacgaggct gatgactgcc ctgtgctggc caaaagattt 1320
ttattttaaa tgaatagtga gtcagatcta ttgcttctct gtattaccca catgacaact 1380
gtctataatg agtttactgc ttgccagctt ctagcttgag agaagggata ttttaaatga 1440
gatcattaac gtgaaactat tactagtata tgtttttgga gatcagaatt cttttccaaa 1500
gatatatgtt tttttctttt ttaggaagat atgatcatgc tgtacaacag ggtagaaaat 1560
gataaaaata gactattgac tgacccagct aagaatcgtg ggctgagcag agttaaacca 1620
tgggacaaac ccataacatg ttcaccatag tttcacgtat gtgtattttt aaatttcatg 1680
cctttaatat ttcaaatatg ctcaaattta aactgtcaga aacttctgtg catgtattta 1740
tatttgccag agtataaact tttatactct gatttttatc cttcaatgat tgattatact 1800
aagaataaat ggtcacatat cctaaaagct tcttcatgaa attattagca gaaaccatgt 1860
ttgtaaccaa agcacatttg ccaatgctaa ctggctgttg taataataaa cagataaggc 1920
tgcatttgct tcatgccatg tgacctcaca gtaaacatct ctgcctttgc ctgtgtgtgt 1980
tctgggggag gggggacatg gaaaaatatt gtttggacat tacttgggtg agtgcccatg 2040
aaaacatcag tgaacttgta actattgttt tgttttggat ttaaggagat gttttagatc 2100
agtaacagct aataggaata tgcgagtaaa ttcagaattg aaacaatttc tccttgttct 2160
acctatcacc acattttctc aaattgaact ctttgttata tgtccatttc tattcatgta 2220
acttcttttt cattaaacat ggatcaaaac tgacaaaaaa aaaaaaaaa 2269

<210> SEQ ID NO 16
<211> LENGTH: 7091
<212> TYPE: DNA
<213> ORGANISM: Homo sapiens

<400> SEQUENCE: 16
gctacccact tccgccccct ccccctgcca ttggaactag ctgagccgaa ctagttgcgg 60
ccaccgagca gccggctctc ggcacctcct cctccgcctc cctgtctcct gttccattcg 120
cctttcctct tctttcctgg cccacgccgc tccgaggcct cgcgaccgcc gagcctgcag 180
cctgccccgc ggccaacatg agcttcttgt tgagttctca gcctgaagtt gactggaact 240
ttcagttaac aagtatttat cgaatacctg atctgtagtg ttggacttag acctatggaa 300
ggagctactg atgtgaatga aagtggtagt cgctcttcta aaacttttaa accaaagaag 360
aacattccag agggttctca ccagtatgag ctcttaaaac acgcagaagc cacacttggc 420
agtggcaacc ttcggatggc tgtcatgctt cctgaagggg aagatctcaa tgaatgggtt 480
gcagttaaca ctgtggattt cttcaatcag atcaacatgc tttatggaac tatcacagac 540
ttctgtacag aagagagttg tccagtgatg tcagctggcc caaaatatga gtatcattgg 600
gcagatggaa cgaacataaa gaaacctatt aagtgctctg caccaaagta tattgattac 660
ttgatgactt gggttcagga ccagttggat gatgagacgt tatttccatc aaaaattggt 720
gtcccgttcc caaagaattt catgtctgtg gcaaaaacta tactcaaacg cctctttagg 780
gtttatgctc acatttatca tcagcatttt gaccctgtga tccagcttca ggaggaagca 840
catctaaata catctttcaa gcactttatt ttttttgtcc aggaattcaa ccttattgat 900
agaagagaac ttgcaccact ccaagaactg attgaaaaac tcacctcaaa agacagataa 960
aaggatgcag agctgtgcaa attgttcctc aaatgaagca gtgtggagtg tattggggat 1020
tttgttatat tttgttttta tctggattgt ttttgtccta ggtttggggg cgggggcttg 1080
tttgggttcc tttttcttta ttctgattat gtgaaaccat attctattgc taggggaagc 1140
caagaaccat tctctataca cttgataagg gtaaatttat cttagtgttt ttaaacttgg 1200
ttttggttac ttgaggagtt ttttaataat attgtgtgct gcaagaaagt gcttgttgat 1260
tgaactgccg atggattggt ttctgtgtgg tataaattgt ggcccattta tgaagtcccc 1320
aaaagagtta tgtttttaag tgccttggca ggctcacttc tgaggtgcaa aacatagata 1380
tagaactgaa cagggcttga aacaatatta ggattactac ccagggcact tactggtgca 1440
tgttgtaaca tatctatgat aaaagccata gtttacctaa aatggtgatt tccagccttt 1500
actgctttga agaaacagaa tttgtaaagg tatgcatgta gaacataaaa aatatttctt 1560
aattattttt tatattgatg gtaatatatt acgttcaaca atgcttaaag ctctacaagc 1620
aggtcttttc ccacctcttg atatctgtga tactgaaact tgaggatgtt gaaatgtatt 1680
acattttggc ttctttctac atgttaactg cactgtagat gtaaaaaattc aggttatata 1740
taggattgcc atcttcagag gtgatgctga actgtgaggt ttcctagtaa ttgccaaatg 1800
agccgtaagt ctgcagaatt cccttctact ttgaagagaa ggggatagga atgtatattt 1860
ggctgggggc atggagatgt tcgtatgtat gaggagttag ggatggggag tcaagttcta 1920
gaaagttttg tctgaaaacc tttgaataga atggcatgaa gattttaatc aattacttat 1980
aaacaaagtc ttagagactt ccttttagga atcaacttcc atgagaagtt aaaaataaat 2040
tattaatttt aggtacagac attaaacatg gaatttaagg actgttgggg gaaattgatc 2100
acttcttagc atttccattc agtgaatgga gctgatgttt gcctgtcatt ttaagatgat 2160
accatacctt ctttggttat tataggtcca gtttgaagca ttctgacttc tggtttttcc 2220
accctgaaag gaaatgtttt tctttgcagc agtattagat aatgaaaaat gctaattcag 2280
tagttattaa cttctaaatt ttattcgcca tgactttcta gtgaattatt accataaata 2340
acaatttcag aaacttagtt tttagaataa atattaattt ttccacttca gttttattct 2400
agaaaatacc ctttttagaa atccagtttt agttttgtca ttttcgataa atctttcttc 2460
agttagaaat atatatcctt ccttcagttg aaacatatac ctttttcaca tctaggaaga 2520
aatgcttgct ctgaaatagt atagattaaa aacactcagt agaaaagaat ctaaaattaa 2580
atgaatttgt tttgccatta aagtagagca gtgatacaat ttaatgccat tacaattatg 2640
ttgactagaa actgcctttt tctccacttc atttctagca attatttacc aagtaccaac 2700
agtagaagta acaggaaagc ctggcagagt taaatatctt ggacatttat tggtaaagct 2760
tatttataaa ctgcagtcag agctagttaa tttccttaaa tctttttgta ttcagataga 2820
taatatgaat cattatgggt tgattcagaa ataaaatttg tgaggtgatt ttgaatcttg 2880
tccatatagg aaaatgaagc acagaattac tcagtcttcc atattgtatt tgacttcata 2940
tcaatctagt aaaaaaggag ttgcaatagc caagtataga gagaatagtg aaaaattaat 3000
cttgcccttt caagccttat acagtagtac actgtacttg tttttagtag taagacctac 3060
tttcccacta tatgtagata gtttgttttc actgtgccag aatctcaggt gcctgcttag 3120
agtatttctt taatcacagt cactgggaag taaggagatg tatatatgtg tatatatggt 3180
aacaaagcat agcagttctc taggggagag gcctggcatt gcacatggtg ttacatggct 3240
acaagtaagg aaaaaatcag aaagtgaaag aactgatgta ataaaaggtt gatttggttg 3300
gttcccatga aagttagtaa gatgcccttt taaatataag gatcagtgct ttgttctgca 3360
gcagagtttg ctgataaatg tctgttggat tctttttgga tttctttaat taatttgtaa 3420
gtaaccaaga taattatttt ccccttgct ctctatatta atacgtagct ataaagcaac 3480
agttggtttt cttatccttt gataaaagca tcccataaaa tataaagtag taagttaaca 3540
tagtattatt gtcacacaca atgctttttt tggttaaatg ttgatacgaa gcaatgtttt 3600
ggaattactt taattgatgg agtagtggtg gtagagagaa attaataaca aaaagagtga 3660
aaatatttta attagcagta gatggtgcta ctggctttca tttgctgact tgattattcc 3720
ctttctctta aaaaccatgg cattagactg cactaaatta acaagcatgt tagttgctgg 3780
tagaggtttt ggaggttaat ttaccttaaa ttggaagact tttaattgca gtctctttct 3840
accttccctc tgttagtcat ttgtaaattc taaatggtca ccataaaatg tattaggtag 3900
gagaagatac gttttatgta taatatatct cagactgagt tactgcctgt cttatcagga 3960
tggataaaac actacagtct cttatcagga aatagagatg atgtggatat ttatatatta 4020
catatataac caccagactc cattttatat attagcattt tccttgctta tgggaaaata 4080
gcaaaacaac atttcattta tacttttgtt taccctctc tgagacaggt tttgataacc 4140
actgaaatgg tagaatatgt gagatacaaa tattgagttg tagaactttc tttttaaggt 4200
gaataagtca tgccttaaca tccaaataag agttcatctt cagagtggtt cttttgggag 4260
cactgtttat tccagctata ctgcaaaagt ataatgtttt tggaactgtt ctagagcata 4320
ccatgaaaag cagtttgtta ttatgcagga aaatcagttt catcatttta gttacactaa 4380
acactttgg cagcttaata tgaccttttt aaattttttt tatttttttt atttttattt 4440
ctttaagatg gagtcttgct ctgttgcccg ggctggagta caatggcatg atctcagctc 4500
actgcaacct ccacctcctg ggttcaagca tttctcctgc ctcagcctcc caagtagctg 4560
ggattacagg cagcaccaca cctggctaat tttcatattt ttagtagaga tggggtttca 4620
acatattggc caggctggtc tcaaactcct gacctcaagt gatccgccct ccccagcctc 4680
ccaaagtgct gggattacag gtgtgagcca ccacagccag ccagtatgac ctatcttaat 4740
catcagctca actgtaattt aaatttggct gttctctgga gctaaaccat tagggaagtt 4800
caaaggaatg tgccatgatt tccgaatttg cacaagagaa tgttttaagc attggtagca 4860
taattgaata aaagaatagt ttcctgatgt cactattttg aagtggaaat tatcacttgg 4920
atgtggaggt tttactttt aaaaacattc agcttaatta ccttacctta attaccttag 4980
ttagatatac taatggaaaa aaaccaagtc ctttctctag aacttgtttt ctatttttgt 5040
tccttttcat gaaaacttct caatttaatt ttaactactg taggatagta ttgattgaat 5100
ggatactatg gaaaagtgga tccaatattt aagatagaag tagtttaagg agacaacagc 5160
ctttactgcc attttttttt aaatgttttc actcagatga acaatttgac tttaataaaa 5220
gactggagat ttttgtacaa agaaatagga ataagtttca tatactaatt atgctgagtt 5280
ttaagcctac atatcacaaa atatttagaa ttgtataacc ttttcatata tttataactt 5340
ttaatgtctt tttaaaagat gtgggaccaa aaatatattt ataatttgga aatgtgactg 5400
cataccaata agaaaactta ccttattttg aaatttatct gggatattaa agaatctacc 5460
aattcttaaa aacacagatt tatactttaa gcttatttta aaattaaaga atatatacca 5520
attcttagaa acactttaag gactactctt aaataactta aatatcagag ttttgttgta 5580
atattaaaat ttaccgtgga aatcactgtt gttcagctat caccttaatt gtgtatgata 5640
tgataaatgt ttagcagtaa agctatctta agatttaatg gaaaagttta atttgaagat 5700
gtaacaaaaa ttctgaccac agttgattct gaatttttaa ggctttccta ataggctgat 5760
cacagagaat aatccatttt gaaggtataa aactgcactg tatgtctgtc acttgtagct 5820
gaactgattc acattttgac aaaagagaga aaatacaaaa atgagttttg caaatgtaat 5880
aactttttct gcatatagaa ctaaataatt gaaaaatatg ggctatagtt ctcaaaggta 5940
gatagtaaaa tcactggctt tttccagctg tatgtttttc cactgtgcgt gtacacacac 6000
actggaaaat aattaggctg attttgcagg tcttcattgt tagagattct gaagtattta 6060
ctgtcaattc ataggtttca gtttatttag gaaattagtg tttgacagct ttttttaaat 6120
tatttcactg aagctgagat tattagtgat acaaagttaa aatttcaata tttaatttct 6180
ctatatatta ttaatattaa attgtttttt acttataaat tcatgttctc atctgattta 6240
atattaaatt tgtataggtg ggcgtttctt accattttgc acaagttttt gtttttctga 6300
aatacttaat tgtgcaggtt gtaaaaaaga ttagtgcatt ttcattttaa ggatgctttg 6360
ctccttaaat tgttcgacag aaatgacttt ttagggaaag tagttttttt ggagctacta 6420
acttgtattt attattgtac atgcataacc agggtggtga gggcactaat cttgtaggaa 6480
acacttactt gatgttttat ttgaactttt cctataggtt taacttttac tgcatagaat 6540
taacactagg aacagtgtca tgaaatctgg gttgaaggag aatacagtat atatgagaac 6600
acttaaagtt caaatagaaa tcatttctga agacaaaagc agaggaatat tgtcagtgcc 6660
aagtaatgga agaataaggg cggcatttac actgtgcaag tattgagaag agtgcataaa 6720
gacagggaac tactctcatg gagacagttt ctctcttata atcaagtaac tagaagggga 6780
aaaatcatct aagttatgaa atccaacata ggcgctatat tacaaactgt gccggattat 6840
gcaaattgta gttgttactg atcaaagttt aattgcttca tttttgttta aaaagggata 6900
ctgatgtcag aaaatctgta atatgtttta ttcaaaagat gtaaataatg tatacagact 6960
tgtatgtgat gggatgggaa atatttaaat tctaggtgtt tttttttttt taaagaagaa 7020
actcaatgtt tataagaaaa aaatgaataa atagttacgt ttggccatga atcctgaaaa 7080
aaaaaaaaaa a 7091

<210> SEQ ID NO 17
<211> LENGTH: 7003
<212> TYPE: DNA
<213> ORGANISM: Homo sapiens

<400> SEQUENCE: 17
actcgcagtc ctgacgggca ggggctgcgg accgcccggc cttggaccca tccggagcca 60
caggttggag gagataagta gctgtccccg tgctcatcgc cctgtggagc agatcctgtc 120
tccttgctga cggtggagcc cgggagttcc agggcttggg aaggggaagg aaacctctct 180
gaaatctgac acctgctctc ccggcaagga aacttcgcag gctgaccgac caagaccatc 240
actatgaccg atggagacta tgattatctg atcaaactcc tggccctcgg ggattcaggg 300
gtggggaaga caacatttct ttatagatac acagataata aattcaatcc caaattcatc 360
actacagtag gaatagactt tcgggaaaaa cgtgtggttt ataatgcaca aggaccgaat 420
ggatcttcag ggaaagcatt taaagtgcat cttcagcttt gggacactgc gggacaagag 480
cggttccgga gtctcaccac tgcatttttc agagacgcca tgggcttctt attaatgttt 540
gacctcacca gtcaacagag cttcttaaat gtcagaaact ggatgagcca actgcaagca 600
aatgcttatt gtgaaaatcc agatatagta ttaattggca acaaggcaga cctaccagat 660
cagagggaag tcaatgaacg gcaagctcgg gaactggctg acaaatatgg cataccatat 720

```
tttgaaacaa gtgcagcaac tggacagaat gtggagaaag ctgtagaaac ccttttggac    780
ttaatcatga agcgaatgga acagtgtgtg gagaagacac aaatccctga tactgtcaat    840
ggtggaaatt ctggaaactt ggatggggaa aagccaccag agaagaaatg tatctgctag    900
actctacata gaaactgaac atcaagaacc ccaccaaaat attactttta aaaacaatga    960
caaaccacac aattgttgtt gagtaaacca cgcacaatgg catgtctttc tttttctgcc   1020
agaaaatcta ttttaagaaa ccagaatagt caacagtgtt caaaagaatt gactagttat   1080
ccctgaggcc ctttcaaaca tgatcaaaga tttcccaatg tgatctcatc atcatggata   1140
ctcaatttgt tttttcttat agagaaaatg agtatataag acaatataca agaagaaata   1200
tcagtgagtt ttaaatcaga acaagttacc tgtcacattg aagaaaaggg taggcactaa   1260
agggagaaca cagaaagaag aatttctaaa atattggatt tacttcttat attgagtcag   1320
atgcatactt ttagatttgc attggggaaa atgtactagc taaaaatgga tacacaatga   1380
agaattctat ttggctaatt aagaatgata tactatgtac acccaataag ctgtactaga   1440
atgaataaat tactgataag gttacaaata ggtaaatgtc acacttctgt taaaatgcag   1500
gaggtagtgt cataatgccg tctttatatt cttaataaat agcactttga caagaacagg   1560
actgtaaatg atgaagtaca agacaaatac cctgggaaaa aaaatgaaag tatgagaaat   1620
tggcatttct acagctgaaa ttcaatgtat ctgttagaga tgtctggaag ggttacttag   1680
ccaaatttta ctcaagccaa ttaggagctg atattatcag ttggaattaa gagaactcca   1740
gaggtttcca tttcaaacaa aattttagaa attggtttgg tgttcagctt cacatttcat   1800
tttttcttag cacatgttga taaaatagtc acaaggagaa attaccagtt acggtttatt   1860
aaatctcttt taaaatgcag tcaaggaaaa ctagccttga atttttttta gataaaataa   1920
gatggtgata tgaaacaaaa agtggcaatt attgcaggtt tccttttagt ttacaaaagt   1980
actggaaact aaatcatatt tcttccctcc aaatttcacc cattcctgac tttgaatcaa   2040
ttgcagaaat gcaggtgtgt tactttgttg atcaataact ttggaacaat tatggatcaa   2100
ttctatggtc actctgaatt ttcatgtcat taatcacata aaaattgata atacctcatt   2160
ctgtattaca atatgatttt attttgccaa aggcaagaca cctatagttg agctgtattt   2220
tgggggattg ggtgaggaag gacttctgat cttatctcaa caaaaaactg gccagtattt   2280
ttgttaatgt aaagcttcct tttctttcta aaaaatagta acaaaattat ttttcattgg   2340
cctattctgt tcttgtgtct aaactaacat tacattaatt tttaatctta gtttctgata   2400
aacacaagcc attcctatca aaatattatt tatttcagtc aattttacca aataacaaag   2460
acaatatatt ttcgtttttt tttattatga gcatatgatt ttttgacagg ctgtttcctc   2520
gtcgtataga ttttttccaa tcaaacctac tttttccata ctctgtgcat atttttttgtg   2580
aagttataca cattgaagac cctaaaaatc ccagtccatc attcagctta cctctgcgaa   2640
cttctatctg gtattgaatc agtttcagaa acacagacag atccaaggaa atgtctcttt   2700
ataatgttct taggatggac tagacccata aatgtgccat gaatcaaaat attaataatt   2760
tgaaagcttt catgctgtta gcccctgatg aaattctcag cattaactgg ccagctcctc   2820
tgatttctgc agcatcgcaa caggttcgaa gatgggttgt ggctgggtat tccctcccat   2880
ggtgtttcct ctgggatgct cttcattatc tcaatgcctg tgccatgaag atagaaaact   2940
gtaagctaac atttaagatg tttcttctgg aaggaaagtg agcaggaaca agttatattg   3000
ccactgctgt ggcaaatttt ggtgaacttt tggggtcatt atatcaattt tttctttgga   3060
```

ttcaaattgt aatgtcccct gcatttcctt aatagggaat gtgaaacctt tataaaactc 3120
taaaagtatt ctgttttgat atgtcttttt gtttctattc attttcagtt atatgattga 3180
tttacttatg ccaagattct gtcactgtca gttatttaat gagtgttttt tcagggtctg 3240
ttttaagatc attatttgat agctgtagca tgaagcagag gttgatgatg cccataattg 3300
caagactatt cctgtaaaaa taacaattat tgggtaataa cttcaagagg aatgagaagt 3360
gacaaaattg atttaaaata ttgttctact tataaataaa tgcttgatat aaaaaatttt 3420
ctccataaag tttgacatct gaccccagat tctatgtaat cattattaga aattccttct 3480
ctcattattt caggattagt agttctgtgt aattcatttt acaatttcaa attgttctgg 3540
tgccataaag tatacagact actttaaaga tttccaaatc ccctaattta ccccacaaca 3600
gcatgtaatt ttagccaaga tatgtcctgt tactaagtat ctcccaatgc tttagtaaaa 3660
cgtatttagg agaaatgttg aaaatgtaca tgaagctcct ttctgatata gaaaccattt 3720
ctggagtatt tacactggtt tgatgtttac attgctctaa ctcggtgcct cagatacctc 3780
tgtgaccaaa tttgtctcca accacatagc tcatttccta taatgttata tcataggaag 3840
ccctcacaga gacactaaca cagctaaaga tcttctgata ttatcagcaa gggatgcaag 3900
gactttattg gaatctggag agtttaactg ccttctcttg gtctcctcac ttacttctta 3960
tgaagttggc attacctgag actcttagct gtgattaggt acaagcttac cttttagggt 4020
agaaaaagaa agatcatttg aaaaatgtat ctaaaataat ccagagaaca taatgtttgt 4080
cttggtctga taatgataag aagtcaagga ttggcagaga aaatactaaa cgccaagagt 4140
tgagcctgtg ggtctctcca taagagtttt aaaactcttg ccagttacca ctttatccaa 4200
tttgctatca ttttcgtatt atcagctatc gccctgtaaa atattcaaaa ctagctattt 4260
ctaaagtaaa cattttatct gttactttta accagatagg tgtctttgtc atccttctac 4320
tataaattgt tctttgccaa cctgtacagg tagatgaacc aggcgagagt tttaatcagc 4380
cttttcttgt ccccttttgta agaaagagat gcttgccata gagaaggaca tgagtacatt 4440
aaaaataatt taatagccac aatatgatgt tctttaagct gcaaattgag tacactggga 4500
atcaacaaat ttgatgaagc ctgtctgtct cttcaccagt ggagtgagtg cagcagttag 4560
aaagagaagc aatattgtgc aactggtgca gtggtgagtt aatcatagtg tataaccttg 4620
tgttcatgaa acaggttgtt cattgttctg catctctctt catttaaaaa ggatacacaa 4680
ttctttcctc attgcatatt acaccaaacg tttgagggaa aaatcctcat tcgtaaagga 4740
ttttggatgt ataatctaaa actcaacaat aaagaaataa tattccaagt ctctggtttc 4800
ctaagataca taataactgt ttataaagaa ggtctaagag ctgatatttg ccaaagtgat 4860
agaagagttg tttttcctc tctactacca agctttaaga cattaaaaga agtctagtgt 4920
atttgaatat tttagagaaa gctttatcat tttttaagat gccaagatgc tgcctacgtt 4980
tgcaaaagtt gtctaagaat tcaccatgag ctatattttc ttctggatct ttgaccaagg 5040
tgatgtcagc ttatttctgg ggaaggtgtt gagctcttat acatgaaaat ggatataggc 5100
tattctctgg gatgagtgtc atttcaatgc tttataaatc catgaagctg cttgtctcat 5160
aaagtagaac tgatacaaat tttggttgga tatatagaga attttataaa tgtattgcct 5220
tagaatttct gggtggagac ccaactacaa tgacattgtc atgccagaac tataaagata 5280
attagagtta aaagttgttt aaattgtgcc cttaaataca gcagaacctg gagaaggtca 5340
tacttcaaag gtcgattttg agtccgaata aagaaagacc tagtaacaga tagttttttt 5400
ttgttcattt tcttctacca agtagaggtt tatgccctca gaactaaact agtaaaaata 5460
tctgaacaaa aaacctttcg ttgttggcat aaaaatgtga tacacttaga gacattttgt 5520
ttattgcata taaatctaat ttttccataa attagattta tgatattttc ataaagcact 5580
tgattagttt ttcaaggcgt accatcacaa agatgctttc ctgcagagtt ctttgtatca 5640
acagcctatg gttgagatgt tttctcattt cctgtagaga gagaatacca ctaacaaaca 5700
aacaaaaact ttagtgccaa aatagtggaa ctattttgtc atcttttgag aaaaaaatat 5760
acaaagaagt catcttttca ttaagtggat tccctggttc ctttccagct ggttgtggaa 5820
gtaatggcta acatccttca gctgactttg tctacaagga ttattagcaa attctgtagg 5880
agcaagcatg tctgacctta acttaatgga tcccttattc aatcagtggc ttctgtcttt 5940
atgtctgttg gcatatcaaa atggtttctg ttcctagaaa agtaataaca tatgcttatc 6000
tttattcttt ttccaggtga ttttgttttc aaatgctcct tgtgaaaaca cctagtgttg 6060
tagaaaggaa agtggccaga aagaacaact tgggaccatg agtaggtcat taaatagctt 6120
agtgatttat cctcatatag ggcttataaa ccctgtatgt gtttatatgt gcttcacaga 6180
gttcgtgtca ggctcaaagg agatatgtat aagaaagtgg tttgtaaatt atgttccatt 6240
tcataaatag acactattca caaactaaaa tctaataaaa aaccacagtt gtaatttaaa 6300
ctgcttgata taaaaagagg tatcatagca gggaaaacac actaattttc atacagtaga 6360
ggtattgaaa actgaaaatg ggaaggcaac ttgaagtcat tgtatttgat tgaaaatgtt 6420
taatacatct cattattgac aaaatatgtc atcttgtatt tatttcaagg aaaccaatga 6480
attctaggta gtatattaca agttggtcaa aatattccat gtacaaatag ggcttctgtg 6540
tccatagcct tgtaagagat actgattgta tctgaaatta tttttaaaa aaataaatta 6600 tcctgcttta gttagtgtgt taaaagtaga cgatgttcta atataacact gaagtgcttc 6660
attgtatccc aacagtttac cttcaagtaa tattatcttt atttttaggc taagcacgtt 6720
tgattatttt gtctgtctcc tatatagatc tgttttgtct agtgctatga atgtaactta 6780
aaactataaa cttgaagttt ttattctata tgccccttaa tagactgtgg ttcctgacgc 6840
acactgttag gtcattattt tgttgtacca aagttctagt ggcttcagaa atcatagcat 6900
ccaatgattt tttggtgtct ggctatgaat actatggttg agaattgtat tcagtgattg 6960
tttctgcaca cttttcaaat aaaaaatgaa tttttatcaa tta 7003

<210> SEQ ID NO 18
<211> LENGTH: 2158
<212> TYPE: DNA
<213> ORGANISM: Homo sapiens

<400> SEQUENCE: 18
agttctgcat ttctgcagag acagaaagaa acgcagctct tgacttcttt tttgtaaaca 60
ttactgtaag agttgtgata actttttatt ctactatgta tatgtatgga atagtattaa 120
taaatgaact agggaaggat gtaataaatt agacatctct tcattttaga gagaagatgg 180
aaacaacatt gcttttcttt tctcaaataa atatgtgtga atcaaaagaa aaaacttttt 240
tcaagttaat acatggttca ggaaaagaag aaacaagcaa agaagccaaa atcagagcta 300
aggaaaaaag aaatagacta agtcttcttg tgcagaaacc tgagtttcat gaagacaccc 360
gctccagtag atctgggcac ttggccaaag aaacaagagt ctcccctgaa gaggcagtga 420
aatggggtga atcatttgac aaactgcttt cccatagaga tggactagag gcttttacca 480
gatttcttaa aactgaattc agtgaagaaa atattgaatt ttggatagcc tgtgaagatt 540

```
tcaagaaaag caagggacct caacaaattc accttaaagc aaaagcaata tatgagaaat    600

ttatacagac tgatgcccca aaagaggtta accttgattt tcacacaaaa gaagtcatta    660

caaacagcat cactcaacct accctccaca gttttgatgc tgcacaaagc agagtgtatc    720

agctcatgga acaagacagt tatacacgtt ttctgaaatc tgacatctat ttagacttga    780

tggaaggaag acctcagaga ccaacaaatc ttaggagacg atcacgctca tttacctgca    840

atgaattcca agatgtacaa tcagatgttg ccatttggtt ataaagaaaa ttgattttgc    900

tcatttttat gacaaactta tacatctgct tctaacatat cgcatgttta tgttaagatt    960

tggtcccatc ctttaaactg aaatatgtca tgtgaaatta ttttaaaaat gtaaaaacaa   1020

aactttctgc taacaaaata catacagtat ctgccagtat attctgtaaa accttctatt   1080

tgatgtcatt ccatttataa tcagaaaaaa aacttatttc ttaatcaaaa ggcagtacaa   1140

aaaaagtaat aatgttttat aagattgtag agttaagtaa aagttaagct tttgcaaagt   1200

tgtcaaaagt tcaaacaaaa gtctagttgg gatttttttac caaagcagca taatatgtgt   1260

tatataaaca taataatact cagatatcca aatgttcaga tagcattttt cataatgaat   1320

gttctctttt ttttggtaat agtgtagaag tgatctggtt cttacaatgg gagatgaaga   1380

acatttatta ttgggttact actaaccctg tcccaagaat agtaatatca cctctagtta   1440

taagccagca acaggaactt ttgtgaagac acattcatct ctacagaact tcagattaaa   1500

tataatctag attaatgact gagaataaga tccacatttg aactcattcc taagtgaaca   1560

tggacgtacc cagttataca aagtacttct gttggtcaca gaaacatgac cagattttgc   1620

atatctccag gtagggaact aagtagacta ccttatcacc ggctaagaaa acttgctact   1680

aaactattag gccatcaatg gcttgaataa aaaccagaga aggtttttcc caggacgtct   1740

catgtttggc cctttagaat tggggtagaa atcagaaatg agatgagggg aagaagcaag   1800

gagtctaagg ccctagcgat ttgggcatct gccacattgg ttcatattca gaaagtgtta   1860

tctcattgat tatattcttg ttaagcaaat ctccttaagt aattattatt caaataagat   1920

tatactcata catctatatg tcactgtttt aaagagatat ttaattttta atgtgtgtta   1980

catggtctgt aaatatttgt atttaaaaat gccatgcatt aggctttgga aatttaatgt   2040

tagttgaaat gtaaaatgtg aaaactttag atcatttgta gtaataaata tttttaactt   2100

cattcataca gttaagttta tctgacaata aaagctctga ctgaaaaaaa aaaaaaaa     2158
```

<210> SEQ ID NO 19
<211> LENGTH: 5852
<212> TYPE: DNA
<213> ORGANISM: Homo sapiens

<400> SEQUENCE: 19

```
ttttgccgga tgttgttgta tgtccgagag acacgtgagg ttctgctacg tcattaccag     60

gcacgcgcag gaaacatggc ggcggcgggt gttgtgagcg ggaaggtttt tggtttcttc    120

ttgattcaat cttgataagt agtatgtgtc caggacttta tccatactcc agtttgttgg    180

agtatggtag gagtatgatt atatatgaac aagaaggagt atatattcac tcatcttgtg    240

gaaagaccaa tgaccaagac ggcttgattt caggaatatt acgtgtttta gaaaaggatg    300

ccgaagtaat agtggactgg agaccattgg atgatgcatt agattcctct agtattctct    360

atgctagaaa ggactccagt tcagttgtag aatggactca ggccccaaaa gaaagaggtc    420

atcgaggatc agaacatctg aacagttacg aagcagaatg ggacatggtt aatacagttt    480

catttaaaag gaaaccacat accaatggag atgctccaag tcatagaaat gggaaaagca    540
```

```
aatggtcatt cctgttcagt ttgacagacc tgaaatcaat caagcaaaac aaagagggta    600
tgggctggtc ctatttggta ttctgtctaa aggatgacgt cgttctccct gctctacact    660
ttcatcaagg agatagcaaa ctactgattg aatctcttga aaaatatgtg gtattgtgtg    720
aatctccaca ggataaaaga acacttcttg tgaattgtca gaataagagt ctttcacagt    780
cttttgaaaa tcttcttgat gagccagcat atggtttaat acaaaaaatt aaaaaggacc    840
cttatacggc aactatgata ggattttcca aagtcacaaa ctacattttt gacagtttga    900
gaggcagcga tccctctaca catcaacgac caccttcaga aatggcagat tttcttagtg    960
atgctattcc aggtctaaag ataaatcaac aagaagaacc aggatttgaa gtcatcacaa   1020
gaattgattt gggggaacgc cctgttgttc aaaggagaga accggtatca ctggaagaat   1080
ggactaagaa cattgattct gaaggaagaa ttttaaatgt agataatatg aagcagatga   1140
tatttagagg gggacttagt catgcattga gaaagcaagc atggaaattt cttctgggtt   1200
attttccctg ggacagtacc aaggaggaaa gaacccaatt acaaaagcaa aaaactgatg   1260
aatacttcag aatgaaactg cagtggaaat ccatcagcca ggaacaagag aaaagaaatt   1320
cgaggttaag agattataga agtcttatcg aaaaagatgt taacagaaca gatcgaacaa   1380
acaagtttta tgaaggccaa gataatccag ggttgatttt acttcatgac attttgatga   1440
cctactgtat gtatgatttt gatttaggat atgttcaagg aatgagtgat ttactttccc   1500
ctcttttata tgtgatggaa aatgaagtgg atgccttttg gtgctttgcc tcttacatgg   1560
accaaatgca tcagaatttt gaagaacaaa tgcaaggcat gaagacccag ctaattcagc   1620
tgagtacctt acttcgattg ttagacagtg gattttgcag ttacttagaa tctcaggact   1680
ctggatacct ttatttttgc ttcaggtggc ttttaatcag attcaaaagg gaatttagtt   1740
ttctagatat tcttcgatta tgggaggtaa tgtggaccga actaccatgt acaaatttcc   1800
atcttcttct ctgttgtgct attctggaat cagaaaagca gcaaataatg gaaaagcatt   1860
atggcttcaa tgaaatactt aagcatatca atgaattgtc catgaaaatt gatgtggaag   1920
atatactctg caaggcagaa gcaatttctc tacagatggt aaaatgcaag gaattgccac   1980
aagcagtctg tgagatcctt gggcttcaag gcagtgaagt tacaacacca gattcagacg   2040
ttggtgaaga cgaaaatgtt gtcatgactc cttgtcctac atctgcattt caaagtaatg   2100
ccttgcctac actctctgcc agtggagcca gaaatgacag cccaacacag ataccagtgt   2160
cctcagatgt ctgcagatta acacctgcat gatcactgtt cttgcttttt tgggaagaga   2220
cactttgttg caaccctttt tcaagtactt gaaagttgaa aatttgaaat cttggtattg   2280
atcatgcttt aaggtttatg taaagaaagt gtactgatgt tcttacatta aagctttaca   2340
aagatttaaa ctaattattt ttgtagttac ttctaccaaa tagcctttcc ttttcgataa   2400
cattcctcag tatttttata gccaagtaca ttttattttc ttgctgatga actggaattg   2460
gataaatatt gcaagtggat gagttggaaa ttatgcactt tgaaaaacat tcactttgtt   2520
taagcttatt gggtttcaga tttgattaaa ttaaatgtgg aggctttcta tagcattcta   2580
agctgagaag tagattgtta cccagtaatg aaataaaaaa taaaaataaa aggatttttt   2640
tctctattgt ttacgacagt actcagctta aatatttatg ctggtcaaat gtgatttaaa   2700
ttggacattt tcatcaatgc agtctaatgt gtagataaat atttcaacca taataagtgg   2760
attggcagta tattttttac attgaacttt tcttcacttg tatataaaga ttatatataa   2820
gtacttattt atgagtataa gaaaggttag gcatattttc attaactgaa taaacgactt   2880
```

```
gatttatata acctggttta tcaaaattta acatggcttc agtatgagat ctttttcaaa   2940
actattttct taaacattta tttcatgaga ttatgttcaa ccctgtacct ggtgtaattt   3000
taaaattaat tgcttgtaac ctcactttac taataatgtt tattatcttt cctaataatg   3060
cattaactga ttaatcaggt gtttaaattt ttataaaata ctcttgcaaa aagtttattt   3120
gaaaaatttc tagatggtct catgagtttc aaaataataa tttttgtgta tgaacaaagc   3180
tgttgttttt accatgcagt attgcatgat tttaagttat gtggaattaa cataactgat   3240
tttgttttaa ttgtaagttg ttaactcctg tatatatcat taaaataaat ctgaagttga   3300
agtagtgttt ttagttaaat tatacttaga aatagtctgc tttttaaaa ttttttttct   3360
tgagaaagag tcttgctctg ttgcccaggc tggagtgcag tggcgcagtc ctggctcact   3420
gcagcctccg ccttctgggt tcaagcgatt ctcctgtctc agcctcccga gcagctggga   3480
ctacaggctt gtgccatcgc gcctgactaa tttttgtatt ttgagtagag atggggtttc   3540
accatgttgg ccaggctggt ctcgaactct tgacctcaag tgatccactc gcttcagcct   3600
cccaaagtgc tgagattaca ggtgtgagcc actgtgcccg gctaattctt taatagaaga   3660
aaaaacatcc aagatggacc tcaattcatc tcttattttt atatgattaa aatgataatc   3720
tggccgggcg cggtggctca cgcctgtaat cccagcactt tgggaggccg aggcgggcgg   3780
atcacgaggt caggagatcg agaccatccc ggctaaaacg gtgaaacccc gtctctacta   3840
aaaatacaaa aaattagccg ggcgtagtgg cgggcgcctg tagtcccagc tacttgggag   3900
gctgaggcag gagaatggcg tgaacccggg aggcggagct tgcagtgagc cgagatcccg   3960
ccactgcact ccagcctggg cgacagagcg agactccgtc tcaaaaaaaa aaaaaaaaaa   4020
atgataatct gaataagtta tggaaatgaa aaccatcctt tttataactg aaaaaaaatt   4080
ttcattagca tggaaatggg cacagtgttg ccttgaaaga tacagttatt tgactcagta   4140
aagcagctta ttacaactga tgctaatagt atagagaaaa aagttgtgca gttctaaaat   4200
ggtcctagag attgactttt ttccccccaag aaagttaggg aacaaaacga actttttttcc   4260
tggttgagca ttaactgaca atcacgacag tagaaccgtt agagtttagt ttttaatatt   4320
atgtgtgtta tctttcatca gttaataatg agtaagccta ttcagaaaaa gaacataaac   4380
tgatcaaaaa ctcagcatct ccagcctttc atttcctgct attcaggaaa ttgcttagaa   4440
catcttgatg tcctccttgt tcttcctgga cagtgacttt ttgggagttt gttcctgctg   4500
cgtaatgtga tacccacttc agattttttt tttatcaata catttagtaa gttgaacttc   4560
tgtcaagttt tattacaaaa ttacttgtta aaacaatttt tactaaactg catttctatc   4620
tagcatattt ttgatatgga agtgatagta tagtatagtt ccaggagaag tcttaaatca   4680
gtccacagag tccagttagc aaatactctg tgccattaag attgctaaaa tacacagttc   4740
aggtaaattt actagtgttt tttaaaggtt tatttgtttt cacaagatgc tctgtccaca   4800
cccttataac atgtaaaata ttgtgtgctg tattatgtgg taaagttgtt aaaattcagt   4860
ttctaacatt aacttaaaag tacagacaat ctaacatgat gatttgactt acaaactttc   4920
aactaaattt atgatggctt taaagcagtg cactgaatag aaaccatact ttgagtaccc   4980
atacagccat ttttcacttt tactacaata ttctataaat cacatgagat atttaacact   5040
ttattataaa ataggctttg tgttagatga ttttgcccaa atgtaaacta atgtagtgtt   5100
ctgagcatgt ttaagttagg gtaggctaaa ctatgtttgg taggttagat gtattaaaag   5160
catttttgat taatgatgtc ttcaatttat gatgtgttta ttggaacata acctcaatat   5220
aagttgaaaa gcatatgtat tttcaattct ggcatgaacc tatgggaatc ttttgcattt   5280
```

aagaacctcc ccattttaat aatttcatgg gtctaagatt cttcatctgt ttataaggaa 5340
ctttagtctt agtgattaga gactaaattt tttttgagc agtaagaaaa cagccttttg 5400
ggacagatag tgagtgattc ttaggaactt gacattgcca agaaatttta tagatgccga 5460
agaattctta tgtgaaattc acataagcat gcccattact aaagacagtt tgtataaagt 5520
aaccctaaat gtttattgag gaacctacag cttcaactga cttacgtgca gatatgtacc 5580
aggagaacat cattttagct tgggcgtctt tacttggggt tttcagagga tccaggaacc 5640
tcactgtatg caaagtcttg tggatgtacc tgaatgtttt tggaggcagg tcacatagtt 5700
tctgaaagtg ttctcttatt ttcctcaaat gtaggtaacc attgttacaa gttatttaac 5760
aggagaatag taacaatgtc taacttatgc taatgatttt gtgtgctgag ctcccattaa 5820
ttaaaatgtc ttcagaaaaa aaaaaaaaaa aa 5852

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ccaaccgcga gaagatgac 19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
tagcacagcc tggatagcaa 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
tgagaaagga ggctgcatca 20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ctgctgcaac tgctgaaca 19

<210> SEQ ID NO 24
<211> LENGTH: 23
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 24
gcctcttcca gaaactagga gaa 23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggggctttct ttgtgtaagc aa 22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacagctgcc aggatcctaa 20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtctggcaca tgtttgtcta ca 22

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagtgcgcca caagcaaa 18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgccttatgg cgagttcca 19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cagcggcagc tgattgttaa 20

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
cagagagatc acccttcaag tca 23

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
acccagatga ctcccacaaa 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
caaggattgg ctgctgctta 20

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
aaggccgtgg tcctgac 17

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
tcagctggct gaagtagtcc 20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
gcaaggtggc agaagtcaa 19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
atggccagag atgcttcca 19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gcgcctttct tcatcatcca 20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gatggtgatg gtagggtttt cc 22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
tcctggaact gaagcactca 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gcagcacaag aatgggtaca 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ccccttcctg gctctcagta 20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ggtctgggct gctctcca 18

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ggacagtgac cctcaacca 19

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cagcagggca aatctcttgt ta 22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tggaaaggtg gtgtggaaac 20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gtcagctggt ggttgctaa 19

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tgatgtcagt gctgctactc c 21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ctgtgtatcc aagacagcag tca 23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ctcagttcag gcttcctaca 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tcttttggca caaggcttac 20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
cacaatagaa ccttcagcag ac 22

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
gaaaagtgtc ttcatgtatc cagtta 26

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54

-continued attccagctt caacccctca 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
atgactaggt gcctgggaac 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccaactaatg ccaccaccaa 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cgaagagact ggctgttgac 20

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ccccttgcct acaagaagct a 21

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tcccgttggg ccaatcc 17

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
agcaagaacg ccaaggacaa 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
cggccacgat tctcttccaa 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
agattgcatg tcccctggaa 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
gggtgggttc cagaaggtta 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tatgcctgcc acaccactaa 20

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gccaggagaa cttccttgta cta 23

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
tcaaccgccc tgaacaca 18

```
<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

acaccgacaa tgtgaccaga a                                              21


<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

agccttccaa gcccatcc                                                  18


<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

tgcggattga gaagccttta                                                20


<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

cgtggtcagg atggctagta                                                20


<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

ccaatcggca gcaatgtcta                                                20


<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

gtcctctgtg aaggggtcaa a                                              21
```

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
tcttcaggca agttagagtt ggtta 25

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tgacaaccca gagctcatcc 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
ggacgccatg ttgtttggaa 20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
cgtccaggtg tcagaggatt a 21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
accttgttct ccaggatacc c 21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
tgaagtggct ggttacatcc 20

<210> SEQ ID NO 79

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
agaggctggt catagggtaa 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gtcttgacca gcctctctca 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
acggtgcttt gagggataca 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
acaagagacc ggctctagga 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
ttgccactag gtgagctgtc 20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
cgttccgtta tccaggcttt t 21

<210> SEQ ID NO 85
<211> LENGTH: 21

<212> TYPE: DNA
<213> ORGANISM: Artificial Sequence
<220> FEATURE:
<223> OTHER INFORMATION: Description of Artificial Sequence: Synthetic primer

<400> SEQUENCE: 85
actcctggta ggtgtcaatg g 21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
ttagagctgc tccacatctc c 21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
accaggttgt tggtgaaggt a 21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
tccatcacca agagggtgaa 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
caggatgctt tccccaaaca 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
acgtgcattg tgctctctca 20

<210> SEQ ID NO 91
<211> LENGTH: 22
<212> TYPE: DNA

<213> ORGANISM: Artificial Sequence
<220> FEATURE:
<223> OTHER INFORMATION: Description of Artificial Sequence: Synthetic
primer

<400> SEQUENCE: 91
cagcactgat ttggtcatct cc 22

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
tgggcaccaa agaaggtta 19

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
ttcctgtgca gagtaaacca 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
atctctacgc ccaccagtcc 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
agcgagtccg agtcatccaa 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
gacgaaagct tggctccaaa 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
gttccatagc gacgttctcc 20

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
tgggataaaa gctctgctct tca 23

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
tgttcgccgg cagaatacta 20

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
acaaggccaa gaattccctc a 21

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
tgccggggct tcttaaaca 19

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
ttcgtcccca gccaacaa 18

<210> SEQ ID NO 103
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 103
tggcttcccg ttcactatcc 20

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcagtgactt tctcagcaac a 21

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ttgggacagc ttggatcaca 20

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ctctgccgtc gcagcaa 17

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tggattagcc cgttgcagac 20

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gccggagcaa aacttaggaa a 21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
aggcggagtt cacaccaata 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
gccaagctct ggaggaagaa 20

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
gagaagaaca ggccgatggt ta 22

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
atcctggtgc tgctgac 17

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
ggccagatct tctgcttca 19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
agttcagaag agcccgagac 20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
gcgctgtctt ttggtgaaaa c 21

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
taccgggaga actacgtatc ca 22

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
atgcgccggt tctggaa 17

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
aggaatgtga gctggagaca 20

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
ttgtcacctt ccaactgaac c 21

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gctacctgga agctgaccaa 20

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
ccacctgcct agtggcaaa 19

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ggaaaggggt ggatgtgtca 20

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cacccaggat gtccttgttc ta 22

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
atgttagagc tcagttggtt gata 24

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
tactgcatga ccctcgacaa 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
atattgtcgc accccatgca 20

<210> SEQ ID NO 127
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
acctcctttc ctgataattt cctcac 26

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gccagcagca ctttgagtta 20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
tgagtcaaca cggagctgta 20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
gaaacccagc cagaaagcaa 20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
aggtggtggt gtcagacaaa 20

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
cctctgccct ccacttaatg tta 23

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
cagctataga gccttccacc aa 22

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
ccggacctga gcgtcatgta 20

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
gcacaccacg tgctcaca 18

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
gaacgggaag cttgtcatca a 21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
atcgccccac ttgattttgg 20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
tcagtttgga aacctgcaga a 21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
gctgcccata gctctttgaa 20

<210> SEQ ID NO 140
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
cccgtcgcct gtacca 16

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
tgttggaata gactctgaga agca 24

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
cggctacgac ctgaaactct a 21

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
tgagtgaggt gttgatgaac ca 22

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
ccagaggcag tgcaaacata a 21

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
agaaattggg tccggggtta 20

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
actccggaca gcacataca 19

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
ccaactgaag cactccgaaa 20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
aagacctggc aacggatgac 20

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
ttgagaatcc tttccaaccc agac 24

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
acaacttgtc catcgtttca c 21

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
accagccatc acacacaa 18

```
<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152

agaactgaac agcgcaaca                                                 19


<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153

gctgggtatt caccatggaa                                                20


<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154

ggtgaccgtt ttggcaatcc                                                20


<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155

cactggccac tccagtcac                                                 19


<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

gcctggcgca ttacaacaa                                                 19


<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

caattccccg ggtagcagta                                                20


<210> SEQ ID NO 158
```

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
cggcaaagct gaaggagaag ta 22

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
caggaccctt tgcaccatca 20

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
acacagtgct aggtgcagtt a 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
tccatactcc cagcctttca c 21

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
aagttcatcc ggcccttca 19

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
ggtgtcttca tccacctcca 20

<210> SEQ ID NO 164
<211> LENGTH: 23

<212> TYPE: DNA
<213> ORGANISM: Artificial Sequence
<220> FEATURE:
<223> OTHER INFORMATION: Description of Artificial Sequence: Synthetic primer

<400> SEQUENCE: 164
tggacgtaag ggactcaaaa tcc 23

<210> SEQ ID NO 165
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
cccaggcctg cgttaca 17

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
tgtgccttac gacccatgta 20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
gttgttcagg gcctcgttta 20

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
gcaagaaggt ggcattgttt cta 23

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
tctggggaaa gtgaggcaaa 20

<210> SEQ ID NO 170
<211> LENGTH: 22
<212> TYPE: DNA

<213> ORGANISM: Artificial Sequence
<220> FEATURE:
<223> OTHER INFORMATION: Description of Artificial Sequence: Synthetic
primer

<400> SEQUENCE: 170
agagaagaga aggctggtga ac 22

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 171
tccaggttgt caggagcaaa 20

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
tcccatctca aagcccatta ca 22

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 173
ctcgtctgag cgggagaa 18

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 174
ctggcaggac tgtgagtaca a 21

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 175
atttcgtact gctcctcttc cc 22

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
tgaccgacga gatcaacttc c 21

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
tgtgccttga cctcagcaa 19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
tgaaggcatt ggggctgtg 19

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 179
agcctgacac gcagaggt 18

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
tgtgcatcta tgtgcgtcac 20

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
ggaatcgatg ggcaaagttg ta 22

<210> SEQ ID NO 182
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 182
caaaagacgg gcctcaccaa 20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cgtaagaggt tgcgcctgaa 20

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
catcggtgga acgcacaa 18

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gggcacttcc ctcaaacaaa 20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gccttggttg gactggaaaa 20

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tttgaagagc aacatggggt ac 22

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
ctcccaggaa ccgtacttca 20

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
ctctgataaa agccacgtct cc 22

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
catcaagatg tggcaggagt a 21

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
tgcagtacca tgacactgaa ata 23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
gactccattc ctttggtctt tcc 23

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
ccatggattc ctcggagtca 20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
tggtctgatg ggtggagacc 20

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
tgagtttcgg ggattgccat ac 22

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
tctcacaatg ggattctctc ca 22

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
caggcaagtt cctgaagtcc 20

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
tgccgaagaa acatggacca a 21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
agccccaaag aatggccaaa 20

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
agaaggccaa accccagaa 19

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
atgctgaggc cttgtttgc 19

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
gagagttgtc cagtgatgtc a 21

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
gtcctgaacc caagtcatca 20

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 204
catcggtacc cagttcagga a 21

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 205
tgctgcatgc tgaacacac 19

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 206
tcctctccaa caccaaagtc c 21

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 207
aggattccgg cacagtcaa 19

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 208
tggaagccac ggtggataa 19

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 209
tgtgcggata tgcttgttcc 20

<210> SEQ ID NO 210
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 210
tctgctccct tccattccc 19

<210> SEQ ID NO 211
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 211
gaattcttca ttcccttgaa ctgaac 26

<210> SEQ ID NO 212
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 212
cgcctcatgt tctgctaca 19

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 213
tagaagagtg cgttggtcac 20

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 214
cgagccgacc atgtcttca 19

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 215
aagctgaagg ttcggagcaa 20

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 216
ccaggctttc caaggttacc a 21

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 217
tggctttctg ggcaagca 18

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 218
actggataca ttcaaaccct cca 23

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
tggtgcacag actggtgtta 20

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
gtactgtggc gatggcatta tac 23

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
agaaaaggga gcagccatca 20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
acagtggaag cctgggttaa 20

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
acagtgtggg agcagttatc a 21

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
ctggcatcca gttgacgaaa 20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
catcagggcc tagcaggtaa 20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
gtgcagcact accacatgaa 20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
tatacgagcc cgtcttctcc 20

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
gccagctgct atatcacaca aa 22

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
aaacccaggg ctacttccaa 20

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
gccacatttc aaaggaaact gac 23

```
<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231

tccctgcagc caatcagata                                                20


<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232

ccaccaagaa gccactttcc                                                20


<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233

taccagcaat gccagggtta                                                20


<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234

agaaactgcg tccgttttcc                                                20


<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235

ggagtcagat gtccttggga taa                                            23


<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236

cggatcaaac tgggatttac cc                                             22


<210> SEQ ID NO 237
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237

cgagaacacg ttgccataca                                                   20


<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238

tctggcttcc tccaccaaa                                                    19


<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239

cagcggagtt cagcatacaa                                                   20


<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240

gttcggctcc tggctgat                                                     18


<210> SEQ ID NO 241
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241

caaagatgga caccagcgaa tc                                                22


<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242

ggggcagttt ctgctcttca                                                   20


<210> SEQ ID NO 243
<211> LENGTH: 21
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 243
tcatcctcag gcagcgtctt a 21

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
gcaggatcct acaccttaca ca 22

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
tgctggagat ggagggctta 20

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
ctggcgagga aagctcca 18

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 247
cagaaatgac atcacagctg cta 23

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 248
ctccccagca tttacccttc a 21

<210> SEQ ID NO 249
<211> LENGTH: 19
<212> TYPE: DNA

<213> ORGANISM: Artificial Sequence
<220> FEATURE:
<223> OTHER INFORMATION: Description of Artificial Sequence: Synthetic primer

<400> SEQUENCE: 249
ggttagactc ggcgaagca 19

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
acccagtcac cctgaatgtc 20

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
gcaggacaag tagaggtttt gtc 23

<210> SEQ ID NO 252
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
gtcggtctgc tggtctcc 18

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
tgtgtcttgc agtgctcaac 20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 254
aggcacagat atgggacaca 20

<210> SEQ ID NO 255
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 255

ataaggcacc tacagctcca                                                20


<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256

accagatcag agggaagtca                                                20


<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257

cagttgctgc acttgtttca                                                20


<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258

ggaagcagga tggatgaaca                                                20


<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259

ctcgggtatg gaatgtagtc c                                              21


<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260

tgaagacacc cgctccagta                                                20


<210> SEQ ID NO 261
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 261
ccccatttca ctgcctcttc a 21

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
tgggaaggtg gtcatcacac 20

<210> SEQ ID NO 263
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
cagcacccgc tgagatca 18

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
gccaagatcc catctctcca 20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
aggcacttca gctcaggaaa 20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ctggctgtgg gtgtggtact 20

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
cgctccactc cctctaggc 19

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 268
gctagagacc gagtgtcctc a 21

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 269
ccagaatgag gaactcctgg aa 22

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 270
tcaaagagct ggtgcgaaaa 20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 271
atttgtgtcc aggtcctcca 20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 272
gaaggagcta ccaggcttcc 20

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 273
agcaatttat ccacggcatc c 21

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
cttcgagaag tcttgcaacc 20

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
gccagaataa gagggaagct a 21

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
tttgccaaag tggctgcaaa 20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 277
tttctgggct tgggttctcc 20

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
tgcaccagtg ggtgtcata 19

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
gtggaactga aggtgccaaa 20

<210> SEQ ID NO 280
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 280
agaagtggaa ccgcttacta ca 22

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 281
agtgtggctc caaggtcata 20

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 282
gctgccatcg tgtatttcta ca 22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
agacctcatc caccggaaaa 20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 284
gggagcactt ggcacttttc a 21

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
gcaggatgtg ccacagatca 20

<210> SEQ ID NO 286
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
ggtccttccc atctacagtg aa 22

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
agcatccccg tgatggaaat a 21

<210> SEQ ID NO 288
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
tgctgccgct catcttca 18

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
caaaggttgc cttggcatca 20

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
gacctggcgc tccagttta 19

<210> SEQ ID NO 291
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
cctctgtgaa gcatctcagc ta 22

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
aagacggctt gatttcagga a 21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
gcatcatcca atggtctcca 20

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
tgttaagcag gacgactttc c 21

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
cctttctggc tgggcttaaa 20

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
ggtgcctctg ccttccaa 18

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
ttgtgccagc catagtcaca 20

```
<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298

agagtgaagg tgtgatgctg aa                                          22


<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299

gcacggtttg tgacaggtac                                             20
```

NONINVASIVE MOLECULAR CLOCK FOR FETAL DEVELOPMENT PREDICTS GESTATIONAL AGE AND PRETERM DELIVERY

CROSS REFERENCE TO RELATED APPLICATIONS

This application is a national phase application of PCT Application No. PCT/US2018/057142, filed Oct. 23, 2018, which claims benefit of U.S. Provisional Application No. 62/576,033 (filed Oct. 23, 2017) and No. 62/578,360 (filed Oct. 27, 2017), each of which is hereby incorporated by reference in its entirety.

FIELD OF THE INVENTION

The invention is in the field of medicine.

SEQUENCE LISTING

The instant application contains a Sequence Listing which has been submitted electronically in ASCII format and is hereby incorporated by reference in its entirety. Said ASCII copy, created on Oct. 17, 2018, is named 103182-1107145_(000300PC)_SL.txt and is 159,304 bytes in size.

BACKGROUND

Understanding the timing and program of human development has been a topic of interest for thousands of years. In antiquity, the ancient Greeks had surprisingly detailed knowledge of various details of stages of fetal development, and they developed mathematical theories to try to account for the timing of important landmarks during development including delivery of the baby (Hanson 1995; Hanson 1987; Parker 1999). In the modern era, biologists have put together a detailed cellular and molecular portrait of both fetal and placental development. However, these results relate to pregnancy in general and have not led to molecular tests, which might enable monitoring of development and prediction of delivery for a given set of parents. The most widely used molecular metrics of development are determining the levels of human chorionic gonadotropin (HCG) and alpha-fetoprotein (AFP), which can be used to detect conception and fetal complications, respectively; however, neither molecule either individually or in conjunction has been found to precisely establish gestational age (Dugoff et al. 2005; Yefet et al. 2017).

Due to the lack of a useful molecular test, most clinicians use either ultrasound imaging or the patient's estimate of last menstruation period (LMP) in order to establish gestational age and a rough estimate for delivery date. However, these methods are neither particularly precise nor useful for predicting preterm delivery, which is a substantial source of mortality and cost in prenatal healthcare. Moreover, inaccurate dating can misguide the assessment of fetal development even for normal term pregnancies, which has been shown to ultimately lead to unnecessary induction of labor and cesarean sections, extended post-natal care, and increased expendable medical expenses (Bennett et al. 2004; Whitworth et al. 2015).

It would be useful both to develop a more precise approach to measure the gestational age of the fetus at various points in pregnancy, and more generally to monitor fetal and placental development for signs of abnormality or preterm delivery. Approximately 15 million neonates are born preterm every year worldwide (Blencowe et al. 2013). As the leading cause of neonatal death and the second cause of childhood death under the age of 5 years (Liu et al. 2012), premature delivery is estimated to annually cost the United States upward of $26.2 billion (Institute of Medicine (US) Committee on Understanding Premature Birth and Assuring Healthy Outcomes 2007). The complications continue later into life as preterm birth is a leading cause of life years lost to ill health, disability, or early death (Murray et al. 2012). Two-thirds of preterm delivery occur spontaneously, and the only predictors are a history of preterm birth, multiple gestations, and vaginal bleeding (Institute of Medicine (US) Committee on Understanding Premature Birth and Assuring Healthy Outcomes 2007). Efforts to find a genetic cause have had only limited success (Ward et al. 2005; York et al. 2009) and therefore most effort is focused on phenotypic and environmental causes (Muglia and Katz 2010).

BRIEF SUMMARY

Gestational age or time to delivery may be determined by (a) generating an expression profile using cfRNA or protein from a maternal sample, and (b) comparing the expression profile with one or more reference profiles that reflect an expression profile characteristic of a defined gestational age.

Risk of preterm delivery may be determined by (a) generating an expression profile using cfRNA (or protein) from a maternal sample, and (b) determining whether the expression profile is or is not characteristic of a population with a history of preterm delivery and/or whether the expression profile is or is not characteristic of a population with a history of full-term delivery.

In a first aspect, the disclosure provides a method of estimating gestational age of a fetus comprising, analyzing a maternal sample to determine an expression profile from a panel comprising one or more placental genes.

In some embodiments, the method includes an expression profile comprising three or more placental genes. In some embodiments, the method includes an expression profile from a panel comprising only of placental genes.

In some embodiments, the method further includes the expression level of each of the placental genes changing during the course of pregnancy. In some embodiments, the method includes the expression level of at least one placental gene is that is higher in the first trimester compared to the third trimester. In some versions, the expression level of all of the placental genes are lower in the first trimester compared to the third trimester. In some embodiments, the method includes the expression level of at least one placental gene that is lower in the first trimester compared to the third trimester.

In some embodiments, the method includes the placental genes selected from genes in TABLE 1. In some embodiments, the method includes the placental genes selected from CGA, CAPN6, CGB, ALPP, CSHL1, PLAC4, PSG7, PAPPA, and LGALS14.

In some embodiments, the method includes determining the expression profiles for three to nine placental genes. In some embodiments, the method includes determining the expression profile by measuring cell-free RNAs (cfRNAs) in the maternal sample. In some embodiments, the method includes determining the expression profile by measuring placental proteins in the maternal sample.

In some embodiments, the method includes a maternal sample from blood, blood plasma, blood serum, or urine. In some embodiments, the method includes a maternal sample obtained from the mother during the third trimester of pregnancy. In some embodiments, the method includes a maternal sample obtained from the mother during the second trimester of pregnancy.

In some embodiments, the method includes the steps: comparing the expression profile with a plurality of reference profiles, wherein each reference profile is characteristic of a defined gestational age, determining which of the plurality of reference profiles corresponds to the expression profile based on the comparing, and deducing the estimated gestational age of the fetus at the time the maternal sample was obtained based on the defined gestational age of the corresponding reference profile.

In a second aspect, the disclosure provides a method for estimating gestational age of a fetus including the steps: (a) obtaining a maternal expression profile for a sample, comprising expression levels for a panel of genes according to any of the embodiments of the first aspect, and (b) comparing expression levels to reference expression levels for the panel of genes, wherein the reference expression levels are obtained from a full-term delivery population, to determine whether the maternal expression profile is similar to, or is different from, the reference expression levels within a threshold.

In some embodiments, the method includes one or more reference expression levels for the full-term population are established using a machine learning technique. In some versions, the method further includes obtaining a plurality of training samples, each labeled as preterm or full-term, obtaining one or more measured expression levels for the panel of genes for each of the plurality of training samples, and iteratively adjusting the one or more reference expression levels using the machine learning technique to increase a number of the training samples that are classified correctly as a result of comparing the one or more measured expression levels to the one or more reference expression levels.

In some embodiments, the method further includes the steps: comparing the expression levels to other reference expression levels for the panel of genes, wherein the other reference expression levels are obtained from a preterm delivery population, to determine whether the maternal expression profile is similar to, or is different from, the other reference expression levels within a threshold.

In a third aspect, the disclosure provides a method for estimating gestational age of a fetus including the steps of: (i) determining a maternal expression profile of a panel comprising at least one placental RNA, and (ii) comparing the maternal expression profile to a reference profile, wherein the comparison of the maternal expression profile to the reference profile allows for the for estimation of gestational age. In some embodiments, the gestational age is known for the reference profile. In some embodiments, the comparison of the maternal expression profile to the reference profile is performed by comparing the maternal expression profile to a gestational function that provides a gestational age based on an input of one or more expression levels, wherein the gestational function is determined by fitting a model to a plurality of calibration samples having measured expression levels and of which a gestational age is known. In some versions, the method uses a regression model.

In some embodiments, the method includes a profile panel described in any of the embodiments of the first aspect. In some embodiments, the method is carried out by a computer.

In some embodiments, the method includes determining a first gestational age according to the method of the first or second aspect using a first maternal sample and determining a second gestational age according to the method of the first or second aspect using a second maternal sample obtained later in pregnancy.

The method of the first aspect, wherein the expression levels of individual placental genes are determined by qPCR or massively parallel sequencing.

The method of the first aspect, wherein the expression levels of individual placental genes are determined by mass spectrometry or using an antibody array.

The method of the first, second, or third aspect, wherein the expression of at least one additional gene is determined, and the additional gene is not a placental gene.

In a fourth aspect, the disclosure provides a composition comprising, primers for multiplex amplification of at least three and no more than fifty placental genes selected TABLE 1.

In a fifth aspect, the disclosure provides a kit comprising, primers suitable for multiplex amplification of at least three, and no more than fifty, placental genes selected from TABLE 1.

In a sixth aspect, the disclosure provides an antibody array for detecting at least three and no more than one hundred placental proteins isolated from maternal blood or urine.

In a seventh aspect, the disclosure provides a method for assessing risk of preterm delivery by a pregnant woman comprising, analyzing a maternal sample to determine an expression profile from a panel comprising one or more genes selected from TABLE 2.

In some embodiments, the method includes a panel comprising three or more genes from TABLE 2. In some embodiments, the method includes genes having higher expression levels in a preterm population than in a term population. In some embodiments, the method includes genes selected from: CLCN3, DAPP1, POLE2, PPBP, LYPLAL1, MAP3K7CL, MOB1B, RAB27B, RGS18, and TBC1D15, or from: CLCN3, DAPP1, PPBP, MAP3K7CL, MOB1B, RAB27B, and RGS18. In some embodiments, the method includes a panel comprising three genes selected from any combination of three from: CLCN3, DAPP1, POLE2, PPBP, LYPLAL1, MAP3K7CL, MOB1B, RAB27B, RGS18, and TBC1D15 (ten transcript panel), or from: CLCN3, DAPP1, PPBP, MAP3K7CL, MOB1B, RAB27B, and RGS18 (seven transcript panel).

In some embodiments, the method includes the expression profiles in which a panel of three to ten genes are determined. In some embodiments, the method includes the expression profile in which a panel comprising exactly three genes are determined.

In some versions the method includes, determining the expression profile by measuring cell-free RNAs (cfRNAs) in the maternal sample. In some embodiments, the method includes determining the expression profile by measuring proteins in the maternal sample.

In some embodiments, the method includes a maternal sample from blood, blood plasma, blood serum, or urine. In some embodiments, the method includes a maternal sample obtained more than 28 days prior to preterm delivery. In some embodiments, the method includes a maternal sample obtained more than 45 days prior to preterm delivery. In some embodiments, the method includes a maternal sample obtained after the second month and prior to the eighth month of pregnancy. In some embodiments, the method includes a maternal sample obtained during the second trimester of pregnancy.

In some versions, a maternal sample is obtained during the third trimester of pregnancy.

In some embodiments, the method of the seventh aspect includes, a maternal sample obtained at a specified week of pregnancy, comprising the steps: comparing the expression profile to a time matched reference profile, wherein the time matched reference profile is characteristic of a normal term pregnancy at the specified week of pregnancy, and identifying the pregnant woman as an elevated risk for preterm delivery if the expression profile differs significantly from the time matched reference profile within a threshold.

In some embodiments, the method of the seventh aspect includes a maternal sample obtained at a specified week of pregnancy, comprising the steps: comparing the expression profile to a time matched reference profile, wherein the time matched reference profile is characteristic of a preterm pregnancy, and identifying the pregnant woman as an elevated risk for preterm delivery if the expression profile is significantly similar to the time matched reference profile within a threshold.

In an eighth aspect, the disclosure provides a method for assessing risk of preterm delivery of a pregnant woman comprising the steps: (a) obtaining a maternal expression profile for a sample, comprising expression levels for a panel of genes according to the seventh aspect of the disclosure, and (b) comparing the expression levels to reference expression levels for the panel of genes, wherein the reference expression levels are obtained from a preterm delivery population, a full-term delivery population, or both populations, to determine whether the maternal expression profile is similar to, or is different from, the reference expression levels within a threshold.

In some embodiments, the method one or more reference levels are established using a machine learning technique.

In some embodiments, the methods of the seventh or eighth aspect are carried out by a computer.

In a ninth aspect, the disclosure provides a method including carrying out the steps of the claims provided in the seventh or eighth aspect with two or more maternal samples obtained at different times during the course of a pregnancy.

The method of the seventh aspect, wherein the expression levels of individual genes are determined by qPCR or massively parallel sequencing.

The method of the seventh aspect, wherein the expression levels of individual genes are determined by mass spectrometry or an antibody array.

In a tenth aspect, the disclosure provides a composition comprising primers for multiplex amplification of at least three genes selected from TABLE 2 and no more than one hundred different genes.

In an eleventh aspect, the disclosure provides a kit comprising primers for multiplex amplification of at least three genes selected from TABLE 2 and no more than one hundred different genes.

In a twelfth aspect, the disclosure provides a method of estimating time to delivery comprising analyzing a maternal sample to determine an expression profile from a panel comprising one or more placental genes.

In some embodiments, the method includes an expression profile from a panel comprising three or more placental genes.

In some embodiments, the method includes an expression profile from a panel comprised only of placental genes.

In some embodiments, the method includes the expression level of each of the placental genes changes during the course of pregnancy. In some embodiments, the method includes the expression level of at least one placental gene that is higher in the first trimester compared to the third trimester. In some embodiments, the method includes the expression level of at least one placental gene that is lower in the first trimester compared to the third trimester. In some versions, the expression levels of all of the placental genes are lower in the first trimester compared to the third trimester.

In some embodiments, the method includes determining the expression profile by measuring cell-free RNAs (cfRNAs) in the maternal sample. In some embodiments, the method includes determining the expression profile by measuring placental proteins in the maternal sample.

In some embodiments, the method includes a maternal sample from blood, blood plasma, blood serum, or urine.

In some embodiments, the method includes a maternal sample obtained from the mother during the third trimester of pregnancy.

In some embodiments, the method includes a maternal sample obtained from the mother during the second trimester of pregnancy.

In some embodiments, the method includes the steps: comparing the expression profile with a plurality of reference profiles, wherein each reference profile is characteristic of a time to delivery, determining which of the plurality of reference profiles corresponds to the expression profile, and deducing the estimated time to delivery at the time the maternal sample was obtained based on the time to delivery of the corresponding reference profile.

In a thirteenth aspect, the disclosure provides a method for estimating time to delivery including the steps: (a) obtaining a maternal expression profile for a sample, comprising expression levels for a panel of genes according to any one of the embodiments of the ninth and seventh aspect, and (b) comparing the expression levels to reference expression levels for the panel of genes, wherein the reference expression levels are obtained from a full-term delivery population to determine whether the maternal expression profile is similar to, or is different from, the reference expressions levels within a threshold.

In some embodiments, the method includes one or more reference levels for the full-term population are established using a machine learning technique. In some embodiments, the method is carried out by a computer.

In some embodiments, the method includes determining a first time to delivery according to the method of the twelfth or thirteenth aspect using a first maternal sample and determining a second time to delivery according to the method of the twelfth or thirteenth aspect using a second maternal sample obtained later in pregnancy.

The method of the twelfth aspect, wherein the expression levels of individual placental genes are determined by qPCR or massively parallel sequencing.

The method of the twelfth aspect, wherein the expression levels of individual placental genes are determined by mass spectrometry or an antibody array.

The method of the twelfth or thirteenth aspect, wherein expression of at least one additional gene is determined, and the additional gene is not a placental gene.

In a fourteenth aspect, the disclosure provides a composition comprising, primers for multiplex amplification of at least three placental genes selected from TABLE 1 and no more than one hundred different genes.

In a fifteenth aspect, the disclosure provides a kit comprising, primers for the multiplex amplification of at least three genes selected from TABLE 1 and no more than one hundred placental genes.

In a sixteenth aspect, the disclosure provides an antibody array for detecting at least three and no more than one hundred placental proteins isolated from maternal blood or urine.

BRIEF DESCRIPTION OF THE DRAWINGS

FIG. 2C shows an exemplary random forest model prediction of time to delivery for training data ($n=21$, $R=0.91$, $P<2.2\times10^{-16}$, cross-validation). FIG. 2D shows an exemplary random forest model prediction of time to delivery for validation data ($n=10$, $R=0.89$, $P<2.2\times10^{-16}$).

FIG. 6A shows an exemplary random forest model prediction of gestational age for training data ($n=21$, $R=0.91$, $P<2.2\times10^{-16}$, cross-validation) and FIG. 6B shows an exemplary random forest model prediction of gestational age for validation data ($n=10$, $R=0.90$, $P<2.2\times10^{-16}$)

FIGS. 10A-10D provide an exemplary list of genes found to be significantly different between spontaneous preterm delivery and normal delivery samples using three statistical analyses.

DETAILED DESCRIPTION OF THE INVENTION

1. INTRODUCTION

Figure 1A:
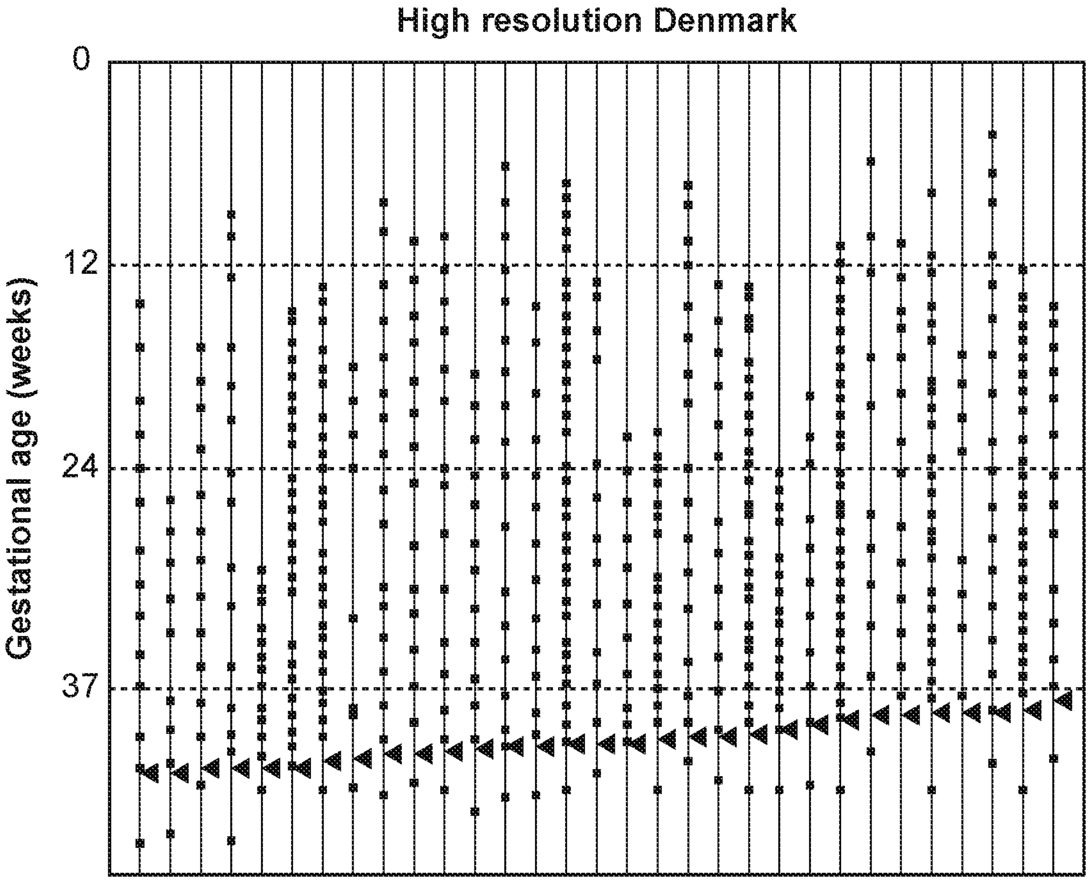
FIGS. 1A-1B are temporal graphs showing collection timelines from pregnant women in three different cohorts: Denmark (FIG. 1A), Pennsylvania and Alabama (FIG. 1B). Squares, inverted triangles, and lines indicate sample collection, delivery date, and individual patients, respectively.

We have discovered a panel of genetic biomarkers for non-invasively predicting gestational age or time to delivery of a fetus in a pregnant woman. We have also discovered an orthogonal set of genetic biomarkers for non-invasively predicting whether a woman is at risk for preterm delivery of a fetus. The discovery that a set of genetic markers for predicting gestational age or time to delivery of a fetus is significant, in part, because of the potential advantages of replacing ultrasounds as the gold standard for predicting gestational age and thus avoiding substantial health care expenses associated with ultrasounds and sonographers. Additionally, the discovery that a set of genetic markers for predicting whether a woman is at risk for preterm delivery is also significant, in part, because of the potential advantages of prophylactically treating women at risk from preterm delivery and thus negating substantial health care expenses associated with neonatal intensive care units (NICU's).

We performed a high time-resolution study of normal human development by measuring cfRNA in blood from pregnant women longitudinally during each week of pregnancy. Analysis of tissue-specific transcripts in these samples enabled us to follow fetal and placental development with high resolution and sensitivity, and also to detect gene-specific response of the maternal immune system to pregnancy. The data from this study establish a "clock" for normal human development and enable a direct molecular approach to establish expected delivery date with comparable accuracy to ultrasound at a fraction of the cost. We also identified an orthogonal gene set that accurately discriminates women at risk of preterm delivery up to two months in advance of labor, forming the basis of a screening or diagnostic test for risk of prematurity.

2. DEFINITIONS

As used herein, the terms "cell free RNA" or "cfRNA" refer to RNA, especially mRNA, expressed by cells of the mother, fetus and/or placenta and recoverable from the non-cellular fraction of maternal blood, and includes fragments of full-length RNA transcripts. In some embodiments "cfRNA" does not include rRNA. In some embodiments "cfRNA" does not include miRNA. In some embodiments "cfRNA" refers to mRNA. Cf RNA can also be recovered from maternal urine.

As used herein, the terms "placental gene," "placental gene product," "placental cfRNA," or "placental protein" refer to a gene or corresponding gene product that is expressed in the placenta but not expressed (or expressed at significantly lower levels) by maternal or fetal tissues. Publicly available resources exist to identify placental genes including databases such as Tissue-Specific Gene Expression and Regulation (TiGER) which identifies 377 RefSeq (NCBI Reference Sequence Database) genes as being preferentially expressed in the placenta (http://bioinfo.wilmer.jhu.edu/tiger). Other databases such as Expression Atlas (https://www.ebi.ac.uk/gxa/home) can also be used to identify placental genes. Placental gene products include mRNA and protein.

As used herein, the term "expression profile," refers to the level of expression of one or a plurality of gene products obtained from a maternal sample. The gene products may be cfRNAs or proteins. For gene products recovered from maternal plasma, expression levels may be expressed as the number of transcripts of a specified RNA per mL maternal plasma, mass of a specified polypeptide per mL maternal plasma, transcript count calculated from RNA-Seq, or any other suitable units. Analogous units may be used for gene products obtained from other maternal samples, such as urine. Expression of gene products may be determined using any suitable method (e.g., as described below). Measured values are typically normalized to account for variations in the quantity and quality of the sample, reverse-transcription efficiency, and the like. When an expression profile reflects expression from multiple different gene products (e.g., different cfRNA transcripts) the gene products may be given different weights when generating or comparing expression profiles or reference profiles. For example, when comparing an expression profile comprising cfRNA 1 and cfRNA 2 in a sample from a pregnant woman with a reference profile (discussed below), a 2-fold difference in values for cfRNA 1 may be given more weight than a 2-fold difference in values for cfRNA 2 in determining a degree of similarity or difference between the expression profile and the reference profile. An expression profile from a maternal (e.g., patient) sample is sometimes referred to as a "maternal expression profile" and a maternal expression profile from a sample collected at a specified time may be referred to as a "[time] maternal expression profile," e.g., a "24 week maternal expression profile."

As used herein, a "reference profile" is an expression profile derived from a reference population. For illustration, examples of reference populations are pregnant women, pregnant women who delivered at term, or pregnant women who delivered prematurely. In some embodiments the reference population is a subpopulation of pregnant women characterized by maternal age (e.g., women 20-25 years old who delivered at term), race or ethnicity (e.g., African-American women who delivered at term), and the like. A reference profile is generated by combining expression profiles of a statistically significant number of women in the population and, for a specified gene product, may reflect the mean transcript level in the population, the median transcript level in the population, or may be determined using any of a number of methods known in the fields of epidemiology and medicine. A reference population will typically comprise at least 10 subjects (e.g., 10-200 subjects), sometimes 50 or more subjects, and sometimes 1000 or more subjects.

As used herein, the term "profile panel" refers to the set of gene products measured in a particular assay. For example, in an assay for six (6) different cfRNAs ("RNAs A-F"), those six cfRNAs would be the profile panel. Likewise, in an assay for six (6) different proteins from maternal plasma or urine, those six proteins would be the profile panel. As another illustration, in an assay in which expression data are collected for transcripts of a large number of genes (e.g., the entire transcriptome, or a large number of placental gene transcripts) the subset used for estimating gestational age or time to delivery, or assessing risk of preterm delivery may be referred to as the profile panel. It will be recognized that measurements of RNAs or proteins not included in the panel may be used as controls, to normalize measurements within or across samples, or for similar uses. In some embodiments a profile panel may include a set of gene products that includes both cfRNAs and proteins. A profile panel is sometimes referred to as a "panel."

As used herein, the terms "preterm pregnancy," "preterm delivery," "full-term pregnancy," "full-term delivery," and "normal term pregnancy" have their normal meanings. Full-term refers to delivery after the fetus reached a gestational age of 37 weeks and preterm refers to delivery prior to the fetus reaching a gestational age of 37 weeks. In some contexts preterm refers to delivery in the period from 16 weeks to 35 weeks gestational age or 24 weeks to 30 weeks gestational age. Preterm populations used in the studies discussed below (see Examples) delivered a fetus prior to 29 weeks gestational age in one case (Pennsylvania cohort) and 33 weeks gestational age in another (Alabama cohort). See FIG. 1.

As used herein, "maternal sample" refers sample of a body fluid obtained from a pregnant woman. The body fluid is typically serum, plasma, or urine, and is usually serum. In some embodiments a sample of a different body fluid may be used, such as saliva, cerebrospinal fluid, pleural effusions, and the like. Maternal samples may be obtained at multiple different time points during pregnancy and stored (e.g., frozen) until assayed. It will be appreciated that the date of collection of a maternal sample is an integral property of the sample.

As used herein, "time to delivery" refers to the number of weeks from a specified time (present time, date of maternal sample collection) to the delivery date or predicted delivery date. Time to delivery is calculated as (gestational age at delivery) minus (gestational age at sample collection).

As used herein, the terms "protein" and "polypeptide" are used interchangeably. Reference to a protein obtained from a maternal sample does not necessarily imply that the protein is a full-length gene expression product. Portions, fragments, and cleavage products may be detected and identifed according to the invention.

3. ILLUSTRATIVE METHODS AND EMBODIMENTS USING CELL-FREE RNA EXPRESSION PROFILES

The invention relates to discovery of a high resolution molecular clock for fetal development and the invention of methods to establish time to delivery, fetal gestational age, and risk of preterm delivery. In one aspect, methods and materials for estimating gestational age or time to delivery of a fetus using expression profiles of placental gene(s) are described. In another aspect, methods and materials for assessing risk of preterm delivery are described.

For illustration and not limitation, gestational age or time to delivery may be determined by (a) generating an expression profile using cfRNA (or protein) from a maternal sample and (b) comparing the expression profile with one or more reference profiles that reflect an expression profile characteristic of a defined gestational age. For illustration, the maternal expression profile is compared to 37 reference profiles (characteristic of 1 through 37 weeks of gestational age) and gestational age or time to delivery is estimated based on the relatedness of the maternal expression profile to one of the 37 reference profiles. For illustration and not limitation, risk of preterm delivery may be determined by (a) generating an expression profile using cfRNA (or protein) from a maternal sample and (b) determining whether the expression profile is or is not characteristic of a population with a history of preterm delivery and/or whether the expression profile is or is not characteristic of a population with a history of full-term delivery. In another approach, machine learning (e.g., random forest regression, support vector machines, elastic net, lasso) is used to predict gestational age, time to delivery, and risk of prematurity based on the maternal expression profile generated from a maternal sample.

3.1 Obtaining the Maternal Sample

A maternal sample (e.g., plasma or urine) may be collected and cfRNA may be isolated from the sample immediately or after storage. See Example 1 below. Art-known methods may be employed to guard the RNA fraction against degradation including, for example, use of special collection tubes (e.g. PAXgene RNA tubes from Preanalytix, Tempus Blood RNA tubes from Applied Biosystems) or additives (e.g. RNAlater from Ambion, RNAsin from Promega) that stabilize the RNA fraction.

Multiple maternal samples may be collected. For example, maternal samples can be collected each trimester, or monthly for a period during the course of pregnancy (e.g., months 3-8). When indicated, maternal samples may be collected more frequently. For example, gestational age or time to delivery may be monitored frequently (e.g., biweekly) as a method for monitoring fetal health.

As another example, a woman identified at 24 weeks as at risk of preterm delivery may elect biweekly assays to monitor risk. In cases in which intervention to avoid preterm delivery (e.g., progesterone supplementation) has been used, a maternal sample may be obtained after the initiation of the intervention to assess whether the intervention has changed the maternal expression profile. Remarkably, methods of the invention may be used to accurately discriminate women at risk of preterm delivery up to two months in advance of labor. See Example 6. In some embodiments of the invention a maternal sample is obtained more than 28 days prior to the preterm delivery. In some embodiments of the invention a maternal sample is obtained more than 45 days prior to the preterm delivery. In some embodiments a maternal sample is obtained after the second month and prior to the eighth month of pregnancy. In some embodiments a maternal sample is obtained during the second trimester of pregnancy In some embodiments a maternal sample is obtained during the third trimester of pregnancy. As discussed above, in many cases a maternal sample may be obtained and assayed more than once during the course of a pregnancy.

3.2 Isolation of cfRNA

Cell-free RNA can be isolated from a maternal sample using techniques well known in the art. See Example 1 below. Isolation of cfRNA from blood or blood fractions is described in Qin et al., *BMC Res. Notes.,* 26; 6:380 (2013) and Mersy et al., *Clin. Chem.,* 61(12)1515-23 (2015), both of which are incorporated herein by reference. Kits for isolating cfRNA from blood are known and are commercially available (e.g., PaxGene Blood RNA kit (Qiagen, Catalog No. 762164). Kits for isolating cfRNA from plasma/serum are known and are commercially available (e.g., Plasma/Serum RNA Purification Kit from Norgen Biotek Corporation, Canada, Catalog No.: 56900 and Quick-cfRNA™ Serum & Plasma from Zymo Research, Catalog No.: R1059; NextPrep Magnazol cfRNA Isolation Kit (Bioo Scientific); Quick-cfRNA™ Serum & Plasma Kit (Zymo Research), and the QIAamp® Circulating Nucleic Acid Kit (Qiagen).

Isolation of cfRNA from urine has been described (see, e.g., Zhao et al., 2015, *Int J. Cancer,* 1; 136(11):2610-5, incorporated herein by reference, describing use of cfRNA for identification of biomarkers and monitoring disease status). Kits for isolating cfRNA from urine are known and are commercially available (e.g., Urine Cell Free Circulating RNA Purification Kit from Norgen Biotek Corporation, Canada, Catalog No.: 56900).

3.3 Quantification of cfRNA Transcripts

Quantification of specific transcripts from a cell free RNA sample can be accomplished in a variety of ways including, but not limited to, array-based methods, amplification-based methods (e.g., RT-qPCR), and high-throughput sequencing (RNA-Seq). The methods of the invention are not limited to a particular method of quantitation.

3.3.1 RT-qPCR Assays

RT-qPCR assays are described in Example 1, below. Briefly, RNA is transcribed into complementary DNA (cDNA) by reverse transcriptase from total RNA or messenger RNA (mRNA). Alternatively, cDNA is generated using template-specific primers specific for selected RNA transcripts (e.g., one of more of SEQ ID NOS:1-19). The cDNA is then used as the template for the qPCR reaction.

RT-qPCR can be performed in a one-step or a two-step assay. One-step assays combine reverse transcription and PCR in a single tube and buffer, using a reverse transcriptase along with a DNA polymerase. One-step RT-qPCR only utilizes sequence-specific primers. In two-step assays, the reverse transcription and PCR steps are performed in separate tubes, with different optimized buffers, reaction conditions, and priming strategies (such as random primers, oligo-(dT) or sequence specific primers in the reverse transcription followed by sequence specific primers in the qPCR step. As described above, it will be apparent that reference to RT-qPCR herein includes either a one or two step RT-qPCR assay.

RT-qPCR can be performed using various buffers and optimizations. See Example 1 below. Isolation of cfRNA from blood and subsequent analysis by RT-qPCR is known in the art (for example, see US Patent Publication No.: 20140199681, incorporated herein by reference). Kits for performing one step RT-qPCR are known and are commercially available (e.g., TaqPath™ 1-step RT-qPCR Master Mix, CG (Thermo Fisher Scientific, Catalog No. A15299). Kits for performing two step RT-qPCR are known and are commercially available (e.g., Maxima First Strand cDNA Synthesis Kit for RT-qPCR (Thermo Fisher Scientific, Catalog No. K1641).

3.3.2 RNA-Seq Assays

RNA-Seq (RNA-sequencing) assays also known as whole transcriptome shotgun sequencing uses next-generation sequencing (NGS) to reveal the presence and quantity of RNA in a sample at a given point in time (see, Zhong et al. *Nat. Rev. Gen.* 10 (1): 57-63 (2009), incorporated herein by reference). RNA-Seq assays are described in Example 1, below. RNA-Seq facilitates the ability to look at changes in gene expression over time or differences in gene expression in different groups or treatments (see, Maher et al. *Nature.* 458 (7234): 97-101 (2009), incorporated herein by reference).

The following sets forth an exemplary method to analyze cfRNAs isolated from a maternal body fluid sample. Briefly, cfRNAs are isolated from a maternal sample, for example using sequence specific primers, oligo(dT) or random primers to generate cDNA molecules. In one approach cDNA is generated using template-specific primers specific for selected RNA transcripts (e.g., corresponding to genes listed in TABLES 1 and 2; one of more of SEQ ID NOS:1-19). The cDNA molecules can be fragmented and optimized such that sequencing linkers are added to the 3' and 5' ends of the cDNA molecules to produce a sequencing library. Fragmentation is typically not needed for cfRNA. The optimized cDNAs are then sequenced using an NGS sequencing platform. Suitable kits for amplifying cDNA and analyzing sequencing products in accordance with the methods of the invention include, for example, the Ovation™ RNA-Seq System (NuGen). Other methods for preparing RNA-Seq libraries for use with a sequencing platform are known such as Podnar et al., 2014, "Next-Generation Sequencing RNA-Seq Library Construction" *Curr Protoc Mol Biol.* 2014 Apr. 14; 106:4.21.1-19. doi: 10.1002/0471142727.mb0421s106; Schuierer et al., 2017, "A comprehensive assessment of RNA-Seq protocols for degraded and low-quantity samples. *BMC Genomics.* 2017 Jun 5; 18(1):442. doi: 10.1186/s12864-017-3827-y; Hrdlickova R, 2017, RNA-Seq methods for transcriptome analysis, Wiley *Interdiscip Rev RNA.* 2017 January; 8(1). doi: 10.1002/wrna.1364), all of which are incorporated herein by reference.

Sequencing libraries suitable for use with RNA-Seq assays can include cDNAs derived from cfRNAs isolated from a maternal sample. It will also be apparent that the sequencing libraries can include cDNAs derived from other RNA species (e.g., miRNAs) that may have been collected during total RNA isolation rather than a cfRNA isolation procedure. Accordingly, either a partial or complete transcriptome analysis can be performed on the RNA content obtained from the maternal sample. In one embodiment, it is preferred that only cfRNAs obtained from the maternal sample are used as the input material for preparing cDNAs suitable for RNA-Seq.

3.4 Profile Panels

The inventors have discovered that certain combinations of gene products are of particular use in practicing the invention. That is, certain combinations of gene products have been identified as sufficient or preferred for providing accurate estimates of gestational age, time to delivery or predicting likelihood of preterm delivery. For example, as described in Example 4, a subset of 9 placental genes provided more predictive power for estimating gestational age or time to delivery than a larger gene panel.

It will be appreciated that, although certain features of panels are discussed in this section, the invention is not limited to these particular described embodiments. It also will be understood that although this section describes panels by reference to cfRNA transcript expression, panels based on expression levels of circulating proteins encoded by the those gene subsets may also be used to determine gestational age or time to delivery and identify women at risk of preterm delivery. See Section 4, below.

In some approaches, multiple different profile panels are used during the course of a woman's pregnancy. For example, a first profile panel may be used in the second trimester and a different profile panel may be used in the third trimester.

3.4.1 Profile Panels for Determining Gestational Age or Time to Delivery

In one aspect, the invention provides a method for estimating gestational age or time to delivery of a fetus by analyzing a maternal sample to determine an expression profile of placental genes (e.g., cfRNA or protein encoded by a placental gene). Suitable panels may be selected based on the information provided in this disclosure. In one embodiment the panel includes one, at least 2, or at least 3 placental genes. In some embodiments, the profile panel can include at least 1, 2, 3, 4, 5, 6, 7, 8, 9, 10, 11, 12, 13, 14, 15, 16, 17, 18, 19, or 20 placental genes. In some embodiments, the profile panel can include exactly 1, 2, 3, 4, 5, 6, 7, 8, 9, 10, 11, 12, 13, 14, 15, 16, 17, 18, 19, or 20 placental genes. In some embodiments the profile panel includes fewer than 100 genes, e.g., fewer than 100 placental genes, sometimes fewer than 50 placental genes, sometimes fewer than 20 placental genes, sometimes fewer than 15 placental genes, sometimes fewer than 10 placental genes, and sometimes fewer than 5 placental genes.

In some embodiments the expression level of each of the placental genes in the profile panel changes during the course of pregnancy. See Examples below. Thus, in one embodiment, the expression level of at least one placental gene in the panel is higher in the first trimester compared to the third trimester. In some embodiments the expression levels of most or all placental genes in the panel are higher in the first trimester compared to the third trimester. In some embodiments, the expression level of at least one placental gene is lower in the first trimester compared to the third trimester. In some embodiments the expression levels of most or all placental genes in the panel are lower in the first trimester compared to the third trimester In some embodiments at least one placental gene is selected from genes in TABLE 1. In some embodiments all of the placental genes in a profile panel are genes listed TABLE 1.

In some embodiments the expression profile includes at least 1, at least 2, at least 3, at least 4, at least 5, at least 6, at least 7, at least 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9]. In some embodiments the expression profile includes 1, 2, 3, 4, 5, 6, 7, 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9]. In one approach the set of placental genes includes at least one gene other than CGA and CGB. In one approach, the profile panel comprises from three (3) to nine (9) cfRNAs selected from SEQ ID NOS:1-9.

In one embodiment gestational age is determined using a profile panel profile of 9 genes: CGA, CAPN6, CGB, ALPP, CSHL1, PLAC4, PSG7, PAPPA, and LGALS14. We trained several distinct models on subpopulations of women (i.e., nulliparous or multiparous women, women carrying male or female fetuses) to determine the importance of the 9 genes that compose the transcriptomic signature identified. Training 4 distinct models for women carrying male or female fetuses and nulliparous or multiparous women revealed that 2 of the 9 genes identified in the main text were sufficient to (CGA, CSHL1) or female (CGA, CAPN6) fetuses and multiparous (CGA, CSHL1) women. However, all 9 genes were necessary to optimally predict time until delivery for nulliparous women, highlighting the importance of the transcriptomic signature identified. In some embodiments of the invention the panel comprises CGA and CSHL1 or CGA and CAPN6.

The nine transcripts used to predict gestational age were weighted by the model in the following order of importance (from most to least): CGA, CAPN6, CGB, ALPP, CSHL1, PLAC4, PSG7, PAPPA, and LGALS14. Thus, in some embodiments the determined level of expression for individual genes are given different weights (or coefficients) when compared to expression in a reference profile. For example, when all 9, or a subset comprising fewer than 9 genes in this group (e.g., 2, 3, 4, 5, 6, 7 or 8) expression values for each gene are ranked CGA>CAPN6>CGB>ALPP>CSHL1>PLAC4>PSG7>PAPPA>LGALS14.

In one embodiment the panel includes one, at least 2, or at least 3 genes from TABLE 1. In some embodiments, the profile panel can include at least 1, 2, 3, 4, 5, 6, 7, 8, 9, 10, 11, 12, 13, 14, 15, 16, 17, 18, 19, or 20 genes from TABLE 1. In some embodiments, the profile panel can include exactly 1, 2, 3, 4, 5, 6, 7, 8, 9, 10, 11, 12, 13, 14, 15, 16, 17, 18, 19, or 20 genes from TABLE 1. In some embodiments the profile panel includes fewer than 100 genes, sometimes fewer than 50 genes, sometimes fewer than 20 genes, sometimes fewer than 15 genes, sometimes fewer than 10 genes, and sometimes fewer than 5 genes. In certain approaches the profile panel comprises a number of genes in the range 1-100 genes, 1-50 genes, 1-25 genes, 3-100 genes, 3-50 genes, 3-25 genes, or 3-10 genes.

In some versions the placental genes are selected from genes in TABLE 1. In some embodiments, the placental genes are selected from CGA, CAPN6, CGB, ALPP, CSHL1, PLAC4, PSG7, PAPPA, and LGALS14. In some embodiments, the genes include at least one gene other than CGA. In some embodiments, the genes include at least two, three, four, five, six, seven or eight genes other than CGA. In some embodiments, the genes include at least one gene other than CGB. In some embodiments, the genes include at least two, three, four, five, six, seven or eight genes other than CGB. In some embodiments, the genes include at least one gene other than CGA and CGB. In some embodiments, the method includes determining the expression profile for three (3) to nine placental genes.

3.4.2 Profile Panels for Determining Risk of Preterm Delivery

In one aspect, the invention provides a method for estimating risk of preterm delivery by analyzing a maternal sample to determine an expression profile. In one embodiment, the profile panel used for such a determination comprises one or more cfRNA transcripts with higher expression levels in a preterm population than in a term population. In one embodiment, a preterm population refers to a set of women who delivered a fetus prior to 37 weeks gestational age. In another embodiment, a preterm population refers to women who delivered a fetus prior to 33 weeks gestational age. In another embodiment, a preterm population refers to women who delivered a fetus prior to 29 weeks gestational age. In yet another embodiment, a preterm population refers to women who delivered a fetus between 12 and 33 weeks gestational age. In another embodiment, a preterm population refers to a set of women who delivered a fetus between 16 and 29 weeks gestational age. In an embodiment, a preterm population refers to a set of women who delivered a fetus between 16 and 33 weeks gestational age. As noted above, one preterm population used in the Examples consisted of women who delivered a fetus prior to 29 weeks gestational age and this population (or subpopulations thereof) is preferred for making reference profiles characteristic of high risk of prematurity. The Examples also show that biomarkers discovered in a population of women who delivered a fetus prior to 29 weeks are applicable in a population of women who delivered a fetus prior to 33 weeks gestational age.

In one approach the profile panel includes 1 or more, preferably 3 or more, genes listed in TABLE 2.

In one approach the profile panel includes three (3) or more genes are selected from the ten transcript panel CLCN3 [SEQ ID NO:10], DAPP1 [SEQ ID NO:11], POLE2 [SEQ ID NO:12], PPBP [SEQ ID NO:13], LYPLAL1 [SEQ ID NO:14], MAP3K7CL [SEQ ID NO:15], MOB1B [SEQ ID NO:16], RAB27B [SEQ ID NO:17], RGS18 [SEQ ID NO:18], and TBC1D15 [SEQ ID NO:19]. In one approach the profile panel comprises three (3) or more genes. In one approach the profile panel comprises three (3) or more genes selected from SEQ ID NOS:10-19. In one approach the profile panel comprises exactly three (3) genes selected from SEQ ID NOS:10-19. In some embodiments the panel comprises only genes selected from SEQ ID NOS:10-19. For example, in various embodiments, the profile panel will comprise the following combinations: (i) CLCN3, DAPP1, POLE2; (ii) DAPP1, POLE2, PPBP; (iii) POLE2, PPBP, LYPLAL1; (iv) PPBP, LYPLAL1, MAP3K7CL; (v) LYPLAL1, MAP3K7CL, MOB1B; (vi) MAP3K7CL, MOB1B, RAB27B; (vii) MOB1B, RAB27B, RGS18; and (viii) RAB27B, RGS18, TBC1D15. It will be appreciated that the full list of combinations of 3 genes selected from SEQ ID NOS:10-19 is easily generated, and this paragraph is intended to convey possession of each said combination of 3 genes.

In one approach the profile panel includes three (3) or more genes are selected from the seven transcript panel CLCN3 [SEQ ID NO:10], DAPP1 [SEQ ID NO:11], PPBP

[SEQ ID NO:13], MAP3K7CL [SEQ ID NO:15], MOB1B [SEQ ID NO:16], RAB27B [SEQ ID NO:17], and RGS18 [SEQ ID NO:18]. In one approach the profile panel comprises three (3) or more genes. In one approach the profile panel comprises three (3) or more genes selected from SEQ ID NOS:10, 11, 13, and 15-18. In one approach the profile panel comprises exactly three (3) genes selected from SEQ ID NOS: 10, 11, 13, and 15-18. In some embodiments the panel comprises only genes selected from SEQ ID NOS: 10, 11, 13, 15, and 16-18.

In one approach the profile panel comprises exactly three genes selected from TABLE 2. In one approach the profile panel comprises exactly three genes selected from SEQ ID NO:10-19. In one approach the profile panel comprises exactly three genes selected from SEQ ID NOS: 10, 11, 13, 15, and 16-18.

The seven transcripts used to identify women at elevated risk or preterm delivery were weighted by the model in the following order of importance (from highest to lowest): RAB27B>PPBP>DAPP1>RGS18>(MOB1B, MAP3K7CL, and CLCN3), where MOB1B, MAP3K7CL, and CLCN3 are equally ranked. Thus, in some embodiments the determined level of expression for individual genes are given different weights (or coefficients) when compared to expression in a reference profile. For example, when all 7, or a subset comprising fewer than 7 genes in this group (e.g., 2, 3, 4, 5, 6) expression values for each gene are ranked): RAB27B>PPBP>DAPP1>RGS18>(MOB1B, MAP3K7CL, and CLCN3).

Figure 3A:
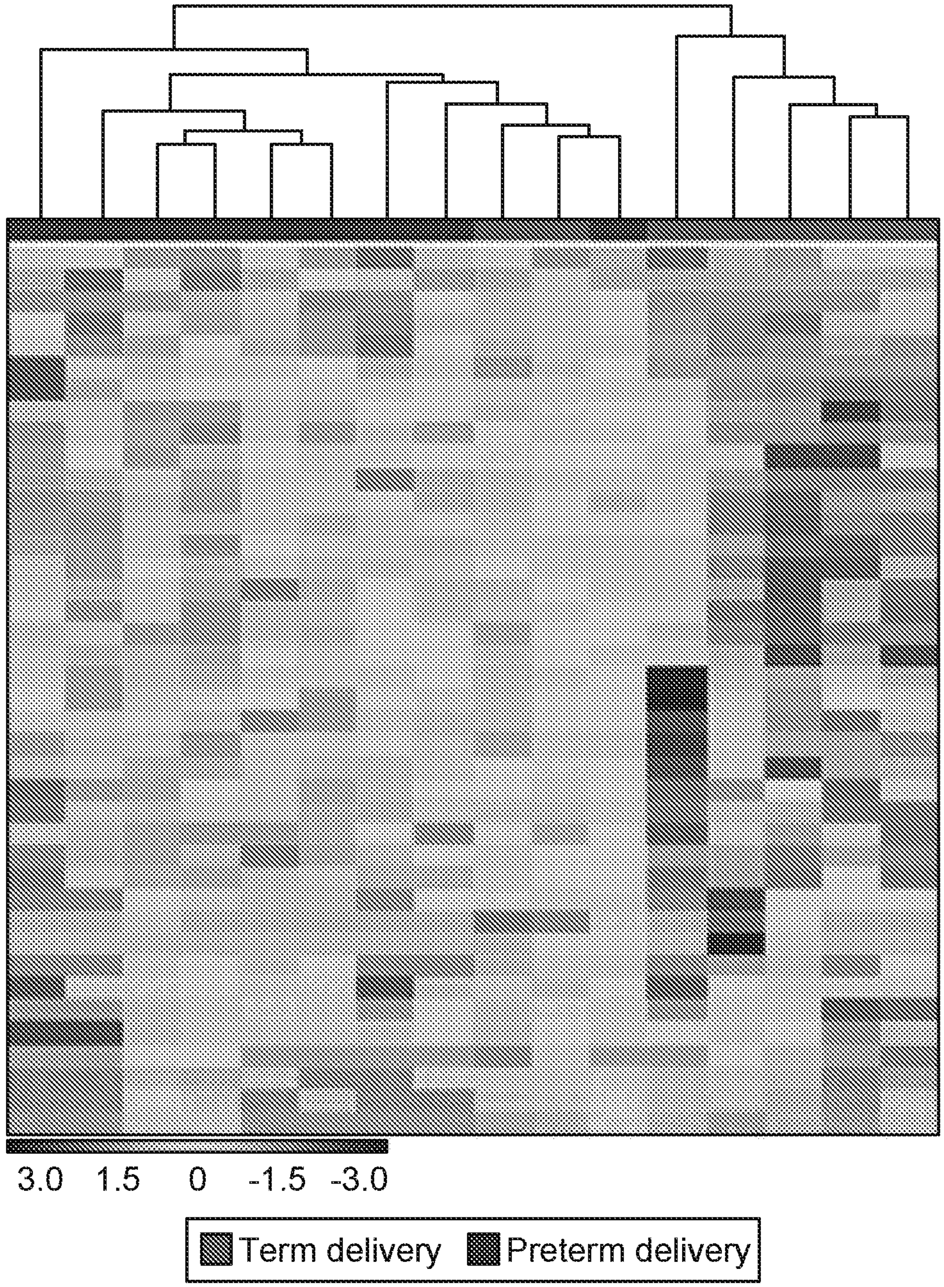
FIG. 3A shows a heat map for 40 differentially expressed genes ($p<0.001$) between preterm deliveries and normal deliveries. RNA-Seq was performed on samples from Pennsylvania.

In one aspect, the invention provides a method for determining risk of preterm delivery by analyzing a maternal sample to determine an expression profile of a set of genes (e.g., cfRNA or protein) listed in TABLE 2, such as SEQ ID NOS: 10, 11, 13, 15, and 16-18. In one embodiment the panel includes one, at least 2, or at least 3 genes from TABLE 2. In some embodiments, the profile panel can include at least 1, 2, 3, 4, 5, 6, 7, 8, 9, 10, 11, 12, 13, 14, 15, 16, 17, 18, 19, or 20 genes from TABLE 2. In some embodiments, the profile panel can include exactly 1, 2, 3, 4, 5, 6, 7, 8, 9, 10, 11, 12, 13, 14, 15, 16, 17, 18, 19, or 20 genes from TABLE 2. In some embodiments the profile panel includes fewer than 100 genes, sometimes fewer than 50 genes, sometimes fewer than 20 genes, sometimes fewer than 15 genes, sometimes fewer than 10 genes, and sometimes fewer than 5 genes. In certain approaches the profile panel comprises a number of genes in the range 1-100 genes, 1-50 genes, 1-25 genes, 3-100 genes, 3-50 genes, 3-25 genes, or 3-10 genes. In one approach at least one of the genes in the profile panel does not listed in FIG. 3A and/or FIG. 3B and/or FIG. 4 of US Patent Publication No. 2013/0252835.

In one approach a maternal sample is obtained at a specified week of pregnancy and the maternal expression profile is compared to a time matched reference profile, wherein the time matched reference profile is characteristic of a full-term pregnancy profile at the specified week of pregnancy. In one approach a maternal sample is obtained at a specified trimester (e.g, first, second or third trimester) of pregnancy and the maternal expression profile is compared to a time matched reference profile, wherein the time matched reference profile is characteristic of a full-term pregnancy profile at the specified trimester of pregnancy. Significant deviations of the maternal profile from the reference profile is indicative that the woman as at elevated risk of preterm delivery. It will be immediately apparent that, in an alternative approach, a maternal sample is obtained at a specified week of pregnancy and the maternal expression profile is compared to a time matched reference profile, wherein the time matched reference profile is characteristic of a preterm pregnancy profile at the specified week of pregnancy. Significant similarities between the maternal profile and the reference profile is indicative that the woman as at elevated risk of preterm delivery. In one approach a machine learning model is used to compare the maternal profile and the reference profile.

4. ILLUSTRATIVE METHODS AND EMBODIMENTS USING CIRCULATING PROTEIN EXPRESSION

4.1 Isolation Of Proteins from Maternal Blood or Urine

Proteins can be isolated from a maternal sample using methods well known in the art. In one appropach total protein is from a maternal blood fraction or urine and assayed for the presence and/or quantity of particular proteins. In one approach an assay is carried out using a protein fraction (e.g., a fraction enriched for protein(s) of interest. In one approach an assay is carried out using one or more purified proteins. Isolation and fractionation of proteins can be performed using fractionation by molecular weight, protein charge, solubility/hydrophobicity, protein isoelectric point (pI), affinity purification (e.g., using a an antiligand, such as an antibody or aptamer, specific from a protein among other methods. Kits for isolating proteins from blood are known and are commercially available (e.g., Total Protein Assay Kit from ITSIBiosciences, Catalog No.: K-0014-20). Kits for isolating proteins from plasma/serum are known and are commercially available (e.g., Antibody Serum Purification Kit (Protein A) from Abcam, Catalog No.: ab109209). Kits for isolating protein and RNA from the sample are also known (e.g., Protein and RNA Isolation System (PARIS) from Thermo Fisher Scientific, Catalog No. AM1921).

4.2 Detecting Proteins from a Maternal Sample

Specific proteins from a maternal sample can be identifed and/or quantified using well know methods, including enzyme-linked immunoadsorbent assay (ELISA); radioimmunoassay (RA) (see, e.g., Anthony et al., *Ann. Clin. Biochem.,* 34:276-280 (1997) describing detection of low levels of protein undetectable using comparable ELISA conditions, incorporated herein by reference); proximity ligation and proximity extension assays (see, e.g., US Pat. Pub. Nos. 20170211133; 20160376642; 20160369321; 20160289750: 20140194311; 20140170654; 20130323729; and 20020064779, incorporated herein by reference), protein binding arrays (e.g., antibody or aptamer arrays), mass spectroscopy (see, e.g., Han, X. et al.(2008), incorporated herein by reference. Mass Spectrometry for Proteomics. Current Opinion in Chemical Biology, 12(5), 483-490. http://doi.org/10.1016/j.cbpa.2008.07.024; Serang, O et al (2012). A review of statistical methods for protein identification using tandem mass spectrometry. Statistics and Its Interface, 5(1), 3-20, incorporated herein by reference). Any suitable method may be used.

Protein binding arrays may be used to detect and quantitate proteins, including but not limited to antibody based arrays and aptamer based arrays (see, e.g., Gold L, et al. (2010) Aptamer-Based Multiplexed Proteomic Technology for Biomarker Discovery. PLoS ONES(12): e15004. https://doi.org/10.1371/journal.pone.0015004, incorporated herein by reference). An antibody array (also known as antibody microarray) is a specific form of protein array. In this technology, a collection of capture antibodies are fixed on a solid surface such as glass, plastic, membrane, or silicon chip, and the interaction between the antibody and its target antigen is detected (see, e.g., U.S. Pat. Nos. 4,591,570; 4,829,010; and 5,100,777, all of which are incorporated herein by reference). Antibody arrays can be used to detect protein expression from various biological fluids including serum, plasma, urine and cell or tissue lysates (see, Knickerbocker T., MacBeath G. Detecting and Quantifying Multiple Proteins in Clinical Samples in High-Throughput Using Antibody Microarrays. In: Wu C. (eds) Protein Microarray for Disease Analysis. Methods in Molecular Biology (Methods and Protocols), vol 723. Humana Press (2011), incorporated herein by reference).

Kits for performing antibody arrays are known and are commercially available (e.g., custom designed antibody arrays or predetermined antibody arrays from RayBiotech, Norcross, Ga.).

5. STATISTICAL ANALYSIS

A maternal expression profile may be compared with a reference profile(s) in a variety of ways. In one approach, a comparison between two data sets is performed to determine whether one data set differs or is similar to another data set, e.g., to within statistical significance. In one embodiment, a first data set can comprise a maternal expression profile, and a second data set comprises a reference profile, where the first and second data sets include one or more data points (for example, median values) for gene expression data for one or more genes, collected over one or more time points during pregnancy (e.g., once a week or once a trimester during the course of the pregnancy). In some embodiments, the second data set comprises a plurality of data points from a preterm maternal sample or a maternal sample having a known gestational age.

Accordingly, a maternal data set can be a measured value of an expression level of one or more genes, where the expression level can be determined from individual expression values for each of the genes, e.g., as an average, weighted average, or median of the individual expression levels. In other embodiments, the individual expression levels can be treated as different dimensions of a multi-dimensional data point, e.g., for use in clustering. For determining a gestational age or time to delivery, the comparison can be between a measured expression level(s) of a maternal sample and the reference expression level(s) of each of a plurality of reference having different known gestational ages, thereby identifying a group or representative data point that is closest (e.g., least difference in a distance between the measured expression level(s) and the reference expression level(s)). The known gestational age of the closest reference sample (or representative data point of a group of reference samples all having a same gestational age) can be used as the gestational age or time to delivery of the maternal sample. Such a comparison can be performed by comprising the measured expression level(s) to a gestational function that is determined from the reference samples, e.g., a linear function that defines a functional relationship between the expression level(s) (e.g., in a multi-dimensional space when individual expression levels correspond to different dimensions or in a 2D-plot when individual expression levels are combined to provide a single metric).

In embodiments where a discrimination is made between term and preterm samples, the comparison can involve determining whether the measured expression level(s) are more similar to preterm reference level(s) or term reference level(s). Such a comparison can involve determining which cluster of reference levels is closest to the measured expression level(s). One or more values may be used for determining whether the measured expression level(s) are sufficiently close (e.g., as measured by a distance or a weight distance where differences along one dimension are weighted differently) for the measured level(s) to be considered part of either cluster of term or preterm samples. An indeterminate classification may result if the expression level(s) are not sufficiently close. A threshold can be used to determine whether the measured expression levels are sufficiently close to reference expression levels of a term or preterm population. A threshold can be selected based on a desired sensitivity and specificity, as will be apparent to one skilled in the art.

To determine the reference level(s), a set of training samples can be labeled with different classifications, e.g., term or preterm. Then, the reference levels can be chosen as being representative of a classification or as values that separate the different classifications, e.g., as cutoffs for assigning different classifications to a new sample. A machine learning technique can analyze different expression levels of different genes to determine which set of expression levels (features) provide the best discrimination for an optimized set of reference levels. A tradeoff between specificity and sensitivity can be optimized, e.g., by a ROC (receiver operating characteristic) curve. In some embodiments, a plurality of training samples, each labeled as preterm or full-term, can be obtained. In some embodiments, training samples are labeled as nulliparous, multiparous women, carrying male fetus, carrying female fetus, or the like. One or more measured expression levels for the panel of genes can be obtained for each of the plurality of training samples. Using the machine learning technique (e.g., by optimizing a cost function as defined by the model), the one or more reference expression levels can be iteratively adjusted to increase a number of the training samples that are classified correctly as a result of comparing the one or more measured expression levels to the one or more reference expression levels.

In some aspects, the first and second data sets can be analyzed to establish relative differences or similarities (e.g., fold increase or fold decrease) between the data sets (e.g., the expression level(s) of the data sets). Such a procedure can be performed when a single expression level is determine for a panel of genes. In another aspect, a pairwise comparison of expression level(s) at each time point for each gene across the duration of pregnancy can be used to identify which reference level(s) are most similar, where each set of reference level(s) can correspond to a different gestational age. In some embodiments, the pairwise comparison (e.g., pairwise between expression levels of different genes and/or between reference level(s) at different times) can include statistical analysis via a range of statistical methodologies, including but not limited to Fisher's exact test, Wilcox rank test, permutation test, linear regression, generalized linear models and quasi-likelihood tests coupled with the appropriate multiple hypothesis correction (e.g., Benjamini Hochberg).

In one embodiment, differentiating gene activity (e.g., between preterm and term maternal samples, see Example 1 and FIGS. 11A-11D) across the pregnancy can include using a quantile adjusted conditional maximum likelihood method, a generalized linear model (GLM) likelihood ratio test, and/or a quasi-likelihood F-test implemented in R using the edgeR software (Bioconductor, available at https://bioconductor.org/packages/release/bioc/html/edgeR.html).

In another aspect, a sample data set can be analyzed using a random forest model (see, e.g., Chen and Ishwaran, *Genomics,* 99:323-329 (2012), incorporated herein by reference) that was generated using the second data set. See Examples. Random forest is a form of machine learning that selects training sets randomly for building multiple models (e.g., decision trees or regression models) and uses the outputs of this ensemble of models to determine a final output (e.g., via majority voting for a term/preterm classification or an average when determining gestational age or time to delivery). Each model can have the same or different features (e.g., expression levels of genes), but have different reference levels as determined from the different training sets that are randomly selected. It will be recognized that other techniques of machine learning can be used to compare two data sets, including but not limited to, support vector machines, elastic net, lasso or neural networks. It will also be apparent that machine learning models (e.g., supervised machine learning; see, for example Mohri et al. (2012) *Foundations of Machine Learning,* The MIT Press, incorporated herein by reference) can be developed to account for particular attributes of a population such as ethnicity and that multiple models can be prepared based on different needs (e.g., an Eastern European model versus a North African model).

In one aspect, a machine learning model (e.g., to predict gestational age or time to delivery) can be prepared as follows:

(1) Curate a labeled training set (e.g., where gestational age of each sample is known);

(2) Iterate through selecting features of interest (e.g., recursive feature selection);

(3) Build a regression model (e.g., random forest) based on the selected features; and (4) Select a regression model and feature subset using cross validation data (e.g., by withholding part of the training set and determining how accurately the regression model evaluated the withheld data).

In one embodiment, once the regression model is prepared, it can be saved and used for future data interpretations. In other embodiments, a single regression model can be determined, e.g., by fitting a line or a curve to a set of measured expression level(s) that are measured at known gestational ages. The regression model can be considered a gestational function, e.g., when a model (e.g., a linear or non-linear function) is fit to expression levels of a plurality of calibration samples having measured expression levels and of which a gestational age is known. Accordingly, the comparison of the maternal expression profile to the reference profile can be performed by comparing the maternal expression profile to a gestational function that provides a gestational age based on an input of one or more expression levels.

In another aspect, the first and second data sets can be analyzed using SAMS (Scoring Algorithm of Molecular Subphenotypes) available at http://statweb.stanford.edu/~tibs/SAM/ (see, Tusher et al., *PNAS,* 98:5116-5121 (2001), incorporated herein by reference). SAMS is a classification algorithm of gene expression data generated from the calculation of two scores (e.g., an up score and a down score). In one embodiment, a maternal expression profile data set of the instant invention (e.g., cfRNAs) can be compared to a reference expression profile data set and a maternal sample having an up score above the median value (as compared to the reference expression profile) and a down score above the median value (as compared to the reference expression profile) can be classified as statistically significant (see., e.g., Herazo-Maya, *Lancet Respir Med,* September 20, (2017) doi:org/10.1016/52213-2600(17)30349-1 and Dinu et al., *BMC Bioinformatics,* 8:242 (2007), both incorporated herein by reference). Other evaluations of a first data set and a second data set using SAMS can be performed according to the SAMS user manual (available at http://www-stat.stanford.edu/~tibs/SAM/sam.pdf).

Various additional statistical analyses exist for the comparison of a first and second data set directed to gene expression data (e.g., preterm data set versus a maternal sample) including for example, methods set forth by Efron and Tibshirani (On Testing the Significance of Sets of Genes. *Ann Appl. Stat.,* 1. 107-129 (2007) and Zhao et al. (Gene expression profiling predicts survival in conventional renal cell carcinoma, PLOS Medicine, 3. E13. 13. 10.1371/journal.pmed.0030013. (2006), both incorporated herein by reference).

As discussed above, maternal expression profiles may be compared to reference profiles and a measure of similarity or difference may be made. In one approach, comparing a maternal expression profile to a reference profile includes compiling gene expression data (e.g., the number or relative number of transcripts of a specified cfRNA sequence on a computer-readable medium) and processing said data on said computer to identify degrees of similarity and difference between said profiles.

6. MEDICAL INTERVENTIONS FOR WOMEN AT RISK OF PRETERM DELIVERY

Women identified as at risk for preterm delivery may elect medical interventions (e.g., progesterone supplementation, cervical cerclage), behavioral changes (smoking cessation), or ultrasound imaging to monitor and reduce the likelihood of preterm delivery or to extend the pregnancy for as long as possible. See Newnham et al. "Strategies to Prevent Preterm Birth." *Frontiers in Immunology* 5 (2014):584, incorporated herein by reference. Progesterone may be used to treat and/or prevent the onset of preterm labor in women identified as at risk for preterm delivery. In some embodiments, a pregnant woman may be administered an amount of progesterone, e.g., as a vaginal gel, that is sufficient to prolong gestation by delaying the shortening or effacing of cervix. The administration can be as infrequent as weekly, or as often as 4 times daily. Antibiotic treatment (amoxicillin, ampicillin, erythromycin, azithromycin, and cephalosporin) is indicated in some women with premature rupture of the membranes (PROM), a precursor of premature delivery, and may be administered to women identified as at risk for preterm delivery. When a woman is identified as at risk of preterm delivery the medical provider may recommend an ultrasound examination at least once per four week period, biweekly, or weekly.

7. THERANOSTIC AND PROGNOSTIC USES OF THE INVENTION FOR WOMEN AT RISK OF PRETERM DELIVERY

In some embodiments, the methods described herein are used for theranosis. In one approach a first maternal expression profile is obtained from a woman at risk of preterm delivery at a first point in time, medically appropriate steps (e.g., medical interventions) are initiated or carried out, and then a second maternal expression profile is obtained from the woman at a second point in time. Each maternal expression profile is compared to an appropriate reference profile (e.g., time matched, population matched, etc.). If the difference between the second maternal expression profile and the appropriate corresponding reference profile is less than the difference between the first maternal expression profile and its appropriate corresponding reference profile this is an indication that the steps carried out have a beneficial therapeutic effect. In some cases, the first and second maternal expression profiles are compared to the same reference profile. In one approach the process is carried out without any medical intervention, in which case a spontaneous improvement may be observed.

In some embodiments, the methods described herein are used for prognosis. It is believed that certain maternal expression profiles are indicative of particular prognoses. For example, certain maternal expression profiles may be used to estimate time until preterm delivery (absent intervention). Reference profiles for this purpose can be generated from sub-populations grouped by specific pregnancy outcomes (dates of prematurity), by genetic risk, or by phenotypic factors such as age and previous pregnancy history. The methods disclosed herein may also be used for identifying and monitoring fetuses having congenital defects; in some cases the methods may be used to inform decisions about in utero treatment. Maternal expression profiles can be used to estimate time to delivery and gestational age for the fetus, and the results used for providing advice or treatment for either the mother or the fetus. Similarly, with appropriately chosen genes such profiles can be used to estimate the risk of adverse events such as preterm delivery.

8. COMPUTER IMPLEMENTED METHODS & DATABASE OF REFERENCE VALUES

Methods of the invention may be implemented using a computer-based system. As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

In some embodiments, a database comprising reference profiles is used in methods of the invention. In some embodiments, a database comprising expression data from a plurality of women, and optionally different subpopulations of women, is provided. Accordingly, aspects of the invention provide systems and methods for the use and development of a database. In some approaches the database is used in combination with an algorithm that enables generation of new reference profiles selected based on characteristics of an individual woman.

Any of the computer systems mentioned herein may utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

A computer system can include a plurality of the same components or subsystems, e.g., connected together by external interface, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

The databases may be provided in a variety of forms or media to facilitate their use. "Media" refers to a manufacture that contains the expression information of the present invention. The databases of the present invention can be recorded on computer readable media, e.g. any medium that can be read and accessed directly by a computer (e.g., an internet database). Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable media can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

9. PRIMERS, PROBES, AND COMPOSITIONS

Primers and probes that specifically hybridize to or amplify cfRNA from placental genes (including genes in TABLE 1) and other informative genes (including genes in TABLE 1 and TABLE 2) may be used in the practice of aspects of the invention. In particular, useful primers and probes include those that specifically hybridize to or amplify SEQ ID NOS: 1-19. These primers and probes are used for amplification (including multiplex PCR, multiplex RT-qPCR, or other amplification methods), for reverse transcription, for construction of sequencing libraries (e.g., RNA-seq libraries), for addition of adaptor sequences, for hybrid capture of RNAs of interest, for construction nucleic acid arrays, for primer extension and for other uses known to the practitioner with knowledge of the art. It is well within the ability of persons of ordinary skill in the art to design probes and primers for their intended uses, taking into account methods of amplification (e.g., addition of adaptors or universal primers), target sequence composition, base composition, avoiding artifacts such as primer dimer formation, as well as the fragmented nature of cfRNA.

For example, it is within the ability of persons of ordinary skill in the art to use SEQ ID NOS:1-19 to design primers, primers pairs, and probes that are specific for each gene and work for their intended purposes (e.g., use in a multiplex reaction). It will be appreciated that for each RNA transcript there are many different primers and combinations of primers that can amplify at least a portion of the transcript. A person of skill in the art can therefore design primer combinations to amplify informative sequences of any of SEQ ID NOS:1-19 or any combination thereof, as well as other gene sequences identified in TABLES 1 and 2. Exemplary primers and probes are described in TABLES 3-5. Probes may be nucleic acid probes, such as RNA or DNA probes. Primers or probes may be immobilized (e.g., for capture based enrichment) or detectably labeled (e.g., with fluorescent, enzymatic, or chemiluminescent moieties or the like).

9.1 Gestational Age or Time to Delivery Compositions

In one aspect, the invention provides primers for multiplex amplification of at least 3 and not more than 50, optionally no more than 25, optionally no more than 10 genes, selected from genes in TABLE 1. In some embodiments, the invention provides primers for multiplex amplification of at least 3 mRNA transcripts provided in TABLE 1. In another embodiment, the invention provides primers for multiplex amplification of any combination of at least 3 mRNA transcripts selected from SEQ ID NOS:1-9. In one embodiment, the primers are for multiplex amplification, wherein the primers comprise at least one pair, and optionally three or more primer pairs. Exemplary primer pairs are provided in TABLE 3. In another embodiment, the primers for multiplex amplification comprise at least three and no more than 100 primer pairs, optionally no more than 50, optionally no more than 25, optionally no more than 10 primer pairs selected from any of the primer pairs provided in TABLE 3.

In a related aspect, the invention provides compositions comprising primer(s) or primer pair(s) as described above. The composition may be an admixture. The composition may be a solution. The composition may additionally contain one or more of (a) maternal cfRNA, (b) buffer, (c) enzymes (e.g., one or a combination of reverse transcriptase, DNA polymerase, RNA or DNA ligase), (d) dNTPs.

In one aspect a composition is provided, comprising (1) cfRNAs with cfRNA sequences corresponding to at least 2 genes in TABLE 1, or amplicons of, or cDNAs from, said cfRNA sequences and (2) primers for amplifying said cfRNA sequences or amplicons or cDNAs, or probes for detecting said cfRNA sequences or amplicons or cDNAs, with the proviso that the composition does not comprise primers for amplifying more than a threshold number of different genes, amplicons or cDNAs; and does not comprise probes for detecting more than the threshold number of different cfRNA sequences or amplicons or cDNAs. In one embodiment the composition does not comprise cfRNAs with cfRNA sequences corresponding to more than the a threshold number of different genes from the human genome, or amplicons of, or cDNAs from more than the threshold number of different genes. In some embodiments the threshold number is 200. In some embodiments the threshold number is 150. In some embodiments the threshold number is 100. In some embodiments the threshold number is 50. In some embodiments the threshold number is 25.

In a related aspect, the invention provides nucleic acid arrays comprising primer(s), primer pair(s), or probes as described above.

9.2 Preterm Risk Compositions

In one aspect, the invention provides primers for multiplex amplification of at least 3 and no more than 100 genes, optionally no more than 50, optionally no more than 25, optionally no more than 10 genes, selected from genes in TABLE 2. In some embodiments, the invention provides primers for multiplex amplification of at least 3 mRNA transcripts provided in TABLE 2 (i.e., RefSeq identifiers). In another embodiment, the invention provides primers for multiplex amplification of any combination of at least 3 mRNA transcripts selected from SEQ ID NOS:10-19, or, alternatively at least 3 mRNA transcripts selected from SEQ ID NOS: 10, 11, 13, and 15-18. In one embodiment, the primers are for multiplex amplification, wherein the primers comprise at least one pair, and optionally three or more primer pairs. Exemplary primer pairs are provided in TABLE 3. In another embodiment, the primers for multiplex amplification comprise at least three and no more than 100 primer pairs, optionally no more than 50, optionally no more than 25, optionally no more than 10 pairs selected from any of the primer pairs provided in TABLE 3.

In a related aspect, the invention provides compositions comprising primer(s) or primer pair(s) as described above. The composition may be an admixture. The composition may be a solution. The composition may additionally contain one or more of (a) maternal cfRNA, (b) buffer, (c) enzymes (e.g., reverse transcriptase, DNA polymerase, RNA or DNA ligase), (d) dNTPs.

In a related aspect, the invention provides kits comprising primer(s) or primer pair(s) as described above packaged together. In one approach, a mixture of different primers are combined in a single mixture. In another approach, primers specific for individual cfRNAs are packaged together in separate vials. The kit may additionally contain one or more of (a) maternal cfRNA, (b) buffer, (c) enzymes (e.g., reverse transcriptase, DNA polymerase, RNA or DNA ligase), (d) dNTPs.

In one aspect a composition is provided, comprising (1) cfRNAs with cfRNA sequences corresponding to at least 2 genes in TABLE 2, or amplicons of, or cDNAs from, said cfRNA sequences and (2) primers for amplifying said cfRNA sequences or amplicons or cDNAs, or probes for detecting said cfRNA sequences or amplicons or cDNAs, with the proviso that the composition does not comprise primers for amplifying more than a threshold number of different genes, amplicons or cDNAs; and does not comprise probes for detecting more than the threshold number of different cfRNA sequences or amplicons or cDNAs. In one embodiment the composition does not comprise cfRNAs with cfRNA sequences corresponding to more than the a threshold number of different genes from the human genome, or amplicons of, or cDNAs from more than the threshold number of different genes. In some embodiments the threshold number is 200. In some embodiments the threshold number is 150. In some embodiments the threshold number is 100. In some embodiments the threshold number is 50. In some embodiments the threshold number is 25.

In a related aspect, the invention provides nucleic acid arrays comprising primer(s) or primer pair(s) as described above.

10. METHODS

This section describes implementation of the methods for determination of gestational age and risk of preterm delivery. Examples in this section are intended as illustrations and are in no sense limiting.

In one approach a maternal sample(s) is collected, frozen, and shipped to a centralized laboratory for analysis. In one approach methods of the invention are carried out in a local medical facility (e.g., hospital lab) optionally using a kit for isolation of cfRNA, production of cDNA, qPCR and/or sequencing. In one approach the kit includes reagent for cfRNA isolation. The use of a standardized kit is advantageous in ensuring uniformity of sample collection, cfRNA isolation, and analysis by qPCR or transcriptome sequencing. The kit may contain reagents for cfRNA, production of cDNA, qPCR and/or sequencing as well as primers or probes described herein for determining expression levels of cfRNA transcripts or combinations of transcripts described herein. In one approach cfRNA, cDNA, or a library is produced and shipped to a centralized laboratory for analysis.

In one approach a maternal sample(s) is collected and an expression profile is determined using a distributed system including client systems and server systems communicating over a computer network server-client, frozen, and shipped to a centralized laboratory for analysis. The server system may comprise databases of reference profiles and may receive data (e.g., expression profile information) from a client system. The expression profile information from the patient is compared to the reference profile using a computer product, e.g., comprising a computer readable medium storing a plurality of instructions for controlling a computer system to perform a method of the invention. the method of any one of the preceding claims. The databases of reference profiles may be produced using the machine learning approaches described herein. Advantageously, as expression profiles from individual patients is collected that information may be used as training data. This may be particularly useful when training and validation data are collected from demographically distinct patient populations (e.g., populations identified by age, race or ethnicity, geographical location, or other criteria).

Patient expression profiles will be most useful when they are tied to particular outcomes (e.g., term delivery or preterm delivery) or gestational age at birth. Thus, in one aspect the invention involves (1) collecting cfRNA from a pregnant woman one or multiple times during pregnancy, determining an expression profile using the cfRNA (i.e., an expression profile corresponding to a set of genes identified herein, e.g., genes from TABLE 1, TABLE 2, or TABLE 6 or combinations or subsets described herein); and recording the expression profile, e.g., on a suitable non-transitory computer readable medium; and then (2) determining the delivery date for the woman, categorizing the delivery as term or preterm (and if preterm, by how many days) or otherwise characterizing the outcome of the pregnancy, and (3) associating the information in (2) with the expression profiles in (1), e.g., by linking the information and expression profile(s) in the computer readable medium.

Determination of Gestational Age

In one approach a method performed using a computer for estimating gestational age of a fetus is provided comprising: (a) obtaining one or more expression profiles from a maternal sample of a pregnant woman carrying a fetus, wherein the expression profile(s) corresponds to the expression of cfRNA transcripts from a first panel of genes; (b) comparing, using a computer system, the expression profile(s) to one or more reference profile(s) characteristic of a defined gestational age(s) to estimate the gestational age of the fetus, wherein the reference profile(s) characteristic of the defined gestational age(s) are determined using a machine learning model that analyzes first training samples that are cfRNA expression profiles labeled with a defined gestational age; (c) updating, using the computer system, the reference profile(s) by: (1) receiving second training samples, wherein the second training samples are cfRNA expression profiles labeled with a defined gestational age, and (2) iteratively adjusting the reference profile(s) via a machine learning model to increase the number of the first and second training samples that are classified correctly. The reference profiles can form a line or curve or be discrete values. In some embodiments the first panel of genes comprises any combination of genes disclosed herein as predictive of gestational age, including placental genes, placental genes listed in Table 1, and at least 1, at least 2, at least 3, at least 4, at least 5, at least 6, at least 7, at least 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9].

Also provided is a computer system comprising: (a) a database comprising reference profile(s), each including a level of expression in a population of pregnant women of cfRNA transcripts corresponding to a first panel of genes and corresponding to a defined gestational age; (b) a user interface configured to interact with a client computer over a network and to receive expression profile(s) including the level of expression in a pregnant woman carrying a fetus of cfRNA transcripts corresponding to the first panel of genes; and (c) one or more processors configured to analyze the reference profile and expression profile, including comparing the reference profile(s) and expression profile(s) to determine gestational age of the fetus; and (d) a network interface that transmits the gestational age of the fetus to the client computer. In one embodiment the the reference profile (s) and expression profile(s) comprise expression levels of a panel of cfRNAs in any combination disclosed herein, including transcripts from placental genes; placental genes listed in Table 1; and at least 1, at least 2, at least 3, at least 4, at least 5, at least 6, at least 7, at least 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9].

Risk of Preterm Delivery

In one approach a method performed using a computer for assessing risk of preterm delivery by a pregnant woman is provided comprising: (a) obtaining one or more expression profiles from a maternal sample of a pregnant woman, wherein the expression profile(s) corresponds to the expression of a plurality of cfRNA transcripts from a first panel of genes; (b) comparing, using a computer system, the expression profile(s) to one or more reference profile(s) characteristic of a woman with (a) a high risk of preterm delivery or (b) a low risk of preterm delivery, or characteristic of a woman with a defined length of pregnancy, wherein the reference profiles are determined using a machine learning model that analyzes first training samples that are cfRNA expression profiles preterm or full-term, or labeled with a length of pregnancy (c) updating, using the computer system, the reference profile(s) by: (1) receiving second training samples, wherein the second training samples are cfRNA expression profiles labeled as preterm or full-term or labeled with a length of pregnancy, and (2) iteratively adjusting the reference profile(s) via a machine learning model to increase the number of the first and second training samples that are classified correctly. The reference profiles can form a line or curve or be discrete values. In some embodiments the first panel of genes comprises any combination of any combination of genes disclosed herein as predictive of risk of premature delivery, including genes listed in Table 1, and at least 2, at least 3, at least 4, at least 5, at least 6, at least 7, at least 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9] or at least least 2, at least 3, at least 4, at least 5, at least 6, or 7 genes selected from CLCN3 [SEQ ID NO:10], DAPP1 [SEQ ID NO:11], PPBP [SEQ ID NO:13], MAP3K7CL [SEQ ID NO:15], MOB1B [SEQ ID NO:16], RAB27B [SEQ ID NO:17], and RGS18 [SEQ ID NO:18]. In some embodiments the first panel of genes comprises at least one combination selected from (1) RGS18; DAPP1; PPBP; (2) RGS18; RAB27B; PPBP; (3) RGS18; MOB1B; PPBP; (4) RGS18; PPBP; MAP3K7CL; (5) RGS18; PPBP; CLCN3; (6) DAPP1; RAB27B; PPBP; (7) DAPP1; MOB1B; PPBP; (8) DAPP1; PPBP; CLCN3; (9) RAB27B; MOB1B; PPBP; (10) RAB27B; PPBP; MAP3K7CL; (11) RAB27B; PPBP; CLCN3; (12) MOB1B; PPBP; MAP3K7CL; and (13) MOB1B; PPBP; CLCN3.

For determining risk of preterm delivery maternal samples can be labeled "preterm" and "term"; or with the gestational age of the child at birth; or with the length of the pregnancy (e.g., week of delivery), combinations of these, or labels suitable for quantitatively or qualitatively distinguishing a full-term delivery from a preterm delivery.

Also provided is a computer system comprising: (a) a database comprising reference profile(s), each including a level of expression in a population of pregnant women of cfRNA transcripts corresponding to a first panel of genes and risk of preterm delivery; (b) a user interface interface configured to interact with a client computer over a network and to receive expression profile(s) including the level of expression in a pregnant woman of cfRNA transcripts corresponding to the first panel of genes; and (c) one or more processors configured to analyze the reference profile and expression profile, including comparing the reference profile (s) and expression profile(s) to determine the risk of preterm delivery; and (d) a network interface that transmits the risk of preterm delivery to the client computer. In some embodiments the reference profile(s) and expression profile(s) comprise expression levels of a panel of cfRNAs in any combination disclosed herein, including genes listed in Table 1 and at least 2, at least 3, at least 4, at least 5, at least 6, at least 7, at least 8, or 9 genes selected from CGA [SEQ ID NO:1], CAPN6 [SEQ ID NO:2], CGB [SEQ ID NO:3], ALPP [SEQ ID NO:4], CSHL1 [SEQ ID NO:5], PLAC4 [SEQ ID NO:6], PSG7 [SEQ ID NO:7], PAPPA [SEQ ID NO:8], and LGALS14 [SEQ ID NO:9] or at least least 2, at least 3, at least 4, at least 5, at least 6, or 7 genes selected from CLCN3 [SEQ ID NO:10], DAPP1 [SEQ ID NO:11], PPBP [SEQ ID NO:13], MAP3K7CL [SEQ ID NO:15], MOB1B [SEQ ID NO:16], RAB27B [SEQ ID NO:17], and RGS18 [SEQ ID NO:18].

11. EXAMPLES

12.1 Example 1

Materials and Experimental Methods

Sample Collection

Blood samples from pregnant Danish women were collected weekly (high-resolution cohort) and at one time point during the second or third trimester from the University of Pennsylvania (preterm discovery cohort) and the University of Alabama at Birmingham (preterm validation cohort) under an Institutional Review Board-approved protocol. Women who participated in the study in Pennsylvania and Alabama were at elevated risk for spontaneous premature delivery. All women who delivered preterm except one patient from Pennsylvania (preeclampsia) experienced spontaneous preterm birth. As per the standard of care, all women with a history of preterm delivery received weekly progesterone injections. The blood samples were collected into EDTA-coated Vacutainer tubes (Becton Dickinson, NJ). Plasma was separated from blood using standard clinical blood centrifugation protocol.

Cell-Free RNA (cfRNA) Isolation

Cell-free RNA was extracted from 0.75-2 mL of plasma using Plasma/Serum Circulating RNA and Exosomal Purification kit (Norgen Biotek Corp, Canada, Catalog No. 42800). The residue of DNA was digested using Baseline-ZERO DNase (Epicentre, WI) and then cleaned by RNA Clean and Concentrator™-5 kit (Zymo Research, CA). The resulting RNA was eluted to 12 μl in elution buffer.

RT-qPCR Assay

RT-qPCR assays consist of two main reactions: reverse transcription/preamplification of extracted cfRNA and qPCR of pre-amplified cDNA. The primers for our gene panels were designed and synthesized by Fluidigm Corporation, CA (TABLE 3). Either 1-2 μl or 10 μl out of the 12 μl of total purified RNA was used for reverse transcription/preamplification reaction using the CellsDirect™ One-Step RT-qPCR Kit (Invitrogen, CA, Catalog No. 11753-100) and a pool of 96 primer pairs from TABLE 3. Preamplification was performed for 20 cycles and residual primers of the reaction were digested using exonuclease I treatment. Multiplex qPCR reactions of 96 samples for the 96 primer pairs were performed using 96×96 Dynamic Array Chip on BioMark System (Fluidigm Corp., CA). The BioMark Dynamic Array Chip loads individual samples (cDNA) and individual reagents (primer pairs) separately into wells on the Dynamic Array chip. The integrated fluidics circuit controllers push samples and reagents through channels until full; then coordinated releasing and closing of fluidic values allows mixing of samples and reagents into individual compartments within the chip. The 96×96 Dynamic Array Chip can simultaneously analyze up to 9,216 reactions. Threshold cycles (Ct values) of qPCR reactions were extracted using Fluidigm real-time PCR analysis software.

cfRNA-Seq Library Preparation

A cell-free RNA sequencing library was prepared by SMARTer Stranded Total RNAseq—Pico Input Mammalian kit (Clontech, CA, Catalog No. 634413) from 6 μl of eluted cfRNA according to the manufacturer's manual. Short read sequencing was performed on Illumina NextSeq™ (2×75 bp) platform (Illumina, CA) to the depth of more than 10 million reads per samples.

Statistical Analysis cfRNA-Seq Differential Expression Analysis 28 samples (14 term and 14 preterm) cfRNA samples of the preterm discovery cohort were sequenced. The sequencing reads were mapped to human reference genome (hg38) using STAR aligner. Duplicates were removed by Picard and then unique reads were quantified using htseq-count. After preprocessing, 16 samples containing sequencing reads that mapped to more than 3000 genes were used for subsequent statistical analyses. Differentiating genes between term and preterm samples were identified using a quantile-adjusted conditional maximum likelihood method, a generalized linear model (GLM) likelihood ratio test, and a quasi-likelihood F-test implemented in R using the edgeR package.

RT-qPCR Sample Analysis

Figure 9:
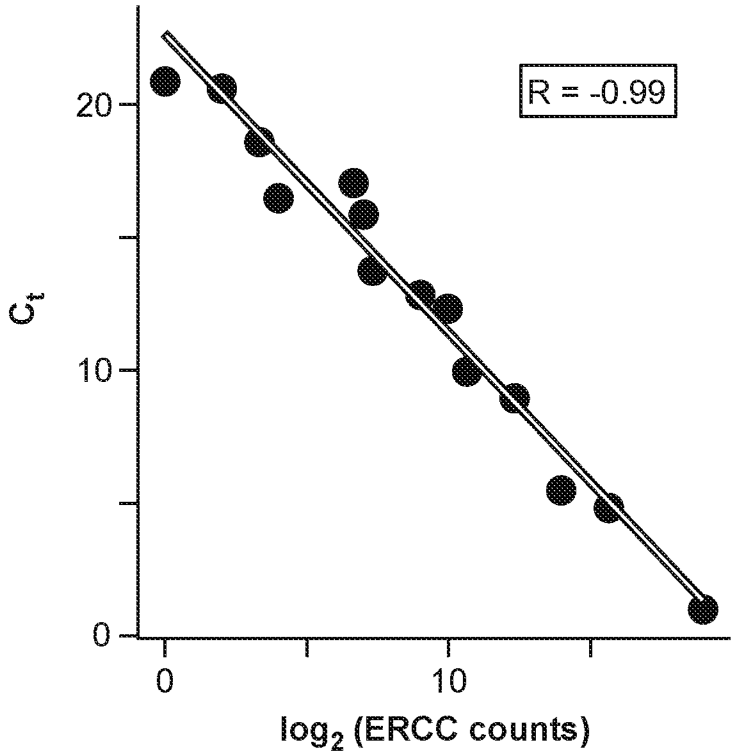
FIG. 9 shows $C_t$ counts for each gene under evaluation are back-calculated from $C_t$ values using a standard curve generated using a common set of external RNA controls developed by the External RNA Controls Consortium (ERCC). The control consists of a set of unlabeled, polyadenylated transcripts designed to be added to an RNA analysis experiment after sample isolation and prior to interrogation. ERCC Spike-In Control Mixes are commercially available, preformulated blends of 92 transcripts, designed to be 250 to 2,000 nucleotides in length, which mimic natural eukaryotic mRNAs (e.g., ERCC RNA Spike-In Mix, Invitrogen, CA, Catalog No. 4456740).

Raw $C_t$ values were quantified in absolute terms. Absolute quantification estimated the transcript counts contained in each sample based on cycle thresholds for known quantities of ERCC (FIG. 9). Estimated transcript counts were then adjusted for dilution, sample volume, and normalized by the volume of processed plasma.

Multivariate Random Forest Modeling

Recursive feature selection and model construction were performed in R using the caret package. Longitudinal data was smoothed using a 3-week centered moving average and divided into a 21 patient training set and a 10 patient validation set. Model selection was performed using 10-fold cross validation repeated 10 times.

Expected Delivery Date Estimation

Expected delivery dates were derived from random forest model predictions. Longitudinal data for this application were not smoothed using a centered moving average. For any given sampling period (second trimester (T2), third trimester (T3), or both (T2&T3), time to delivery estimates were shifted to a specified reference time point and then averaged using the median to establish an expected delivery date.

Preterm Biomarker Candidate Selection and Validation

Absolute RT-qPCR values were normalized using a modified multiple of the median approach as applied in Rose and Mennuti (*Fetal Medicine, West J Med.*, 1993; 159:312-317, incorporated herein by reference) that is both time and epidemiologically invariant, allowing for consistent comparisons across cohorts of different ethnicities. At-term patient medians were quantified by trimester on a cohort level for each gene. Biomarker discovery was performed using the combined criterion of an effect size and significance value threshold calculated using Hedges' g and the Fisher exact test, respectively, as described in Sweeney et al. (*J. Pediatric Infect. Dis. Soc.,* 2017, doi: 10.1093/jpids/pix021, incorporated herein by reference). Genes were considered significantly different between cohorts using an effect size threshold of 0.8 and a false discovery rate (FDR) of 5%. Candidate gene biomarkers were then tested in unique combinations of 3 to estimate their ability to detect both true and false positives. Combinations with a true positive rate of greater than 0.75 and a false positive rate less than 0.05 were selected for further validation using an independent cohort. The ROC curve was based on the fraction of biomarker combinations where all genes showed a fold increase of at least 2.5 over median expression.

11.2 Example 2

Longitudinal Data of Due Dates from Three Distinct Populations

We performed a high time-resolution study of normal human development by measuring cfRNA in blood from pregnant women longitudinally during each week of pregnancy. cfRNA provides a window into the phenotypic state of the pregnancy by providing information about gene expression in fetal, placental and maternal tissues. Koh et al. described using tissue-specific genes for direct measurement of tissue health and physiology, and that these measurements are concordant with the known physiology of pregnancy and fetal development at low time resolution (Koh et al. *PNAS,* Vol. 111, 20:7361-7366, (2014), incorporated herein by reference). Analysis of tissue-specific transcripts in the instant samples enabled us to follow fetal and placental development with high resolution and sensitivity, and also to detect gene-specific response of the maternal immune system to pregnancy. The data from the present study establishes a "clock" for normal human development and enables a direct molecular approach to establish time to delivery and gestational age using nine placental genes. We demonstrate that cfRNA samples from both the second and third trimesters of pregnancy can predict expected delivery date with comparable accuracy to ultrasound, creating the basis for a portable, inexpensive dating method.

We recruited 31 pregnant Danish women from the Danish National Biobank, each of whom agreed to give blood on a weekly basis, resulting in 521 total plasma samples to analyze (FIG. 1A). All women delivered normally at term, defined as a gestational age at delivery of or greater than 37 weeks, and their medical records showed no unusual health changes during pregnancy (TABLE 8). Each sample was analyzed by highly multiplexed real time PCR using a panel of genes that were chosen to be specific to the placenta, fetal tissue, or the immune system.

TABLE 8

| | | Pennsylvania (n = 16) | | Alabama (n = 26) | |
|---|---|---|---|---|---|
| Demographics | Denmark (n = 31) | Preterm (n = 9) | At-term (n = 7) | Preterm (n = 8) | At-term (n = 18) |
| Age (years ± SD) | 29.9 ± 3.2 | | | 23.9 ± 2.8 | 25.8 ± 4.4 |
| Parity (% nulliparous) | 19 (61.3) | | | 0 (0) | 0 (0) |
| BMI (kg/m$^2$, mean ± SD) | 22.1 ± 3.6 | | | 28.9 ± 10.5 | 28.6 ± 7.0 |
| Ethnicity (% Hispanic) | 0 (0) | | | 0 (0) | 0 (0) |
| Caucasian (%) | 31 (100) | | | 0 (0) | 1 (8) |
| African-American (%) | 0 (0) | | | 8 (100) | 17 (94) |
| Gestational age at delivery (weeks, mean ± SD) | 40 ± 1.2 | 26.7 ± 2.3 | 39.4 ± 0.5 | 30.8 ± 2.5 | 38.7 ± 1.2 |
| Mode of delivery | | | | | |
| Spontaneous | 67.7 | | | 7 (88) | 16 (29) |
| Cesarean section | 12.9 | | | 1 (12) | 2 (11) |
| Gender (% male) | 14 (45.2) | | | 5 (63) | 10 (58) |
| Birth weight (kg, mean ± SD) | 3.8 ± 0.6 | | | 1.7 ± 0.7 | 3.1 ± 0.4 |

11.3 Example 3

Gene Expression of Maternal, Placental and Fetal-Tissue Specific Genes in Maternal Plasma Samples from Normal Due Date Deliveries Cell-free RNA was isolated from each of the Denmark cohort individuals blood samples as set forth in Example 1. RT-qPCR assays were performed on the isolated cfRNA essentially as set forth in Example 1. A primer pair for each of the genes set forth in FIG. 9 was added to aliquots of the cfRNA samples and Ct values were calculated using appropriate controls.

Figure 2A:
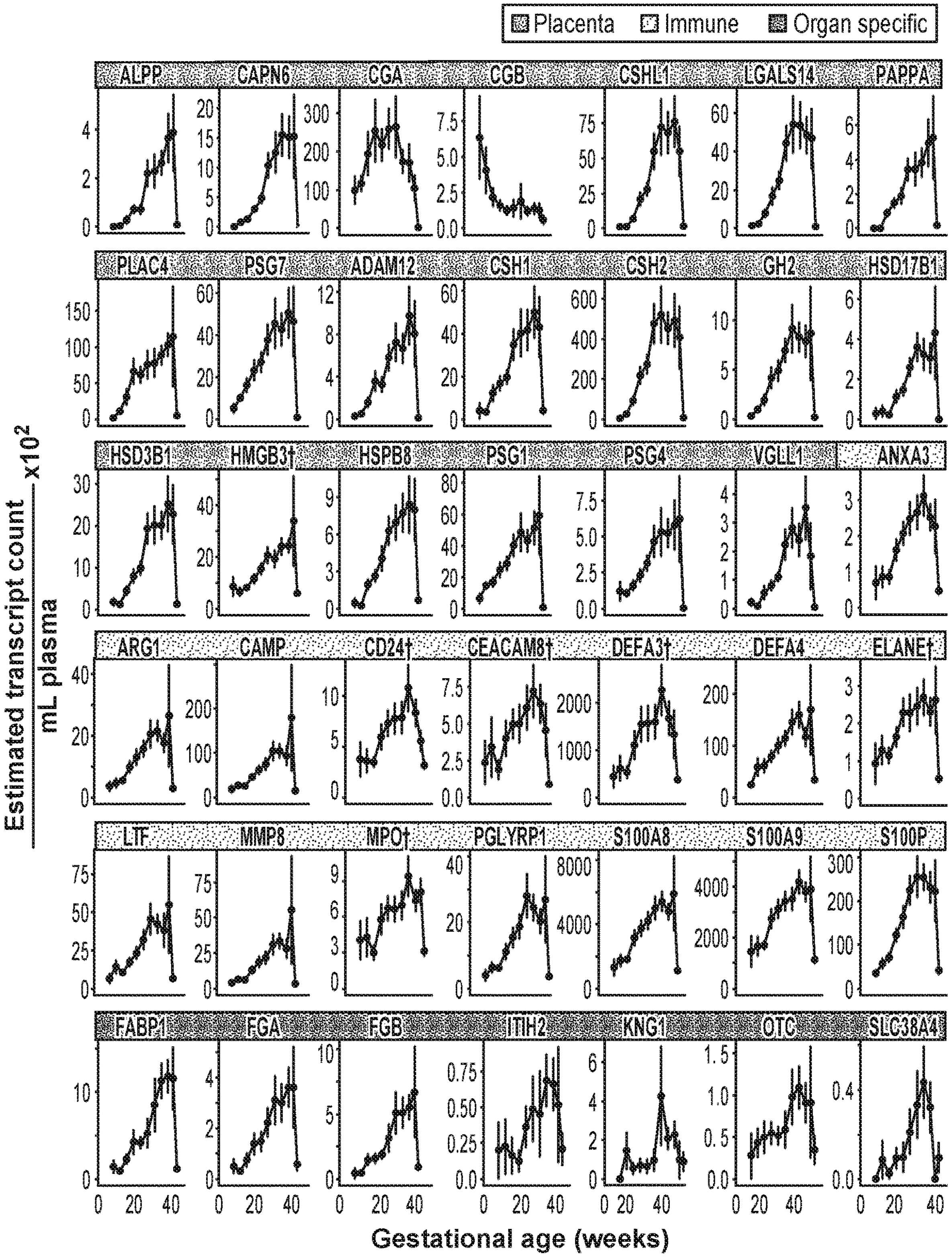
FIG. 2A shows data from representative gene expression arrays of placenta, immune or organ specific genes (last row). Gene-specific inter-patient monthly averages±standard error of the mean (SEM) plotted over the course of gestation (shaded in gray). † represents genes for which data for only 21 patients was available.
Figure 2B:
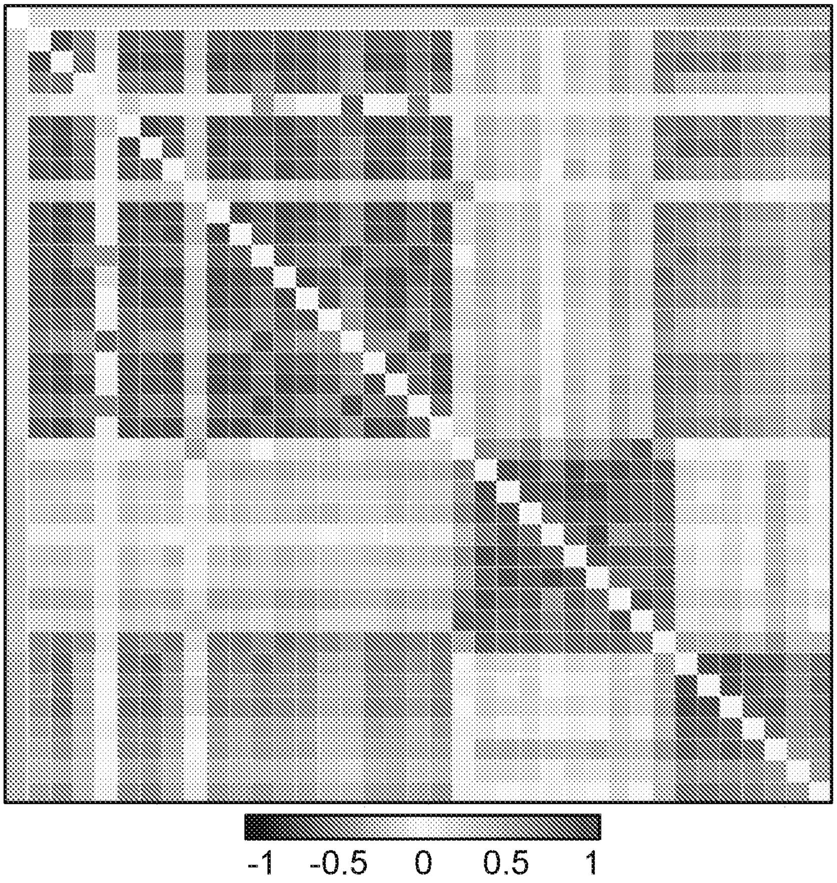
FIG. 2B is a heatmap showing correlation between gene-specific estimated transcript counts. Genes are listed in the same order as FIG. 2A while omitting genes for which data was only available for 21 patients. Placental (rows/columns 1-20), immune (rows/columns 21-29) and organ specific genes (rows/columns 30-36) are shown.
Figure 4:
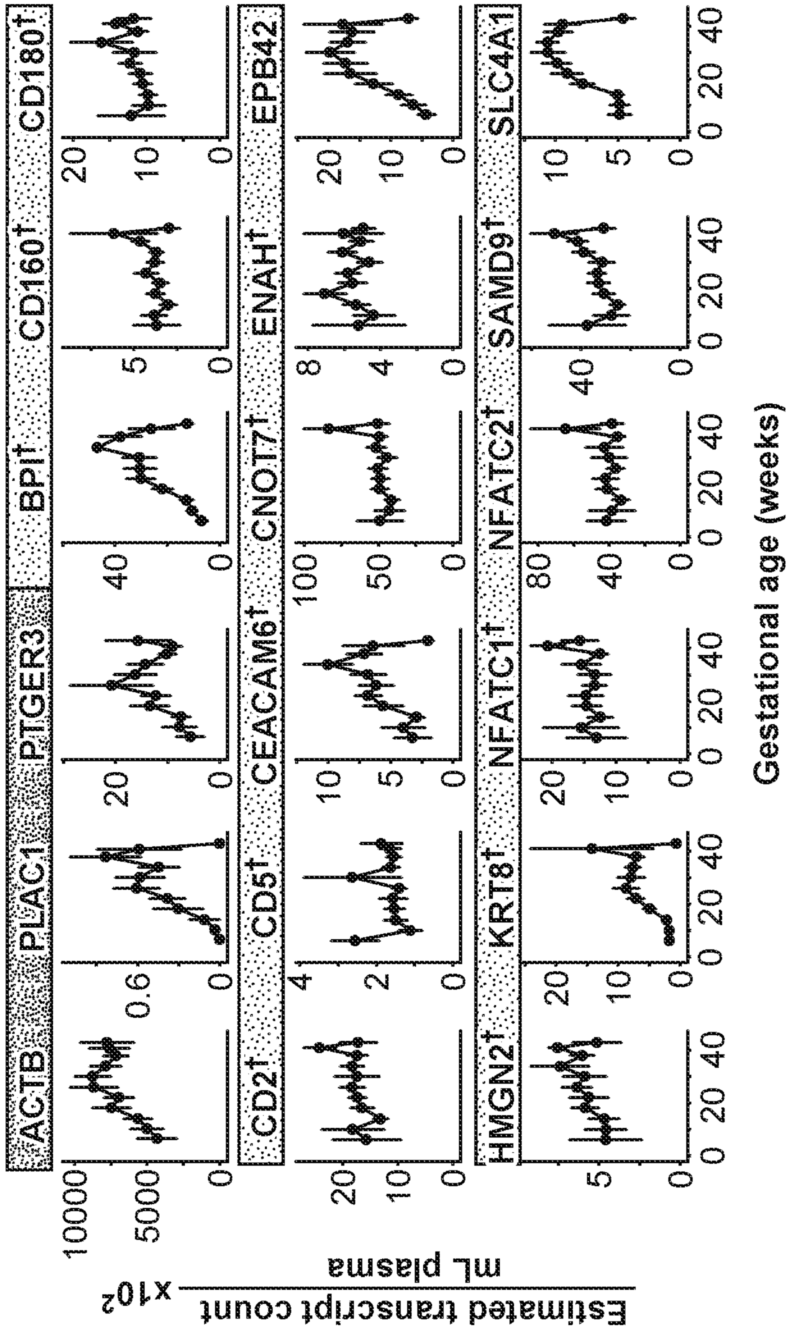
FIG. 4 shows data from representative gene expression arrays of placenta or immune genes. Gene-specific inter-patient monthly averages±standard error of the mean (SEM) plotted over the course of gestation (shaded in gray). t represents genes for which data for only 21 patients was available.

Gene-specific inter-patient monthly averages±standard error of the mean (SEM) were plotted over the course of gestation (FIG. 2A). The average time course of gene expression highlighted interesting behavior that differed by gene function (FIGS. 2A and 4). Placental and fetal genes (blue and yellow) show a clear increase through the course of pregnancy with slightly different trajectories depending on the gene. Some of these genes plateau before delivery and one of them (CGB) decreases from a peak in the first trimester. Immune genes, which are dominated by the maternal immune system but may also include a fetal contribution, have a more complex interpretation but in general show changes in time with measurable baselines early in pregnancy and after delivery. We then calculated the correlation between gene values across all genes and all pregnancies (FIG. 2B) and discovered that genes within each set (i.e. placental, immune, fetal) were highly correlated with each other. Moreover, we found that placental and fetal genes also showed a moderate degree of cross correlation, suggesting that placental cfRNA may provide an accurate estimate of fetal development and gestational age throughout pregnancy.

11.4 Example 4

Model for Prediction of Time to Delivery & Comparison with Gold Standard

Figure 2C:
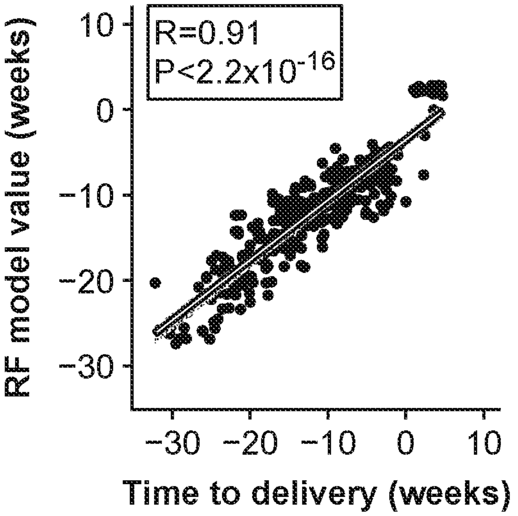
FIGS. 2C-2D show solid lines and shading that indicate linear fit and 95% confidence intervals, respectively.
Figure 2D:
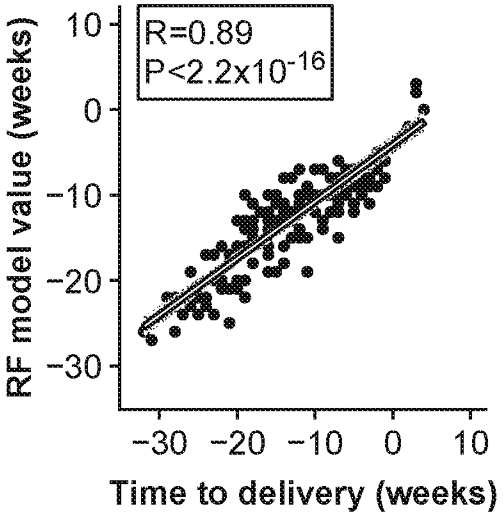
Figure 5:
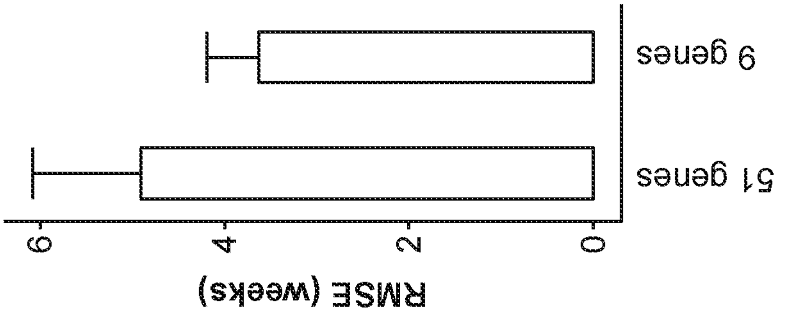
FIG. 5 shows a random forest model built using 9 placental genes outperforming a random forest model built using 51 genes of placental, immune and tissue-specific organ origin to predict gestational age by root mean squared error (RMSE).

The results of the gene expression assays motivated us to apply a machine learning approach in order to build a model, which would predict gestational age or time to delivery from cfRNA measurements. We used a random forest model and were able to show that a subset of nine placental genes provided more predictive power than using the full panel of measured genes (FIG. 5). Using these 9 genes (CGA, CAPN6, CGB, ALPP, CSHL1, PLAC4, PSG7, PAPPA, and LGALS14) we accurately predicted the time from sample collection until delivery (Pearson correlation r=0.91, $P<2.2\times10^{-16}$), which is an objective criterion independent of ultrasound-estimated gestational age (FIG. 2C). Our model's performance improved significantly over the course of gestation (root mean squared error (RMSE)=6.0 (T1), 3.9 (T2), 3.3 (T3), 3.7 (PP) weeks). Remarkably, our model performed equally well (r=0.89, $P<2.2\times10^{-16}$) on a withheld cohort of 10 women during the validation stage (RMSE=5.4 (T1), 4.2 (T2), 3.8 (T3), 2.7 (PP) weeks) (FIG. 2D).

Figure 6A:
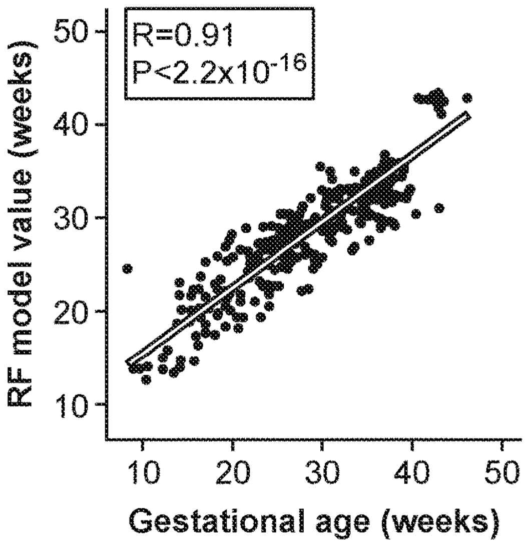
FIGS. 6A and 6B show solid lines and shading indicating a linear fit and 95% confidence intervals, respectively.
Figure 6B:
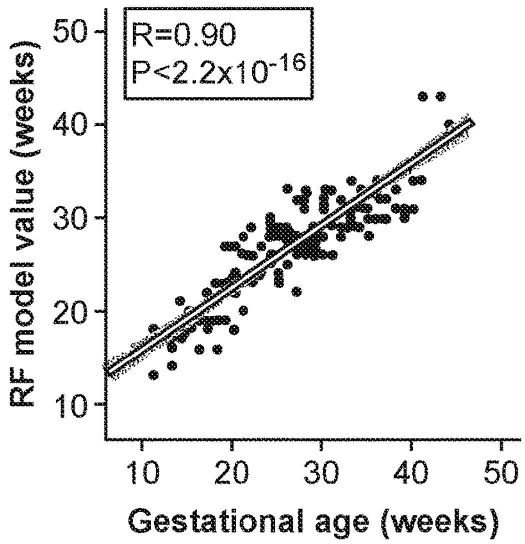

We also built a separate model to predict gestational age (as estimated by ultrasound) and using the same nine placental genes, the model performed comparably well both on training (r=0.91, $P<2.2\times10^{-16}$) and validation data (r=0.90, $P<2.2\times10^{-16}$) (FIGS. 6A and 6B).

The random forest model selects placental genes as most predictive of time from sample collection until delivery and gestational age. Although several of these genes show similar time trajectories, their detection rate early on pregnancy varies, suggesting that redundancy may improve accuracy at early time points, when both placental and fetal cfRNA are low and lead to drop-out effects. As cfRNA increases during gestation, the accuracy of the model improves. This is in contrast with the efficacy of ultrasound dating, which relies on a constant fetal growth rate, an assumption that deteriorates over time (Savitz et al. 2002; Papageorghiou et al. 2016).

Further investigating drivers of the model reveals markers with known roles during pregnancy. CGA and CGB, the two main model drivers together with CAPN6, behave differently from other genes in the model. CGA and CGB are the two subunits of HCG, known to play a major role in pregnancy initiation and progression and involved in trophoblast differentiation (Jaffe et al. 1969). The trend observed for these two genes is compatible with what is known from protein levels during pregnancy (Cocquebert et al. 2012). Free CGB and PAPPA are also used as biochemical markers for at risk of Down Syndrome in the first trimester (Wald and Hackshaw 1997), and other genes selected by the model are related to trophoblast development (e.g., LGALS14, PAPPA).

Figure 2E:
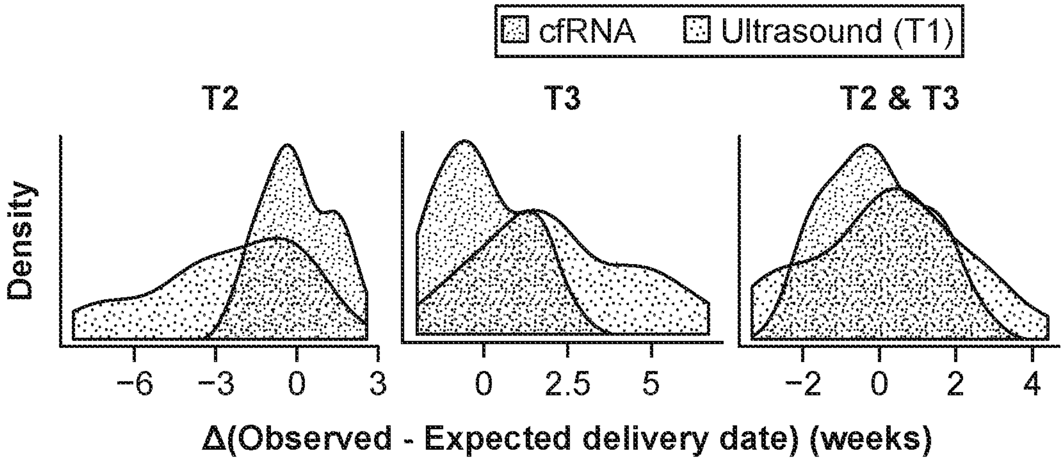
FIG. 2E are graphs showing comparison of expected delivery date prediction during the second, third trimester, or both second and third trimesters, by ultrasound or cell-free RNA methods of the invention.

We then used our model to estimate expected delivery date from samples taken during the second, third, or both trimesters (FIG. 2E). We found that 32% (T2), 23% (T3), 45% (T2&T3), and 48% (T1 Ultrasound) of patients delivered within one week of their expected delivery dates (TABLE 9).

TABLE 9

| | Δ(Observed-Expected delivery date) (%) | | | | |
|---|---|---|---|---|---|
| Method | <−2 weeks | −1 to −2 weeks | ±1 week | +1 to +2 weeks | >+2 weeks |
| cfRNA (T2) | 50 | 18 | 32 | 0 | 0 |
| cfRNA (T3) | 0 | 6 | 23 | 29 | 42 |
| cfRNA (T2 & T3) | 19 | 6 | 45 | 10 | 20 |
| Ultrasound (T1) | 0 | 26 | 48 | 23 | 3 |

Prior studies report that under normal circumstances it is possible to determine the week in which a woman may deliver with 57.8% accuracy using ultrasound and 48.1% using LMP (Savitz et al. 2002). Our results are not only comparable to ultrasound measurements at a fraction of the cost but also use a method that is more easily ported to resource challenged settings.

For gestational age prediction, we trained several distinct models on subpopulations of women (i.e., nulliparous or multiparous women, women carrying male or female fetuses) to determine the importance of the 9 genes that compose the transcriptomic signature identified. Training 4 distinct models for women carrying male or female fetuses and nulliparous or multiparous women revealed that 2 of the 9 genes identified in the main text were sufficient to predict time to delivery for women carrying male (CGA, CSHL1) (Root mean squared error (RMSE) of 5.43 and 4.80 in the second and third trimesters respectively) or female (CGA, CAPN6) fetuses (RMSE of 5.58 and 4.60 in the second and third trimesters respectively) and multiparous (CGA, CSHL1) women (RMSE of 5.22 and 4.56 in the second and third trimesters respectively). However, all 9 genes were necessary to predict time until delivery for nulliparous women (RMSE of 5.09 and 4.50 in the second and third trimesters respectively), highlighting the importance of the transcriptomic signature identified. The nine transcripts used to predict gestational age were weighted by the model in the following order of importance (from most to least): CGA, CAPN6, CGB, ALPP, CSHL1, PLAC4, PSG7, PAPPA, and LGALS14. See TABLE 10.

TABLE 10

| |
|---|
| 7.70 (T1-multiparous), |
| 5.09 (T2-nulliparous) vs 5.22 (T2-multiparous), |
| 4.50 (T3-nulliparous) vs 4.56 (T3-multiparous), and |
| 3.13 (PP-nulliparous) vs 4.24 (PP-multiparous) weeks. |
| 5.58 (T2-female) vs 5.43 (T2-male), |

TABLE 10-continued

| |
|---|
| 4.60 (T3-female) vs 4.80 (T3-male), and |
| 2.57 (PP-female) vs 2.83 (PP-male) weeks. |

In summary, we have discovered a molecular clock of fetal development which reflects the roadmap of developmental gene expression in the placenta and fetus, and enables prediction of time to delivery, gestational age, and expected delivery date with comparable accuracy to ultrasound. Our method has several advantages to ultrasound, namely cost and applicability later during pregnancy. At a fraction of the cost of ultrasound, cfRNA measurements can be easily ported to resource challenged settings. Even in countries that regularly use ultrasound, cfRNA presents an attractive, accurate alternative to ultrasound, especially during the second and third trimesters, when ultrasound predictions deteriorate to 15 (T2) or 27 (T3) day estimates of delivery (Altman and Chitty 1997). We expect that this clock will also be useful for discovering and monitoring fetuses having congenital defects that can be treated in utero, which represents a rapidly growing part of maternal-fetal medicine.

11.5 Example 5

Figure 7A:
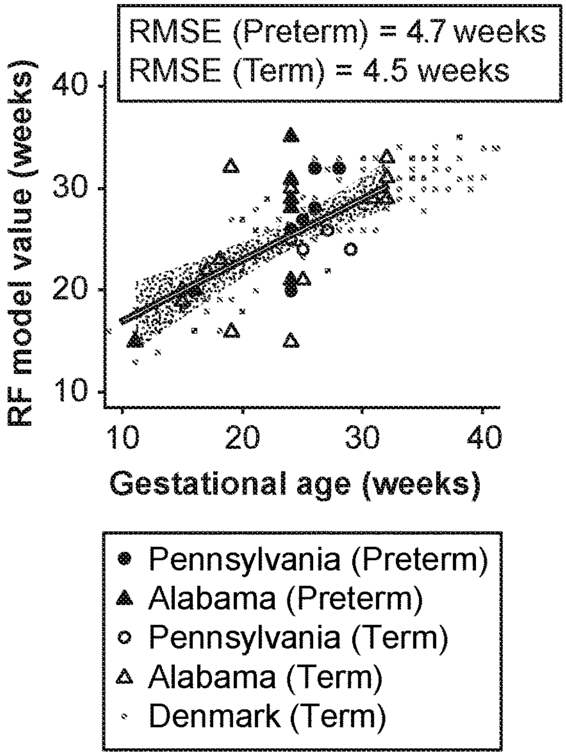
FIGS. 7A and 7B show solid lines and shading indicating a linear fit and 95% confidence intervals, respectively. Training and validation data are reported above each graph. Random forest model prediction of gestational age and time to delivery for normal and preterm samples reveals that although the model works well for prediction of gestational age for normal deliveries (RMSE=4.5) and preterm deliveries (RMSE=4.7) (FIG. 7A), it fails to accurately predict time to delivery in the preterm cases (RMSE=10.5 weeks) (FIG. 7B); while accurately predicting time to delivery for normal deliveries (FIG. 7B).
Figure 7B:
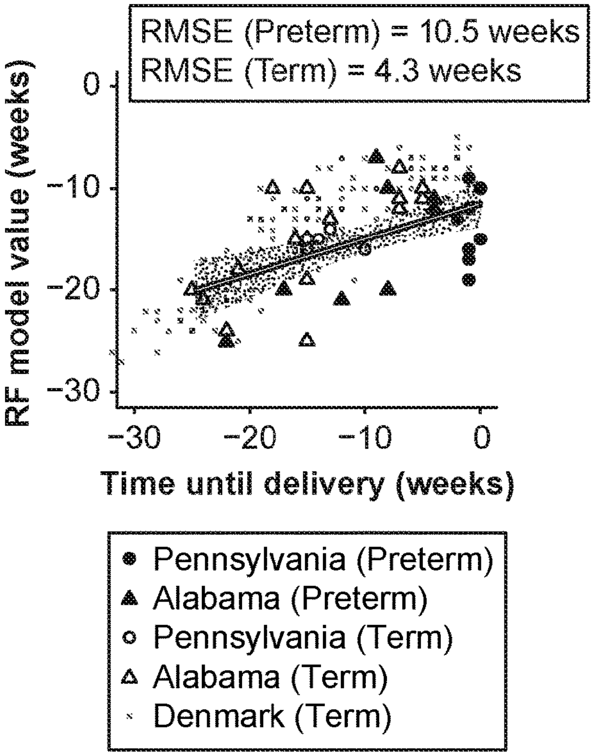

Identification Of Differentially Expressed Genes Between Normal and Preterm Deliveries While the first generation "clock" model is able to predict gestational age and time of delivery for a normal pregnancy, we were also interested in testing its performance on preterm delivery. We therefore used two separately recruited cohorts from communities at high risk for premature delivery recruited at the University of Pennsylvania and the University of Alabama at Birmingham to test performance on preterm pregnancies (see, FIG. 1 and TABLE 1). We discovered that while the model validated performance on normal pregnancy (RMSE=4.3 weeks), it generally failed to predict time until delivery in preterm samples (RMSE=10.5 weeks) (FIG. 7). This suggests that the model's content is reflective of the normal developmental program and may not account for the various outlier physiological events which may lead to preterm birth. In other words, from a molecular perspective, the premature fetus does not appear to have reached full gestation and therefore preterm birth is likely not caused by overmaturation signals from the fetus or placenta, which give the illusion of reaching full-term. This conclusion is supported by the observation that pharmacological agents designed to stop or slow down uterine contractions prevent a small number of preterm deliveries (Romero et al. 2014; Conde-Agudelo and Romero 2016).

To further investigate this question and develop a second generation "clock" model capable of predicting preterm delivery, we performed RNAseq, essentially as set forth in Example 1, on cfRNA obtained from plasma samples from term (n=7) and preterm (n=9) women collected from one of the preterm-enriched cohorts (Pennsylvania) (see, FIG. 1 and TABLE 1) for genes, which may discriminate preterm from normal delivery.

Analysis of this RNAseq data suggested that nearly 40 genes could separate term from preterm with statistical significance (p<0.001) (see, FIG. 3A and FIGS. 10A-10D). When recalculated to exclude one preeclamptic woman (see Examples) it was determined that 37 genes could separate term from preterm with statistical significance.

Figure 8:
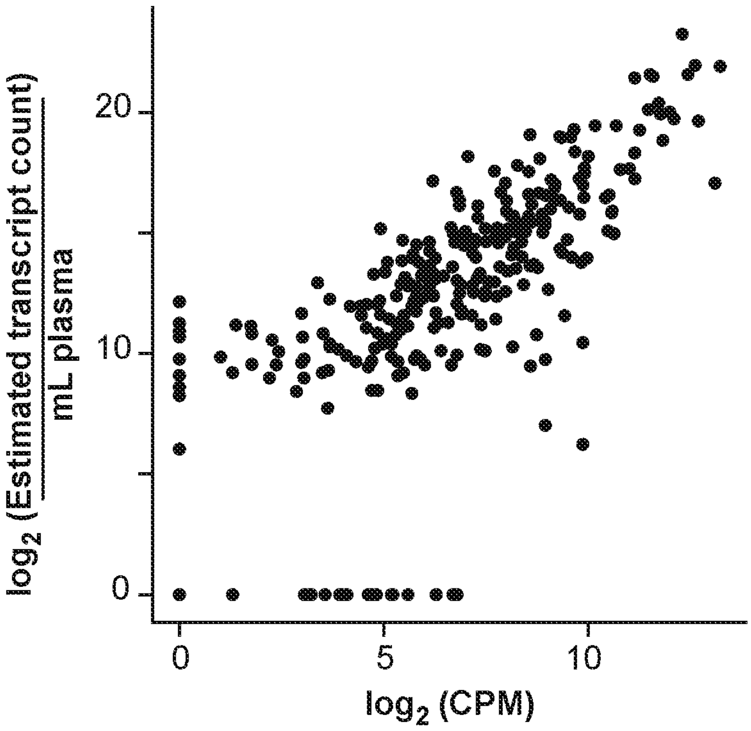
FIG. 8 shows RT-qPCR measurements agree with previously determined RNA-Seq values.

We then created a PCR panel with the highest scoring candidate preterm biomarkers and other immune and placental genes. We confirmed that the differential expression observed in RNAseq was also observed with this qPCR panel (FIG. 8).

11.6 Example 6

Model for Prediction of Preterm Delivery

Figure 3B:
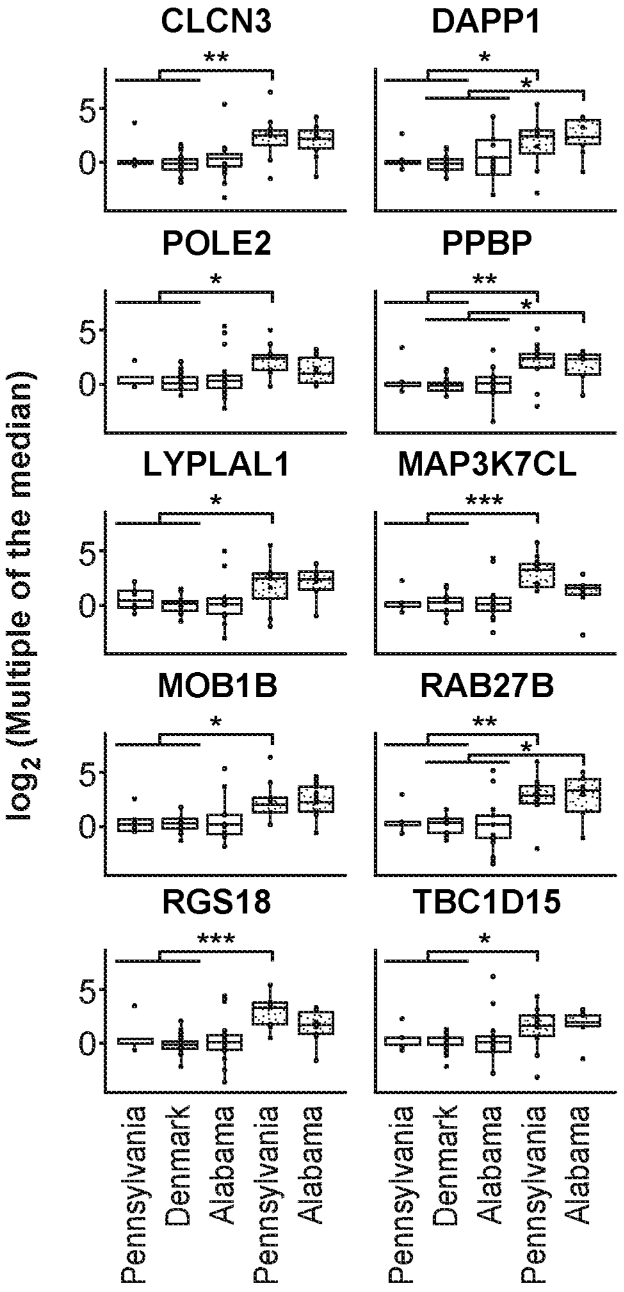
FIG. 3B shows individual plots of 10 genes identified and validated in an independent cohort from Alabama, which accurately predicted preterm delivery using any unique combination of 3 genes from this set. All p-values reported are calculated using the Fisher exact test (FDR<5%). *, , and * indicate significance levels below 0.05, 0.005, and 0.0005, respectively.
Figure 3C:
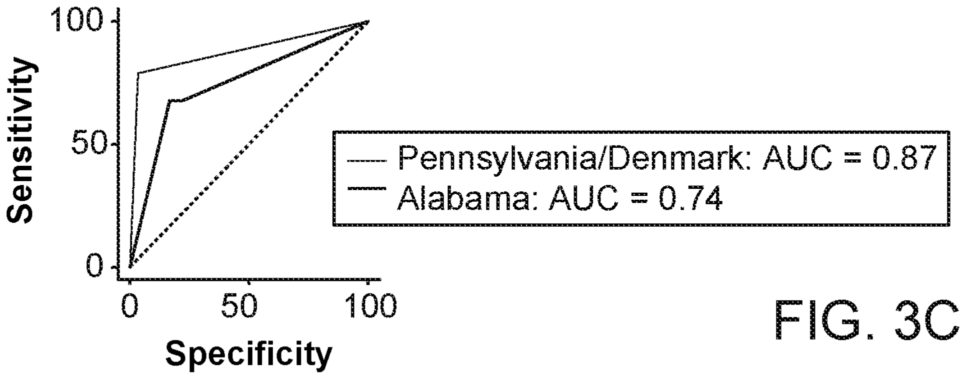
FIG. 3C is a graph showing predictive performance of the 10 validated preterm biomarkers in unique combinations of 3 genes from FIG. 3B. Area under the curve (AUC) values are highlighted both for the discovery (Pennsylvania and Denmark) and validation (Alabama) cohorts.

The top ten genes from this panel (CLCN3, DAPP1, POLE2, PPBP, LYPLAL1, MAP3K7CL, MOB1B, RAB27B, RGS18, TBC1D15) (FDR 5%, Hedge's g≥0.8) (FIG. 3B), accurately classify 7 out of 9 preterm samples (78%) and misclassify only 1 of 26 at-term samples (4%) from both Pennsylvania and Denmark with a mean AUC of 0.87 (FIG. 3C).

Figure 1B:
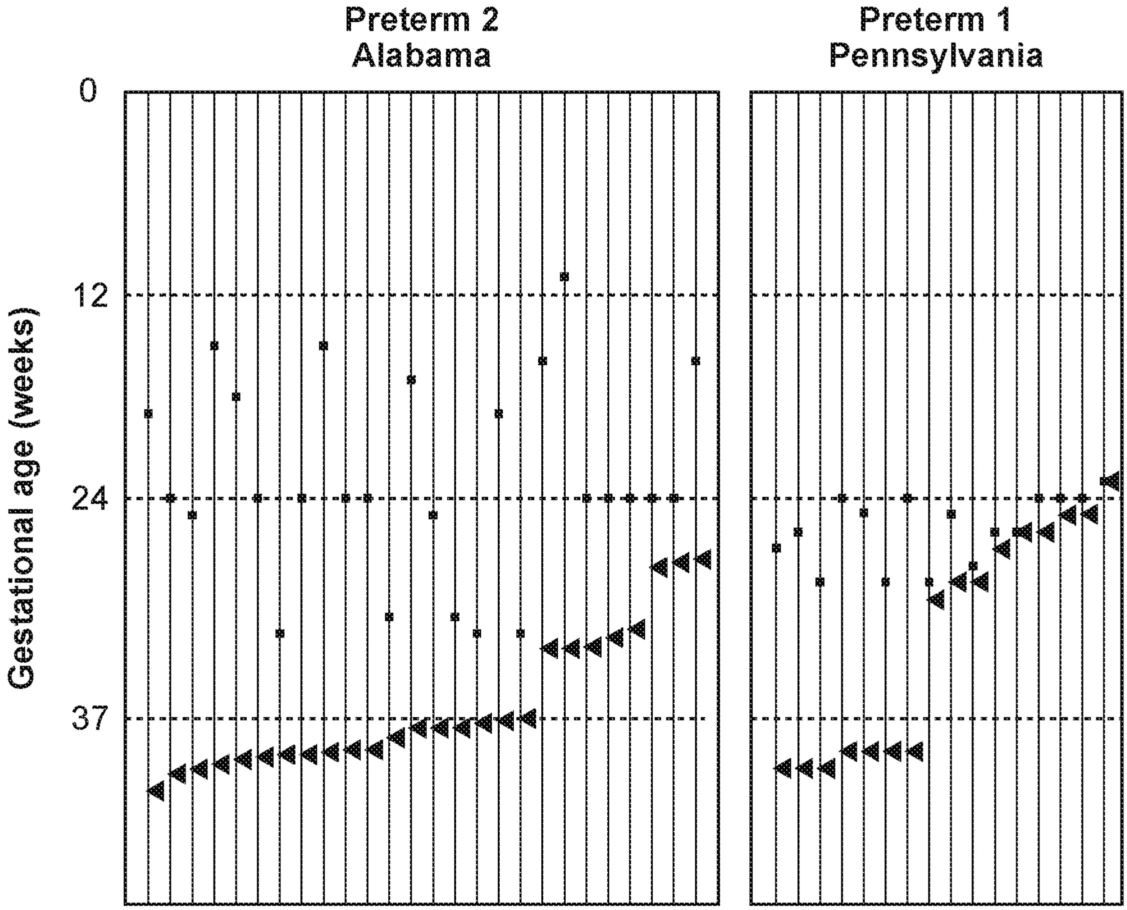

When used in combination, these ten genes also showed successful validation in an independent preterm-enriched cohort from Alabama, accurately classifying 4 out of 6 preterm samples (66%) and misclassifying 3 out of 18 at-term samples (17%) (see, FIG. 1).

Moreover, this independent validation cohort shows that it is possible to discriminate preterm from term pregnancy up to 2 months in advance of labor with an AUC of 0.74 (FIG. 3C). Several of the genes in the response signature were individually significantly more highly expressed in women who delivered preterm (FDR≤5%, Hedge's g≥0.8), demonstrating the robustness of their effect (FIG. 3B). Our data suggests that the genes associated with spontaneous preterm birth are distinct from those found to be most predictive for gestational age and normal time to delivery.

In subsequent refinements we determined that one woman in the cohort experienced induced preterm birth due to preeclampsia rather than spontaneous preterm birth We removed the data points associated with her plasma sample. Rerunning the analysis with this sample removed yielded 7 transcripts (CLCN3, DAPP1, PPBP, MAP3K7CL, MOB1B, RAB27B, RGS18) as opposed to 10, that when used in combinations of 3 produced a true positive rate of greater than 75% and misclassified less than 5%.

As described in Example 7, below, we identified several subcombinations of the 7 transcripts that may be used to determine a woman's likelihood or risk of preterm delivery. Thus, in some approaches one or more of the following panels is used to assess the likelihood of full-term, or preterm, delivery: (1) RGS18; DAPP1; PPBP; (2) RGS18; RAB27B; PPBP; (3) RGS18; MOB1B; PPBP; (4) RGS18; PPBP; MAP3K7CL; (5) RGS18; PPBP; CLCN3; (6) DAPP1; RAB27B; PPBP; (7) DAPP1; MOB1B; PPBP; (8) DAPP1; PPBP; CLCN3; (9) RAB27B; MOB1B; PPBP; (10) RAB27B; PPBP; MAP3K7CL; (11) RAB27B; PPBP; CLCN3; (12) MOB1B; PPBP; MAP3K7CL; and (13) MOB1B; PPBP; CLCN3.

We found that PPBP, DAPP1, and RAB27B were all individually elevated in women who delivered preterm in both the Pennsylvania and Alabama cohorts (FDR≤5%, Hedge's g≥0.8), demonstrating the robustness of their effect. The ranking the weight order (from highest to lowest) is RAB27B>PPBP>DAPP1>RGS18>(MOB1B, MAP3K7CL, and CLCN3).

In summary, we have discovered and validated a set of biomarkers which enables prediction of time to delivery for patients at risk of preterm delivery. Furthermore, our preterm delivery model suggests that the physiology of preterm delivery is distinct from normal development, forming the basis for the first screening or diagnostic test for risk of prematurity.

11.7 Example 7

Gene Combinations Meeting the Criterion of 75% True Positive Rate and Less Than 5% False Positive Rate Seven transcripts of interest RAB27B, PPBP, DAPP1, RGS18, MOB1B, MAP3K7CL, CLCN37 can be grouped in 35 unique combinations of genes. We filtered those combinations using the criterion of 75% true positive rate and less than 5% false positive rate. This yielded 13 combinations shown in TABLE 11. We generated an ROC curve to determine the which combinations predict risk of delivering preterm.

TABLE 11

| Combination | Gene 1 | Gene 2 | Gene 3 |
|---|---|---|---|
| 1 | RGS18 | DAPP1 | PPBP |
| 2 | RGS18 | RAB27B | PPBP |
| 3 | RGS18 | MOB1B | PPBP |
| 4 | RGS18 | PPBP | MAP3K7CL |
| 5 | RGS18 | PPBP | CLCN3 |
| 6 | DAPP1 | RAB27B | PPBP |
| 7 | DAPP1 | MOB1B | PPBP |
| 8 | DAPP1 | PPBP | CLCN3 |
| 9 | RAB27B | MOB1B | PPBP |
| 10 | RAB27B | PPBP | MAP3K7CL |
| 11 | RAB27B | PPBP | CLCN3 |
| 12 | MOB1B | PPBP | MAP3K7CL |
| 13 | MOB1B | PPBP | CLCN3 |

Each of these 13 combinations of 3 genes may be used as a panel for assessing risk of preterm delivery. Thus, in some embodiments a panel comprising one or more of the following combination of genes is used to determine of the following panels Thus, in some approaches a panel comprising one or more of the following combinations of genes is used to assess the likelihood of full-term, or preterm, delivery: (1) RGS18; DAPP1; PPBP; (2) RGS18; RAB27B; PPBP; (3) RGS18; MOB1B; PPBP; (4) RGS18; PPBP; MAP3K7CL; (5) RGS18; PPBP; CLCN3; (6) DAPP1; RAB27B; PPBP; (7) DAPP1; MOB1B; PPBP; (8) DAPP1; PPBP; CLCN3; (9) RAB27B; MOB1B; PPBP; (10) RAB27B; PPBP; MAP3K7CL; (11) RAB27B; PPBP; CLCN3; (12) MOB1B; PPBP; MAP3K7CL; and (13) MOB1B; PPBP; CLCN3.

11.8 Example 8

Body Mass Index (BMI) Does Not Affect Cell-Free RNA (cfRNA) Levels

We have tested for the effect of BMI on circulating cfRNA levels using estimated transcript counts of GAPDH per milliliter of plasma and found no significant difference between underweight (BMI<18.5), normal weight (18.5≤BMI<25), overweight (25≤BMI<30), and obese (BMI≥30) individuals both before and after Bonferroni correction using a Wilcoxon rank sum test.

P-values for distinct tests of GAPDH levels before and after Bonferroni correction, respectively, were as follows: (1) underweight versus normal weight (P=0.58, 1), underweight versus overweight (P=0.12, 0.80), underweight versus obese (P=0.26, 1), normal weight versus overweight (P=0.06, 0.35), normal weight versus obese (P=0.16, 0.95), and overweight versus obese (P=0.72, 1). Similar results were obtained for placental-specific cfRNAs such as CAPN6, CGA, and CGB.

All comparisons were done within cohorts so that differences in BMI distribution between cohorts were not confounding.

12. SELECTED REFERENCES

Altman, D. G., & Chitty, L. S. (1997). New charts for ultrasound dating of pregnancy. Ultrasound in Obstetrics & Gynecology, 10(3), 174-191. doi:10.1046/j.1469-0705.1997. 10030174.x Barr, W. B., & Pecci, C. C. (2004). Last menstrual period versus ultrasound for pregnancy dating. International Journal of Gynaecology and Obstetrics, 87(1), 38-39. doi: 10.1016 /j.ijgo.2004.06.008

Bennett, K. A., Crane, J. M. G., O'shea, P., Lacelle, J., Hutchens, D., & Copel, J. A. (2004). First trimester ultrasound screening is effective in reducing postterm labor induction rates: a randomized controlled trial. American Journal of Obstetrics and Gynecology, 190(4), 1077-1081. doi:10.1016/j.ajog.2003.09.065

Blencowe, H., Cousens, S., Chou, D., Oestergaard, M., Say, L., Moller, A.-B., . . . Born Too Soon Preterm Birth Action Group. (2013). Born too soon: the global epidemiology of 15 million preterm births. Reproductive Health, 10 Suppl 1, S2. doi:10.1186/1742-4755-10-S1-S2

Cocquebert, M., Berndt, S., Segond, N., Guibourdenche, J., Murthi, P., Aldaz-Carroll, L., . . . Fournier, T. (2012). Comparative expression of hCG β-genes in human trophoblast from early and late first-trimester placentas. American Journal of Physiology. Endocrinology and Metabolism, 303 (8), E950-8. doi:10.1152/ajpendo.00087.2012

Conde-Agudelo, A., & Romero, R. (2016). Vaginal progesterone to prevent preterm birth in pregnant women with a sonographic short cervix: clinical and public health implications. American Journal of Obstetrics and Gynecology, 214(2), 235-242. doi:10.1016/j.ajog.2015.09.102

Dugoff, L., Hobbins, J. C., Malone, F. D., Vidaver, J., Sullivan, L., Canick, J. A., . . . FASTER Trial Research Consortium. (2005). Quad screen as a predictor of adverse pregnancy outcome. Obstetrics and Gynecology, 106(2), 260-267. doi:10.1097/01.AOG.0000172419.37410.eb Hanson, A. E. (1987). The Eight Months' Child and the Etiquette of Birth: Obsit Omen! Bulletin of the History of Medicine.

Hanson, A. E. (1995). Paidopoiia: Metaphors for conception, abortion, and gestation in the Hippocratic Corpus. Clio Medica (Amsterdam, Netherlands).

Institute of Medicine (US) Committee on Understanding Premature Birth and Assuring Healthy Outcomes. (2007). Preterm Birth: Causes, Consequences, and Prevention. (R. E. Behrman & A. S. Butler, Eds.). Washington (DC): National Academies Press (US).

Jaffe, R. B., Lee, P. A., & Midgley, A. R. (1969). Serum gonadotropins before, at the inception of, and following human pregnancy. The Journal of Clinical Endocrinology and Metabolism, 29(9), 1281-1283. doi:10.1210/jcem-29-9-1281

Koh, W., Pan, W., Gawad, C., Fan, H. C., Kerchner, G. A., Wyss-Coray, T., . . . Quake, S. R. (2014). Noninvasive in vivo monitoring of tissue-specific global gene expression in humans. Proceedings of the National Academy of Sciences of the United States of America, 111(20), 7361-7366. doi: 10.1073/pnas.1405528111

Liu, L., Johnson, H. L., Cousens, S., Perin, J., Scott, S., Lawn, J. E., . . . Child Health Epidemiology Reference Group of WHO and UNICEF. (2012). Global, regional, and national causes of child mortality: an updated systematic analysis for 2010 with time trends since 2000. The Lancet, 379(9832), 2151-2161. doi:10.1016/S0140-6736(12) 60560-1

Lund, S. P., Nettleton, D., McCarthy, D. J., & Smyth, G. K. (2012). Detecting differential expression in RNA-sequence data using quasi-likelihood with shrunken dispersion estimates. Statistical Applications in Genetics and Molecular Biology, 11(5). doi:10.1515/1544-6115.1826

McCarthy, D. J., Chen, Y., & Smyth, G. K. (2012). Differential expression analysis of multifactor RNA-Seq experiments with respect to biological variation. Nucleic Acids Research, 40(10), 4288-4297. doi:10.1093/nar/gks042

Muglia, L. J., & Katz, M. (2010). The enigma of spontaneous preterm birth. The New England Journal of Medicine, 362(6), 529-535. doi:10.1056/NEJMra0904308

Murray, C. J. L., Vos, T., Lozano, R., Naghavi, M., Flaxman, A. D., Michaud, C., . . . et al. (2012). Disability-adjusted life years (DALYs) for 291 diseases and injuries in 21 regions, 1990-2010: a systematic analysis for the Global Burden of Disease Study 2010. The Lancet, 380(9859), 2197-2223. doi:10.1016/50140-6736(12)61689-4

Papageorghiou, A. T., Kemp, B., Stones, W., Ohuma, E. O., Kennedy, S. H., Purwar, M., . . . International Fetal and Newborn Growth Consortium for the 21st Century (INTERGROWTH-21st). (2016). Ultrasound-based gestational-age estimation in late pregnancy. Ultrasound in Obstetrics & Gynecology, 48(6), 719-726. doi:10.1002/uog.15894

Parker, H. (1999). Greek Embryological Calendars and a Fragment from the Lost Work of Damastes, on the Care of Pregnant Women and of Infants. The Classical Quarterly.

Robinson, M. D., McCarthy, D. J., & Smyth, G. K. (2010). edgeR: a Bioconductor package for differential expression analysis of digital gene expression data. Bioinformatics, 26(1), 139-140. doi:10.1093/bioinformatics/btp616

Robinson, M. D., & Smyth, G. K. (2008). Small-sample estimation of negative binomial dispersion, with applications to SAGE data. Biostatistics, 9(2), 321-332. doi: 10.1093/biostatistics/kxm030

Romero, R., Dey, S. K., & Fisher, S. J. (2014). Preterm labor: one syndrome, many causes. Science, 345(6198), 760-765. doi:10.1126/science.1251816

Rose, N. C., & Mennuti, M. T. (1993). Maternal serum screening for neural tube defects and fetal chromosome abnormalities. The Western Journal of Medicine, 159(3), 312-317.

Savitz, D. A., Terry, J. W., Dole, N., Thorp, J. M., Siega-Riz, A. M., & Herring, A. H. (2002). Comparison of pregnancy dating by last menstrual period, ultrasound scanning, and their combination. American Journal of Obstetrics and Gynecology, 187(6), 1660-1666. doi:10.1067/mob.2002.127601

Sweeney, T. E., Haynes, W. A., Vallania, F., Ioannidis, J. P., & Khatri, P. (2017). Methods to increase reproducibility in differential gene expression via meta-analysis. Nucleic Acids Research, 45(1), e1. doi:10.1093/nar/gkw797

Wald, N. J., & Hackshaw, A. K. (1997). Combining ultrasound and biochemistry in first-trimester screening for Down's syndrome. Prenatal Diagnosis, 17(9), 821-829. doi: 10.1002/(SICI)1097-0223(199709)17:9<821::AID-PD154>3.0.CO; 2-5

Ward, K., Argyle, V., Meade, M., & Nelson, L. (2005). The heritability of preterm delivery. Obstetrics and Gynecology, 106(6), 1235-1239. doi:10.1097/01.AOG.0000189091.35982.85

Whitworth, M., Bricker, L., & Mullan, C. (2015). Ultrasound for fetal assessment in early pregnancy. Cochrane Database of Systematic Reviews, (7), CD007058. doi: 10.1002/14651858.CD007058.pub3

Yefet, E., Kuzmin, O., Schwartz, N., Basson, F., & Nachum, Z. (2017). Predictive Value of Second-Trimester Biomarkers and Maternal Features for Adverse Pregnancy Outcomes. Fetal Diagnosis and Therapy. doi:10.1159/000458409

York, T. P., Strauss, J. F., Neale, M. C., & Eaves, L. J. (2009). Estimating fetal and maternal genetic contributions to premature birth from multiparous pregnancy histories of twins using MCMC and maximum-likelihood approaches. Twin Research and Human Genetics, 12(4), 333-342. doi: 10.1375/twin.12.4.333

Zhang, G., et al. (2017). Genetic Associations with Gestational Duration and Spontaneous Preterm Birth. The New England Journal of Medicine, 377(12), 1156-1167. doi: 10.1056/NEJMoa1612665

Rose and Mennuti (*Fetal Medicine, West J Med.,* 1993; 159:312-317)

Sweeney et al. (*J. Pediatric Infect. Dis. Soc.,* 2017, doi: 10.1093/jpids/pix021.)

13. TABLES 1-5

TABLE 1

PREDICTING TIME TO DELIVERY

| Gene | RefSeq | Gene ID | Tissue Specificity | Tissue | Function |
|---|---|---|---|---|---|
| CGA | NM_001252383.1 | 1081 | Yes | Placenta | Subunit of HCG |
| CAPN6 | NM_014289.3 | 827 | Yes | Placenta | Calcium-dependent cysteine protease |
| CGB | NM_000737.3 | 1082 | Yes | Placenta | Subunit of HCG |
| LGALS14 | NM_020129.2 | 56891 | Yes | Placenta | Carbohydrate recognition |
| PSG7 | NM_002783.2 | 5676 | Yes | Placenta | Immunoglobin-like proteins, known to be released into maternal circulation |
| ALPP | NM_001632.3 | 250 | Yes | Placenta | Alkaline phosphatase |
| CSHL1 | NM_001318.2 | 1444 | Yes | Placenta | Growth control, located at growth hormone locus, expressed in placental villi |
| PAPPA | NM_002581.3 | 5069 | Yes | Placenta | Metalloproteinase which cleaves insulin growth factors that can then bind IGF receptors |
| PLAC4 | NM_182832.2 | 191585 | Yes | Placenta | Expressed in placental syncytiotrophoblasts, associated with preeclampsia and trisomy 21 |
| ACTB | NM_001101.3 | 60 | No | | |
| HSD3B1 | NM_000862.2 | 3283 | Yes | Placenta | |
| S100A8 | NM_002964.4 | 6279 | Yes | Immune | Immune indicates bone marrow specificity |
| HAL | NM_002108.2 | 15109 | No | | |
| HSPB8 | NM_014365.2 | 26353 | No | | |
| VGLL1 | NM_016267.3 | 51442 | Yes | Placenta | |
| S100A9 | NM_002965.3 | 6280 | Yes | Immune | Immune indicates bone marrow specificity |
| ITIH2 | NM_002216.2 | 3698 | Yes | Liver | |
| ANXA3 | NM_005139.2 | 306 | Yes | Immune | |
| S100P | NM_005980.2 | 6286 | No | | |
| KNG1 | NM_000893.3 | 3827 | Yes | Liver | |
| CYP3A7 | NM_000765.3 | 1551 | Yes | Liver | |
| CSH1 | NM_001317.5 | 1442 | Yes | Placenta | |
| CAMP | NM_004345.4 | 820 | Yes | Immune | Immune indicates bone marrow specificity |
| OTC | NM_000531.5 | 5009 | Yes | Liver | |
| DCX | NM_000555.3 | 1641 | Yes | Brain | |
| FSTL3 | NM_005860.2 | 10272 | Yes | Placenta | |
| CSH2 | NM_022644.3 | 1443 | Yes | Placenta | |
| PLAC1 | NM_021796.3 | 10761 | Yes | Placenta | |

TABLE 1-continued

PREDICTING TIME TO DELIVERY

| Gene | RefSeq | Gene ID | Tissue Specificity | Tissue | Function |
|---|---|---|---|---|---|
| DEFA4 | NM_001925.1 | 1669 | Yes | Immune | Immune indicates bone marrow specificity |
| FABP1 | NM_001443.1 | 2168 | Yes | Liver | |
| SERPINA7 | NM_000354.5 | 6906 | Yes | Liver | |
| FRZB | NM_001463.3 | 2487 | No | | |
| SLC2A2 | NM_000340.1 | 6514 | Yes | Liver | |
| LTF | NM_001199149.1 | 4057 | Yes | Immune | Immune indicates bone marrow specificity |
| FGA | NM_000508.3 | 2243 | Yes | Liver | |
| SLC4A1 | NM_000342.3 | 6521 | Yes | Immune | Immune indicates bone marrow specificity |
| GNAZ | NM_002073.2 | 2781 | No | | |
| ADAM12 | NM_003474.4 | 8038 | Yes | Placenta | |
| GH2 | NM_022557.3 | 2689 | Yes | Placenta | |
| PSG1 | NM_006905.2 | 5669 | Yes | Placenta | |
| MMP8 | NM_002424.2 | 4317 | Yes | Immune | Immune indicates bone marrow specificity |
| FGB | NM_005141.4 | 2244 | Yes | Liver | |
| ARG1 | NM_001244438.1 | 383 | Yes | Liver | |
| MEF2C | NM_001131005.2 | 4208 | No | | |
| HSD17B1 | NM_000413.2 | 3292 | Yes | Placenta | |
| PSG4 | NM_002780.4 | 5672 | Yes | Placenta | |
| PGLYRP1 | NM_005091.2 | 8993 | Yes | Immune | Immune indicates bone marrow specificity |
| SLC38A4 | NM_018018.4 | 55089 | Yes | Liver | |
| EPB42 | NM_000119.2 | 2038 | Yes | Immune | Immune indicates bone marrow specificity |
| PTGER3 | NM_198717.1 | 5733 | No | | |

TABLE 2

PREDICTING PRETERM DELIVERY

| Gene | RefSeq | Gene ID | Tissue Specificity | Tissue | "Druggable?" | Function |
|---|---|---|---|---|---|---|
| TBC1D15 | NM__001146214 | 64786 | No | | Yes - involved in signalling | Encodes Ras-like protein. Regulator of intracellular traffic |
| RGS18 | NM__130782 | 64407 | No | | Yes - involved in signalling | Regulator of G-protein signaling |
| DAPP1 | NM__001306151 | 27071 | No | | Yes - involved in signalling | B-cell receptor signaling pathway |
| RAB27B | NM__004163 | 5874 | No | | Yes - involved in signalling | Prenylated, membrane bound proteins involved in vesicular fusion and trafficking |
| MOB1B | NM__001244766 | 92597 | No | | Yes - involved in cell cycle | Kinase essential for spindle pole body duplicaiton and mitotic checkpoint regulation |
| PPBP | NM__002704 | 5473 | Yes | Immune | Unclear | Platelet dereived growth factor |
| LYPLAL1 | NM__138794 | 127018 | No | | Unclear | Unknown, links to childhood obesity and hypertension |

TABLE 2-continued

| PREDICTING PRETERM DELIVERY | | | | | | |
|---|---|---|---|---|---|---|
| Gene | RefSeq | Gene ID | Tissue Specificity | Tissue | "Druggable?" | Function |
| MAP3K7CL | NM_001286617 | 56911 | No | | Unclear | Unknown |
| CLCN3 | NM_173872 | 1182 | No | | Probably not given its ubiquitous nature across cell types | Voltage-gated chloride channel present in all cell types |
| POLE2 | NM_002692 | 5427 | No | | Yes - involved in cell cycle | Involved in DNA repair and replication |
| CGB | NM_000737.3 | 1082 | Yes | Placenta | | |
| PKHD1L1 | NM_177531 | 93035 | Yes | Thyroid | | |
| APLF | NM_173545 | 200558 | No | | | |
| DGCR14 | NR_134304 | 8220 | Yes | Testis | | |
| MMD | NM_012329 | 23531 | Yes | Fat | | |
| VCAN | NM_004385 | 1462 | No | | | |
| P2RY12 | NM_022788 | 64805 | Yes | Brain | | |
| RAB11A | NM_004663 | 8766 | No | | | |
| FRMD4B | NM_015123 | 23150 | No | | | |
| PLAC4 | NM_182832.2 | 191585 | Yes | Placenta | | |
| ADAM12 | NM_003474.4 | 8038 | Yes | Placenta | | |
| CYP3A7 | NM_000765.3 | 1551 | Yes | Liver | | |
| VGLL1 | NM_016267.3 | 51442 | Yes | Placenta | | |
| GH2 | NM_022557.3 | 2689 | Yes | Placenta | | |
| CAPN6 | NM_014289.3 | 827 | Yes | Placenta | | |
| PSG4 | NM_002780.4 | 5672 | Yes | Placenta | | |
| RPL23AP7 | NR_024528 | 118433 | No | | | |
| ANXA3 | NM_005139.2 | 306 | Yes | Immune | | |
| HSPB8 | NM_014365.2 | 26353 | No | | | |
| PKHD1L1 | NM_177531 | 93035 | Yes | Thyroid | | |
| AVPR1A | NM_000706 | 552 | No | | | |
| KLF9 | NM_001206 | 687 | No | | | |
| CSHL1 | NM_001318.2 | 1444 | Yes | Placenta | | |
| PSG7 | NM_002783.2 | 5676 | Yes | Placenta | | |
| CGA | NM_001252383.1 | 1081 | Yes | Placenta | | |
| PAPPA | NM_002581.3 | 5069 | Yes | Placenta | | |
| PSG1 | NM_006905.2 | 5669 | Yes | Placenta | | |
| CSH2 | NM_022644.3 | 1443 | Yes | Placenta | | |
| LGALS14 | NM_020129.2 | 56891 | Yes | Placenta | | |
| KRT8 | NR_045962 | 3856 | No | | | |
| CD180 | NM_005582 | 4064 | No | | | |
| NFATC2 | NM_012340 | 4773 | No | | | |
| PLAC1 | NM_021796.3 | 10761 | Yes | Placenta | | |
| RAP1GAP | NM_001145657 | 5909 | No | | | |
| CAMP | NM_004345.4 | 820 | Yes | Immune | | |
| ENAH | NM_001008493 | 55740 | No | | | |
| CPVL | NM_019029 | 54504 | No | | | |
| ELANE | NM_001972 | 1991 | Yes | Immune | | |
| LTF | NM_001199149.1 | 4057 | Yes | Immune | | |
| PGLYRP1 | NM_005091.2 | 8993 | Yes | Immune | | |
| FAM212B-AS1 | NR_038951 | 100506343 | No | | | |
| Immune | indicates | bone | marrow | specificity | | |

TABLE 3

| Exemplary primer pairs. | | | | |
|---|---|---|---|---|
| Gene | SEQ ID NO: | Forward Primer | Reverse Primer | SEQ ID NO: |
| ACTB | 20 | CCAACCGCGAGAAGATGAC | TAGCACAGCCTGGATAGCAA | 21 |
| ADAM12 | 22 | TGAGAAAGGAGGCTGCATCA | CTGCTGCAACTGCTGAACA | 23 |
| AFP | 24 | GCCTCTTCCAGAAACTAGGAGAA | GGGGCTTTCTTTGTGTAAGCAA | 25 |
| ALPP | 26 | GACAGCTGCCAGGATCCTAA | GTCTGGCACATGTTTGTCTACA | 27 |
| ANXA1 | 28 | AAGTGCGCCACAAGCAAA | TGCCTTATGGCGAGTTCCA | 29 |
| ANXA3 | 30 | CAGCGGCAGCTGATTGTTAA | CAGAGAGATCACCCTTCAAGTCA | 31 |

TABLE 3-continued

Exemplary primer pairs.

| Gene | SEQ ID NO: | Forward Primer | Reverse Primer | SEQ ID NO: |
|---|---|---|---|---|
| APLF | 32 | ACCCAGATGACTCCCACAAA | CAAGGATTGGCTGCTGCTTA | 33 |
| APOA4 | 34 | AAGGCCGTGGTCCTGAC | TCAGCTGGCTGAAGTAGTCC | 35 |
| ARG1 | 36 | GCAAGGTGGCAGAAGTCAA | ATGGCCAGAGATGCTTCCA | 37 |
| AVPR1A | 38 | GCGCCTTTCTTCATCATCCA | GATGGTGATGGTAGGGTTTTCC | 39 |
| BPI | 40 | TCCTGGAACTGAAGCACTCA | GCAGCACAAGAATGGGTACA | 41 |
| CALCB | 42 | CCCCTTCCTGGCTCTCAGTA | GGTCTGGGCTGCTCTCCA | 43 |
| CAMP | 44 | GGACAGTGACCCTCAACCA | CAGCAGGGCAAATCTCTTGTTA | 45 |
| CAPN6 | 46 | TGGAAAGGTGGTGTGGAAAC | GTCAGCTGGTGGTTGCTAA | 47 |
| CCL20 | 48 | TGATGTCAGTGCTGCTACTCC | CTGTGTATCCAAGACAGCAGTCA | 49 |
| CD160 | 50 | CTCAGTTCAGGCTTCCTACA | TCTTTTGGCACAAGGCTTAC | 51 |
| CD180 | 52 | CACAATAGAACCTTCAGCAGAC | GAAAAGTGTCTTCATGTATCCAGTTA | 53 |
| CD2 | 54 | ATTCCAGCTTCAACCCCTCA | ATGACTAGGTGCCTGGGAAC | 55 |
| CD24 | 56 | CCAACTAATGCCACCACCAA | CGAAGAGACTGGCTGTTGAC | 57 |
| CD5 | 58 | CCCCTTGCCTACAAGAAGCTA | TCCCGTTGGGCCAATCC | 59 |
| CDK5R1 | 60 | AGCAAGAACGCCAAGGACAA | CGGCCACGATTCTCTTCCAA | 61 |
| CEACAM6 | 62 | AGATTGCATGTCCCCTGGAA | GGGTGGGTTCCAGAAGGTTA | 63 |
| CEACAM8 | 64 | TATGCCTGCCACACCACTAA | GCCAGGAGAACTTCCTTGTACTA | 65 |
| CGA | 66 | TCAACCGCCCTGAACACA | ACACCGACAATGTGACCAGAA | 67 |
| CGB | 68 | AGCCTTCCAAGCCCATCC | TGCGGATTGAGAAGCCTTTA | 69 |
| CLCN3 | 70 | CGTGGTCAGGATGGCTAGTA | CCAATCGGCAGCAATGTCTA | 71 |
| CNOT7 | 72 | GTCCTCTGTGAAGGGGTCAAA | TCTTCAGGCAAGTTAGAGTTGGTTA | 73 |
| COL17A1 | 74 | TGACAACCCAGAGCTCATCC | GGACGCCATGTTGTTTGGAA | 75 |
| COL21A1 | 76 | CGTCCAGGTGTCAGAGGATTA | ACCTTGTTCTCCAGGATACCC | 77 |
| CPVL | 78 | TGAAGTGGCTGGTTACATCC | AGAGGCTGGTCATAGGGTAA | 79 |
| CRP | 80 | GTCTTGACCAGCCTCTCTCA | ACGGTGCTTTGAGGGATACA | 81 |
| CSH1 | 82 | ACAAGAGACCGGCTCTAGGA | TTGCCACTAGGTGAGCTGTC | 83 |
| CSH2 | 84 | CGTTCCGTTATCCAGGCTTTT | ACTCCTGGTAGGTGTCAATGG | 85 |
| CSHL1 | 86 | TTAGAGCTGCTCCACATCTCC | ACCAGGTTGTTGGTGAAGGTA | 87 |
| CUX2 | 88 | TCCATCACCAAGAGGGTGAA | CAGGATGCTTTCCCCAAACA | 89 |
| CYP3A7 | 90 | ACGTGCATTGTGCTCTCTCA | CAGCACTGATTTGGTCATCTCC | 91 |
| DAPP1 | 92 | TGGGCACCAAAGAAGGTTA | TTCCTGTGCAGAGTAAACCA | 93 |
| DCX | 94 | ATCTCTACGCCCACCAGTCC | AGCGAGTCCGAGTCATCCAA | 95 |
| DEFA3 | 96 | GACGAAAGCTTGGCTCCAAA | GTTCCATAGCGACGTTCTCC | 97 |
| DEFA4 | 98 | TGGGATAAAAGCTCTGCTCTTCA | TGTTCGCCGGCAGAATACTA | 99 |
| DGCR14 | 100 | ACAAGGCCAAGAATTCCCTCA | TGCCGGGGCTTCTTAAACA | 101 |
| DLX2 | 102 | TTCGTCCCCAGCCAACAA | TGGCTTCCCGTTCACTATCC | 103 |
| EGFR | 104 | GCAGTGACTTTCTCAGCAACA | TTGGGACAGCTTGGATCACA | 105 |

TABLE 3-continued

Exemplary primer pairs.

| Gene | SEQ ID NO: | Forward Primer | Reverse Primer | SEQ ID NO: |
|---|---|---|---|---|
| ELANE | 106 | CTCTGCCGTCGCAGCAA | TGGATTAGCCCGTTGCAGAC | 107 |
| ENAH | 108 | GCCGGAGCAAAACTTAGGAAA | AGGCGGAGTTCACACCAATA | 109 |
| EPB42 | 110 | GCCAAGCTCTGGAGGAAGAA | GAGAAGAACAGGCCGATGGTTA | 111 |
| EPOR | 112 | ATCCTGGTGCTGCTGAC | GGCCAGATCTTCTGCTTCA | 113 |
| EPX | 114 | AGTTCAGAAGAGCCCGAGAC | GCGCTGTCTTTTGGTGAAAAC | 115 |
| EVX1 | 116 | TACCGGGAGAACTACGTATCCA | ATGCGCCGGTTCTGGAA | 117 |
| FABP1 | 118 | AGGAATGTGAGCTGGAGACA | TTGTCACCTTCCAACTGAACC | 119 |
| FABP7 | 120 | GCTACCTGGAAGCTGACCAA | CCACCTGCCTAGTGGCAAA | 121 |
| FAM212B-AS1 | 122 | GGAAAGGGGTGGATGTGTCA | CACCCAGGATGTCCTTGTTCTA | 123 |
| FGA | 124 | ATGTTAGAGCTCAGTTGGTTGATA | TACTGCATGACCCTCGACAA | 125 |
| FGB | 126 | ATATTGTCGCACCCCATGCA | ACCTCCTTTCCTGATAATTTCCTCAC | 127 |
| FOXG1 | 128 | GCCAGCAGCACTTTGAGTTA | TGAGTCAACACGGAGCTGTA | 129 |
| FRMD4B | 130 | GAAACCCAGCCAGAAAGCAA | AGGTGGTGGTGTCAGACAAA | 131 |
| FRZB | 132 | CCTCTGCCCTCCACTTAATGTTA | CAGCTATAGAGCCTTCCACCAA | 133 |
| FSTL3 | 134 | CCGGACCTGAGCGTCATGTA | GCACACCACGTGCTCACA | 135 |
| GAPDH | 136 | GAACGGGAAGCTTGTCATCAA | ATCGCCCCACTTGATTTTGG | 137 |
| GCA | 138 | TCAGTTTGGAAACCTGCAGAA | GCTGCCCATAGCTCTTTGAA | 139 |
| GH2 | 140 | CCCGTCGCCTGTACCA | TGTTGGAATAGACTCTGAGAAGCA | 141 |
| GNAZ | 142 | CGGCTACGACCTGAAACTCTA | TGAGTGAGGTGTTGATGAACCA | 143 |
| GPR116 | 144 | CCAGAGGCAGTGCAAACATAA | AGAAATTGGGTCCGGGGTTA | 145 |
| GRHL2 | 146 | ACTCCGGACAGCACATACA | CCAACTGAAGCACTCCGAAA | 147 |
| GSN | 148 | AAGACCTGGCAACGGATGAC | TTGAGAATCCTTTCCAACCCAGAC | 149 |
| GYPB | 150 | ACAACTTGTCCATCGTTTCAC | ACCAGCCATCACACACAA | 151 |
| HAL | 152 | AGAACTGAACAGCGCAACA | GCTGGGTATTCACCATGGAA | 153 |
| HBG2 | 154 | GGTGACCGTTTTGGCAATCC | CACTGGCCACTCCAGTCAC | 155 |
| HIST1H2BM | 156 | GCCTGGCGCATTACAACAA | CAATTCCCCGGGTAGCAGTA | 157 |
| HMGB3 | 158 | CGGCAAAGCTGAAGGAGAAGTA | CAGGACCCTTTGCACCATCA | 159 |
| HMGN2 | 160 | ACACAGTGCTAGGTGCAGTTA | TCCATACTCCCAGCCTTTCAC | 161 |
| HS6ST1 | 162 | AAGTTCATCCGGCCCTTCA | GGTGTCTTCATCCACCTCCA | 163 |
| HSD17B1 | 164 | TGGACGTAAGGGACTCAAAATCC | CCCAGGCCTGCGTTACA | 165 |
| HSD3B1 | 166 | TGTGCCTTACGACCCATGTA | GTTGTTCAGGGCCTCGTTTA | 167 |
| HSPB8 | 168 | GCAAGAAGGTGGCATTGTTTCTA | TCTGGGGAAAGTGAGGCAAA | 169 |
| ITIH2 | 170 | AGAGAAGAGAAGGCTGGTGAAC | TCCAGGTTGTCAGGAGCAAA | 171 |
| KLF9 | 172 | TCCCATCTCAAAGCCCATTACA | CTCGTCTGAGCGGGAGAA | 173 |
| KNG1 | 174 | CTGGCAGGACTGTGAGTACAA | ATTTCGTACTGCTCCTCTTCCC | 175 |
| KRT8 | 176 | TGACCGACGAGATCAACTTCC | TGTGCCTTGACCTCAGCAA | 177 |
| KRT81 | 178 | TGAAGGCATTGGGGCTGTG | AGCCTGACACGCAGAGGT | 179 |

TABLE 3-continued

Exemplary primer pairs.

| Gene | SEQ ID NO: | Forward Primer | Reverse Primer | SEQ ID NO: |
|---|---|---|---|---|
| LGALS14 | 180 | TGTGCATCTATGTGCGTCAC | GGAATCGATGGGCAAAGTTGTA | 181 |
| LHX2 | 182 | CAAAAGACGGGCCTCACCAA | CGTAAGAGGTTGCGCCTGAA | 183 |
| LIPC | 184 | CATCGGTGGAACGCACAA | GGGCACTTCCCTCAAACAAA | 185 |
| LRRN3 | 186 | GCCTTGGTTGGACTGGAAAA | TTTGAAGAGCAACATGGGGTAC | 187 |
| LTF | 188 | CTCCCAGGAACCGTACTTCA | CTCTGATAAAAGCCACGTCTCC | 189 |
| LYPLAL1 | 190 | CATCAAGATGTGGCAGGAGTA | TGCAGTACCATGACACTGAAATA | 191 |
| MAP3K7CL | 192 | GACTCCATTCCTTTGGTTTTTTCC | CCATGGATTCCTCGGAGTCA | 193 |
| MEF2C | 194 | TGGTCTGATGGGTGGAGACC | TGAGTTTCGGGGATTGCCATAC | 195 |
| MMD | 196 | TCTCACAATGGGATTCTCTCCA | CAGGCAAGTTCCTGAAGTCC | 197 |
| MMP8 | 198 | TGCCGAAGAAACATGGACCAA | AGCCCCAAAGAATGGCCAAA | 199 |
| MN1 | 200 | AGAAGGCCAAACCCCAGAA | ATGCTGAGGCCTTGTTTGC | 201 |
| MOB1B | 202 | GAGAGTTGTCCAGTGATGTCA | GTCCTGAACCCAAGTCATCA | 203 |
| MPO | 204 | CATCGGTACCCAGTTCAGGAA | TGCTGCATGCTGAACACAC | 205 |
| NFATC1 | 206 | TCCTCTCCAACACCAAAGTCC | AGGATTCCGGCACAGTCAA | 207 |
| NFATC2 | 208 | TGGAAGCCACGGTGGATAA | TGTGCGGATATGCTTGTTCC | 209 |
| NPY1R | 210 | TCTGCTCCCTTCCATTCCC | GAATTCTTCATTCCCTTGAACTGAAC | 211 |
| NTSR1 | 212 | CGCCTCATGTTCTGCTACA | TAGAAGAGTGCGTTGGTCAC | 213 |
| OAZ1 | 214 | CGAGCCGACCATGTCTTCA | AAGCTGAAGGTTCGGAGCAA | 215 |
| OTC | 216 | CCAGGCTTTCCAAGGTTACCA | TGGCTTTCTGGGCAAGCA | 217 |
| P2RY12 | 218 | ACTGGATACATTCAAACCCTCCA | TGGTGCACAGACTGGTGTTA | 219 |
| PAPPA | 220 | GTACTGTGGCGATGGCATTATAC | AGAAAAGGGAGCAGCCATCA | 221 |
| PAPPA2 | 222 | ACAGTGGAAGCCTGGGTTAA | ACAGTGTGGGAGCAGTTATCA | 223 |
| PCDH11X | 224 | CTGGCATCCAGTTGACGAAA | CATCAGGGCCTAGCAGGTAA | 225 |
| PGLYRP1 | 226 | GTGCAGCACTACCACATGAA | TATACGAGCCCGTCTTCTCC | 227 |
| PKHD1L1 | 228 | GCCAGCTGCTATATCACACAAA | AAACCCAGGGCTACTTCCAA | 229 |
| PLAC1 | 230 | GCCACATTTCAAAGGAAACTGAC | TCCCTGCAGCCAATCAGATA | 231 |
| PLAC4 | 232 | CCACCAAGAAGCCACTTTCC | TACCAGCAATGCCAGGGTTA | 233 |
| POLE2 | 234 | AGAAACTGCGTCCGTTTTCC | GGAGTCAGATGTCCTTGGGATAA | 235 |
| POU3F2 | 236 | CGGATCAAACTGGGATTTACCC | CGAGAACACGTTGCCATACA | 237 |
| PPBP | 238 | TCTGGCTTCCTCCACCAAA | CAGCGGAGTTCAGCATACAA | 239 |
| PRDX5 | 240 | GTTCGGCTCCTGGCTGAT | CAAAGATGGACACCAGCGAATC | 241 |
| PRG2 | 242 | GGGGCAGTTTCTGCTCTTCA | TCATCCTCAGGCAGCGTCTTA | 243 |
| PSG1 | 244 | GCAGGATCCTACACCTTACACA | TGCTGGAGATGGAGGGCTTA | 245 |
| PSG2 | 246 | CTGGCGAGGAAAGCTCCA | CAGAAATGACATCACAGCTGCTA | 247 |
| PSG4 | 248 | CTCCCCAGCATTTACCCTTCA | GGTTAGACTCGGCGAAGCA | 249 |
| PSG7 | 250 | ACCCAGTCACCCTGAATGTC | GCAGGACAAGTAGAGGTTTTGTC | 251 |
| PTGER3 | 252 | GTCGGTCTGCTGGTCTCC | TGTGTCTTGCAGTGCTCAAC | 253 |

TABLE 3-continued

| Exemplary primer pairs. | | | | |
|---|---|---|---|---|
| Gene | SEQ ID NO: | Forward Primer | Reverse Primer | SEQ ID NO: |
| RAB11A | 254 | AGGCACAGATATGGGACACA | ATAAGGCACCTACAGCTCCA | 255 |
| RAB27B | 256 | ACCAGATCAGAGGGAAGTCA | CAGTTGCTGCACTTGTTTCA | 257 |
| RAP1GAP | 258 | GGAAGCAGGATGGATGAACA | CTCGGGTATGGAATGTAGTCC | 259 |
| RGS18 | 260 | TGAAGACACCCGCTCCAGTA | CCCCATTTCACTGCCTCTTCA | 261 |
| RHCE | 262 | TGGGAAGGTGGTCATCACAC | CAGCACCCGCTGAGATCA | 263 |
| RNASE2 | 264 | GCCAAGATCCCATCTCTCCA | AGGCACTTCAGCTCAGGAAA | 265 |
| RPL23AP7 | 266 | CTGGCTGTGGGTGTGGTACT | CGCTCCACTCCCTCTAGGC | 267 |
| S100A8 | 268 | GCTAGAGACCGAGTGTCCTCA | CCAGAATGAGGAACTCCTGGAA | 269 |
| S100A9 | 270 | TCAAAGAGCTGGTGCGAAAA | ATTTGTGTCCAGGTCCTCCA | 271 |
| S100P | 272 | GAAGGAGCTACCAGGCTTCC | AGCAATTTATCCACGGCATCC | 273 |
| SAMD9 | 274 | CTTCGAGAAGTCTTGCAACC | GCCAGAATAAGAGGGAAGCTA | 275 |
| SATB2 | 276 | TTTGCCAAAGTGGCTGCAAA | TTTCTGGGCTTGGGTTCTCC | 277 |
| SEMA3B | 278 | TGCACCAGTGGGTGTCATA | GTGGAACTGAAGGTGCCAAA | 279 |
| SERPINA7 | 280 | AGAAGTGGAACCGCTTACTACA | AGTGTGGCTCCAAGGTCATA | 281 |
| SLC12A8 | 282 | GCTGCCATCGTGTATTTCTACA | AGACCTCATCCACCGGAAAA | 283 |
| SLC2A2 | 284 | GGGAGCACTTGGCACTTTTCA | GCAGGATGTGCCACAGATCA | 285 |
| SLC38A4 | 286 | GGTCCTTCCCATCTACAGTGAA | AGCATCCCCGTGATGGAAATA | 287 |
| SLC4A1 | 288 | TGCTGCCGCTCATCTTCA | CAAAGGTTGCCTTGGCATCA | 289 |
| SLITRK3 | 290 | GACCTGGCGCTCCAGTTTA | CCTCTGTGAAGCATCTCAGCTA | 291 |
| TBC1D15 | 292 | AAGACGGCTTGATTTCAGGAA | GCATCATCCAATGGTCTCCA | 293 |
| TFIP11 | 294 | TGTTAAGCAGGACGACTTTCC | CCTTTCTGGCTGGGCTTAAA | 295 |
| VCAN | 296 | GGTGCCTCTGCCTTCCAA | TTGTGCCAGCCATAGTCACA | 297 |
| VGLL1 | 298 | AGAGTGAAGGTGTGATGCTGAA | GCACGGTTTGTGACAGGTAC | 299 |

TABLE 4

Key: "Forward" Forward primer comprises sequence corresponding to bases a-b of SEQ ID NO: X. E.g., Forward primer comprises bases 30-45 of SEQ ID NO: 1. "Reverse" Reverse primer comprises reverse complement of sequence corresponding to bases c-d of SEQ ID NO: X.E.g., Reverse primer comprises reverse complement of bases 500-520 of SEQ ID NO: 1.

| Gene | SEQ ID NO: X | Exemplary Primer Pair A | | Exemplary Primer Pair B | | Exemplary Primer Pair C | |
|---|---|---|---|---|---|---|---|
| | | FORWARD | REVERSE | FORWARD | REVERSE | FORWARD | REVERSE |
| CGA mRNA transcript 861 bp | 1 | 30-45 | 500-520 | 45-60 | 400-420 | 100-120 | 600-620 |
| CAPN6 mRNA transcript 3604 bp | 2 | 30-45 | 500-520 | 45-60 | 400-420 | 100-120 | 600-620 |
| CGB mRNA transcript 933 bp | 3 | 30-45 | 500-520 | 45-60 | 400-420 | 100-120 | 600-620 |
| ALPP mRNA transcript 2883 bp | 4 | 30-45 | 500-520 | 45-60 | 400-420 | 100-120 | 600-620 |
| CSHL1 mRNA transcript 661 bp | 5 | 30-45 | 500-520 | 45-60 | 400-420 | 100-120 | 600-620 |
| PLAC4 mRNA transcript 10009 bp | 6 | 30-45 | 500-520 | 45-60 | 400-420 | 100-120 | 600-620 |
| PSG7 mRNA transcript 2046 bp | 7 | 30-45 | 500-520 | 45-60 | 400-420 | 100-120 | 600-620 |
| PAPPA mRNA transcript 11025 bp | 8 | 30-45 | 500-520 | 45-60 | 400-420 | 100-120 | 600-620 |
| LGALS14 mRNA transcript 794 bp | 9 | 30-45 | 500-520 | 45-60 | 400-420 | 100-120 | 600-620 |
| CLCN3 mRNA transcript 6299 bp | 10 | 30-45 | 500-520 | 45-60 | 400-420 | 100-120 | 600-620 |
| DAPP1 mRNA transcript 3006 bp | 11 | 30-45 | 500-520 | 45-60 | 400-420 | 100-120 | 600-620 |
| POLE2 mRNA transcript 1861 bp | 12 | 30-45 | 500-520 | 45-60 | 400-420 | 100-120 | 600-620 |

TABLE 4-continued

Key: "Forward" Forward primer comprises sequence corresponding to bases a-b of SEQ ID NO: X. E.g., Forward primer comprises bases 30-45 of SEQ ID NO: 1. "Reverse" Reverse primer comprises reverse complement of sequence corresponding to bases c-d of SEQ ID NO: X.E.g., Reverse primer comprises reverse complement of bases 500-520 of SEQ ID NO: 1.

| | SEQ ID | Exemplary Primer Pair A | | Exemplary Primer Pair B | | Exemplary Primer Pair C | |
|---|---|---|---|---|---|---|---|
| Gene | NO: X | FORWARD | REVERSE | FORWARD | REVERSE | FORWARD | REVERSE |
| PPBP mRNA transcript 1307 bp | 13 | 30-45 | 500-520 | 45-60 | 400-420 | 100-120 | 600-620 |
| LYPLAL1 mRNA transcript 1922 bp | 14 | 30-45 | 500-520 | 45-60 | 400-420 | 100-120 | 600-620 |
| MAP3K7CL mRNA transcript 2269 bp | 15 | 30-45 | 500-520 | 45-60 | 400-420 | 100-120 | 600-620 |
| MOB1B mRNA transcript 7091 bp | 16 | 30-45 | 500-520 | 45-60 | 400-420 | 100-120 | 600-620 |
| RAB27B mRNA transcript 7003 bp | 17 | 30-45 | 500-520 | 45-60 | 400-420 | 100-120 | 600-620 |
| RGS18 mRNA transcript 2158 bp | 18 | 30-45 | 500-520 | 45-60 | 400-420 | 100-120 | 600-620 |
| TBC1D15 mRNA transcript 5852 bp | 19 | 30-45 | 500-520 | 45-60 | 400-420 | 100-120 | 600-620 |

TABLE 5

Key: Probe comprises sequence corresponding to bases a-b of SEQ ID NO: X. or the complement thereof

| Gene | SEQ ID NO: X | Exemplary Probe A | Exemplary Probe B | Exemplary Probe C |
|---|---|---|---|---|
| CGA mRNA transcript 861 bp | 1 | 100-140 | 200-240 | 300-340 |
| CAPN6 mRNA transcript 3604 bp | 2 | 100-140 | 200-240 | 300-340 |
| CGB mRNA transcript 933 bp | 3 | 100-140 | 200-240 | 300-340 |
| ALPP mRNA transcript 2883 bp | 4 | 100-140 | 200-240 | 300-340 |
| CSHL1 mRNA transcript 661 bp | 5 | 100-140 | 200-240 | 300-340 |
| PLAC4 mRNA transcript 10009 bp | 6 | 100-140 | 200-240 | 300-340 |
| PSG7 mRNA transcript 2046 bp | 7 | 100-140 | 200-240 | 300-340 |
| PAPPA mRNA transcript 11025 bp | 8 | 100-140 | 200-240 | 300-340 |
| LGALS14 mRNA transcript 794 bp | 9 | 100-140 | 200-240 | 300-340 |
| CLCN3 mRNA transcript 6299 bp | 10 | 100-140 | 200-240 | 300-340 |
| DAPP1 mRNA transcript 3006 bp | 11 | 100-140 | 200-240 | 300-340 |
| POLE2 mRNA transcript 1861 bp | 12 | 100-140 | 200-240 | 300-340 |
| PPBP mRNA transcript 1307 bp | 13 | 100-140 | 200-240 | 300-340 |
| LYPLAL1 mRNA transcript 1922 bp | 14 | 100-140 | 200-240 | 300-340 |
| MAP3K7CL mRNA transcript 2269 bp | 15 | 100-140 | 200-240 | 300-340 |
| MOB1B mRNA transcript 7091 bp | 16 | 100-140 | 200-240 | 300-340 |
| RAB27B mRNA transcript 7003 bp | 17 | 100-140 | 200-240 | 300-340 |
| RGS18 mRNA transcript 2158 bp | 18 | 100-140 | 200-240 | 300-340 |
| TBC1D15 mRNA transcript 5852 bp | 19 | 100-140 | 200-240 | 300-340 |

TABLE 6

LIST OF EXEMPLARY mRNA TRANSCRIPTS:

| SEQ ID NO: | Specification Identity | Accession No. |
|---|---|---|
| 1 | CGA mRNA transcript 861 bp | NM_001252383.1 |
| 2 | CAPN6 mRNA transcript 3604 bp | NM_014289.3 |
| 3 | CGB mRNA transcript 933 bp | NM_000737.3 |
| 4 | ALPP mRNA transcript 2883 bp | NM_001632.3 |
| 5 | CSHL1 mRNA transcript 661 bp | NM_001318.2 |
| 6 | PLAC4 mRNA transcript 10009 bp | NM_182832.2 |
| 7 | PSG7 mRNA transcript 2046 bp | NM_002783.2 |
| 8 | PAPPA mRNA transcript 11025 bp | NM_002581.3 |
| 9 | LGALS14 mRNA transcript 794 bp | NM_020129.2 |
| 10 | CLCN3 mRNA transcript 6299 bp | NM_173872 |
| 11 | DAPP1 mRNA transcript 3006 bp | NM_001306151 |
| 12 | POLE2 mRNA transcript 1861 bp | NM_002692 |
| 13 | PPBP mRNA transcript 1307 bp | NM_002704 |
| 14 | LYPLAL1 mRNA transcript 1922 bp | NM_138794 |
| 15 | MAP3K7CL mRNA transcript 2269 bp | NM_001286617 |
| 16 | MOB1B mRNA transcript 7091 bp | NM_001244766 |
| 17 | RAB27B mRNA transcript 7003 bp | NM_004163 |
| 18 | RGS18 mRNA transcript 2158 bp | NM_130782 |
| 19 | TBC1D15 mRNA transcript 5852 bp | NM_001146214 |

TABLE 7

SEQUENCES OF EXEMPLARY mRNA TRANSCRIPTS:

CGA mRNA transcript 861 bp

SEQ ID NO: 1

```
   1 acactctgct ggtataaaag caggtgagga cttcattaac tgcagttact gagaactcat
  61 aagacgaagc taaaatccct cttcggatcc acagtcaacc gccctgaaca catcctgcaa
 121 aaagcccaga gaaaggagcg ccatggatta ctacagaaaa tatgcagcta tctttctggt
 181 cacattgtcg gtgtttctgc atgttctcca ttccgctcct gatgtgcagg agacagggtt
 241 tcaccatgtt gcccaggctg ctctcaaact cctgagctca agcaatccac ccactaaggc
 301 ctcccaaagt gctaggatta cagattgccc agaatgcacg ctacaggaaa acccattctt
 361 ctcccagccg ggtgccccaa tacttcagtg catgggctgc tgcttctcta gagcatatcc
 421 cactccacta aggtccaaga agacgatgtt ggtccaaaag aacgtcacct cagagtccac
 481 ttgctgtgta gctaaatcat ataacagggt cacagtaatg gggggtttca aagtggagaa
 541 ccacacggcg tgccactgca gtacttgtta ttatcacaaa tcttaaatgt tttaccaagt
 601 gctgtcttga tgactgctga ttttctggaa tggaaaatta agttgtttag tgtttatggc
 661 tttgtgagat aaaactctcc ttttccttac cataccactt tgacacgctt caaggatata
 721 ctgcagcttt actgccttcc tccttatcct acagtacaat cagcagtcta gttcttttca
 781 tttggaatga atacagcatt tagcttgttc cactgcaaat aaagcctttt aaatcatcat
 841 tcaaaaaaaa aaaaaaaaaa a
```

CAPN6 mRNA transcript 3604 bp

SEQ ID NO: 2

```
   1 gagcagagct tggtacagcc caaatagttt tcaggttaag aaagccagaa tctttgttca
  61 gccacactga ctgaacagac ttttagtggg gttacctggc taacagcagc agcggcaacg
 121 gcagcagcag cagcagcagc agcagcagca gcagcagggc tcctgggata actcaggcat
 181 agttcaacac tatgggtcct cctctgaagc tcttcaaaaa ccagaaatac caggaactga
 241 agcaggaatg catcaaagac agcagacttt tctgtgatcc aacatttctg cctgagaatg
 301 attctctttt ctacaaccga ctgcttcctg gaaaggtggt gtggaaacgt ccccaggaca
 361 tctgtgatga cccccatctg attgtgggca acattagcaa ccaccagctg acccaaggga
 421 gactggggca caagccaatg gtttctgcat tttcctgttt ggctgttcag gagtctcatt
 481 ggacaaagac aattcccaac cataaggaac aggaatggga ccctcaaaaa acagaaaaat
 541 acgctgggat atttcacttt cgtttctggc attttggaga atggactgaa gtggtgattg
 601 atgacttgtt gcccaccatt aacggagatc tggtcttctc tttctccact tccatgaatg
 661 agttttggaa tgctctgctg gaaaaagctt atgcaaagct gctaggctgt tatgaggccc
 721 tggatggttt gaccatcact gatattattg tggacttcac gggcacattg gctgaaactg
 781 ttgacatgca gaaaggaaga tacactgagc ttgttgagga gaagtacaag ctattcggag
 841 aactgtacaa aacatttacc aaaggtggtc tgatctgctg ttccattgag tctcccaatc
 901 aggaggagca agaagttgaa actgattggg gtctgctgaa gggccatacc tataccatga
 961 ctgatattcg caaaattcgt cttggagaga gacttgtgga agtcttcagt gctgagaagg
1021 tgtatatggt tcgcctgaga aaccccttgg gaagacagga atggagtggc ccctggagtg
1081 aaatttctga agagtggcag caactgactg catcagatcg caagaacctg gggcttgtta
1141 tgtctgatga tggagagttt tggatgagct tggaggactt ttgccgcaac tttcacaaac
1201 tgaatgtctg ccgcaatgtg aacaacccta tttttggccg aaaggagctg gaatcggtgt
1261 tgggatgctg gactgtggat gatgatcccc tgatgaaccg ctcaggaggc tgctataaca
```

TABLE 7-continued

| SEQUENCES OF EXEMPLARY mRNA TRANSCRIPTS: |
| --- |
| 1321 accgtgatac cttcctgcag aatccccagt acatcttcac tgtgcctgag gatgggcaca |
| 1381 aggtcattat gtcactgcag cagaaggacc tgcgcactta ccgccgaatg ggaagacctg |
| 1441 acaattacat cattggcttt gagctcttca aggtggagat gaaccgcaaa ttccgcctcc |
| 1501 accacctcta catccaggag cgtgctggga cttccaccta tattgacacc cgcacagtgt |
| 1561 ttctgagcaa gtacctgaag aagggcaact atgtgcttgt cccaaccatg ttccagcatg |
| 1621 gtcgcaccag cgagtttctc ctgagaatct tctctgaagt gcctgtccag ctcagggaac |
| 1681 tgactctgga catgcccaaa atgtcctgct ggaacctggc tcgtggctac ccgaaagtag |
| 1741 ttactcagat cactgttcac agtgctgagg acctggagaa gaagtatgcc aatgaaactg |
| 1801 taaacccata tttggtcatc aaatgtggaa aggaggaagt ccgttctcct gtccagaaga |
| 1861 atacagttca tgccattttt gacacccagg ccattttcta cagaaggacc actgacattc |
| 1921 ctattatagt acaggtctgg aacagccgaa aattctgtga tcagttcttg gggcaggtta |
| 1981 ctctggatgc tgaccccagc gactgccgtg atctgaagtc tctgtacctg cgtaagaagg |
| 2041 gtggtccaac tgccaaagtc aagcaaggcc acatcagctt caaggttatt tccagcgatg |
| 2101 atctcactga gctctaaatc tgcaatccca gagaatcctg acaaagcgtg ccaccctttt |
| 2161 attttccgtc aggtgccagg tcttagttaa gattcacaat ctttagaaag aatgagattc |
| 2221 acaataatta actcttcctc tcttctgata aattccccat acctcccaat ccaagtagca |
| 2281 tctgtagcta cataacctat atacctccag cagctggaca tggggaggcg acagtcctat |
| 2341 ctagacatca tacacatttg ccaagaaagg atctctgggg cttccggggg tgagattcaa |
| 2401 gcaggacaat aacaagaggc tggacaccct acagatgtct ttgatgtttt cagttgtttg |
| 2461 atatatctcc cctgtagggc atgttgagga aggaggaggg ctgatcaagg ccaagctggt |
| 2521 ctagcctgac atcctagctc ctgactgaac actatagact tcccagcagc atttcaccca |
| 2581 gcagccagag ccggctttaa gtccccaacc cttacagaca ccactgccac caccaccaac |
| 2641 cacgaccacc accaccacca ccactcacca ccatcatcac ctccggaaag tgtagtcctg |
| 2701 ccctaaccca agtcaccccc gacagtaaat tttaccttca tgttgagaaa gcttcctggt |
| 2761 gcttaatcaa gagctggagt tcaatgagtc ctagacagtg agaggggcct gagcttcagc |
| 2821 tcaatggaag cctgctgtgt gccacaagac ggaaaagtgg aagaagctgc agtgggagac |
| 2881 aaagcctcgg tcccccaccc atccacacac acctacactc acacacgcgc acatgggcgc |
| 2941 gcacgaacta ccattcaggc agtcagtggg caagaggaaa gataagtaag taccatacac |
| 3001 acctaaaaga tgagagaatt catccagaca tattacagcc agtttggggc ccctgactgc |
| 3061 aatgtgaaac ctctcgctgc tgctaggttt acaaacaagc ccattgtcct gtgcctccta |
| 3121 atatcatttg tactgaagac cccatctggg gacttgagac tttggtccca gcccagactc |
| 3181 ctcagacttt tctctcagtt gggatgcttc actcgctggg ggtgtttgtt tgccctctca |
| 3241 tttttcagta cttctacaga attttctcta gagtcagtca ttatgaaatg tacttccctc |
| 3301 catcttaacc tatcaacttt ctgcccctcc ttcaaggccc agtataaatg ccacctcctc |
| 3361 catgaagcct tccctaattc caccccaaac ccccaccttc aacaatattt caacgcttct |
| 3421 gcaatgatga aaaagaaaca tagttgtagt acttagccta cctagaccag caagcattca |
| 3481 tttttagctc gctcattttt taccatgttt tccagtctgt ttaacttctg cagtgccttc |
| 3541 actacactgc cttacataaa ccaaatcaca ataaagttca tattcagtac attgaaaaaa |
| 3601 aaaa |

TABLE 7-continued

SEQUENCES OF EXEMPLARY mRNA TRANSCRIPTS:

CGB mRNA transcript 933 bp

SEQ ID NO: 3

```
  1 tgcaggaaag cctcaagtag aggagggttg aggcttcagt ccagcacctt tctcgggtca
 61 cggcctcctc ctggctccca ggaccccacc ataggcagag gcaggccttc ctacacccta
121 ctccctgtgc ctccagcctc gactagtccc tagcactcga cgactgagtc tctgaggtca
181 cttcaccgtg gtctccgcct caccccttggc gctggaccag tgagaggaga gggctggggc
241 gctccgctga gccactcctg cgcccccctg gccttgtcta cctcttgccc cccgaggggt
301 tagtgtcgag ctcaccccag catcctatca cctcctggtg gccttgccgc cccccacaacc
361 ccgaggtata aagccaggta cacgaggcag gggacgcacc aaggatggag atgttccagg
421 ggctgctgct gttgctgctg ctgagcatgg gcgggacatg ggcatccaag gagccgcttc
481 ggccacggtg ccgccccatc aatgccaccc tggctgtgga gaaggagggc tgccccgtgt
541 gcatcaccgt caacaccacc atctgtgccg gctactgccc caccatgacc cgcgtgctgc
601 agggggtcct gccggccctg cctcaggtgg tgtgcaacta ccgcgatgtg cgcttcgagt
661 ccatccggct ccctggctgc ccgcgcggcg tgaaccccgt ggtctcctac gccgtggctc
721 tcagctgtca atgtgcactc tgccgccgca gcaccactga ctgcgggggt cccaaggacc
781 accccttgac ctgtgatgac cccccgcttcc aggactcctc ttcctcaaag gcccctcccc
841 ccagccttcc aagcccatcc cgactcccgg ggccctcgga caccccgatc ctcccacaat
901 aaaggcttct caatccgcaa aaaaaaaaaa aaa
```

ALPP mRNA transcript 2883 bp

SEQ ID NO: 4

```
   1 tcagccagtg tggcttcagg tcaagaggct gggcagggtc aaggtggcaa cgaggggaga
  61 agccgggaca cagttctccc tgatttaaac ccgggcagcc tggagtgcag ctcatactcc
 121 atgcccagaa ttcctgcctc gccactgtcc tgctgccctc cagacatgct ggggccctgc
 181 atgctgctgc tgctgctgct gctgggcctg aggctacagc tctccctggg catcatccca
 241 gttgaggagg agaacccgga cttctggaac cgcgaggcag ccgaggccct gggtgccgcc
 301 aagaagctgc agcctgcaca gacagccgcc aagaacctca tcatcttcct gggcgatggg
 361 atgggggtgt ctacggtgac agctgccagg atcctaaaag ggcagaagaa ggacaaactg
 421 gggcctgaga taccccctggc catggaccgc ttcccatatg tggctctgtc caagacatac
 481 aatgtagaca aacatgtgcc agacagtgga gccacagcca cggcctacct gtgcggggtc
 541 aagggcaact tccagaccat tggcttgagt gcagccgccc gctttaacca gtgcaacacg
 601 acacgcggca acgaggtcat ctccgtgatg aatcgggcca agaaagcagg gaagtcagtg
 661 ggagtggtaa ccaccacacg agtgcagcac gcctcgccag ccggcaccta cgcccacacg
 721 gtgaaccgca actggtactc ggacgccgac gtgcctgcct ccgcccgcca ggaggggtgc
 781 caggacatcg ctacgcagct catctccaac atggacattg acgtgatcct aggtggaggc
 841 cgaaagtaca tgtttcgcat gggaacccca gaccctgagt acccagatga ctacagccaa
 901 ggtgggacca ggctggacgg gaagaatctg gtgcaggaat ggctggcgaa gcgccagggt
 961 gcccggtatg tgtggaaccg cactgagctc atgcaggctt ccctggaccc gtctgtgacc
1021 catctcatgg gtctctttga gcctggagac atgaaatacg agatccaccg agactccaca
1081 ctggacccct ccctgatgga gatgacagag gctgccctgc gcctgctgag caggaacccc
1141 cgcggcttct tcctcttcgt ggagggtggt cgcatcgacc atggtcatca tgaaagcagg
1201 gcttaccggg cactgactga gacgatcatg ttcgacgacg ccattgagag ggcgggccag
```

TABLE 7-continued

| SEQUENCES OF EXEMPLARY mRNA TRANSCRIPTS: |
|---|
| 1261 ctcaccagcg aggaggacac gctgagcctc gtcactgccg accactccca cgtcttctcc |
| 1321 ttcggaggct accccctgcg agggagctcc atcttcgggc tggcccctgg caaggcccgg |
| 1381 gacaggaagg cctacacggt cctcctatac ggaaacggtc caggctatgt gctcaaggac |
| 1441 ggcgcccggc cggatgttac cgagagcgag agcgggagcc ccgagtatcg gcagcagtca |
| 1501 gcagtgcccc tggacgaaga gacccacgca ggcgaggacg tggcggtgtt cgcgcgcggc |
| 1561 ccgcaggcgc acctggttca cggcgtgcag gagcagacct tcatagcgca cgtcatggcc |
| 1621 ttcgccgcct gcctggagcc ctacaccgcc tgcgacctgg cgccccccgc cggcaccacc |
| 1681 gacgccgcgc acccggggcg gtccgtggtc cccgcgttgc ttcctctgct ggccgggacc |
| 1741 ctgctgctgc tggagacggc cactgctccc tgagtgtccc gtccctgggg ctcctgcttc |
| 1801 cccatcccgg agttctcctg ctccccacct cctgtcgtcc tgcctggcct ccagcccgag |
| 1861 tcgtcatccc cggagtccct atacagaggt cctgccatgg aaccttcccc tccccgtgcg |
| 1921 ctctggggac tgagcccatg acaccaaacc tgccccttgg ctgctctcgg actccctacc |
| 1981 ccaaccccag ggactgcagg ttgtgccctg tggctgcctg caccccagga aaggaggggg |
| 2041 ctcaggccat ccagccacca cctacagccc agtgggtacc aggcaggctc ccttcctggg |
| 2101 gaaaagaagc acccagaccc cgcgccccgc tgatctttgc ttcagtcctt gaatcacctg |
| 2161 tgggacttga ggactcggga tcttcaggac gcctggagaa gggtggtttc ctgccaccct |
| 2221 gctggccaag gaggctcctg gggtggggat caccaggggg attttgacac agccttcggc |
| 2281 tgccccccac taagctaatt ccacacccct gtaccccccc agggggccct ctgcctcatg |
| 2341 gcaaaggctt gccccaaatc tcaacttctc agacgttcca tacccccaca tgccaatttc |
| 2401 agcacccaac tgagatccga ggagctcctg ggaagccctg ggtgcaggac actggtcgag |
| 2461 agccaaaggt ccctccccag acatctggac actgggcata gatttctcaa gaaggaagac |
| 2521 tcccctgcct ccccagggcc tctgctctcc tgggagacaa agcaataata aaaggaagtg |
| 2581 tttgtaatcc cagcactttg ggaggccgag gtgggcggat cacgaggtca ggagatggag |
| 2641 accatcctgg ctaacacggt gaaacccctt atctatgcgc ctgtagtccc agctacccag |
| 2701 gaggctgaag caggataatc gcttgaaccc gggcggcgga gattgcagtg agccgaggtc |
| 2761 atgccactgc actgcagcct gggcgacaga gcgagattct gcctcaaaaa taaacaaata |
| 2821 aattttaaaa ataaataaat aataaaagga agtgttagac aatgtaaaaa aaaaaaaaaa |
| 2881 aaa |
| CSHL1 mRNA transcript 661 bp |
| SEQ ID NO: 5 |
| 1 agcatcccaa ggcccgactc cccgcaccac tcagggtcct gtggacagct cacctagcgg |
| 61 caatggctgc aggaagaagc ctatatcaca aaggaacaga agtattcatt cctgcatgac |
| 121 tcccagacct ccttctgctt ctcagactct attccgacat cctccaacat ggaggaaacg |
| 181 cagcagaaat ccaacttaga gctgctccac atctccctgc tgctcatcga gtcgcggctg |
| 241 gagcccgtgc ggttcctcag gagtaccttc accaacaacc tggtgtatga cacctcggac |
| 301 agcgatgact atcacctcct aaaggaccta gaggaaggca tccaaatgct gatggggagg |
| 361 ctggaagacg gcagccacct gactgggcag accctcaagc agacctacag caagtttgac |
| 421 acaaactcgc acaaccatga cgcactgctc aagaactacg ggctgctcca ctgcttcagg |
| 481 aaggacatgg acaaggtcga gacattcctg cgcatggtgc agtgccgctc tgtggagggc |
| 541 agctgtggct tctaggggcc cgcgtggcat cctgtgaccc ctccccagtg cctctcctgg |

TABLE 7-continued

SEQUENCES OF EXEMPLARY mRNA TRANSCRIPTS:

601 ccctgaaggt gccactccag tgcccaccag ccttgtctta ataaaattaa gttgtattgt 661 t

PLAC4 mRNA transcript 10009 bp

SEQ ID NO: 6

1 cgtagctcat aatccatttt tataacacct tgctatctat atttacacct ttaaagaaca 61 cgggaattta agagggaaga gtaactaggc ttttgctaaa cttgggctaa taaaaccctc 121 tgtagagaga tccttaatat aggcatgggg acaacaagga gtatcccaag ggactcgccg 181 ctagggtgtc ttttaagcta ttggagcaaa ttcaaatttg gcttaaagaa aaagaaactc 241 attttgtatt gcaacaccat ttgggttaaa tacaagttag atgacgaata tatctggcct 301 aaacatggtt ctatatacta tagtgatatt ttacgattag gcttattttg taaaagagaa 361 ggaaaatggg aagagatccc ttatgtacag gcttttatgg ctctatactg gatcacgtta 421 cttccaggca ttagaatgcc atgcataagg gatccccacc tagctgctcc ccatagaaag 481 ttcataagcc tccccagagt ctcttcagtc ccccagtcct gagtgggggt tctcgccaat 541 tccctaatga gattccaccc caatatcatc aggcaccttt cccccttatc caactagccc 601 tagcctatac cctctgctgc ccaagaaaat gagcccaacc agtacaccag gagtggggct 661 ccatatcagc ccctaaggtc aagcctgtgt ccactgtgga aagtagttga tggaaatgag 721 ggaacactca aagagtacat atgccacttt ccatgtctaa ttagacctta taaaaggaaa 781 gaattggcca gttttcagat aaaccagaaa agcttataca agagtttgtt acgttgacta 841 tgttcttcaa attgccacga tttacaaata ttgtcatccg cttgctgtgc tgtggggaaa 901 aaaaagtaga ggaaaaagtg tgtggttaag ccagtcaatt atgacaaggt taaagaagta 961 actcggggaa aagatgaaaa tcccgctctg tttcagggtc ttttagttga agcactcagg 1021 aaatatacta atgcaggccc agacacccca gaagggcaag ctctcctggg tatacatttt 1081 ctcattcaat cttctcctga cattaggagg aatctacaaa aagcagcaat gggaccttca 1141 agtcctatga aacgacgctt aaacatagcc tttaaagttt acaacaacag ggacagggca 1201 aaagagggga gtaaaaagaa atagccaaaa agtacaattg ttaacagtga ctttaagcct 1261 ccttgcccct caggattact catcttgaga aaatgttaca aaattagcat ctgggatgcc 1321 tagacaagac ttgatgcctg acttgctgac ccctgggcca gaatcactgc gcctactata 1381 cgcaaaaggg cccctggcaa tgcaaatgtc ctaactgctc tggtgagaga gaacaataac 1441 aacaaaaagc ttccatcaat actagagcta accttctcct actagcccca gtgagctgct 1501 tagctcaagt aagtttactg tcccagagga cagctttcca cagtggcaga taagcagccg 1561 cctgaacatt tttctttggt atttccacca ctgagtgtgc tctccagtgg cgtggggact 1621 ccagaatctc cttttgagca atgcagtttg cttcctcccc tttttagttg atgctatggg 1681 attccctgtc ctgccttttc ctgttttcca tacctatcgg ggcaaacaaa atttggccag 1741 gtagatgggt cccagttctg taaataactt gaatccagtt gtcttgtata ggtcatttta 1801 tttaatatgt ttttgggtat atgtacatgt attgtgatgt gtgttacatc tagcgtgctg 1861 tcaaactggc ttatagataa aagaacactc atacattcaa caaataagac tactgaaagc 1921 ttattagttt gaagagaatc ttgtatcttc taaaatttaa ctttaggatt tttacctagg 1981 taagtcactg atgttcatag gctttaaaat ggttaaaatg gctttaaatg gtgaccagct 2041 ttgcatggta ccttggttct cggtgatcta gataaagtta aaagtgaaat aattaaatac 2101 acgtaaatgg gatatgctta atgtgtggtt taaaatcata aaatggtaga atggttctca TABLE 7-continued

| SEQUENCES OF EXEMPLARY mRNA TRANSCRIPTS: |
|---|
| 2161 gttatagaat gacaatgtct agtgtgaagt tcatgacttc ttccttccta ggtttccata |
| 2221 aaatgtgcta aagaaatgta ttctttattg agaaaaaatt ttttgtctaa tccggaagtt |
| 2281 actaaatggg aggttcaaaa catgagtgaa ccagtgagta gaaaagagag atgtaaagaa |
| 2341 tattatgaat agaaaatgta ttttttgttt gttttgcaag gaaggatata aagaaagagt |
| 2401 aattttatat gtggaggaat cctgtatagt aaattcccta tcctagagta aaataacttt |
| 2461 aagaaagagg tagtatagaa catgtcagga aattcagcta tgttgtagat ggtctgtgta |
| 2521 agtcatctgc acagtgcatg agtgtggagg tgggcgggca ctcattggcc cttgaactcc |
| 2581 ttttgagcag tatggaagcc aagaactaga agccaggaaa tggggttgta aaactgattt |
| 2641 gtctatggat tttatgtgtt gagctgctgt ggtcttggct tgtagtaatt acctatatga |
| 2701 accttccccc ctcccctttta gaatttagga caggttcaaa aggccctcca atataaaaat |
| 2761 aaaatactgt ccttccccac aaaggaaaaa atagctcccc ggttcaacca ggagacttag |
| 2821 tcttgctaaa accttaaaga cagggtaaag acagggatac cccaagaatc aattacaatg |
| 2881 aaatggaagg ggccttatca ggtattgtta agtaccccca ctgctgttaa acttcaggga |
| 2941 acacctactt gggcacacag atccaggact aaacctgttt cttatgagtc acaggcacaa |
| 3001 aggaagggca ctacaaccac aaccaatatc agtaaagctt tggaagacct ctgctaccta |
| 3061 tttaaaataa tcaacactca gccagaagag gtaatgtaat gctgtagatg ggaataggag |
| 3121 cattgatctt gctcttcttc ctgactgtag tacttccttt ctatggcttt aaccagccac |
| 3181 ctcctcctgg gaaacatctc ctgtgggctt gttgggtata gaagctactc taagacccaa |
| 3241 ccagatacca tgatgccact gttaattctg tttgctcttc taattaacct aagctagtgt |
| 3301 gtatgtggac agggagggtg gacaaaattc tacagtaaat atttcaaaaa ttatagcatc |
| 3361 atagaatcat ctttatggct gccagatttg tcatcaacac ccccaggata gacagtttca |
| 3421 tcttccgacc tatctggaaa atctcaggac catgtcccca gacctcctaa ctaaccatag |
| 3481 caccccaaaa tacccaaacc cctattgtga agtggaactc ttccccactt agtggatccc |
| 3541 ccctggaccc tgctgtcccc ctgccctgac cactattatc ggaatctggg aagttgggca |
| 3601 tctatatctc cagtgcactc ataactctaa catttgcatc cactcttgca ttaatgacac |
| 3661 aaaagtggaa gcttccctgc gatgctctgg tccaactcta gttgccaagt ttccaagacc |
| 3721 acggggaggt aaatgagatt ccatttgtga gtgaaaagac catatatggt accttctccc |
| 3781 ggatgggaac atacaaagga aaaacaactg cctgatctgg gaaggtgaca gtactacctt |
| 3841 cttctagaaa acaaagattg ttcaaccacc accatgagaa caggtggaaa atatctctat |
| 3901 agacccaacc tggcaatgaa gtataaacat cgcaccccgc agggcttctc ttggtgccct |
| 3961 agttgggttc atttttgttt gtgactatga atgggaagaa gtcacaccct gtaaccactc |
| 4021 caactcccta aggagtcacc tcttctttaa ggaatagctt tcccttgtat ctaaaaaact |
| 4081 tggaactgac atgaatgaac gttggccact cttacccctc caggggtcac aatctataac |
| 4141 gcctaggacc caagaatatc agaaataagt aagcaataaa actaattctg gcaggaatca |
| 4201 gggtggcaat aggactagca gcaccctggg gtggctttgc ctaccatgag ttaacgctaa |
| 4261 agaacttggc tcaaatccta gaatccttag ccaccaacgg agatcaggca ttaaagagaa |
| 4321 ttcaagagtt ccccagactc tggaaaatgt agttgttgat aacagactag cattggatta |
| 4381 tttactagct gaacaaggtg gggtcttgtg cagttattaa taaaacctgc tgcacatata |
| 4441 ttaactctgg acaggttgag gttaacattc aaaagatcta tgagcaagct acctagttac |

TABLE 7-continued

| SEQUENCES OF EXEMPLARY mRNA TRANSCRIPTS: |
|---|
| 4501 atagatataa ccagggcact gcccccaact atatctggtc aaccatcaaa agtgccttcc |
| 4561 caagtctcac ctgtttttca cctcttctag gacctttgac aactgtcttg ttacaaatgt |
| 4621 ttggtccttg cttctttaac ctcttagtaa agtttgtgta ttctagatta ccacagttcc |
| 4681 agagacaatg ctggcacaag gcttccagcc catcctgtcc actgacacgg agaatgaaat |
| 4741 cgtcctgcct ctgggctcct tagatcaggt atccagagat ttttactcct ccagtgccag |
| 4801 gcagggccta cgtccataaa ctcagcagga agtagttacg gaaaacagat ctccgcccctt |
| 4861 ctgcagcccc cttaagatta aggaggagta tctaatctct gaagggggaa tgaggtagga |
| 4921 ggtgggactc aactctggaa gtggggctca ggcactcaga ccaaactgag cactagctaa |
| 4981 aataggtcca gggcagatgc tagtttccat aggacacacc gacctgtgtc aagtcagttc |
| 5041 accatggctc tggcagcacc cagaagttac caccctcacc ctggaaatgt ctgcataaac |
| 5101 tgccccttca tttgcatata attaaaagtg gatacaaata ccactgcaga actgcctctg |
| 5161 agctgctact gtgggcgcac agcctgtagg gcagccctgc tttgcaagga gcagcgcctc |
| 5221 tgctgctgct gtgcacagcc ggccgcttca ataaaagttg ctaacaccac tggcttgccc |
| 5281 ttgagttcct tcctgggcaa agctaagaac cctcccgggc tatgcttcaa tcttagggct |
| 5341 cgcctgtcct gcatcactgg gatcatctcc cagtaaacta gccacactta catccatgtg |
| 5401 tcagggacat ttctggagaa agcagcccag gacactgttg aataaaacac acaatagtct |
| 5461 ctgtggtctt ctccacccca ccccacacca ggcaccctca gcttgattct cctttttaat |
| 5521 tgcctgtaag cagggaagca caatgttttc acattctttg taaggccttt gttctactaa |
| 5581 aatctaacct cagagcacaa ttttaaacta gatgaaagag ttgctgcgcc tgaagcactg |
| 5641 caaacacctc ctcaccacac atgtgcactc accctggaca ccctcactca ccctgacacc |
| 5701 ctcactcctc accctggaca ccctcactca ccccagacac cgtcactcct caccctggac |
| 5761 acctcactct gcaccctgga caccctcact caccctggac acgttcactc accctgacac |
| 5821 cctcactcac cctggacacc ctcactcacc ctggataccc tcactcctca ccctggacac |
| 5881 cctcactcac cctggatacc ctcactcctc accctggaca ctctcactca ccctgacacc |
| 5941 ctcaatcctc accctggact ccctcactcc tcaccctgga ctccctcact cctcaccctg |
| 6001 gacaccctca ctcctcatcc tggacaccct cactcaacct ggacaccctc actcctcacc |
| 6061 ctgacaccct cactcctcac cctggacacc ctcactcctc accctgacac cctcactcct |
| 6121 caccctggca ccctcagtca ccctgacacc ctcactcctc accctgacac cctcaagtct |
| 6181 tcacctccct ggctgcagcc tgggacacgc tttccctaac ttctgaaggc tcagtcctcc |
| 6241 tcaagccaat ctcatctcaa attgcacctc ctcagagagg tcttccataa ccgcccttat |
| 6301 aaagcaggat tctttcacca ataccccttc ccacatggca ctgtctcaca gcactcctct |
| 6361 aaaagtctgt ttacttcctt gacaatctgt cttccttata aggggaggtt ctgtaaaagc |
| 6421 caagactctc tctgtctagt tgactgttgc ataccagggc ttagaccaag gccctgacat |
| 6481 gcagtaggtg cttaatatgt tttgaggcaa ggtcttgctc tgttgcacat gctggagtgc |
| 6541 agtggcacaa tcgtaattca ttgcagcctt gaactcctga gctcaagtga tcctcctgcc |
| 6601 tcagcctcct gagtagctgg gactacaggc atgcaccacc aagcttggct aatttaaaaa |
| 6661 aaaaattata tagataggga cttgctatgt tgcctaggct gatcttgaac tcctaacctc |
| 6721 aagcaatcct cccacctcgg ccttccaaag tgctgggata ataggcatgg agccgccaca |
| 6781 cccagccaat gtgccgaaga aagaaagaaa aacatgctca tcctttgagt caggttcaaa |

TABLE 7-continued

| SEQUENCES OF EXEMPLARY mRNA TRANSCRIPTS: |
|---|
| 6841 tttttctcc tctttaaccc ccagtcactc cagttataag tgatttttaa ctcttctcac |
| 6901 actttaatgc atctggcaag aagatccacg tggtgttagg aacaatacag gaccttaagg |
| 6961 atgggggaat cagcaggtgt cagcgtgccc tgtatgctca gggcagctgt ttccactgga |
| 7021 cattctccct ttgcctctct gggcagcaac tcctaggcca gccgacctgc tgtgtcgagt |
| 7081 aaccaggatt tctcaatctt ggcatggttg ccattttgga ccagatcgtt ctttgttgtg |
| 7141 ggggctgccc tgtacggcaa agaatgccga gcagcacttc cagtctccac ccacaggacg |
| 7201 ccagtagcac cctctaagtt gtgagaactc aaaatgtccc cagaggatgc cagatgtccc |
| 7261 ctggggtggg gacacaatca ccccaggttg agatccatgg agccaggtct gtttgccacc |
| 7321 aaggggtaaa gctccattcc caccttagga gggctaggag gcagcatcgt ggggccacag |
| 7381 aaggcctggg tttgcagtca gaggacagga tgcacattcc ttcaagatac agacccagat |
| 7441 tgttgggcat ctagttcttg ggttttctgt tgttgctgtt ccgttttgtc tgtcttccct |
| 7501 cctttgttta ctagcagcct ggaatttgcc actttttcta aacgaagatt tatggaacac |
| 7561 ttaccacacg gctgacgctg cgcgaggcta aggttctaat acaccgcagc tcacttaact |
| 7621 ctcgcaatac cataaacgca cactgtttca tcttgaccct ttcttgggaa ggtgacagag |
| 7681 aggtaggagg gcaaacatct tgtgtgcccc gtcccaaggg tattactggt ggaataatat |
| 7741 ccgcccccca ccccagtttc taatttgctg taggctgtga cgctgtgggg caagactagg |
| 7801 agtcctgttg aaattaggaa taagtgtgct gtgagggaag ggctgcctta ttttagagca |
| 7861 cagattttct gaatatctat tttgacaggt tcgatcctct ccccttcctg ccttccttct |
| 7921 gtcgattttc aatgtcttga tggtgtccca cctgagtggc ctttagagat gtgagttgtg |
| 7981 aggcactggg gaggcaggca cacgtcctcc agcccaagac tgcctaattt aacagggatt |
| 8041 tctgcattct ggaacaagcc tccatttcc ccaagcagga ttactccaga gggcaaaaca |
| 8101 cagcccaata gtatcacatt tcctttctgc tttagcaaaa ataaccactg tctcattcat |
| 8161 gggaaaaggc cgccaaacaa atttgttact ggaaccattt gtaacaactt ctagtttgca |
| 8221 ctgccttgga gcaagcacac tttgtagagg agggatttgc agttacttgg gcaacaaggt |
| 8281 aaccactgat cattacagga agcttcagaa accgtgggac cagtgtagaa gaatggacta |
| 8341 tctgtccaaa ctaagaataa aaagaatgac acttgtattt tgtatgtctt tttcactttg |
| 8401 cctttctagt aattcatttt tcttgatatt tacaccttgt ggccctgtga tagactggaa |
| 8461 atctcaaaaa cacacgttca gcaccaagat tttcagcagc accgcctcag aatgagaccc |
| 8521 ctagaaaaaa ctgcgtgttt tccacttgcc caacacgagg agtttttgga acacgacctg |
| 8581 cttgaggtgg agattttcta gatgggcaaa gagaaggaaa cacttaacct aggaagagta |
| 8641 tttaggaaga agaaagaaca cagcctttct gcacaggaaa ccgccgagca gaggggcatc |
| 8701 tggcctctgc agtggcctcc aaatagagtc caatggctgg ggccagcgtg gctgcttaaa |
| 8761 ggggactcaa gggatataat aaaatgcaga ttctcaggtc ctagtgcaga caggctcacc |
| 8821 caataagtct ggactgcata tgggaatctc tatttctagg cccttctgca aggtattcct |
| 8881 gctctttcca ggaaccatcg gcagctggtt tggggaaaga agcaacgact ccaagtgtga |
| 8941 cctgtgagct ggcagcagcc accctcagct ctgctctcgg tcactgaatc cgattctgca |
| 9001 ttttaacagg accccaggtg ttgcacccac acaaagctga agcagattgg tctgggggca |
| 9061 aaaaattaga gctatggaga ttctctcaaa tgaaatagat gatatcattg actgttagag |
| 9121 cttctagaag gaatctgagg tcacttgttc aaattccctg atttacagat gaggaaacag |

TABLE 7-continued

SEQUENCES OF EXEMPLARY mRNA TRANSCRIPTS:

```
9181  aggctcagac agctcaaatg acttctctcc aatacccaac attcgacaag tagcagctct
9241  gggactagta cccaaagcac ctagctctcc aatcactgcg caagccacac aattctgtct
9301  gcttgtcagt ggcttttctg attcaaaaaa agcttaggaa tttccccagg aggcagcacg
9361  atgtagtggg aagggctctg gatgtctctc caaggcttct ggaattcatg cccacctcca
9421  ccaagaagcc actttcctgc cagctacagg tgctcacctg aaaagcaagc cagaccatat
9481  taaccctggc attgctggta cctggaagac tttctgattc aatgctttcc acctcctcct
9541  acccctcacc acccccgtgg catgaaatcc tgggggctgc tttagaaatt gttttctttg
9601  gctgctggtg gggtgctgc tggtgggggt ttgcacagct ggcacactgc accagtctgg
9661  tgggggtttg cacagctggc acactgcacc agtctcctgc ctgctgccaa caaggccatt
9721  tcccaagcac tggctttgga gaagttgggg ctctgaagtg ggaacacaag gctgcctttt
9781  gcaggccagg tgtaaattct ccccctgcca ctttcagcct agcgtgaaac agatggagtg
9841  tgcattccca cttcccttta tggtaccctg gaatgatgga gctgcccagg gcatcgccac
9901  gttactctct agacagtctc tttgtcttcc tgcaatggca gcgccgaggt tgtatatttc
9961  taggtgcagg tatatgattg ccatataata aaaatctgaa aacatccca
```

PSG7 mRNA transcript 2046 bp

SEQ ID NO: 7

```
   1  agtgcagaag gaggaaggac agcacagctg acagccgtgc tcaggaagat tctggatcct
  61  aggctcatct ccacagagga gaacacgcag ggagcagaga ccatggggcc cctctcagcc
 121  cctccctgca cacagcatat aacctggaaa gggctcctgc tcacagcatc acttttaaac
 181  ttctggaacc cgcccaccac agcccaagtc acgattgaag cccagccacc aaaagtttcc
 241  gaggggaagg atgttcttct acttgtccac aatttgcccc agaatcttac tggctacatc
 301  tggtacaaag gacaaatcag ggacctctac cattatgtta catcatatat agtagacggt
 361  caaataatta aatatgggcc tgcatacagt ggacgagaaa cagtatattc caatgcatcc
 421  ctgctgatcc agaatgtcac ccaggaagac acaggatcct acactttaca catcataaag
 481  cgaggtgatg ggactggagg agtaactgga cgtttcacct tcaccttata cctggagact
 541  cccaaaccct ccatctccag cagcaatttc aaccccaggg aggccacgga ggctgtgatt
 601  ttaacctgtg atcctgagac tccagatgca agctacctgt ggtggatgaa tggtcagagc
 661  ctccctatga ctcacagctt gcagctgtct gaaaccaaca ggaccctcta cctatttggt
 721  gtcacaaact atactgcagg accctatgaa tgtgaaatac ggaacccagt gagtgccagc
 781  cgcagtgacc cagtcaccct gaatctcctc ccgaagctgc ccaagcccta catcaccatc
 841  aataacttaa accccaggga gaataaggat gtctcaacct tcacctgtga acctaagagt
 901  gagaactaca cctacatttg gtggctaaat ggtcagagcc tcccggtcag tcccagggta
 961  aagcgacgca ttgaaaacag gatcctcatt ctacccagtg tcacgagaaa tgaaacagga
1021  ccctatcaat gtgaaatacg ggaccgatat ggtggcatcc gcagtgaccc agtcaccctg
1081  aatgtcctct atggtccaga cctccccaga atttaccctt cattcaccta ttaccattca
1141  ggacaaaacc tctacttgtc ctgctttgcg gactctaacc caccggcaca gtattcttgg
1201  acaattaatg ggaagtttca gctatcagga caaaagcttt ctatccccca gattactaca
1261  aagcatagcg ggctctatgc ttgctctgtt cgtaactcag ccactggcaa ggaaagctcc
1321  aaatccgtga cagtcagagt ctctgactgg acattaccct gaattctact agttcctcca
1381  attccatctt ctcccatgga acctcaaaga gcaagaccca ctctgttcca gaagccctat
```

TABLE 7-continued

| SEQUENCES OF EXEMPLARY mRNA TRANSCRIPTS: |
|---|
| 1441 aagtcagagt tggacaactc aatgtaaatt tcatgggaaa atccttgtac ctgatgtctg |
| 1501 agccactcag aactcaccaa aatgttcaac accataacaa cagctgctca aactgtaaac |
| 1561 aaggaaaaca agttgatgac ttcacactgt ggacagcttt tcccaagatg tcagaataag |
| 1621 actccccatc atgatgaggc tctcacccct cttagctgtc cttgcttgtg cctgcctctt |
| 1681 tcacttggca ggataatgca gtcattagaa tttcacatgt agtataggag cttctgaggg |
| 1741 taacaacaga gtgtcagata tgtcatctca acctcagact tttacataac atctcaggag |
| 1801 gaaatgtggc tctctccatc ttgcatacag ggctcccaat agaaatgaac acagagatat |
| 1861 tgcctgtgtg tttgcagaga agatggtttc tataaagagt aggaaagctg aaattatagt |
| 1921 agactcccct ttaaatgcac attgtgtgga tggctctcac catttcctaa gagatacatt |
| 1981 gtaaaacgtg acagtaagac tgattctagc agaataaaac atgtactaca tttgctaaaa |
| 2041 aaaaaa |
| PAPPA mRNA transcript 11025 bp |
| SEQ ID NO: 8 |
| 1 gagcatcttt tggggggagg gaattcagcg gatcagtctt aagaggagct tttttttgaa |
| 61 gcgagaaatc atataaaata aaatgaaata aaacaaggag gaaggcaacc agctgttagg |
| 121 ggaaaaataa ggcagataaa ggagcgggga gagaaattaa ttgccaacca ggaggagttg |
| 181 ggctgtattt ttcaaaggtg gggagagtgg agcacacacc ttgaggagga aagcgagaaa |
| 241 gaaaagaaaa aagcaagtgg aaagggggc tcgcccaaga agggtgaaga agcgaagaaa |
| 301 gtcgaggcgc cgaggctccc aaagctggca gctccgggtg gcggtgcagg ggcgaagggg |
| 361 gggcgggggg aaccgtcgga catgcggctc tggagttggg tgctgcacct ggggctgctg |
| 421 agcgccgcgc tgggctgcgg gctggccgag cgtccccgcc gggcccggag agacccgcgg |
| 481 gccggccgac ccccgcgccc cgccgccggc ccggccacct gcgccacccg ggcggcccgc |
| 541 ggccgccgcg cctcgccgcc gccgccgccg ccgccgggcg gtgcctggga agccgtgcgc |
| 601 gtcccccggc ggcggcagca gcgggaggcg aggggcgcca ccgaggagcc gagcccgccg |
| 661 agccgggcgc tctatttcag cgggcgaggc gagcagctgc gcctccgggc cgacctcgag |
| 721 ctgccccggg acgcgttcac gctgcaagtg tggctgcgag cggagggggg ccagaggtct |
| 781 ccggcagtga tcacagggct gtatgacaaa tgttcttata tctcacgtga ccgaggatgg |
| 841 gtcgtgggca ttcacaccat cagtgaccaa gacaacaaag acccacgcta ctttttctcc |
| 901 ttgaagacag accgagcccg gcaagtgacc accatcaatg cccaccgcag ctacctccca |
| 961 ggccagtggg tatacctagc tgccacctat gatgggcagt tcatgaagct ctatgtgaat |
| 1021 ggtgcccagg tggccacctc tggggaacaa gtgggtggca tattcagccc actgacccag |
| 1081 aagtgcaaag tgctcatgtt agggggcagt gccctgaatc acaactaccg gggctacatc |
| 1141 gagcacttca gtctgtggaa ggtggccagg actcagcggg agatactgtc tgacatggaa |
| 1201 acccatggcg cccacactgc tctacctcag ctcctcctcc aggagaactg ggacaatgtg |
| 1261 aagcatgcct ggtcccccat gaaggatggc agcagcccca aagtggaatt cagcaatgcc |
| 1321 cacggctttc tgctggacac gagtctggag cctcctctgt gcggacagac attgtgtgac |
| 1381 aacacagagg tcattgccag ctacaatcag ctctcaagtt tccgccagcc caaggtggtg |
| 1441 cgctaccgcg tggtcaacct ctatgaagat gatcataaga acccgacggt gacgcgcgag |
| 1501 caggtggact tccagcacca tcagctggct gaggccttca agcaatacaa catctcctgg |
| 1561 gagctggacg tgctggaggt gagcaactcc tcccttcgcc gccgcctcat cctggccaac |

TABLE 7-continued

| SEQUENCES OF EXEMPLARY mRNA TRANSCRIPTS: |
|---|
| 1621 tgtgacatca gcaagattgg ggatgagaac tgtgaccccg agtgcaacca cacgctgacg |
| 1681 ggccacgacg gcggggattg ccgccacctg cgccaccctg ccttcgtgaa gaagcagcac |
| 1741 aacggggtgt gtgacatgga ctgcaactat gaacggttca actttgatgg tggagagtgc |
| 1801 tgtgaccctg aaatcaccaa tgtcactcag acttgctttg accccgactc tccacacaga |
| 1861 gcctacttgg atgttaatga gctgaagaac attcttaaat tggatggatc aacacatctc |
| 1921 aatattttct ttgcaaaatc ctcagaggag gagttggcag gagtagcaac ttggccatgg |
| 1981 gacaaggagg ccctgatgca cttaggtggc attgtcttga acccatcttt ctatggcatg |
| 2041 cctgggcaca cccacaccat gatccatgag attggtcaca gcctgggcct ctatcacgtc |
| 2101 ttccgaggca tctcagaaat ccagtcctgc agtgacccct gcatggagac agagccctcc |
| 2161 ttcgagactg gagacctctg caatgatacc aacccagccc ctaaacacaa gtcctgtggt |
| 2221 gacccagggc caggaaatga cacctgtggc tttcatagct tcttcaacac tccttacaac |
| 2281 aacttcatga gctatgcaga tgacgactgt acggactcct tcacgcccaa tcaagtcgcc |
| 2341 agaatgcact gttacctgga cctggtctac cagggctggc agccctccag gaaaccagcg |
| 2401 cctgttgccc tcgcccccca agttctgggc cacacaacgg actctgtgac actggagtgg |
| 2461 ttcccaccta tagatggcca tttctttgaa agagaattgg gatcagcatg tcatctttgc |
| 2521 ctggaaggga gaatcctggt gcagtatgct tccaacgctt cctccccaat gccctgcagc |
| 2581 ccatcaggac actggagccc tcgtgaagca gaaggtcatc ctgatgttga acagccctgt |
| 2641 aagtccagtg tccgcacctg gagcccaaat tcagctgtca acccacacac ggttcctcca |
| 2701 gcctgccctg agcctcaagg ctgctacctc gagctggagt tcctctaccc cttggtccct |
| 2761 gagtctctga ccatttgggt gacctttgtc tccactgact gggactctag tggagctgtc |
| 2821 aatgacatca aactgttggc tgtcagtggg aagaacatct ccctgggtcc tcagaatgtc |
| 2881 ttctgtgatg tcccactgac catcagactc tgggacgtgg gcgaggaggt gtatggcatc |
| 2941 caaatctaca cgctggatga gcacctggag atcgatgctg ccatgttgac ctccactgca |
| 3001 gacaccccac tctgtctaca gtgtaagccc ctgaagtata aggtggtccg ggaccctcct |
| 3061 ctccagatgg atgtggcctc catcctacat ctcaatagga aattcgtaga catggatcta |
| 3121 aatcttggca gtgtgtacca gtattgggtc ataactattt caggaactga agagagtgag |
| 3181 ccatcacctg ctgtcacata catccatgga agtgggtact gtggcgatgg cattatacaa |
| 3241 aaagaccaag gtgaacaatg cgacgacatg aataagatca atggtgatgg ctgctccctt |
| 3301 ttctgccgac aagaagtctc cttcaattgt attgatgaac ccagccggtg ctatttccat |
| 3361 gatggtgatg gggtatgtga ggagtttgaa caaaaaacca gcattaagga ctgtggtgtc |
| 3421 tacacgcccc agggattcct ggatcagtgg gcatccaatg cttcagtatc tcatcaagac |
| 3481 cagcaatgcc caggctgggt catcatcgga cagccagcag catcccaggt gtgtcgaacc |
| 3541 aaggtgatag atctcagtga aggcatttcc cagcatgcct ggtacccttg caccatcagc |
| 3601 tacccatatt cccagctggc tcagaccact ttttggctcc gggcgtattt ttctcaacca |
| 3661 atggttgccg cagctgtcat tgtccacctg gtgacggatg ggacatatta tggggaccaa |
| 3721 aagcaggaga ccatcagcgt gcagctgctt gataccaaag atcagagcca cgatctaggc |
| 3781 ctccatgtcc tgagctgcag gaacaatccc ctgattatcc ctgtggtcca tgacctcagc |
| 3841 cagcccttct accacagcca ggcggtacgt gtgagcttca gttcgcccct ggtcgccatc |
| 3901 tcgggggtgg ccctccgttc cttcgacaac tttgaccccg tcaccctgag cagctgccag |

TABLE 7-continued

SEQUENCES OF EXEMPLARY mRNA TRANSCRIPTS:

| | | | | | | |
|---|---|---|---|---|---|---|
| 3961 | agaggggaga | cctacagccc | tgccgagcag | agctgcgtgc | acttcgcatg | tgagaaaact |
| 4021 | gactgtccag | agctggctgt | ggagaatgct | tctctcaatt | gctccagcag | cgaccgctac |
| 4081 | cacggtgccc | agtgtactgt | gagctgccgg | acaggctacg | tgctccagat | acggcgggat |
| 4141 | gatgagctga | tcaagagcca | gacgggaccc | agcgtcacag | tgacctgtac | agagggcaag |
| 4201 | tggaataagc | aggtggcctg | tgagccagtc | gactgcagca | tcccagatca | ccatcaagtc |
| 4261 | tatgctgcct | ccttctcctg | ccctgagggc | accacctttg | gcagtcaatg | ttccttccag |
| 4321 | tgccgtcacc | ctgcacaatt | gaaaggcaac | aacagcctcc | tgacctgcat | ggaggatggg |
| 4381 | ctgtggtcct | tcccagaggc | cctgtgtgag | ctcatgtgcc | tcgctccacc | ccctgtgccc |
| 4441 | aatgcagacc | tccagaccgc | ccggtgccga | gagaataagc | acaaggtggg | ctccttctgc |
| 4501 | aaatacaaat | gcaagcctgg | ataccatgtg | cctggatcct | ctcggaagtc | aaagaaacgg |
| 4561 | gccttcaaga | ctcagtgtac | ccaggatggc | agctggcagg | agggagcttg | tgttcctgtg |
| 4621 | acctgtgacc | cacctccacc | aaaattccat | gggctctacc | agtgtactaa | tggcttccag |
| 4681 | ttcaacagtg | agtgtaggat | caagtgtgaa | gacagtgatg | cctcccaggg | acttgggagc |
| 4741 | aatgtcattc | attgccggaa | agatggcacc | tggaacggct | ccttccatgt | ctgccaggag |
| 4801 | atgcaaggcc | agtgctcggt | tccaaacgag | ctcaacagca | acctcaaact | gcagtgccct |
| 4861 | gatggctatg | ccatagggtc | ggagtgtgcc | acctcgtgcc | tggaccacaa | cagcgagtcc |
| 4921 | atcatcctgc | caatgaacgt | gaccgtgcgt | gacatccccc | actggctgaa | ccccacacgg |
| 4981 | gtagagagag | ttgtctgcac | tgctggtctc | aagtggtatc | ctcaccctgc | tctgattcac |
| 5041 | tgtgtcaaag | gctgtgagcc | cttcatggga | gacaattatt | gtgatgccat | caacaaccga |
| 5101 | gccttttgca | actatgacgg | tggggattgc | tgcacctcca | cagtgaagac | caaaaaggtc |
| 5161 | accccattcc | ctatgtcctg | tgatctacaa | ggtgactgtg | cttgtcggga | cccccaggcc |
| 5221 | caagaacaca | gccggaaaga | cctccgggga | tacagccatg | gctaaggaag | gacaagaagt |
| 5281 | tgtcaaagaa | ttcccaacgc | caggacccac | atccctttgg | tattgatttc | acagtcagct |
| 5341 | gctcaacgga | atggcctctc | cacaccaggg | atccttagca | cccaaccggt | ctgcctttaa |
| 5401 | ttttacccag | gaaggactca | cattggggcg | aatgaaccaa | gtttcgccat | gctggatgat |
| 5461 | gaaatggatt | cccatcccaa | agtctgagat | ggattgcata | tacagtgtgc | agtcccagag |
| 5521 | cctcctaaaa | ttctagccat | ttgtcacaca | accacagcaa | gaaacgtgtt | ctatatctag |
| 5581 | agtgtgccca | tctgtgttta | gtacacatgc | atgcatacac | acccatacaa | acatctgtgt |
| 5641 | gagggcagtt | ctggagatga | gcagagagag | accggaataa | actcaatctt | ttctttccca |
| 5701 | agctcctagc | caacactatc | cttgggagaa | agaaatttgc | agaaactgct | aagaccaagt |
| 5761 | gtggagatgt | caagctagtt | cacactctga | ggctcagaat | atgtaggaca | tgcacaattg |
| 5821 | tgcagtcctt | tgggattgga | agtgaaacag | tctgtgatcc | cctaccttct | agggaactag |
| 5881 | gacctaggaa | gaggtaaaga | ttatcaggta | tgcaaagcgc | cccaattctt | ctgctgccat |
| 5941 | gggggatttt | accccaactc | cagggttcga | ggccaatctg | agaatggctt | aggattgcaa |
| 6001 | tgtcaaggta | ttatatcagc | cccttgcttg | aggcttgagg | tcataatatc | cctctaggac |
| 6061 | ttacctgttc | ccccagatct | tgccttggga | ccacatttgc | tgctactttt | cctgctgctc |
| 6121 | tatcctatac | attgaataat | ccaagatggt | agaactaggt | taggaaaaat | tccacacaac |
| 6181 | caaacagtct | gccttaaaag | tgacccacat | ttttccatag | ctcctcactt | tttagccctt |
| 6241 | ctgcaagaga | aaaaccctca | tgggtccaca | tggtgagaag | ttaagtttcc | tgtaagtggg |

TABLE 7-continued

| SEQUENCES OF EXEMPLARY mRNA TRANSCRIPTS: |
| --- |
| 6301 cctctcaccc tggaaaggag ttgagggaca tcagatgctg gaaccctcac tgaaagtcca |
| 6361 gaatgtctaa gccagtgtta gattttgtaa acaagtggaa cagtgttaaa tttctatgat |
| 6421 gttggagcca tccagagact actggaattg tcgagacttt tggattatta tccttatcct |
| 6481 tatcctaatc ttcctagccc ttcaggctag agtaggcttc gatcctgaga accttgctgt |
| 6541 tgctctgagg agatataatt ctgggagaaa gaatctttta taagaacagt acagattgtt |
| 6601 ctcaagaggg ccatcagaag gaagccaaag agttcacagc ctcagcacca acaactcaac |
| 6661 atggtcatca tgttttctat atggtttttc cagctagcag tactcccttc catacctgtg |
| 6721 actgggcagt gcttttctct ctcccatgtc tagcctccaa aagttaagtg aaaattagtc |
| 6781 aactgcacgt ggaagccccc accactttgg ggatctcttt atttcttttc agccagggac |
| 6841 ctgtccactc cctttgaatt aatatgggaa gaaattaata caggatgaac tggagagaag |
| 6901 ggttgagtgt ggcatacttt ctgaaacctg gagctgggaa ttgcggagaa gggaaggtct |
| 6961 agactagtta catcacatag ggattactgt aaatcaagtc atctcaagtc tagtgaagac |
| 7021 agccaacaga aacaaaacct agcataggga tagaaaatac catgcacgtg tgcagcccca |
| 7081 cctaattcct gcatccaagg caggtgttgt taatctatca tagcacttaa aaaaaaaaaa |
| 7141 aaaaagagac caaaaataac tttaggaacc accatattat atcactccca atagcactga |
| 7201 cctggtgatc aaaaacactt gagaagacat ctattggcca tctctggcca attacactaa |
| 7261 gaaacatatc aaggtgcttt tggcacaggt gcccacaaat acggatgcag tgctgagata |
| 7321 gtttatgaga cttgtaccat ttcacaaact ctgaaattgg gttccatatt ggcaaggctg |
| 7381 ccacagttgt taagaataat cctctatgtt tcttcctcac aaaaccatat ctcatttata |
| 7441 tccagaccat tacttcacta taattacaag gacaaattat tagcaagaaa taagaatagt |
| 7501 attagaagaa ttgatcctat tttgaacccc tctccagtat cttcacactc ttgtcaactc |
| 7561 tccaggcctc tctcttgccc tgagttatca gcctgtgtgg tgttaactac cttagaaggt |
| 7621 acaagctaag aaatgtaaca gtatcaaccc tcccagttgc ttaattatac ccataggtaa |
| 7681 tacaaaaagc tctgaagacc caaagatgac attactaatg atgtgatttc aggagccaca |
| 7741 gaagaacctt accagcttcc ctcaaatcag tccttatcct ctttctatct tcactcccat |
| 7801 catcatctat tttcacacta tccagctaag caaagattcc tggaggctga cttgtatctt |
| 7861 cagactcaca gagtgaattc agctcttctg aatcaagacc cacccagtct ctttcattca |
| 7921 gacctgttgc taacaaattt atatttgcca aggatattag gcaaaagagg ctacttgatt |
| 7981 ggtggccaac ctcgtgccca catggaaggt atctttaata gggtcttttc aaaccttagt |
| 8041 ggaggagggt cagctcaatt tgggcaatgc atttgttccc agtttcattt tcttcctggg |
| 8101 aattaactcg tcatttcatt ccttcagtca tcttctgtgt aggtgaccgg agcactgaga |
| 8161 ggcagctctg atgcactatt gtgtgtcagc agctcaaagg ccctaaaaca ctgaaggttc |
| 8221 tgcatctgaa gtattagatt gttagcagca aaatatgaaa gatgaggtgg acagtcctct |
| 8281 aagccctatt tagggaagct tttccaagcc acaatcttaa ctacctaccc aaaggatttg |
| 8341 cattaccccc agattctgtg ccaacaacct tttaaggaaa tacagtcctt gggaaatgag |
| 8401 ttttgatggt gaattggggt gttaaggaag ggaaagattg tcatagatgg tagggctttg |
| 8461 aaaatgcagg gtatcagctg ccactcctgg cttcaacaca ttgagtcact gcctagacgg |
| 8521 ttctcttggt cttattccca tcctggccaa tgcttaaata ctatttgttg aaaataattc |
| 8581 tttgagacag atttcagcta cctcccttcc aggttcgatt taacttggtt gtaattgtca |

TABLE 7-continued

| SEQUENCES OF EXEMPLARY mRNA TRANSCRIPTS: |
|---|
| 8641 atttgttgtt ataggtctta cctgtgtgaa agaaagaaaa agaaagaaag aaagaaagag |
| 8701 aaaggaaatt ataaggtcaa gttaacagtt ttgaggtttt gtgttttttt ctggaactac |
| 8761 ttcaagtgag aaaataaaaa aaaatggtga caaagctgta cagatagaga taatagaaga |
| 8821 caaagagatt aaaaggaaat aaaaatgcat gattaaaaac taagaataaa aaacctattt |
| 8881 ttatgtttcc taaaggaaat tgtttattct acagcctcag taggtagaca caaacataaa |
| 8941 gatttcccta gaagacatag agtgggattt gataacactg tctgttattt tctgtacatt |
| 9001 gtggtaggtc caggaaatat gacattttcc cccttgatgt gttattgttg ttgttgggtg |
| 9061 gggtgggcat tttgtttatt tgtttggtgg caatcagtgg tagtagggag tgggagggct |
| 9121 tatattggtt tttccagcta ttaaggggac atattgtgtc gttgtgcttt tcacgttata |
| 9181 aaatgtttat atttaccagt acagcactgg gctttataaa gactgcactc agaaccacac |
| 9241 tgcacagtcc agtttttttaa aaagctgcta catgacagac aggtaatccc actgagtgag |
| 9301 ttttgagaaa caaatcaaac gaagtaaaca agaaacataa aaaccaaata gcaaatgaat |
| 9361 aaaagcctgt tcttgtaact tattcaactt ttgccaaatt cctaccaatc acttgctttt |
| 9421 taaaagaaat gtataatagc caaaagagaa attatgtccc tgttgtacag aagttagaat |
| 9481 ttttgactcc aggcagcagt ttgctcagtg atcttgaaca agttatccaa ttgcctctac |
| 9541 atttgcatca gtttctctag ctgcaaaatg gggataatac tatataccta cctcacagtg |
| 9601 ggagggcagg agattttgag gccctgaggt tttaggtggg ctgtgagggc caacgcttga |
| 9661 cacaaagtcc atgggttatt attcaagaat gcacaggccc atcggccttt tagaaagaca |
| 9721 agacagggag tgcttgtttg atatttcaag gaataaagcc ggagctcctg aattgtagtc |
| 9781 caccttaaaa gagagacctg tattggagaa tattttattt ttttggcaaa tttgatctta |
| 9841 ccctttacca gttctataat ttggttaaaa gctgattatg tcctacaatg tcaaagtcag |
| 9901 ctaactgtcg tctacttaag acttctggtc atttccaact tatagaggaa gggagtctct |
| 9961 aaaatctctt cttcagaagg cacctcactt ctcagactta aaattccaca tcaagtgttc |
| 10021 cattaaaaga agataaggca ttctgagtgc aaacaaatgg gggcttctta aactacacac |
| 10081 cagcagtcag tgaggaaaac tttgaacaat tattgagttg ctttcttggg tctctataat |
| 10141 caataacctg tctgcagata tctatctata taaagatatt atatataaat ataaatttac |
| 10201 atatatatgc acatgtatat atagttgtac atatatgtgt gtatatatat acttaaatgt |
| 10261 aatatttaca aaataaaact gtgatctcgt ctagagaaaa tgtattcata ttacaaactg |
| 10321 ctcttccata tttatgtacc atattatacc tttttattat tgttataatt attatgggta |
| 10381 tttctaatta atatgatgtt gaaacctgtt tggcaccttc tggaagctac caaaaaaatg |
| 10441 acactccatt gaagtgctta aaagctgttc tcataagaat tctactggcc tattgtaaaa |
| 10501 aagaaaaaaa aaaagaaaaa gaagaaagac acaaagaaaa taatctaaac accaaaaact |
| 10561 aaacacaatt ccaatccttt ttctgtacct cacgcgcata aatttgctgc tcctattttt |
| 10621 ttttctgttt atgtgttttt atggatctaa gttaaatctt ttggcaatat ataaaaatgt |
| 10681 aaatagtaaa ctttatttat taagaatgtc atcttttttta atttatattt acacaattgt |
| 10741 tcatctaatt tattttttct atacagtttt aaatactcag acatattttg ctgttcatga |
| 10801 tatttttatc ctgttctcat ggatttgttt tcccatactg ttttctctga tctcaattac |

TABLE 7-continued

SEQUENCES OF EXEMPLARY mRNA TRANSCRIPTS:

10861 aggttggatc tcacaaataa taatgtcaga gacagaaata ttttgccact gttgattact
10921 atactttaaa gttctatatt atgaaaatat ataatagctt gtacgcttca aaaaaaaaaa
10981 aaaaaaaaaa aaaaaaaaaa aaaaaaaaaa aaaaaaaaaa aaaaa LGALS14 mRNA transcript 794 bp

SEQ ID NO: 9

1 gctgcattac agacacagac ctgcaaacat ctatggttgt gacagagttt ctttctgaca
61 cctgagtctt tctcctgctg cacggaaagc ttgctgggag gggcttggaa tctggcatga
121 agccaaaggg catctctgag ttgcagcatt taaatgatcc cactcagaga ttcacacaga
181 agactggaca caattccgaa gagctgccca gaaggagaga acaatgtcat cactacccgt
241 accatacaca ctgcctgttt ccttgcctgt tggttcgtgc gtgataatca cagggacacc
301 gatcctcact tttgtcaagg acccacagct ggaggtgaat ttctacactg ggatggatga
361 ggactcagat attgctttcc aattccgact gcactttggt catcctgcaa tcatgaacag
421 ttgtgtgttt ggcatatgga gatatgagga gaaatgctac tatttaccct ttgaagatgg
481 caaaccattt gagctgtgca tctatgtgcg tcacaaggaa tacaaggtaa tggtaaatgg
541 ccaacgcatt tacaactttg cccatcgatt cccgccagca tctgtgaaga tgctgcaagt
601 cttcagagat atctccctga ccagagtgct tatcagcgat tgagggagat gatcagactc
661 ctcattgttg aggaatccct ctttctacct gaccatggga ttcccagagc ctactaacag
721 aataatccct cctcacccct tcccctacac ttgatcatta aaacagcacc aaacttcaaa
781 aaaaaaaaaa aaaa CLCN3 mRNA transcript 6299 bp

SEQ ID NO: 10

1 gtgacgtcac gcgtcgacgc tggggcgtac ctttcgggct cctgactcct gccgcttctc
61 ttccccttcc gtgggtcagg gccggtccgg tccggaacct gcagcccctt tcccagtgtt
121 ctagttcgcc cgtgacccgg aataatgagc aaggagggtg tggtgggttg aaagccatcc
181 tactttactc ccgagttaga gcatggattc agttttagtc ttaaggggga agtgagattg
241 gagattttta tttttaattt tgggcagaag caggttgact ctagggatct ccagagcgag
301 aggatttaac ttcatgttgc tcccgtgttt gaaggaggac aataaaagtc ccaccgggca
361 aaattttcgt aacctctgcg gtagaaaacg tcaggtatct tttaaatcgc gatagttttc
421 gctgtgtcag gctttcttcg gtggagctcc gagggtagct aggttctagg tttgaaacag
481 atgcagaatc caaaggcagc gcaaaaaaca gccaccgatt ttgctatgtc tctgagctgc
541 gagataatca gacagctaaa tggagtctga gcagctgttc catagaggct actatagaaa
601 cagctacaac agtataacaa gtgcaagtag tgatgaggaa cttttagatg gagcaggtgt
661 tattatggac tttcaaacat ctgaagatga caatttatta gatggtgaca ctgcagttgg
721 aactcattat acaatgacaa atggaggcag cattaacagt tctacacatt tactggatct
781 tttggatgaa ccaattccag gtgttggtac atatgatgat ttccatacta ttgattgggt
841 gcgagaaaaa tgtaaagaca gagaaaggca tagacggatc aacagcaaaa agaaagaatc
901 agcatgggaa atgacaaaaa gtttgtatga tgcgtggtca ggatggctag tagtaacact
961 aacaggattg gcatcagggg cactggccgg attaatagac attgctgccg attggatgac
1021 tgacctaaag gagggcattt gccttagtgc gttgtggtac aaccacgaac agtgctgttg
1081 gggatctaat gaaacaacat ttgaagagag ggataaatgt ccacagtgga aaacatgggc
1141 agaattaatc ataggtcaag cagagggtcc tggttcttat atcatgaact acataatgta TABLE 7-continued

| SEQUENCES OF EXEMPLARY mRNA TRANSCRIPTS: |
| --- |
| 1201 catcttctgg gccttgagtt ttgcctttct tgcagtttcc ctggtaaagg tatttgctcc |
| 1261 atatgcctgt ggctctggaa ttccagagat taaaactatt ttaagtggat tcatcatcag |
| 1321 aggttacttg ggaaaatgga ctttaatgat taaaaccatc acattagtcc tggctgtggc |
| 1381 atcaggtttg agtttaggaa aagaaggtcc cctggtacat gttgcctgtt gctgcggaaa |
| 1441 tatcttttcc tacctctttc caaagtatag cacaaacgaa gctaaaaaaa gggaggtgct |
| 1501 atcagctgcc tcagctgcag gggtttctgt agcttttggt gcaccaattg gaggagttct |
| 1561 ttttagcctg gaagaggtta gctattattt tcctctcaaa actttatgga gatcattttt |
| 1621 tgctgcttta gtggctgcat ttgttttgag gtccatcaat ccatttggta acagccgtct |
| 1681 ggtccttttt tatgtggagt atcatacacc atggtacctt tttgaactgt ttccttttat |
| 1741 tcttctaggg gtatttggag ggctttgggg agccttttc attagggcaa atattgcctg |
| 1801 gtgtcgtcga cgcaagtcca cgaaatttgg aaagtatccc gttctggaag tcattattgt |
| 1861 tgcagccatt actgctgtga tagccttccc taatccatac actaggctaa acaccagtga |
| 1921 actgatcaaa gagcttttta cagactgtgg tcccctggaa tcctcttctc tttgtgacta |
| 1981 cagaaatgac atgaatgcca gtaaaattgt cgatgacatt cctgatcgtc cagcaggcat |
| 2041 tggagtatat tcagctatat ggcagttatg cctggcactc atatttaaaa tcataatgac |
| 2101 agtattcact tttggcatca aggttccatc aggcttgttc atccccagca tggccattgg |
| 2161 agcgatcgca ggaaggattg tggggattgc ggtggagcag cttgcctact atcaccacga |
| 2221 ctggtttatc tttaaggagt ggtgtgaggt cggggctgat tgcattacac ctggccttta |
| 2281 tgccatggtt ggtgctgctg catgcttagg tggtgtgaca agaatgactg tctccctggt |
| 2341 ggttattgtt tttgagctta ctggaggctt ggaatatatt gttcccctta tggctgcagt |
| 2401 catgaccagt aaatgggttg gagatgcctt tggcagggaa ggcatttatg aagcacacat |
| 2461 ccgattaaat ggataccctt tcttggatgc aaaagaagaa ttcactcata ccaccctggc |
| 2521 tgctgacgtt atgagacctc gaaggaatga tcctccctta gctgtcctga cacaggacaa |
| 2581 tatgacagtg gatgatatag aaaacatgat taatgaaacc agctacaatg gatttcctgt |
| 2641 cataatgtca aaagaatctc agagattagt gggatttgcc ctcagaagag acctgacaat |
| 2701 tgcaatagaa agtgccagga aaaaacaaga aggtatcgtt ggcagttctc gggtgtgttt |
| 2761 tgcacagcac accccatctc ttccagcaga aagtcctcgg ccattgaagc ttcgaagcat |
| 2821 tcttgacatg agccctttta cagtgacaga ccacacccca atggagatcg tggtggatat |
| 2881 tttccgaaag ctgggactga ggcagtgcct tgtaactcac aatgggattg tcttggggat |
| 2941 catcacaaag aagaacatat tagagcatct cgagcaacta aagcagcacg tcgaaccctt |
| 3001 ggcgcctcct tggcattata acaaaaaaag atatcctccg gcatatggcc cagacggcaa |
| 3061 accaagaccc cgcttcaata atgttcaact gaatctcaca gatgaggaga gagaagaaac |
| 3121 ggaagaggaa gtttatttgt tgaatagcac aactctttaa cctgagggag tcatctactt |
| 3181 ttttttcctc ctttacaaaa aaagaaagga aatataaaag ccgggttttt gcaacatggt |
| 3241 ttgcaaataa tgctggtgga atggaggagt tgtttgggga gggaaaggag agagaaggaa |
| 3301 aggagtgagg tatttcccgt ctaacagaaa gcagcgtatc aactcctatt gttctgcact |
| 3361 ggatgcattc agctgaggat gtgcctgata gtgcaggctt gcgcctcaac agagatgaca |
| 3421 gcagagtcct cgagcacctg gcctgttgct ccaacattgc aaagacacat tatcagtccc |
| 3481 tatttctaga gggattactt tgaattgagc catctataaa actgcaaggt cttgcccttt |

TABLE 7-continued

SEQUENCES OF EXEMPLARY mRNA TRANSCRIPTS:

3541 tttttaatca aaactgttct gtttaattca tgaattgtat agttaagcat tacctttcta
3601 cattccagaa gagcctttat ttctctctct ctctctctct ctctctctct ctctactgag
3661 ctgtaacaaa gcctctttaa atcggtgtat ccttttgaag cagtcctttc tcatattgag
3721 atgtactgtg attttactga ggtttcatca caagaaggga gtgtttcttg tgccattaac
3781 catgtagttt gtaccatcac taaatgcttg gaacagtaca catgcaccac aacaaaggct
3841 catcaaacag gtaaagtctc gaaggaagcg agaacgaaat ctctcattgt gtgccgtgtg
3901 gctcaaaacc gaaaacaatg aagcttggtt ttaaaggata aagttttctt ttttgttttc
3961 ctctcagact ttatggataa tgtgaccggg tcttatgcaa attttctatt tctaaaacta
4021 ctactatgat atacaagtgc tgttgagcat aattaaataa aatgctgctg ctttgacagt
4081 aaagagaagg aagtattctg attagctgta tctggtatta attgcatgtt aaaacactgg
4141 aatttttaaa attgaaatta gatcagtcat tcttttcttt tctcaagata tctcatggct
4201 gacactgaag aagaaatgta attcataact tgcactaaat gtatattttt tttcttaaaa
4261 atttaccatt cttatttata tttttatgga ttaaaattta taaaatacag atcagttaat
4321 attgcactta agtaatttta ccttttttaat gtgattttta tagaataatt cagacttaca
4381 aatacagaga tatgaacaaa gtttacagtg ggaacaaagg tttaaaaaaa ggttgtggtt
4441 ctctctctgt gatccagtgt gcacataaac ctttctctga tctttcactg ccatcctctg
4501 gattatgtct tctgacctgt ccattttgac ccattaactg gaaagttgaa aaactacatt
4561 aactggaaag ttgaaaaact acattacttt ggagaataaa accgaaagtt cgtgtatacc
4621 ttcttaaaaa aaaaatcaaa ccaaaaatgt gaaaacaata gaattgcaaa gatagcagtt
4681 aaaattttaa tctgaaaata acctttgaat ctcgggctag gttacgtcca tatttgaagt
4741 ggtcagtgat ggtttgaaca ttttttgcag gatgagtgaa aatgcactgg attatatttg
4801 ggatttttgt ttttggaatt gtctgtttta atcacagcct taattcacaa ttggcaaagg
4861 cagtttactc aaaggactgg gctaaatatt ctgtaattat gcatttttga taggaaaatg
4921 aaatttttgc aaacagacat tttctttttt tttggctgga gtgcagtggg gcatggtctt
4981 ggctcactgc agcgttgacc acctgggctc aagtgatact cccgcctcag ccacccaagt
5041 agctggcact acgggcacac gccaccatgc ccagctaatt tttttgtatt tttagtagag
5101 atggggtttt gccatgctgc ccaggctggt ctcaactcct cagctcaagc aatctgcctg
5161 cgtgagcctc ccaaagtggt ggaattacag gcgtgggcca ctgcgcctgg cccagacaga
5221 cattttctga aacacaactg gcaatgagct gtttttacat tttgaaagtg attcttcact
5281 tcctagttct taattatagt atacctatta agatctgtaa gatcctgaag acataagatc
5341 atgaagccat ataagaatga ggattgaaag ttgagcaaaa ttttcgggat tttgggaaac
5401 attcttagct gtgctatctg cctaaaatta ttccttatta cttctctcct ttgacagact
5461 tcaagttttc ttcatagccc tttcaaagtt ttttgagcca tccagagtaa aatcatttct
5521 aaatgatagt tctgtatatc tccaactcgt cttaagtgta tttgcctgtg tgcaacgtat
5581 tgctagacta tgaactcctc agcatggctg ctggataact taattgtcct gagttaatag
5641 ccttcaaagg acaaatcggt ttctttgcag atagcttcgt aaaacttcac atggagttta
5701 ttttatcata tttccctttt ttatttctgc tcctccttta attgcccatc ttgcttcaga
5761 gactgacatt tcagggtgga tattaattaa agcattaatt ttgttttttg gtatatttct
5821 atccctagta tttctatctt actgctaaaa tacaggaaaa gtgccgtatt tttaatgcat TABLE 7-continued SEQUENCES OF EXEMPLARY mRNA TRANSCRIPTS:

```
5881 ttagtggttt tctttggtgt tatctgttcc atttttcttt ttcatacatt gaagtgtgtc
5941 tccttttcaa ccaaaataat gaaatagtgg agaccatgaa attgttgtgc ctggctaatt
6001 ggcaaattaa tttaccaata taataagtgt agcgccttgt ttgaataccc tttttgagaa
6061 ggtatgatga gaatgggcaa gggtgtcagc atctcttctt cttaataatt aattgttttc
6121 agttttggtt cacgaagaat gcttagttaa tctgtaatgt tgcctagagc tgtatttatc
6181 tgtttttatt tatactagtg tagtaaagct gcatatcatt acagtaaaaa cgactactgt
6241 gatgagttaa tcagaaaatc tattaaaatc tatatgacaa tgaaaaaaaa aaaaaaaaa
```

DAPP1 mRNA transcript 3006 bp

SEQ ID NO: 11

```
   1 gcaggctgct gtctcacaga gcgagaaggt gtcaggagca gcccagttgt gtctctctct
  61 ctacctctgt gaagggcgcg aatgggcaga gcagaacttc tagaagggaa gatgagcacc
 121 caggatccct cagatctgtg gagcagatcc gatggagagg ctgagctgct ccaggacttg
 181 gggtggtatc acggcaacct cacacgccat gctgctgaag ctcttctcct ctcaaatgga
 241 tgtgacggca gctaccttct gagggacagc aatgagacca ccgggctgta ctctctctct
 301 gtgagggcca aagattctgt taaacacttt catgttgaat atactggata ttcatttaaa
 361 tttggcttta atgaattctc atctttgaag gattttgtca agcattttgc aaatcagcct
 421 ttgattggaa gcgagacagg cactctgatg gttctaaaac atccctaccc aagaaaagtg
 481 gaagaaccct ccatttatga atctgtccgg gttcacacag caatgcagac aggaagaaca
 541 gaagatgacc ttgtgcccac agcaccttct ctgggcacca aagaaggtta cctcaccaaa
 601 cagggaggcc tggtcaagac ctggaaaaca agatggttta ctctgcacag gaatgaactg
 661 aaatacttca aagaccagat gtcaccagaa ccaattcgga tcctagacct aacagaatgt
 721 tcagctgtac aattcgatta ttcacaagaa agggtaaact gtttttgttt ggtatttcca
 781 ttcaggacat tttatctctg tgcaaagacc ggagtagaag ctgatgagtg gatcaagata
 841 ttacgctgga aattggtcaa ggacaaaagc tgatttattt tgtctgctct ctgtatatct
 901 cccgaggaga agactgatca caaataagaa aacagctcaa ccaaggggaa ggcacgatcc
 961 gatctcggtc gttcatcttt aaatagatct ttcttgccaa ggaatgctct ggcccaggag
1021 caaggtggaa tgtttccctg acgctgtgat ctgcagcagg cttcaaatga aaaccgacta
1081 aggatttttct ttcaaaaaca aatcagaagc agatgctgat tgggacccat ataccacgtt
1141 gctgactcac gttgctgccc ttccatgatg ttgccatctc cttgagaaca ctgaagcaat
1201 caccattctg atagaaagtg cttaaaccac cactcttagg tctgctcact cttagaacac
1261 acaatggaag aggaagggtt tttgttttca ctcattgtgg tccccaagcc tattgacact
1321 agttgcctag agtcccactg tgagtcatgg tcagcctgtc tgacatccag gttgtgctat
1381 taaccaagaa ggaaacagat acttggaggc ttagatgact tctgcaggat ttatattcag
1441 atagaaaaca tcaaatattt tcaggggaga ggtttttttt tttaattttt ccccctttat
1501 acaaaaaaaa aagaacattt ccaaaactaa aatagaaaat gcttgtggca tttattttct
1561 ctttttaaaa ggttcagaaa tttggcaggt cctttgcttc taatgacaaa actgtgagag
1621 ctagatgtcc tatgggcaat taggtagtat aataaaggta aatgaaggta caatttttaa
1681 accattattt tcaccctgtt ggggtaaatg ttttaaagag tgagaaaaca taaattgaga
1741 aagggtgata aagtaataga taacttttag tttaataata attattgtta ttatactact
1801 aataatagag cacttgtaag cactaagtta tctttatcca acatttctcc aaatggactg
```

TABLE 7-continued

SEQUENCES OF EXEMPLARY mRNA TRANSCRIPTS:

```
1861 aaagaaactt ttcaaggaca gtgtattata acaatccctt tcccagaatt agttgtatag
1921 ggttggccca agagatgtaa gaaaaatctc gcattgctcc ctaagcaccc tgggccttat
1981 taaagagcaa cttctatttc cagtcggggg agtaacacta aagctacaag aaatatgtaa
2041 taatgatagg taataatgtg ttccaaagct ttttcaaact agaataagga ggcaaataga
2101 agaatgagat actgatgtcc acagttcatt ggcagaatct aaccccttct gttatctttt
2161 ttaatactat ttttgtttag atagaagttt caaagaagat aaaaatgctt gaagagcctg
2221 agagtaaaaa gattatgctg caaagctatg atataaactg ctcttgcagt ccaaagggat
2281 acctgattaa agaagtttct tatttaaaca tctcagacgc aaaaaattaca ttaaattttt
2341 gtatatttca acaacatttt aaatgtattt tgttatgttt gtattatata ggataaagca
2401 aatgtcaagt taaaatgtat tgtgttgttt gtaaagtaag aagttactgg ccaggagcgg
2461 cggctcatgc ctgtaatccc aggactttgg taggccaaga caagcagatc acttgaggtc
2521 aggagttcaa catcagcctg gccaacatga tgaaaccttg tctttactaa aaatacaaaa
2581 attagctggg catggtggca ggcgcctgta atcccagcta ctcaggaggc tgaggcagga
2641 gaattgcttg aacccgggag gtggaggttg cagtgaacca agatcgcggc gctgcactct
2701 agcctgggtg acagagtcag actccgtccc aaaaaaacaa acaaacaaaa caaaacaaaa
2761 aaaaacagaa gttacaaatg aatactcacg gatatgtata gttttatgtt tgttttctta
2821 gaaacaaatg tgtttctttg ggtgggtaat attgtgtttt actatgttta ccttttataa
2881 aacataacct gtttatttat attctttggc tttgtttatt aaaaagcatg attttgctgt
2941 gcatgtacca ttttgctatt aaaatttatt tttaatattt gtaacttgaa aaaaaaaaaa
3001 aaaaaa
```

POLE2 mRNA transcript 1861 bp

SEQ ID NO: 12

```
   1 agcctactcg gtccggggtt gcgaactgta aggtctgagt tgctgcggcg caggcagcgg
  61 agaccaagca gggatcttaa cagggtttag cgccacgcgg gccagggccg aggccggagc
 121 tgggaggggc gcgcccggga aggggcggag ctgcggcggt ggcgccaaat cgcaaatatg
 181 gcgccggagc ggctgcggag ccgggcgctc tccgccttca agttgcgggg cttgctgctc
 241 cgtggtgaag ctattaagta cctcacagaa gctcttcagt ctatcagtga attagagctt
 301 gaagataaac tggaaaagat aattaatgca gttgagaagc aacccttgtc atcaaacatg
 361 attgaacgat ctgtggtgga agcagcagtc caggaatgca gtcagtctgt tgatgaaact
 421 atagagcacg ttttcaatat cataggagca tttgatattc cacgctttgt gtacaattca
 481 gaaagaaaaa aatttcttcc tctgttaatg accaaccacc ctgcaccaaa tttatttgga
 541 acaccaagag ataaagcaga gatgtttcgt gagcgatata ccattttgca ccagaggacc
 601 cacaggcatg aattatttac tcctccggtg ataggttctc accctgatga aagcggaagc
 661 aaattccagc ttaaaacaat agaaacctta ttgggtagta caaccaaaat cggagatgcg
 721 attgttcttg gaatgataac gcagttaaaa gagggaaaat tttttctgga agatcctact
 781 ggaacagtcc aactagacct tagtaaagct cagttccata gtggtttata cacagaggca
 841 tgctttgtct tagcagaagg ttggtttgaa gatcaagtgt ttcatgtcaa tgcctttgga
 901 tttccaccca ctgagccctc tagtactact agggcatact atggaaatat taattttttt
 961 ggaggtcctt ctaatacatc tgtgaagact tctgcaaaac taaaacagct agaagaggag
1021 aataaagatg ctatgtttgt gtttttatct gatgtttggt tggaccaggt ggaagtattg
```

TABLE 7-continued

SEQUENCES OF EXEMPLARY mRNA TRANSCRIPTS:

```
1081 gaaaaacttc gcataatgtt tgctggttat tcaccagcac ctccaacctg ctttattctg
1141 tgtggtaatt tttcatctgc accatatgga aaaaatcaag ttcaagcttt gaaagattcc
1201 ctaaaaactt tggcagatat aatatgtgaa tacccagata ttcaccaaag tagtcgtttt
1261 gtgtttgtac ctggtccaga ggatcctgga tttggttcca tcttaccaag gccaccactt
1321 gctgaaagca tcactaatga attcagacaa agggtaccat tttcagtttt tactactaat
1381 ccttgcagaa ttcagtactg tacacaggaa attactgtct tccgtgaaga cttagtaaat
1441 aaaatgtgca gaaactgcgt ccgttttcct agcagcaatt tggctattcc taatcacttt
1501 gtaaagacta tcttatccca aggacatctg actcccctac ctctttatgt ctgcccagtg
1561 tattgggcat atgactatgc tttgagagtg tatcctgtgc ccgatctact tgtcattgca
1621 gacaaatatg atcctttcac tacgacaaat accgaatgcc tctgcataaa ccctggctct
1681 tttccaagaa gtggattttc attcaaagtt ttttatcctt ctaataagac agtagaagat
1741 agcaaacttc aaggcttttg agattcttaa agatcatctg aagaaaattc atcagttttc
1801 tgcttaactc tatatcttat gtgattctga tattacaata aaattatggt aaactttagg
1861 a
```

PPBP mRNA transcript 1307 bp

SEQ ID NO: 13

```
   1 acttatctgc agacttgtag gcagcaactc accctcactc agaggtcttc tggttctgga
  61 aacaactcta gctcagcctt ctccaccatg agcctcagac ttgataccac cccttcctgt
 121 aacagtgcga gaccacttca tgccttgcag gtgctgctgc ttctgccatt gctgctgact
 181 gctctggctt cctccaccaa aggacaaact aagagaaact tggcgaaagg caaagaggaa
 241 agtctagaca gtgacttgta tgctgaactc cgctgcacgt gtataaagac aacctctgga
 301 attcatccca aaaacatcca aagtttggaa gtgatcggga aaggaaccca ttgcaaccaa
 361 gtcgaagtga tagccacact gaaggatggg aggaaaatct gcctggaccc agatgctccc
 421 agaatcaaga aaattgtaca gaaaaaattg gcaggtgatg aatctgctga ttaatttgtt
 481 ctgtttctgc caaacttctt taactcccag gaagggtaga attttgaaac cttgattttc
 541 tagagttctc atttattcag gatacctatt cttactgcat taaaatttgg atatgtgctt
 601 cattctgcct caaaaatcac attttattct gagaaggctg gttaaaagat ggcagaaaga
 661 agatgaaaat aaataagcct ggtttcaacc ctctaattct tgcctaaaca ttggactgta
 721 ctttgcactt ttttctttaa aaatttctat tctaacacaa cttggttgat tttcctggt
 781 ctactttatg gttattagac atactcatgg gtattattag atttcataat ggtcaatgat
 841 aataggaatt acatggagcc caacagagaa tatttgctca atacattttt gttaatatat
 901 ttaggaactt aatggagtct ctcagtgtct tagtcctagg atgtcttatt taaaatactc
 961 cctgaaagtt tattctgatg tttattttag ccatcaaaca ctaaaataat aaattggtga
1021 atatgaacct tataaactgt ggctagccgg tttaaagcga atatattcgc cactagtaga
1081 acaaaaatag atgatgaaaa tgaattaaca tatctacata gttataattc tatcattaga
1141 atgagcctta taaataagta caatatagga cttcaacctt actagactcc taattctaaa
1201 ttctactttt ttcatcaaca gaactttcat tcattttta aaccctaaaa cttataccca
1261 cactattctt acaaaaatat tcacatgaaa taaaaatttg ctattga
```

TABLE 7-continued

| SEQUENCES OF EXEMPLARY mRNA TRANSCRIPTS: |
| --- |

LYPLAL1 mRNA transcript 1922 bp

SEQ ID NO: 14

```
   1 gtgcgcggcc ccgcgcggca acgcaggggc ggaaccgcat gactggcagt ggcatcagcg

  61 atggcggctg cgtcggggtc ggctctgcag cgctgtatcg tgtcgccggc agggaggcat

 121 agcgcctctc tgatcttcct gcatggctca ggtgattctg gacaaggatt aagaatgcgg

 181 atcaagcagg ttttaaatca agatttaaca ttccaacaca taaaaattat ttatccaaca

 241 gctcctccca gatcatacac tcctatgaaa ggaggaacct ccaatgtatg gtttgacaga

 301 tttaaaataa ccaatgactg cccagaacac cttgaatcaa ttgatgtcat gtgtcaagtg

 361 cttactgatt tgattgatga agaagtaaaa agtggcatca agaagaacag gatattaata

 421 ggaggattct ctatgggagg atgcatggca atacatttag catatagaaa tcatcaagat

 481 gtggcaggag tatttgctct ttctagtttt ctgaataaag catctgctgt ttaccaggct

 541 cttcagaaga gtaatggtgt acttcctgaa ttatttcagt gtcatggtac tgcagatgag

 601 ttagttcttc attcttgggc agaagagaca aactcaatgt taaaatctct aggagtgacc

 661 acgaagtttc atagttttcc aaatgtttac catgagctaa gcaaaactga gttagacata

 721 ttgaagttat ggattcttac aaagctgcca ggagaaatgg aaaaacaaaa atgaatgaat

 781 caagagtgat ttgttaatgt aagtgtaatg tctttgtgaa aagtgatttt tactgccaaa

 841 ttataatgat aattaaaata ttaagaaata acactttcct gactttttta ttattaaaat

 901 gcttatcact gtagacagta gctaatctta ttaatgaaaa acaatagaca aacatctgtg

 961 cataattttt cagacacaat tctgtaaata tttggaaacc ttttaagtat ttaaactttt

1021 aaatttttga aataaagtat tctaaactaa tataaataag gacaatgaaa aaacatgaaa

1081 ggacttagca taatgttatt ttatcttttc tacaactttg tttaaattac ctttccaaag

1141 atatttgtgt ttatgtaatt ttccacggaa taacattaat actctaggtt tataaaccgg

1201 tttcacatta tttcatttga tcatcacaag agctttgcga agtaagccga gaagttgtta

1261 ctggtattta ataatagcaa tagaggagtt aaagactttc ccacagcttg caggtcaaga

1321 caagaaattc aggtctccta attctcagtg gagctctatt tctgttaacc caaattgctg

1381 ctctgtttta ggcctcaatt tcatctgtaa aatgatacta atagtactta tcccattgga

1441 tttttgttga gatttaaata aatagccaaa agccaataca taataaacac tcaataaaga

1501 ttaaccacaa ggagagtcat gatctggctc caggaataca ttgttagatg actgaaaaat

1561 tgtattactt caatgaaaat actataaata ataacatttt cacatattag ttggttctca

1621 tgcatacata atctaatttt atttgatcct cacaactgtt taagttttat taaatataca

1681 ttatccctat ttgtataaat agaatcatac aatacctgcc tgctttcatt caacaaaatt

1741 atcatgagat ttttccatgt tgtgtacatc aatagttcat ctattttatt gctcagtaat

1801 attccattgt gtggatgtat cactatttgt ttacacactc accactgata tataagttgc

1861 ttccagtgtg aggctgtttt aaataaagct gctatgaata ttcatgtaag aaaaaaaaaa

1921 aa
```

MAP3K7CL mRNA transcript 2269 bp

SEQ ID NO: 15

```
   1 cgcagccccg gttcctgccc gcacctctcc ctccacacct ccccgcaagc tgagggagcc

  61 ggctccggcc tcggccagcc caggaaggcg ctcccacagc gcagtggtgg gctgaagggc

 121 tcctcaagtg ccgccaaagt gggagcccag gcagaggagg cgccgagagc gagggagggc

 181 tgtgaggact gccagcacgc tgtcacctct caatagcagc ccaaacagat taagacacgg
```

TABLE 7-continued

| SEQUENCES OF EXEMPLARY mRNA TRANSCRIPTS: |
|---|
| 241 gaggtgaaag acaacttgag tggttaaatt actgtcatgc aaagcgacta gatggttcag |
| 301 ctgattgcac ctttagaagt tatgtggaac gaggcagcag atcttaagcc ccttgctctg |
| 361 tcacgcaggc tggaatgcag tggtggaatc atggctcact acagccctga cctcctgggc |
| 421 ccagagatgg agtctcgcta ttttgcccag gttggtcttg aacacctggc ttcaagcagt |
| 481 cctcctgctt ttggcttctt gaagtgcttg gattacagta tttcagtttt atgctctgca |
| 541 acaagtttgg ccatgttgga ggacaatcca aaggtcagca agttggctac tggcgattgg |
| 601 atgctcactc tgaagccaaa gtctattact gtgcccgtgg aaatccccag ctcccctctg |
| 661 gattgtcagt ggctgctatg cagcaggtgc agcctggtct ctcactgagt ctctactcca |
| 721 caaaggcaac gactggccaa ggcagtggct ggctctgggt tacacaagtg cagacactca |
| 781 actaagtgag ctggaagacc caggagaagg cggaggctca ggcgcccaca tgatcagcac |
| 841 agccagggta cctgctgaca agcctgtacg catcgccttt agcctcaatg acgcctcaga |
| 901 tgatacaccc cctgaagact ccattccttt ggtctttcca gaattagacc agcagctaca |
| 961 gcccctgccg ccttgtcatg actccgagga atccatggag gtgttcaaac agcactgcca |
| 1021 aatagcagaa gaataccatg aggtcaaaaa ggaaatcacc ctgcttgagc aaaggaagaa |
| 1081 ggagctcatt gccaagttag atcaggcaga aaaggagaag gtggatgctg ctgagctggt |
| 1141 tcgggaattc gaggctctga cggaggagaa tcggacgttg aggttggccc agtctcaatg |
| 1201 tgtggaacaa ctggagaaac ttcgaataca gtatcagaag aggcagggct cgtcctaact |
| 1261 ttaaattttt cagtgtgagc atacgaggct gatgactgcc ctgtgctggc caaaagattt |
| 1321 ttattttaaa tgaatagtga gtcagatcta ttgcttctct gtattaccca cacgacaact |
| 1381 gtctataatg agtttactgc ttgccagctt ctagcttgag agaagggata ttttaaatga |
| 1441 gatcattaac gtgaaactat tactagtata tgtttttgga gatcagaatt cttttccaaa |
| 1501 gatatatgtt tttttctttt ttaggaagat atgatcatgc tgtacaacag ggtagaaaat |
| 1561 gataaaaata gactattgac tgacccagct aagaatcgtg ggctgagcag agttaaacca |
| 1621 tgggacaaac ccataacatg ttcaccacag tttcacgtat gtgtattttt aaatttcatg |
| 1681 cctttaatat ttcaaatatg ctcaaattta aactgtcaga aacttctgtg catgtattta |
| 1741 tatttgccag agtataaact tttatactct gatttttatc cttcaatgat tgattatact |
| 1801 aagaataaat ggtcacatat cctaaaagct tcttcatgaa attattagca gaaaccatgt |
| 1861 ttgtaaccaa agcacatttg ccaatgctaa ctggctgttg taataataaa cagataaggc |
| 1921 tgcatttgct tcatgccatg tgacctcaca gtaaacatct ctgcctttgc ctgtgtgtgt |
| 1981 tctgggggag gggggacatg gaaaaatatt gtttggacat tacttgggtg agtgcccatg |
| 2041 aaaacatcag tgaacttgta actattgttt tgttttggat ttaaggagat gttttagatc |
| 2101 agtaacagct aataggaata tgcgagtaaa ttcagaattg aaacaatttc tccttgttct |
| 2161 acctatcacc acattttctc aaattgaact ctttgttata tgtccatttc tattcatgta |
| 2221 acttcttttt cattaaacat ggatcaaaac tgacaaaaaa aaaaaaaaa |
| MOB1B mRNA transcript 7091 bp |
| SEQ ID NO: 16 |
| 1 gctacccact tccgccccct ccccctgcca ttggaactag ctgagccgaa ctagttgcgg |
| 61 ccaccgagca gccggctctc ggcacctcct cctccgcctc cctgtctcct gttccattcg |
| 121 cctttcccct tctttcccgg cccacgccgc tccgaggcct cgcgaccgcc gagcctgcag |
| 181 cctgccccgc ggccaacatg agcttcttgt tgagttctca gcctgaagtt gactggaact |

TABLE 7-continued

| SEQUENCES OF EXEMPLARY mRNA TRANSCRIPTS: |
|---|
| 241 ttcagttaac aagtatttat cgaatacctg atctgtagtg ttggacttag acctatggaa |
| 301 ggagctactg atgtgaatga aagtggtagt cgctcttcta aaacttttaa accaaagaag |
| 361 aacattccag agggttctca ccagtatgag ctcttaaaac acgcagaagc cacacttggc |
| 421 agtggcaacc ttcggatggc tgtcatgctt cctgaagggg aagatctcaa tgaatgggtt |
| 481 gcagttaaca ctgtggattt cttcaatcag atcaacatgc tttatggaac tatcacagac |
| 541 ttctgtacag aagagagttg tccagtgatg tcagctggcc caaaatatga gtatcattgg |
| 601 gcagatggaa cgaacataaa gaaacctatt aagtgctctg caccaaagta tattgattac |
| 661 ttgatgactt gggttcagga ccagttggat gatgagacgt tatttccatc aaaaattggt |
| 721 gtcccgttcc caaagaattt catgtctgtg gcaaaaacta tactcaaacg cctctttagg |
| 781 gtttatgctc acatttatca tcagcatttt gaccctgtga tccagcttca ggaggaagca |
| 841 catctaaata catctttcaa gcactttatt ttttttgtcc aggaattcaa ccttattgat |
| 901 agaagagaac ttgcaccact ccaagaactg attgaaaaac tcacctcaaa agacagataa |
| 961 aaggatgcag agctgtgcaa attgttcctc aaatgaagca gtgtggagtg tattggggat |
| 1021 tttgttatat tttgttttta tctggattgt ttttgtccta ggtttggggg cgggggcttg |
| 1081 tttgggttcc tttttcttta ttccgattat gtgaaaccat attctattgc taggggaagc |
| 1141 caagaaccat tctctacaca cttgataagg gtaaatttac cttagtgttt ttaaacttgg |
| 1201 ttccggttac ctgaggagcc ttttaataat attgtgtgct gcaagaaagt gcctgttgat |
| 1261 tgaactgccg atggattggt ttctgtgtgg tataaattgt ggcccattta tgaagtcccc |
| 1321 aaaagagtta tgtttttaag tgccttggca ggctcacttc tgaggtgcaa aacatagata |
| 1381 tagaactgaa cagggcttga aacaatatta ggattactac ccagggcact tactggtgca |
| 1441 tgttgtaaca tatctatgat aaaagccata gtttacctaa aatggtgatt tccagccttt |
| 1501 actgctttga agaaacagaa tttgtaaagg tatgcatgta gaacataaaa aatatttctt |
| 1561 aattattttt tatattgatg gtaatatatt acgttcaaca atgcttaaag ctctacaagc |
| 1621 aggtcttttc ccacctcttg atatctgtga tactgaaact tgaggatgtt gaaatgtatt |
| 1681 acattttggc ctcctcctac atgttaactg cactgtagac gtaaaaactc aggttatata |
| 1741 taggattgcc atcttcagag gtgatgctga actgtgaggt tccctagtaa ttgccaaatg |
| 1801 agccgtaagt ctgcagaatt cccttccact ttgaagagaa ggggatagga atgtatattt |
| 1861 ggctgggggc atggagatgt tcgtatgtat gaggagttag ggatggggag tcaagttcta |
| 1921 gaaagttttg tctgaaaacc tttgaataga atggcatgaa gattttaatc aattacttat |
| 1981 aaacaaagtc ttagagactt ccttttagga atcaacttcc atgagaagtt aaaaataaat |
| 2041 tattaatttt aggtacagac attaaacatg gaatttaagg actgttgggg gaaattgatc |
| 2101 acttcttagc atttccattc agtgaatgga gctgatgttt gcctgtcatt ttaagatgat |
| 2161 accatacctt ctttggctat tataggtcca gtttgaagca ttctgacttc tggtttttcc |
| 2221 accctgaaag gaaatgcttt tctttgcagc agtattagat aatgaaaaat gctaattcag |
| 2281 tagttattaa cctctaaatt ttattcgcca tgactttcta gcgaattatt accataaata |
| 2341 acaatctcag aaacttagtt tttagaataa atattaattt ttccacttca gtcttatcct |
| 2401 agaaaatacc ctttttagaa atccagtttt agttttgtca ttttcgataa atctttcttc |
| 2461 agttagaaat atatatcctt ccttcagttg aaacatacac ctttttcaca tctaggaaga |
| 2521 aatgcttgct ctgaaatagt atagattaaa aacactcagt agaaaagaat ctaaaattaa |

TABLE 7-continued

| SEQUENCES OF EXEMPLARY mRNA TRANSCRIPTS: |
|---|
| 2581 atgaatttgt tttgccatta aagtagagca gtgatacaat ttaatgccat tacaattatg |
| 2641 ttgactagaa actgcctttt tctccacttc atttctagca attatttacc aagtaccaac |
| 2701 agtagaagta acaggaaagc ctggcagagt taaatatctt ggacatttat tggtaaagct |
| 2761 tatttataaa ctgcagccag agctagttaa tttccttaaa tctttttgta ttcagataga |
| 2821 taatatgaat cattatgggt tgattcagaa ataaaatttg tgaggtgatt ttgaatcttg |
| 2881 tccatatagg aaaatgaagc acagaattac tcagtcttcc atattgtatt tgacttcata |
| 2941 tcaatctagt aaaaaaggag ttgcaatagc caagtataga gagaacagtg aaaaattaat |
| 3001 cttgcccttt caagccttat acagtagtac actgtacttg tttttagtag taagacctac |
| 3061 tttcccacta tatgtagata gtttgttttc actgtgccag aatctcaggt gcctgcttag |
| 3121 agtatttctt taatcacagt cactgggaag taaggagatg tatatatgtg tatatatggt |
| 3181 aacaaagcat agcagttctc taggggagag gcctggcatt gcacatggtg ttacatggct |
| 3241 acaagtaagg aaaaaatcag aaagtgaaag aactgatgta ataaaaggtt gatttggttg |
| 3301 gttcccatga aagttagtaa gatgcccttt taaatataag gatcagtgct ttgttctgca |
| 3361 gcagagtttg ctgataaatg tctgttggat tctttttgga tttctttaat taatttgtaa |
| 3421 gtaaccaaga taattatttt ccccccttgcc ctctatatta atacgtagct ataaagcaac |
| 3481 agttggtttt cttatccttt gataaaagca tcccataaaa tataaagtag taagttaaca |
| 3541 tagtattatt gtcacacaca atgctttttt tggttaaatg ttgatacgaa gcaatgtttt |
| 3601 ggaattactt taattgatgg agtagtggtg gtagagagaa attaataaca aaaagagtga |
| 3661 aaatatttta attagcagta gatggtgcta ccggctttca tttgctgact tgattattcc |
| 3721 ctttctctta aaaaccatgg cattagactg cactaaatta acaagcatgt tagttgctgg |
| 3781 tagaggtttt ggaggttaat ttacctcaaa ttggaagact tttaattgca gtctctttct |
| 3841 accttccctc tgttagtcat ttgtaaattc taaatggtca ccataaaatg tattaggtag |
| 3901 gagaagatac gttttacgta taatatatct cagactgagt tactgcctgt cttatcagga |
| 3961 tggataaaac actacagtct cttatcagga aatagagatg atgtggatat ttatatatta |
| 4021 catatataac caccagactc cattttacat attagcattt tccttgctta tgggaaaata |
| 4081 gcaaaacaac atttcattta tacttttgtt taccccctctc tgagacaggt tttgataacc |
| 4141 actgaaatgg tagaatatgt gagatacaaa tattgagttg tagaactttc tttttaaggt |
| 4201 gaataagtca tgccttaaca tccaaataag agttcatctt cagagtggtt cttttgggag |
| 4261 cactgtttat tccagctata ccgcaaaagt acaacgtttt tggaactgtt ctagagcata |
| 4321 ccatgaaaag cagtttgtta ttatgcagga aaatcagttt catcatttta gttacactaa |
| 4381 acacttttgg cagcttaata tgaccttttt aaattttttt tatttttttt atttttattt |
| 4441 ctttaagatg gagtcttgct ctgttgcccg ggctggagta caatggcatg atctcagctc |
| 4501 actgcaacct ccacctcctg ggttcaagca tttctcctgc ctcagcctcc caagtagctg |
| 4561 ggattacagg cagcaccaca cctggctaat tttcatattt ttagtagaga tggggtttca |
| 4621 acatattggc caggctggtc tcaaactcct gacctcaagt gatccgccct ccccagcctc |
| 4681 ccaaagtgct gggattacag gtgtgagcca ccacagccag ccagtatgac ctatcttaat |
| 4741 catcagctca actgtaattt aaatttggct gttctctgga gctaaaccat tagggaagtt |
| 4801 caaaggaatg tgccatgatt tccgaatttg cacaagagaa tgttttaagc attggtagca |
| 4861 taattgaata aaagaatagt ttcctgatgt cactattttg aagtggaaat tatcacttgg |

TABLE 7-continued

| SEQUENCES OF EXEMPLARY mRNA TRANSCRIPTS: |
|---|
| 4921 atgtggaggt tttacttttt aaaaacactc agcttaatta ccttacccta attacctcag |
| 4981 ttagatatac taatggaaaa aaaccaagtc ctttctctag aacttgtttt ctatttttgt |
| 5041 tccttttcat gaaaacttct caatttaatt ttaactactg taggatagta ttgattgaat |
| 5101 ggatactatg gaaaagtgga tccaatattt aagatagaag tagtttaagg agacaacagc |
| 5161 ctttactgcc attttttttt aaatgttttc actcagatga acaatttgac tttaataaaa |
| 5221 gactggagat ttttgtacaa agaaatagga ataagtttca tatactaatt atgctgagtt |
| 5281 ttaagcccac atatcacaaa atatttagaa ttgtataacc ttttcatata tttataactt |
| 5341 ttaatgtctt tttaaaagat gtgggaccaa aaatatattt ataatttgga aatgtgactg |
| 5401 cataccaata agaaaactta ccttattttg aaatttatct gggatattaa agaatctacc |
| 5461 aattcttaaa aacacagatt tatacttcaa gcttattcta aaattaaaga atatatacca |
| 5521 attcttagaa acactttaag gactactctt aaataactta aatatcagag ttttgttgta |
| 5581 atattaaaat ttaccgtgga aatcactgtt gttcagctat caccttaatt gtgtatgata |
| 5641 tgataaatgt ttagcagtaa agctatctta agatttaatg gaaaagttta atttgaagat |
| 5701 gtaacaaaaa ttctgaccac agttgattct gaatttttaa ggctttccta ataggctgat |
| 5761 cacagagaat aatccatttt gaaggtataa aactgcactg tatgtctgtc acttgtagct |
| 5821 gaactgattc acattttgac aaaagagaga aaatacaaaa atgagttttg caaatgtaat |
| 5881 aactttttct gcatatagaa ctaaataatt gaaaaatatg ggctatagtt ctcaaaggta |
| 5941 gatagtaaaa tcactggctt tttccagctg tatgtttttc cactgtgcgt gtacacacac |
| 6001 actggaaaat aattaggctg attttgcagg tcttcatcgt tagagattct gaagtattta |
| 6061 ctgtcaattc ataggtttca gtttattcag gaaattagtg ttcgacagct tttttaaat |
| 6121 tatttcactg aagctgagat tattagtgat acaaagttaa aatttcaata tttaatttct |
| 6181 ctatatatta ttaatattaa attgtttttt acttataaat tcatgttctc atctgattta |
| 6241 atattaaatt tgtataggtg ggcgtttctt accattttgc acaagttttt gtttttctga |
| 6301 aatacttaat tgtgcaggtt gtaaaaaaga ttagtgcatt ttcattttaa ggatgctttg |
| 6361 ctccttaaat tgttcgacag aaatgacttt ttagggaaag tagttttttt ggagctacta |
| 6421 acttgtattt atcattgtac atgcataacc agggtggtga gggcaccaat cttgtaggaa |
| 6481 acacttactt gatgttttat ttgaactttt cctataggtt taacttttac tgcatagaat |
| 6541 taacactagg aacagtgtca tgaaatctgg gttgaaggag aatacagtat atatgagaac |
| 6601 acttaaagtt caaacagaaa tcatttccga agacaaaagc agaggaatat tgtcagtgcc |
| 6661 aagtaatgga agaataaggg cggcatttac actgtgcaag tattgagaag agtgcataaa |
| 6721 gacagggaac tactctcatg gagacagttt ctctcttata atcaagtaac tagaagggga |
| 6781 aaaatcatct aagttatgaa atccaacata ggcgctatat tacaaactgt gccggattat |
| 6841 gcaaattgta gttgttactg atcaaagttt aattgcttca tttttgttta aaaagggata |
| 6901 ctgatgtcag aaaatctgta atatgtttta ttcaaaagat gtaaataatg tatacagact |
| 6961 tgtatgtgat gggatgggaa atatttaaat tctaggtgtt tttttttttt taaagaagaa |
| 7021 actcaatgtt tataagaaaa aaatgaataa atagttacgt ttggccatga atcctgaaaa |
| 7081 aaaaaaaaaa a |

TABLE 7-continued

| SEQUENCES OF EXEMPLARY mRNA TRANSCRIPTS: |
| --- |

RAB27B mRNA transcript 7003 bp

SEQ ID NO: 17

```
   1 actcgcagtc ctgacgggca ggggctgcgg accgcccggc cttggaccca tccggagcca
  61 caggttggag gagataagta gctgtccccg tgctcatcgc cctgtggagc agatcctgtc
 121 tccttgccga cggtggagcc cgggagttcc agggcttggg aaggggaagg aaacctctct
 181 gaaatctgac acctgctctc ccggcaagga aacttcgcag gctgaccgac caagaccatc
 241 actatgaccg atggagacta tgattatctg atcaaactcc tggccctcgg ggattcaggg
 301 gtggggaaga caacatttct ttatagatac acagataata aattcaatcc caaattcatc
 361 actacagcag gaatagactt tcgggaaaaa cgtgtggttt ataatgcaca aggaccgaat
 421 ggatcttcag ggaaagcatt taaagtgcat cttcagcttt gggacactgc gggacaagag
 481 cggttccgga gtctcaccac tgcatttttc agagacgcca tgggcttctt attaatgttt
 541 gacctcacca gtcaacagag cttcttaaat gtcagaaact ggatgagcca actgcaagca
 601 aatgcttatt gtgaaaatcc agatatagta ttaattggca acaaggcaga cctaccagat
 661 cagagggaag tcaatgaacg gcaagctcgg gaactggctg acaaatatgg cataccatat
 721 tttgaaacaa gtgcagcaac tggacagaat gtggagaaag ctgtagaaac ccttttggac
 781 ttaatcatga agcgaatgga acagtgtgtg gagaagacac aaatccctga tactgtcaat
 841 ggtggaaatt ctggaaactt ggatggggaa aagccaccag agaagaaatg tatctgctag
 901 actctacata gaaactgaac atcaagaacc ccaccaaaat attactttta aaaacaatga
 961 caaaccacac aattgttgtt gagtaaacca cgcacaatgg catgtctttc tttttctgcc
1021 agaaaatcta ttttaagaaa ccagaatagt caacagtgtt caaaagaatt gactagttat
1081 ccctgaggcc ctttcaaaca tgatcaaaga tttcccaatg tgatctcatc atcatggata
1141 ctcaatttgt tttttcttat agagaaaatg agtatataag acaatataca agaagaaata
1201 tcagtgagtt ttaaatcaga acaagttacc tgtcacattg aagaaaaggg taggcactaa
1261 agggagaaca cagaaagaag aatttctaaa atattggatt tacttcttat attgagtcag
1321 atgcatactt ttagatttgc attggggaaa atgtactagc taaaaatgga tacacaatga
1381 agaattctat ttggctaatt aagaatgata tactatgtac acccaataag ctgtactaga
1441 atgaataaat tactgataag gttacaaata ggtaaatgtc acacttctgt taaaatgcag
1501 gaggtagtgt cataatgccg tctttatatt cttaataaat agcactttga caagaacagg
1561 actgtaaatg atgaagtaca agacaaatac cctgggaaaa aaaatgaaag tatgagaaat
1621 tggcattcct acagctgaaa ttcaatgcat ctgttagaga tgtctggaag ggttactcag
1681 ccaaatttta ctcaagccaa ttaggagctg atattatcag ttggaattaa gagaactcca
1741 gaggtttcca tttcaaacaa aattttagaa attggtttgg tgttcagctt cacatttcat
1801 tttttcttag cacatgttga taaaatagtc acaaggagaa attaccagtt acggtttatt
1861 aaatctcttt taaaatgcag tcaaggaaaa ctagccttga attttttta gataaaataa
1921 gatggtgata tgaaacaaaa agtggcaatt attgcaggtt tccttttagt ttacaaaagt
1981 actggaaact aaatcatatt tcttccctcc aaatttcacc cattcctgac tttgaatcaa
2041 ttgcagaaat gcaggtgtgt tactttgttg atcaataact ttggaacaat tatggatcaa
2101 ttctatggtc actctgaatt ttcatgtcat taatcacata aaaattgata atacctcatt
2161 ctgtattaca atatgatttt attttgccaa aggcaagaca cctatagttg agctgtattt
2221 tgggggactg ggtgaggaag gacttctgat cttatctcaa caaaaaactg gccagtattt
```

TABLE 7-continued

| SEQUENCES OF EXEMPLARY mRNA TRANSCRIPTS: |
|---|
| 2281 ttgttaatgt aaagcttcct tttctttcta aaaaatagta acaaaattat ttttcattgg |
| 2341 cctattctgt tcttgtgtct aaactaacat tacattaatt tttaatctta gtttctgata |
| 2401 aacacaagcc attcctatca aaatattatt tatttcagtc aattttacca aataacaaag |
| 2461 acaatatatt ttcgtttttt tttattatga gcatatgatt ttttgacagg ctgtttcctc |
| 2521 gtcgtataga ttttttccaa tcaaacctac tttttccata ctctgtgcat attttttgtg |
| 2581 aagttataca cattgaagac cctaaaaatc ccagtccatc attcagctta cctctgcgaa |
| 2641 cttctatctg gtattgaatc agtttcagaa acacagacag atccaaggaa atgtctcttt |
| 2701 ataatgttct taggatggac tagacccata aatgtgccat gaatcaaaat attaataatt |
| 2761 tgaaagcttt catgctgtta gcccctgatg aaattctcag cattaactgg ccagctcctc |
| 2821 tgatttctgc agcatcgcaa caggttcgaa gatgggttgt ggctgggtat tccctcccat |
| 2881 ggtgtttcct ctgggatgct cttcattatc tcaatgcctg tgccatgaag atagaaaact |
| 2941 gtaagctaac atttaagatg tttcttctgg aaggaaagtg agcaggaaca agttatattg |
| 3001 ccactgctgt ggcaaatttt ggtgaacttt tggggtcatt atatcaattt tttctttgga |
| 3061 ttcaaattgt aatgtcccct gcatttcctt aatagggaat gtgaaacctt tataaaactc |
| 3121 taaaagtatt ctgttttgat atgtcttttt gtttctattc attttcagtt atatgattga |
| 3181 tttacttatg ccaagattct gtcactgtca gttatttaat gagtgttttt tcagggtctg |
| 3241 ttttaagatc attatttgat agctgtagca tgaagcagag gttgatgatg cccataattg |
| 3301 caagactatt cctgtaaaaa taacaattat tgggtaataa cttcaagagg aatgagaagt |
| 3361 gacaaaattg atttaaaata ttgttctact tataaataaa tgcttgatat aaaaaatttt |
| 3421 ctccataaag tttgacatct gaccccagat tctatgtaat cattattaga aattccttct |
| 3481 ctcattattt caggattagt agttctgtgt aattcatttt acaatttcaa attgttctgg |
| 3541 tgccataaag tatacagact actttaaaga tttccaaatc ccctaattta ccccacaaca |
| 3601 gcatgtaatt ttagccaaga tatgtcctgt tactaagtat ctcccaatgc tttagtaaaa |
| 3661 cgtatttagg agaaatgttg aaaatgtaca tgaagctcct ttctgatata gaaaccattt |
| 3721 ctggagtatt tacactggtt tgatgtttac attgctctaa ctcggtgcct cagatacctc |
| 3781 tgtgaccaaa tttgtctcca accacatagc tcatttccta taatgttata tcataggaag |
| 3841 ccctcacaga gacactaaca cagctaaaga tcttctgata ttatcagcaa gggatgcaag |
| 3901 gactttattg gaatctggag agtttaactg ccttctcttg gtctcctcac ttacttctta |
| 3961 tgaagttggc attacctgag actcttagct gtgattaggt acaagcttac cttttagggt |
| 4021 agaaaaagaa agatcatttg aaaaatgtat ctaaaataat ccagagaaca taatgtttgt |
| 4081 cttggtctga taatgataag aagtcaagga ttggcagaga aaatactaaa cgccaagagt |
| 4141 tgagcctgtg ggtctctcca taagagtttt aaaactcttg ccagttacca ctttatccaa |
| 4201 tttgctatca ttttcgtatt atcagctatc gccctgtaaa atattcaaaa ctagctattt |
| 4261 ctaaagtaaa cattttatct gttactttta accagatagg tgtctttgtc atccttctac |
| 4321 tataaattgt tctttgccaa cctgtacagg tagatgaacc aggcgagagt tttaatcagc |
| 4381 cttttcttgt ccccttttgta agaaagagat gcttgccata gagaaggaca tgagtacatt |
| 4441 aaaaataatt taatagccac aatatgatgt tctttaagct gcaaattgag tacactggga |
| 4501 atcaacaaat ttgatgaagc ctgtctgtct cttcaccagt ggagtgagtg cagcagttag |
| 4561 aaagagaagc aatattgtgc aactggtgca gcggtgagtt aatcatagtg tataaccttg |

TABLE 7-continued

| SEQUENCES OF EXEMPLARY mRNA TRANSCRIPTS: |
|---|
| 4621 tgttcatgaa acaggttgtt cattgttctg catctctctt catttaaaaa ggatacacaa |
| 4681 ttctttcctc attgcatatt acaccaaacg tttgagggaa aaatcctcat tcgtaaagga |
| 4741 ttttggatgt ataatctaaa actcaacaat aaagaaataa tattccaagt ctctggtttc |
| 4801 ctaagataca taataactgt ttataaagaa ggtctaagag ctgatatttg ccaaagtgat |
| 4861 agaagagttg ttttttcctc tctactacca agctttaaga cattaaaaga agtctagtgt |
| 4921 atttgaatat tttagagaaa gctttatcat tttttaagat gccaagatgc tgcctacgtt |
| 4981 tgcaaaagtt gtctaagaat tcaccatgag ctatattttc ttctggatct ttgaccaagg |
| 5041 tgatgtcagc ttatttctgg ggaaggtgtt gagctcttat acatgaaaat ggatataggc |
| 5101 tattctctgg gatgagtgtc atttcaatgc tttataaatc catgaagctg cttgtctcat |
| 5161 aaagtagaac tgatacaaat tttggttgga tatatagaga attttacaaa tgtattgcct |
| 5221 tagaatttct gggtggagac ccaactacaa tgacattgtc atgccagaac tataaagata |
| 5281 attagagtta aaagttgttt aaattgtgcc cttaaataca gcagaacctg gagaaggtca |
| 5341 tacttcaaag gtcgattttg agtccgaaca aagaaagacc tagtaacaga tagttttttt |
| 5401 ttgttcattt tcttctacca agtagaggtt tatgccctca gaactaaact agtaaaaata |
| 5461 tctgaacaaa aaacctttcg ttgttggcat aaaaatgtga tacacttaga gacattttgt |
| 5521 ttattgcata taaatctaat ttttccataa attagattta tgatattttc ataaagcact |
| 5581 tgattagttt ttcaaggcgt accatcacaa agatgctttc ctgcagagtt ctttgtatca |
| 5641 acagcctatg gttgagatgt tttctcattt cctgtagaga gagaatacca ctaacaaaca |
| 5701 aacaaaaact ttagtgccaa aatagtggaa ctattttgtc atctttcgag aaaaaaatat |
| 5761 acaaagaagt catcttttca ttaagtggat tccctggttc ctttccagct ggttgtggaa |
| 5821 gtaatggcta acatccttca gctgactttg tctacaagga ttattagcaa attctgtagg |
| 5881 agcaagcatg tccgacctta acttaatgga tcccttattc aatcagtggc ttctgtcttt |
| 5941 atgtctgttg gcatatcaaa atggtttctg ttcctagaaa agtaataaca tatgcttatc |
| 6001 tttattcttt ttccaggtga ttttgttttc aaatgctcct tgtgaaaaca cctagtgttg |
| 6061 tagaaaggaa agtggccaga aagaacaact tgggaccatg agtaggtcat taaatagctt |
| 6121 agtgatttat cctcatatag ggcttataaa ccctgtatgt gtttatatgt gcttcacaga |
| 6181 gttcgtgtca ggctcaaagg agatatgtat aagaaagtgg tttgtaaatt atgttccatt |
| 6241 tcataaatag acactattca caaactaaaa tctaataaaa aaccacagtt gtaatttaaa |
| 6301 ctgcttgata taaaaagagg tatcatagca gggaaaacac actaattttc atacagtaga |
| 6361 ggtattgaaa actgaaaatg ggaaggcaac ttgaagtcat tgtatttgat tgaaaatgtt |
| 6421 taatacatct cattattgac aaaatatgtc atcttgtatt tatttcaagg aaaccaatga |
| 6481 attctaggta gtatattaca agttggtcaa aatattccat gtacaaatag ggcttctgtg |
| 6541 tccatagcct tgtaagagat actgattgta tctgaaatta ttttttaaaa aaataaatta |
| 6601 tcctgcttta gttagtgtgt taaaagtaga cgatgttcta atataacact gaagtgcttc |
| 6661 attgtatccc aacagtttac cttcaagtaa tattatcttt atttttaggc taagcacgtt |
| 6721 tgattatttt gtctgtctcc tatatagatc tgttttgtct agtgctatga atgtaactta |
| 6781 aaactataaa cttgaagttt ttattctata tgccccttaa tagactgtgg ttcctgacgc |
| 6841 acactgttag gtcattattt tgttgtacca aagttctagt ggcttcagaa atcatagcat |

TABLE 7-continued

SEQUENCES OF EXEMPLARY mRNA TRANSCRIPTS:

6901 ccaatgattt tttggtgtct ggctatgaat actatggttg agaattgtat tcagtgattg 6961 tttctgcaca cttttcaaat aaaaaatgaa tttttatcaa tta RGS18 mRNA transcript 2158 bp

SEQ ID NO: 18

1 agttctgcat ttctgcagag acagaaagaa acgcagctct tgacttcttt tttgtaaaca 61 ttactgtaag agttgtgata actttttatt ctactatgta tatgtatgga atagtattaa 121 taaatgaact agggaaggat gtaataaatt agacatctct tcattttaga gagaagatgg 181 aaacaacatt gcttttcttt tctcaaataa atatgtgtga atcaaaagaa aaaacttttt 241 tcaagttaat acatggttca ggaaaagaag aaacaagcaa agaagccaaa atcagagcta 301 aggaaaaaag aaatagacta agtcttcttg tgcagaaacc tgagtttcat gaagacaccc 361 gctccagtag atctgggcac ttggccaaag aaacaagagt ctcccctgaa gaggcagtga 421 aatggggtga atcatttgac aaactgcttt cccatagaga tggactagag gcttttacca 481 gatttcttaa aactgaattc agtgaagaaa atattgaatt ttggatagcc tgtgaagatt 541 tcaagaaaag caagggacct caacaaattc accttaaagc aaaagcaata tatgagaaat 601 ttatacagac tgatgcccca aaagaggtta accttgattt tcacacaaaa gaagtcatta 661 caaacagcat cactcaacct accctccaca gttttgatgc tgcacaaagc agagtgtatc 721 agctcatgga acaagacagt tatacacgtt ttctgaaatc tgacatctat ttagacttga 781 tggaaggaag acctcagaga ccaacaaatc ttaggagacg atcacgctca tttacctgca 841 atgaattcca agatgtacaa tcagatgttg ccatttggtt ataaagaaaa ttgattttgc 901 tcatttttat gacaaactta tacatctgct tctaacatat cgcatgttta tgttaagatt 961 tggtcccatc ctttaaactg aaatatgtca tgtgaaatta ttttaaaaat gtaaaaacaa 1021 aactttctgc taacaaaata catacagtat ctgccagtat attctgtaaa accttctatt 1081 tgatgtcatt ccatttataa tcagaaaaaa aacttatttc ttaatcaaaa ggcagtacaa 1141 aaaaagtaat aatgttttat aagattgtag agttaagtaa aagttaagct tttgcaaagt 1201 tgtcaaaagt tcaaacaaaa gtctagttgg gatttttttac caaagcagca taatatgtgt 1261 tatataaaca taataatact cagatatcca aatgttcaga tagcattttt cataatgaa”

1321 gttctctttt ttttggtaat agtgtagaag tgatctggtt cttacaatgg gagatgaaga 1381 acatttatta ttgggttact actaaccctg tcccaagaat agtaatatca cctctagtta 1441 taagccagca acaggaactt ttgtgaagac acattcatct ctacagaact tcagattaaa 1501 tataatctag attaatgact gagaataaga tccacatttg aactcattcc taagtgaaca 1561 tggacgtacc cagttataca aagtacttct gttggtcaca gaaacatgac cagattttgc 1621 atatctccag gtagggaact aagtagacta ccttatcacc ggctaagaaa acttgctact 1681 aaactattag gccatcaatg gcttgaataa aaaccagaga aggtttttcc caggacgtct 1741 catgtttggc cctttagaat tggggtagaa atcagaaatg agatgagggg aagaagcaag 1801 gagtctaagg ccctagcgat ttgggcatct gccacattgg ttcatattca gaaagtgtta 1861 tctcattgat tatattcttg ttaagcaaat ctccttaagt aattattatt caaataagat 1921 tatactcata catctatatg tcactgtttt aaagagatat ttaattttta atgtgtgtta 1981 catggtctgt aaatacttgt atttaaaaat gccatgcatt aggctttgga aatttaatgt 2041 tagttgaaat gtaaaatgtg aaaactttag atcatttgta gtaataaata tttttaactt 2101 cattcataca gttaagttta tctgacaata aaagctctga ctgaaaaaaa aaaaaaaa TABLE 7-continued

| SEQUENCES OF EXEMPLARY mRNA TRANSCRIPTS: |
|---|

TBC1D15 mRNA transcript 5852 bp

SEQ ID NO: 19

```
   1 ttttgccgga tgttgttgta tgtccgagag acacgtgagg ttctgctacg tcattaccag
  61 gcacgcgcag gaaacatggc ggcggcgggt gttgtgagcg ggaaggtttt tggtttcttc
 121 ttgattcaat cttgataagt agtatgtgtc caggacttta tccatactcc agtttgttgg
 181 agtatggtag gagtatgatt atatatgaac aagaaggagt atatattcac tcatcttgtg
 241 gaaagaccaa tgaccaagac ggcttgattt caggaatatt acgtgtttta gaaaaggatg
 301 ccgaagtaat agtggactgg agaccattgg atgatgcatt agattcctct agtattctct
 361 atgctagaaa ggactccagt tcagttgtag aatggactca ggccccaaaa gaaagaggtc
 421 atcgaggatc agaacatctg aacagttacg aagcagaatg ggacatggtt aatacagttt
 481 catttaaaag gaaaccacat accaatggag atgctccaag tcatagaaat gggaaaagca
 541 aatggtcatt cctgttcagt ttgacagacc tgaaatcaat caagcaaaac aaagagggta
 601 tgggctggtc ctatttggta ttctgtctaa aggatgacgt cgttctccct gctctacact
 661 ttcatcaagg agatagcaaa ctactgattg aatctcttga aaaatatgtg gtattgtgtg
 721 aatctccaca ggataaaaga acacttcttg tgaattgtca gaataagagt ctttcacagt
 781 cttttgaaaa tcttcctgat gagccagcat atggtttaat acaaaaaatt aaaaaggacc
 841 cttatacggc aactatgata ggattttcca aagtcacaaa ctacattttt gacagtttga
 901 gaggcagcga tccctctaca catcaacgac caccttcaga aatggcagat tttcttagtg
 961 atgctattcc aggtctaaag ataaatcaac aagaagaacc aggatttgaa gtcatcacaa
1021 gaattgattt gggggaacgc cctgttgttc aaaggagaga accggtatca ctggaagaat
1081 ggactaagaa cattgattct gaaggaagaa ttttaaatgt agataatatg aagcagatga
1141 tatttagagg gggacttagt catgcattga gaaagcaagc atggaaattt cttctgggtt
1201 attttccctg ggacagtacc aaggaggaaa gaacccaatt acaaaagcaa aaaactgatg
1261 aatacttcag aatgaaactg cagtggaaat ccatcagcca ggaacaagag aaaagaaatt
1321 cgaggttaag agattacaga agtcttatcg aaaaagatgt taacagaaca gatcgaacaa
1381 acaagtttta tgaaggccaa gataatccag ggttgatttt acttcatgac attttgatga
1441 cctactgtat gtatgatttt gatttaggat atgttcaagg aatgagtgat ttactttccc
1501 ctcttttata tgtgatggaa aatgaagtgg atgccttttg gtgctttgcc tcttacatgg
1561 accaaatgca tcagaatttt gaagaacaaa tgcaaggcat gaagacccag ctaattcagc
1621 tgagtacctt acttcgattg ttagacagtg gattttgcag ttacttagaa tctcaggact
1681 ctggatacct ttatttttgc ttcaggtggc ttttaatcag attcaaaagg gaatttagtt
1741 ttctagatat tcttcgatta tgggaggtaa tgtggaccga actaccatgt acaaatttcc
1801 atcttcttct ctgttgtgct attctggaat cagaaaagca gcaaataatg gaaaagcatt
1861 atggcttcaa tgaaatactt aagcatatca atgaattgtc catgaaaatt gatgtggaag
1921 atatactctg caaggcagaa gcaatttctc tacagatggt aaaatgcaag gaattgccac
1981 aagcagtctg tgagatcctt gggcttcaag gcagtgaagt tacaacacca gattcagacg
2041 ttggtgaaga cgaaaatgtt gtcatgactc cttgtcctac atctgcattt caaagtaatg
2101 ccttgcctac actctctgcc agtggagcca gaaatgacag cccaacacag ataccagtgt
2161 cctcagatgt ctgcagatta acacctgcat gatcactgtt cttgcttttt tgggaagaga
2221 cactttgttg caacccttt tcaagtactt gaaagttgaa aatttgaaat cttggtattg
```

TABLE 7-continued

| SEQUENCES OF EXEMPLARY mRNA TRANSCRIPTS: |
|---|
| 2281 atcatgcttt aaggtttatg taaagaaagt gtactgatgt tcttacatta aagctttaca |
| 2341 aagatttaaa ctaattattt ttgtagttac ttctaccaaa tagcctttcc ttttcgataa |
| 2401 cattcctcag tatttttata gccaagtaca ttttattttc ttgctgatga actggaattg |
| 2461 gataaatatt gcaagtggat gagttggaaa ttatgcactt tgaaaaacat tcactttgtt |
| 2521 taagcttatt gggtttcaga tttgattaaa ttaaatgtgg aggctttcta tagcattcta |
| 2581 agctgagaag tagattgtta cccagtaatg aaataaaaaa taaaaacaaa aggatttttt |
| 2641 tctctattgt ttacgacagt actcagctta aatatttatg ctggtcaaat gtgatttaaa |
| 2701 ttggacattt tcatcaatgc agtctaatgt gtagataaat atttcaacca taataagtgg |
| 2761 attggcagta tatttttttac attgaacttt tcttcacttg tatataaaga ttatatataa |
| 2821 gtacttattt atgagcataa gaaaggttag gcatattttc attaactgaa taaacgactt |
| 2881 gatttatata acctggttta tcaaaattta acatggcttc agtatgagat ctttttcaaa |
| 2941 actattttct taaacattta tttcatgaga ttatgttcaa ccctgtacct ggtgtaattt |
| 3001 taaaattaat tgcttgtaac ctcactttac taataatgtt tattatcttt cctaataatg |
| 3061 cattaactga ttaatcaggt gtttaaattt ttataaaata ctcttgcaaa aagtttattt |
| 3121 gaaaaatttc tagatggtct catgagtttc aaaataataa tttttgcgta tgaacaaagc |
| 3181 tgttgttttt accatgcagt attgcatgat tttaagttat gtggaattaa cataactgat |
| 3241 tttgttttaa ttgtaagttg ttaactcctg tatatatcat taaaataaat ctgaagttga |
| 3301 agtagtgttt ttagttaaat tatacttaga aatagtctgc ttttttaaaa ttttttttct |
| 3361 tgagaaagag tcttgctctg ttgcccaggc tggagtgcag tggcgcagtc ctggctcact |
| 3421 gcagcctccg ccttctgggt tcaagcgatt ctcctgtctc agcctcccga gcagctggga |
| 3481 ctacaggctt gtgccatcgc gcctgactaa tttttgtatt ttgagtagag atggggtttc |
| 3541 accatgttgg ccaggctggt ctcgaactct tgacctcaag tgatccactc gcttcagcct |
| 3601 cccaaagtgc tgagattaca ggtgtgagcc actgtgcccg gctaattctt taatagaaga |
| 3661 aaaaacatcc aagatggacc tcaattcatc tcttattttt atatgattaa aatgataatc |
| 3721 tggccgggcg cggtggctca cgcctgtaat cccagcactt tgggaggccg aggcgggcgg |
| 3781 atcacgaggt caggagatcg agaccatccc ggctaaaacg gtgaaacccc gtctctacta |
| 3841 aaaatacaaa aaattagccg ggcgtagtgg cgggcgcctg tagccccagc tacttgggag |
| 3901 gctgaggcag gagaa-ggcg tgaacccggg aggcggagct tgcagtgagc cgagatcccg |
| 3961 ccactgcact ccagcctggg cgacagagcg agactccgtc tcaaaaaaaa aaaaaaaaaa |
| 4021 atgataatct gaataagtta tggaaatgaa aaccatcctt tttataactg aaaaaaaatt |
| 4081 ttcattagca tggaaatggg cacagtgttg ccttgaaaga tacagttatt tgactcagta |
| 4141 aagcagctta ttacaactga tgctaatagt atagagaaaa aagttgtgca gttctaaaat |
| 4201 ggtcctagag attgactttt ttccccccaag aaagttaggg aacaaaacga actttttttcc |
| 4261 tggttgagca ttaactgaca atcacgacag tagaaccgtt agagtttagt ttttaatatt |
| 4321 atgtgtgtta tctttcatca gttaataatg agtaagccta ttcagaaaaa gaacataaac |
| 4381 tgatcaaaaa ctcagcatct ccagcctttc atttcctgct attcaggaaa ttgcttagaa |
| 4441 catcttgatg tcctccttgt tcttcctgga cagtgacttt ttgggagttt gttcctgctg |
| 4501 cgtaatgtga tacccacttc agattttttt tttatcaata catttagtaa gttgaacttc |
| 4561 tgtcaagttt tattacaaaa ttacttgtta aaacaatttt tactaaactg catttctatc |

TABLE 7-continued

| SEQUENCES OF EXEMPLARY mRNA TRANSCRIPTS: |
|---|
| 4621 tagcatattt ttgatatgga agtgatagta tagtatagtt ccaggagaag tcttaaatca |
| 4681 gtccacagag tccagttagc aaatactctg tgccattaag attgctaaaa tacacagttc |
| 4741 aggtaaattt actagcgttt tttaaaggtt tatttgtttt cacaagatgc tctgtccaca |
| 4801 cccttataac atgtaaaata ttgtgtgctg tattatgtgg taaagttgtt aaaattcagt |
| 4861 ttctaacatt aacttaaaag tacagacaat ctaacatgat gatttgactt acaaactttc |
| 4921 aactaaattt atgatggctt taaagcagtg cactgaatag aaaccatact ttgagtaccc |
| 4981 atacagccat ttttcacttt tactacaata ttctataaat cacatgagat atttaacact |
| 5041 ttattataaa ataggctttg tgttagatga ttttgcccaa atgtaaacta atgtagtgtt |
| 5101 ctgagcatgt ttaagttagg gtaggctaaa ctatgtttgg taggttagat gtattaaaag |
| 5161 catttttgat taatgatgtc ttcaatttat gatgtgttta ttggaacata acctcaatat |
| 5221 aagttgaaaa gcatacgtat tttcaattct ggcatgaacc tatgggaatc ttttgcattt |
| 5281 aagaacctcc ccattttaat aatttcatgg gtctaagatt cttcatctgt ttataaggaa |
| 5341 ctttagtctt agtgattaga gactaaattt tttttgagc agtaagaaaa cagccttttg |
| 5401 ggacagatag tgagtgattc ttaggaactt gacattgcca agaaatttta tagatgccga |
| 5461 agaattctta tgtgaaattc acataagcat gcccattact aaagacagtt tgtataaagt |
| 5521 aaccctaaat gtttactgag gaacctacag cttcaactga cttacgcgca gatatgtacc |
| 5581 aggagaacat cattttagct tgggcgtctt tacttggggt tttcagagga tccaggaacc |
| 5641 tcactgtatg caaagtcttg tggatgtacc tgaatgtttt tggaggcagg tcacatagtt |
| 5701 tctgaaagtg ttctcttatt ttcctcaaat gtaggtaacc attgttacaa gttatttaac |
| 5761 aggagaatag taacaatgtc taacttatgc taatgatttt gtgtgctgag ctcccattaa |
| 5821 ttaaaatgtc ttcagaaaaa aaaaaaaaaa aa |

Ngo et al., *Science* 360,1133-1136 (2018) is incorporated herein by reference.

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same.

What is claimed is:

1. A method for treating a pregnant subject for elevated risk of having preterm delivery, comprising:

(a) assaying a maternal sample obtained or derived from the pregnant subject to determine an expression profile of a panel of genes, wherein the panel of genes comprises three or more genes selected from the group consisting of CLCN3, DAPP1, POLE2, PPBP, LYPLAL1, MAP3K7CL, MOB1B, RAB27B, RGS18, and TBC1D15;

(b) computer processing the expression profile determined in (a) (i) against reference expression levels of the panel of genes or (ii) with a trained machine learning model;

(c) determining, based at least in part on the computer processing in (b), that the pregnant subject has an elevated risk of having the preterm delivery; and (d) administering to the pregnant subject a therapeutic intervention for the elevated risk of having the preterm delivery, wherein the therapeutic intervention is selected from the group consisting of a progesterone, an antibiotic, a cervical cerclage, a cervical pessary, a folate supplement, and an omega-3 fatty acid supplement.

2. The method of claim 1, wherein the maternal sample is obtained in at least one of months 3 to 8 after pregnancy.

3. The method of claim 1, wherein the reference expression levels are obtained from a first population of subjects having a preterm delivery, a second population of subjects having a full-term delivery, or both.

4. The method of claim 3, wherein one or more of the reference expression levels are determined using a machine learning technique.

5. The method of claim 1, wherein the three or more genes comprise RAB27B.

6. The method of claim 1, wherein the assaying comprises assaying cell-free ribonucleic acid (cfRNA) from the maternal sample obtained or derived from the pregnant subject.

7. The method of claim 1, wherein the maternal sample is selected from the group consisting of a blood sample, a blood plasma sample, a blood serum sample, and a urine sample.

8. The method of claim 7, wherein the maternal sample is the blood plasma sample.

9. The method of claim 1, wherein the assaying comprises performing capture-based enrichment of nucleic acids from the maternal sample for the panel of genes.

10. The method of claim 9, wherein the capture-based enrichment comprises use of primers or probes configured to specifically hybridize to nucleic acid sequences of the panel of genes.

11. The method of claim 1, wherein (b) further comprises determining that the expression profile indicates elevated expression of PPBP in the pregnant subject having the elevated risk of having the preterm delivery.

* * * * *